US009187546B2

(12) United States Patent
DeFrees

(10) Patent No.: US 9,187,546 B2
(45) Date of Patent: *Nov. 17, 2015

(54) COMPOSITIONS AND METHODS FOR THE PREPARATION OF PROTEASE RESISTANT HUMAN GROWTH HORMONE GLYCOSYLATION MUTANTS

(75) Inventor: Shawn DeFrees, North Wales, PA (US)

(73) Assignee: Novo Nordisk A/S, Bagsvaerd (DK)

(*) Notice: Subject to any disclaimer, the term of this patent is extended or adjusted under 35 U.S.C. 154(b) by 663 days.

This patent is subject to a terminal disclaimer.

(21) Appl. No.: 11/910,958

(22) PCT Filed: Apr. 10, 2006

(86) PCT No.: PCT/US2006/013903
§ 371 (c)(1),
(2), (4) Date: May 15, 2008

(87) PCT Pub. No.: WO2006/121569
PCT Pub. Date: Nov. 16, 2006

(65) Prior Publication Data
US 2009/0124544 A1 May 14, 2009

Related U.S. Application Data

(60) Provisional application No. 60/669,736, filed on Apr. 8, 2005, provisional application No. 60/710,401, filed on Aug. 22, 2005, provisional application No. 60/720,030, filed on Sep. 23, 2005.

(51) Int. Cl.
C07K 14/61 (2006.01)
A61K 38/27 (2006.01)
A61P 5/06 (2006.01)
C12N 15/09 (2006.01)
A61K 38/00 (2006.01)

(52) U.S. Cl.
CPC .............. C07K 14/61 (2013.01); A61K 38/27 (2013.01); C12N 15/09 (2013.01); A61K 38/00 (2013.01)

(58) Field of Classification Search
None
See application file for complete search history.

(56) References Cited

U.S. PATENT DOCUMENTS

| | | |
|---|---|---|
| 4,055,635 A | 10/1977 | Green et al. |
| 4,088,538 A | 5/1978 | Schneider |
| 4,179,337 A | 12/1979 | Davis et al. |
| 4,385,260 A | 5/1983 | Watts et al. |
| 4,412,989 A | 11/1983 | Iwashita et al. |
| 4,414,147 A | 11/1983 | Klibanov |
| 4,438,253 A | 3/1984 | Casey et al. |
| 4,451,566 A | 5/1984 | Spencer |
| 4,496,689 A | 1/1985 | Mitra |
| 4,565,653 A | 1/1986 | Ives et al. |
| 4,675,414 A | 6/1987 | DeFusco et al. |
| 4,767,702 A | 8/1988 | Cohenford |
| 4,806,595 A | 2/1989 | Noishiki et al. |
| 4,826,945 A | 5/1989 | Cohn et al. |
| 4,847,325 A | 7/1989 | Shadle et al. |
| 4,879,236 A | 11/1989 | Smith et al. |
| 4,918,009 A | 4/1990 | Nilsson |
| 4,925,796 A | 5/1990 | Bergh et al. |
| 4,980,502 A | 12/1990 | Felder et al. |
| 5,032,519 A | 7/1991 | Paulson et al. |
| 5,047,335 A | 9/1991 | Paulson et al. |
| 5,104,651 A | 4/1992 | Boone et al. |
| 5,122,614 A | 6/1992 | Zalipsky |
| 5,147,788 A | 9/1992 | Page et al. |
| 5,153,265 A | 10/1992 | Shadle et al. |
| 5,154,924 A | 10/1992 | Friden |
| 5,164,374 A | 11/1992 | Rademacher et al. |
| 5,166,322 A | 11/1992 | Shaw et al. |
| 5,169,933 A | 12/1992 | Anderson et al. |
| 5,180,674 A | 1/1993 | Roth |
| 5,182,107 A | 1/1993 | Friden |
| 5,194,376 A | 3/1993 | Kang |
| 5,202,413 A | 4/1993 | Spinu |
| 5,206,344 A | 4/1993 | Katre et al. |
| 5,219,564 A | 6/1993 | Zalipsky et al. |
| 5,272,066 A | 12/1993 | Bergh et al. |
| 5,278,299 A | 1/1994 | Wong et al. |
| 5,281,698 A | 1/1994 | Nitecki |
| 5,288,637 A | 2/1994 | Roth |

(Continued)

FOREIGN PATENT DOCUMENTS

| | | |
|---|---|---|
| AU | 1991/083760 A | 3/1992 |
| AU | 1992/017052 | 12/1992 |

(Continued)

OTHER PUBLICATIONS

Abeijon et al., 1986, J. Biol. Chem. 261(24):11374-11377.
Abuchowski et al., 1977, J. Biol. Chem. 252:3582-3586.
Abuchowski et al., 1984, Cancer Biochem. Biophys. 7:175-186.
Abuchowski et al., 1977, J. Biol. Chem. 252:3578-3581.
Ailor et al., 2000, Glycobiology 10:837-847.
Allegre et al., 2006, J. Membrane Science 269:109-117.
Altmann et al., 1999, Glycoconjugate J. 16:109-123.
Aplin et al., 1981, CRC Crit Rev. Biochem. 259-306.
Beauchamp et al., 1983, Anal Biochem.131:25-33.
Berger et al., 1988, Blood 71:1641-1647.
Berg-Fassman et al. 1993, J. Biol. Chem. 268:14861-14866.
Bhadra et al., 2002, Pharmazie 57:5-29.
Bhatia et al., 1989, Anal. Biochem. 178:408-413.
Bickel et al., 2001, Adv. Drug Deliv. Rev. 46:247-279.
Bjoern, et al., 1992, J. Biol. Chem., 266(17):11051-11057.
Boccu et al., 1983, Z. Naturforsch 38C:94-99.
Boime et al., 1995, Endocrinology 136:2635-2640.

(Continued)

Primary Examiner — Zachary Howard
(74) Attorney, Agent, or Firm — Leydig, Voit & Mayer, Ltd.

(57) ABSTRACT

The present invention relates to protease resistant mutants of human growth hormone, which contain newly introduced proteolysis resistant mutations and N-linked or O-linked glycosylation site(s), such that these recombinantly produced polypeptides have glycosylation patterns distinctly different from that of the naturally occurring human growth hormone. The polynucleotide coding sequences for the mutants, expression cassettes comprising the coding sequences, cells expressing the mutants, and methods for producing the mutants are also disclosed. Further disclosed are pharmaceutical compositions comprising the mutants and method for using the mutants.

39 Claims, 35 Drawing Sheets

(56) References Cited

U.S. PATENT DOCUMENTS

| | | |
|---|---|---|
| 5,308,460 A | 5/1994 | Mazid et al. |
| 5,324,663 A | 6/1994 | Lowe |
| 5,324,844 A | 6/1994 | Zalipsky |
| 5,342,940 A | 8/1994 | Ono et al. |
| 5,346,696 A | 9/1994 | Kim et al. |
| 5,352,670 A | 10/1994 | Venot |
| 5,369,017 A | 11/1994 | Wong et al. |
| 5,374,541 A | 12/1994 | Wong |
| 5,374,655 A | 12/1994 | Kashem et al. |
| 5,384,249 A | 1/1995 | Sasaki et al. |
| 5,399,345 A | 3/1995 | Schumacher et al. |
| 5,405,753 A | 4/1995 | Brossmer |
| 5,409,817 A | 4/1995 | Ito et al. |
| 5,410,016 A | 4/1995 | Hubbell et al. |
| 5,432,059 A | 7/1995 | Bean |
| 5,446,090 A | 8/1995 | Harris |
| 5,492,841 A | 2/1996 | Craig |
| 5,527,527 A | 6/1996 | Friden |
| 5,529,914 A | 6/1996 | Hubbell et al. |
| 5,545,553 A | 8/1996 | Gotschlich |
| 5,567,422 A | 10/1996 | Greenwald |
| 5,583,042 A | 12/1996 | Roth |
| 5,595,900 A | 1/1997 | Lowe |
| 5,605,793 A | 2/1997 | Stemmer |
| 5,614,184 A | 3/1997 | Sytkowski et al. |
| 5,621,039 A | 4/1997 | Hallahan et al. |
| 5,629,384 A | 5/1997 | Veronese et al. |
| 5,635,603 A | 6/1997 | Hansen et al. |
| 5,643,575 A | 7/1997 | Martinez et al. |
| 5,646,113 A | 7/1997 | Attie et al. |
| 5,672,662 A | 9/1997 | Harris et al. |
| 5,672,683 A | 9/1997 | Friden et al. |
| 5,705,367 A | 1/1998 | Gotschlich |
| 5,714,166 A | 2/1998 | Tomalia et al. |
| 5,716,812 A | 2/1998 | Withers et al. |
| 5,723,121 A | 3/1998 | Takenaga et al. |
| 5,728,554 A | 3/1998 | Bayer et al. |
| 5,739,208 A | 4/1998 | Harris |
| 5,762,920 A | 6/1998 | Yung et al. |
| 5,770,420 A | 6/1998 | Lowe et al. |
| 5,798,233 A | 8/1998 | Gotschlich |
| 5,811,238 A | 9/1998 | Stemmer et al. |
| 5,824,778 A | 10/1998 | Ishikawa et al. |
| 5,824,864 A | 10/1998 | Fox et al. |
| 5,830,721 A | 11/1998 | Stemmer et al. |
| 5,833,988 A | 11/1998 | Friden |
| 5,834,251 A | 11/1998 | Maras et al. |
| 5,837,458 A | 11/1998 | Minshull et al. |
| 5,849,535 A | 12/1998 | Cunningham et al. |
| 5,858,751 A | 1/1999 | Paulson et al. |
| 5,858,752 A | 1/1999 | Seed et al. |
| 5,861,374 A | 1/1999 | Berkner et al. |
| 5,874,075 A | 2/1999 | Collins et al. |
| 5,876,980 A | 3/1999 | DeFrees et al. |
| 5,922,577 A | 7/1999 | DeFrees et al. |
| 5,925,739 A | 7/1999 | Spira et al. |
| 5,932,462 A | 8/1999 | Harris et al. |
| 5,945,314 A | 8/1999 | Prieto et al. |
| 5,945,322 A | 8/1999 | Gotschlich |
| 5,955,347 A | 9/1999 | Lowe |
| 5,962,294 A | 10/1999 | Paulson et al. |
| 5,969,040 A | 10/1999 | Hallahan et al. |
| 5,977,307 A | 11/1999 | Friden |
| 6,010,999 A | 1/2000 | Daley et al. |
| 6,015,555 A | 1/2000 | Friden |
| 6,030,815 A | 2/2000 | DeFrees et al. |
| 6,034,223 A | 3/2000 | Maddon et al. |
| 6,037,452 A | 3/2000 | Minamino et al. |
| 6,048,720 A | 4/2000 | Dalborg et al. |
| 6,057,292 A | 5/2000 | Cunningham et al. |
| 6,075,134 A | 6/2000 | Bertozzi et al. |
| 6,087,325 A | 7/2000 | Meers et al. |
| 6,096,512 A | 8/2000 | Elhammer et al. |
| 6,113,906 A | 9/2000 | Greenwald et al. |
| 6,117,651 A | 9/2000 | Schultz et al. |
| 6,127,153 A | 10/2000 | Johnson et al. |
| 6,166,183 A | 12/2000 | Ishikawa et al. |
| 6,183,738 B1 | 2/2001 | Clark |
| 6,251,864 B1 | 6/2001 | Dower et al. |
| 6,261,805 B1 | 7/2001 | Wood |
| 6,268,193 B1 | 7/2001 | Lowe |
| 6,319,695 B1 | 11/2001 | Wong et al. |
| 6,340,742 B1 | 1/2002 | Burg et al. |
| 6,342,382 B1 | 1/2002 | Gotschlich |
| 6,348,558 B1 | 2/2002 | Harris et al. |
| 6,361,977 B1 | 3/2002 | Bauer et al. |
| 6,362,254 B2 | 3/2002 | Harris et al. |
| 6,376,604 B2 | 4/2002 | Kozlowski |
| 6,399,336 B1 | 6/2002 | Paulson et al. |
| 6,399,337 B1 | 6/2002 | Taylor et al. |
| 6,440,703 B1 | 8/2002 | DeFrees |
| 6,458,937 B1 | 10/2002 | Bertozzi et al. |
| 6,465,220 B1 | 10/2002 | Hassan et al. |
| 6,495,365 B1 | 12/2002 | Saito et al. |
| 6,531,121 B2 | 3/2003 | Brines et al. |
| 6,555,346 B1 | 4/2003 | Kretzdorn et al. |
| 6,555,660 B2 | 4/2003 | Nissen et al. |
| 6,586,398 B1 | 7/2003 | Kinstler et al. |
| 6,692,931 B1 | 2/2004 | Reutter et al. |
| 6,693,183 B2 | 2/2004 | Natsuka et al. |
| 6,716,626 B1 | 4/2004 | Itoh et al. |
| 6,743,896 B2 | 6/2004 | Filpula et al. |
| 6,780,624 B2 | 8/2004 | Gotschlich |
| 6,800,740 B1 | 10/2004 | Cunningham et al. |
| 6,949,372 B2 | 9/2005 | Betenbaugh et al. |
| 7,094,530 B1 | 8/2006 | Sasaki et al. |
| 7,125,843 B2 | 10/2006 | DeFrees et al. |
| 7,138,371 B2 | 11/2006 | DeFrees et al. |
| 7,157,277 B2 | 1/2007 | DeFrees et al. |
| 7,173,003 B2 | 2/2007 | DeFrees et al. |
| 7,179,617 B2 | 2/2007 | DeFrees et al. |
| 7,199,223 B2 | 4/2007 | Bossard et al. |
| 7,202,208 B2 | 4/2007 | Papadimitriou |
| 7,214,660 B2 | 5/2007 | DeFrees et al. |
| 7,226,903 B2 | 6/2007 | DeFrees et al. |
| 7,229,962 B2 | 6/2007 | Chung et al. |
| 7,235,638 B2 | 6/2007 | Persson |
| 7,265,084 B2 | 9/2007 | DeFrees et al. |
| 7,265,085 B2 | 9/2007 | DeFrees et al. |
| 7,276,475 B2 | 10/2007 | DeFrees et al. |
| 7,297,511 B2 | 11/2007 | DeFrees et al. |
| 7,304,150 B1 | 12/2007 | Egrie et al. |
| 7,338,933 B2 | 3/2008 | DeFrees et al. |
| 7,368,108 B2 | 5/2008 | DeFrees et al. |
| 7,399,613 B2 | 7/2008 | DeFrees et al. |
| 7,405,198 B2 | 7/2008 | DeFrees et al. |
| 7,416,858 B2 | 8/2008 | DeFrees et al. |
| 7,439,043 B2 | 10/2008 | DeFrees et al. |
| 7,473,680 B2 | 1/2009 | DeFrees et al. |
| 7,524,813 B2 | 4/2009 | Zundel et al. |
| 7,662,933 B2 | 2/2010 | Kinstler et al. |
| 7,691,603 B2 | 4/2010 | DeFrees |
| 7,696,163 B2 | 4/2010 | DeFrees et al. |
| 7,795,210 B2 | 9/2010 | DeFrees et al. |
| 7,803,777 B2 | 9/2010 | DeFrees |
| 7,842,661 B2 | 11/2010 | DeFrees et al. |
| 7,932,364 B2 | 4/2011 | DeFrees et al. |
| 7,956,032 B2 | 6/2011 | DeFrees et al. |
| 8,008,252 B2 | 8/2011 | DeFrees et al. |
| 8,063,015 B2 | 11/2011 | DeFrees et al. |
| 8,178,108 B2 | 5/2012 | Buechler et al. |
| 8,207,112 B2 | 6/2012 | Hinderer et al. |
| 8,247,381 B2 | 8/2012 | DeFrees |
| 8,268,967 B2 | 9/2012 | DeFrees et al. |
| 8,361,961 B2 | 1/2013 | DeFrees et al. |
| 8,633,157 B2 | 1/2014 | DeFrees et al. |
| 8,716,239 B2 | 5/2014 | DeFrees et al. |
| 8,716,240 B2 | 5/2014 | DeFrees et al. |
| 8,791,066 B2 | 7/2014 | DeFrees |
| 8,791,070 B2 | 7/2014 | DeFrees et al. |
| 2001/0041683 A1 | 11/2001 | Schmitz et al. |
| 2001/0043929 A1 | 11/2001 | Zalipsky et al. |
| 2002/0004483 A1 | 1/2002 | Nissen et al. |
| 2002/0016003 A1 | 2/2002 | Saxon et al. |

(56) References Cited

U.S. PATENT DOCUMENTS

| | | |
|---|---|---|
| 2002/0019342 A1 | 2/2002 | Bayer |
| 2002/0037841 A1 | 3/2002 | Papadimitriou |
| 2002/0068347 A1 | 6/2002 | Taylor et al. |
| 2002/0115833 A1 | 8/2002 | Burg et al. |
| 2002/0137134 A1 | 9/2002 | Gerngross et al. |
| 2002/0142370 A1 | 10/2002 | Paulson et al. |
| 2002/0142964 A1 | 10/2002 | Nissen et al. |
| 2002/0148791 A1 | 10/2002 | DeFrees |
| 2002/0150981 A1 | 10/2002 | Canfield |
| 2002/0168323 A1 | 11/2002 | Gonda et al. |
| 2002/0182586 A1 | 12/2002 | Morris et al. |
| 2003/0027257 A1 | 2/2003 | Iatrou et al. |
| 2003/0040037 A1 | 2/2003 | Bayer |
| 2003/0083251 A1 | 5/2003 | Westenfelder |
| 2003/0096338 A1 | 5/2003 | Pedersen et al. |
| 2003/0100075 A1 | 5/2003 | Persson et al. |
| 2003/0119090 A1 | 6/2003 | Wong |
| 2003/0124645 A1 | 7/2003 | Paulson et al. |
| 2003/0166212 A1 | 9/2003 | Taylor et al. |
| 2003/0166525 A1 | 9/2003 | Hoffmann et al. |
| 2003/0170863 A1 | 9/2003 | Persson et al. |
| 2003/0180835 A1 | 9/2003 | Bayer |
| 2003/0186850 A1 | 10/2003 | Clausen et al. |
| 2003/0195338 A1 | 10/2003 | Chung et al. |
| 2003/0207406 A1 | 11/2003 | Johnson et al. |
| 2004/0020857 A1 | 2/2004 | Belew et al. |
| 2004/0043446 A1 | 3/2004 | DeFrees et al. |
| 2004/0063911 A1 | 4/2004 | DeFrees et al. |
| 2004/0077836 A1 | 4/2004 | DeFrees et al. |
| 2004/0082026 A1 | 4/2004 | DeFrees et al. |
| 2004/0102607 A1 | 5/2004 | Danishefsky et al. |
| 2004/0115168 A1 | 6/2004 | DeFrees et al. |
| 2004/0126838 A1 | 7/2004 | DeFrees et al. |
| 2004/0132640 A1 | 7/2004 | DeFrees et al. |
| 2004/0136955 A1 | 7/2004 | Barker |
| 2004/0137557 A1 | 7/2004 | DeFrees et al. |
| 2004/0142856 A1 | 7/2004 | DeFrees et al. |
| 2004/0197875 A1 | 10/2004 | Hauser et al. |
| 2005/0026266 A1 | 2/2005 | Clausen et al. |
| 2005/0031584 A1 | 2/2005 | DeFrees et al. |
| 2005/0064540 A1 | 3/2005 | Defrees et al. |
| 2005/0085631 A1 | 4/2005 | Boyle et al. |
| 2005/0100982 A1 | 5/2005 | DeFrees et al. |
| 2005/0106658 A1 | 5/2005 | DeFrees et al. |
| 2005/0113565 A1 | 5/2005 | Klausen et al. |
| 2005/0118672 A1 | 6/2005 | DeFrees et al. |
| 2005/0143292 A1 | 6/2005 | DeFrees et al. |
| 2005/0250678 A1 | 11/2005 | DeFrees et al. |
| 2005/0269265 A1 | 12/2005 | DeFrees |
| 2005/0271690 A1 | 12/2005 | Gotschlich |
| 2005/0288490 A1 | 12/2005 | Nakamoto et al. |
| 2006/0024286 A1 | 2/2006 | Glidden |
| 2006/0029573 A1 | 2/2006 | Shen et al. |
| 2006/0030521 A1 | 2/2006 | DeFrees et al. |
| 2006/0035224 A1 | 2/2006 | Johansen |
| 2006/0040856 A1 | 2/2006 | DeFrees et al. |
| 2006/0088906 A1 | 4/2006 | DeFrees et al. |
| 2006/0111279 A1 | 5/2006 | DeFrees et al. |
| 2006/0165728 A1 | 7/2006 | Young et al. |
| 2006/0177892 A1 | 8/2006 | De Frees |
| 2006/0182714 A1 | 8/2006 | Behrens et al. |
| 2006/0183198 A1 | 8/2006 | Buechler et al. |
| 2006/0246544 A1 | 11/2006 | Kang et al. |
| 2006/0276618 A1 | 12/2006 | DeFrees et al. |
| 2006/0287223 A1 | 12/2006 | DeFrees et al. |
| 2006/0287224 A1 | 12/2006 | DeFrees et al. |
| 2007/0014759 A1 | 1/2007 | DeFrees et al. |
| 2007/0026485 A1 | 2/2007 | DeFrees et al. |
| 2007/0027068 A1 | 2/2007 | DeFrees et al. |
| 2007/0032405 A1 | 2/2007 | DeFrees et al. |
| 2007/0037966 A1 | 2/2007 | Rasmussen et al. |
| 2007/0042458 A1 | 2/2007 | DeFrees et al. |
| 2007/0059275 A1 | 3/2007 | DeFrees et al. |
| 2007/0105755 A1 | 5/2007 | DeFrees et al. |
| 2007/0111926 A1 | 5/2007 | Zundel et al. |
| 2007/0154992 A1 | 7/2007 | DeFrees |
| 2007/0254834 A1 | 11/2007 | DeFrees et al. |
| 2007/0254836 A1 | 11/2007 | Defrees et al. |
| 2008/0015142 A1 | 1/2008 | DeFrees et al. |
| 2008/0039373 A1 | 2/2008 | Klausen et al. |
| 2008/0050772 A1 | 2/2008 | DeFrees et al. |
| 2008/0070275 A1 | 3/2008 | DeFrees et al. |
| 2008/0102083 A1 | 5/2008 | DeFrees et al. |
| 2008/0108557 A1 | 5/2008 | Behrens et al. |
| 2008/0146494 A1 | 6/2008 | DeFrees et al. |
| 2008/0146782 A1 | 6/2008 | DeFrees et al. |
| 2008/0176790 A1 | 7/2008 | DeFrees |
| 2008/0187955 A1 | 8/2008 | DeFrees et al. |
| 2008/0200651 A1 | 8/2008 | Ostergaard et al. |
| 2008/0206808 A1 | 8/2008 | DeFrees et al. |
| 2008/0206810 A1 | 8/2008 | Johnson et al. |
| 2008/0207487 A1 | 8/2008 | DeFrees et al. |
| 2008/0242607 A1 | 10/2008 | DeFrees |
| 2008/0242846 A1 | 10/2008 | DeFrees et al. |
| 2008/0248959 A1 | 10/2008 | DeFrees |
| 2008/0253992 A1 | 10/2008 | DeFrees et al. |
| 2008/0255026 A1 | 10/2008 | DeFrees et al. |
| 2008/0255040 A1 | 10/2008 | DeFrees |
| 2008/0274958 A1 | 11/2008 | DeFrees |
| 2008/0280818 A1 | 11/2008 | DeFrees |
| 2008/0300173 A1 | 12/2008 | DeFrees |
| 2008/0300175 A1 | 12/2008 | DeFrees et al. |
| 2008/0305518 A1 | 12/2008 | Klausen et al. |
| 2008/0305991 A1 | 12/2008 | DeFrees et al. |
| 2008/0305992 A1 | 12/2008 | DeFrees et al. |
| 2008/0318850 A1 | 12/2008 | DeFrees et al. |
| 2008/0319183 A1 | 12/2008 | DeFrees et al. |
| 2009/0028822 A1 | 1/2009 | DeFrees et al. |
| 2009/0048440 A1 | 2/2009 | Felo et al. |
| 2009/0053167 A1 | 2/2009 | DeFrees |
| 2009/0054623 A1 | 2/2009 | DeFrees |
| 2009/0055942 A1 | 2/2009 | Ostergaard et al. |
| 2009/0076237 A1 | 3/2009 | Turecek et al. |
| 2009/0081188 A1 | 3/2009 | DeFrees et al. |
| 2009/0093399 A1 | 4/2009 | DeFrees et al. |
| 2009/0124544 A1 | 5/2009 | DeFrees |
| 2009/0137763 A1 | 5/2009 | DeFrees et al. |
| 2009/0143292 A1 | 6/2009 | Hinderer et al. |
| 2009/0169509 A1 | 7/2009 | DeFrees et al. |
| 2009/0176967 A1 | 7/2009 | Stennicke |
| 2009/0203579 A1 | 8/2009 | DeFrees et al. |
| 2009/0227504 A1 | 9/2009 | Klausen et al. |
| 2009/0240028 A1 | 9/2009 | Behrens et al. |
| 2009/0247450 A1 | 10/2009 | Mack |
| 2009/0252720 A1 | 10/2009 | Ostergaard et al. |
| 2009/0253166 A1 | 10/2009 | Zundel et al. |
| 2009/0264366 A1 | 10/2009 | Johansen et al. |
| 2009/0292110 A1 | 11/2009 | DeFrees |
| 2009/0305967 A1 | 12/2009 | DeFrees et al. |
| 2010/0009902 A1 | 1/2010 | DeFrees |
| 2010/0015684 A1 | 1/2010 | DeFrees et al. |
| 2010/0028939 A1 | 2/2010 | Behrens et al. |
| 2010/0029555 A1 | 2/2010 | Tonon et al. |
| 2010/0035299 A1 | 2/2010 | DeFrees et al. |
| 2010/0041872 A1 | 2/2010 | Defrees et al. |
| 2010/0048456 A1 | 2/2010 | DeFrees et al. |
| 2010/0056428 A1 | 3/2010 | Behrens |
| 2010/0075375 A1 | 3/2010 | DeFrees et al. |
| 2010/0081791 A1 | 4/2010 | DeFrees et al. |
| 2010/0113743 A1 | 5/2010 | DeFrees et al. |
| 2010/0120666 A1 | 5/2010 | Zopf et al. |
| 2010/0174056 A1 | 7/2010 | Gillies et al. |
| 2010/0174059 A1 | 7/2010 | DeFrees et al. |
| 2010/0210507 A9 | 8/2010 | DeFrees et al. |
| 2010/0286067 A1 | 11/2010 | DeFrees |
| 2010/0322940 A1 | 12/2010 | Bayer |
| 2010/0330645 A1 | 12/2010 | DeFrees et al. |
| 2010/0331489 A1 | 12/2010 | DeFrees |
| 2011/0003744 A1 | 1/2011 | DeFrees et al. |
| 2011/0177029 A1 | 7/2011 | DeFrees |
| 2011/0223646 A1 | 9/2011 | Schwartz et al. |
| 2011/0318780 A1 | 12/2011 | DeFrees |
| 2012/0016105 A1 | 1/2012 | DeFrees et al. |
| 2012/0083600 A1 | 4/2012 | Felo et al. |

(56) References Cited

U.S. PATENT DOCUMENTS

| | | |
|---|---|---|
| 2012/0107867 A1 | 5/2012 | DeFrees et al. |
| 2012/0172300 A1 | 7/2012 | DeFrees |
| 2012/0220517 A1 | 8/2012 | DeFrees et al. |
| 2013/0059780 A1 | 3/2013 | DeFrees |
| 2014/0112903 A1 | 4/2014 | DeFrees et al. |

FOREIGN PATENT DOCUMENTS

| | | |
|---|---|---|
| CA | 2131703 A1 | 9/1993 |
| CA | 2110543 A1 | 6/1994 |
| CA | 2324616 A1 | 9/1999 |
| CA | 2167521 | 10/2003 |
| CA | 2500389 A1 | 4/2004 |
| CA | 2511814 A1 | 7/2004 |
| DE | 2437388 | 2/1975 |
| DE | 19709787 | 9/1998 |
| DE | 19852729 A1 | 5/2000 |
| EP | 0119539 A2 | 9/1984 |
| EP | 0200421 A2 | 12/1986 |
| EP | 0370205 A2 | 5/1990 |
| EP | 0459630 A2 | 12/1991 |
| EP | 0474313 A | 3/1992 |
| EP | 0475354 A2 | 3/1992 |
| EP | 0577580 A2 | 1/1994 |
| EP | 0585109 A | 3/1994 |
| EP | 0605963 A2 | 7/1994 |
| EP | 0775711 A1 | 5/1997 |
| EP | 0863154 A1 | 9/1998 |
| EP | 1260582 A1 | 11/2002 |
| EP | 1270642 A1 | 1/2003 |
| EP | 1428878 | 6/2004 |
| EP | 1481985 A1 | 12/2004 |
| FI | 922515 A | 12/1992 |
| GB | 2256197 A | 12/1992 |
| JP | S59172425 A | 9/1984 |
| JP | H03-503759 A | 8/1991 |
| JP | H06-086684 A | 3/1994 |
| JP | H07-196925 A | 8/1995 |
| JP | H07-223921 A | 8/1995 |
| JP | H08-506023 A | 7/1996 |
| JP | H09-503905 A | 4/1997 |
| JP | H09-208461 A | 8/1997 |
| JP | H10-307356 A | 11/1998 |
| JP | 2000-501607 A | 2/2000 |
| JP | 2001-508783 A | 7/2001 |
| JP | 2001-519784 A | 10/2001 |
| JP | 2003-521930 A | 7/2003 |
| JP | 2005-521635 A | 7/2005 |
| JP | 2005-328782 A | 12/2005 |
| KR | 2002-0010363 A | 2/2002 |
| KR | 10-0396983 B1 | 8/2003 |
| NZ | 532027 A | 9/2008 |
| NZ | 539415 A | 12/2008 |
| NZ | 547554 A | 9/2009 |
| RU | 2005/101348 A | 8/2005 |
| SE | 9501285 | 10/1996 |
| WO | WO 87/00056 | 1/1987 |
| WO | WO 87/05330 A1 | 9/1987 |
| WO | WO 89/06546 A1 | 7/1989 |
| WO | WO 89/10134 A1 | 11/1989 |
| WO | WO 90/07572 | 7/1990 |
| WO | WO 90/08164 A1 | 7/1990 |
| WO | WO 90/08823 A1 | 8/1990 |
| WO | WO 90/12090 A1 | 10/1990 |
| WO | WO 90/13540 A1 | 11/1990 |
| WO | WO 91/06635 A1 | 5/1991 |
| WO | WO 91/09122 A1 | 6/1991 |
| WO | WO 91/14697 A1 | 10/1991 |
| WO | WO 92/01055 A1 | 1/1992 |
| WO | WO 92/15686 A1 | 9/1992 |
| WO | WO 92/16555 A1 | 10/1992 |
| WO | WO 92/16640 A1 | 10/1992 |
| WO | WO 92/18135 | 10/1992 |
| WO | WO 92/22310 A1 | 12/1992 |
| WO | WO 93/08842 A1 | 5/1993 |
| WO | WO 93/13198 A1 | 7/1993 |
| WO | WO 93/15189 A1 | 8/1993 |
| WO | WO 93/18787 A1 | 9/1993 |
| WO | WO 94/04193 A1 | 3/1994 |
| WO | WO 94/05332 | 3/1994 |
| WO | WO 94/09027 A1 | 4/1994 |
| WO | WO 94/15625 A1 | 7/1994 |
| WO | WO 94/17039 A1 | 8/1994 |
| WO | WO 94/18247 A1 | 8/1994 |
| WO | WO 94/25614 A1 | 11/1994 |
| WO | WO 94/25615 A1 | 11/1994 |
| WO | WO 94/26760 A1 | 11/1994 |
| WO | WO 94/27631 A1 | 12/1994 |
| WO | WO 94/28024 A1 | 12/1994 |
| WO | WO 95/02421 A1 | 1/1995 |
| WO | WO 95/04278 A1 | 2/1995 |
| WO | WO 95/05465 A1 | 2/1995 |
| WO | WO 96/10089 A1 | 4/1996 |
| WO | WO 96/11953 A1 | 4/1996 |
| WO | WO 96/12800 A1 | 5/1996 |
| WO | WO 96/40731 | 6/1996 |
| WO | WO 96/21468 A1 | 7/1996 |
| WO | WO 96/21469 A1 | 7/1996 |
| WO | WO 96/32491 | 10/1996 |
| WO | WO 96/32492 A1 | 10/1996 |
| WO | WO 96/34015 A1 | 10/1996 |
| WO | WO 96/36357 A1 | 11/1996 |
| WO | WO 96/40881 A1 | 12/1996 |
| WO | WO 97/05330 | 2/1997 |
| WO | WO 97/21822 A2 | 6/1997 |
| WO | WO 97/47651 A1 | 12/1997 |
| WO | WO 98/05363 | 2/1998 |
| WO | WO 98/31826 | 7/1998 |
| WO | WO 98/31826 A1 | 7/1998 |
| WO | WO 98/32466 A1 | 7/1998 |
| WO | WO 98/41562 A1 | 9/1998 |
| WO | WO 98/51784 A1 | 11/1998 |
| WO | WO 98/58964 | 12/1998 |
| WO | WO 99/00150 A2 | 1/1999 |
| WO | WO 99/13063 A1 | 3/1999 |
| WO | WO 99/14259 A1 | 3/1999 |
| WO | WO 99/22764 A1 | 5/1999 |
| WO | WO 99/28491 A1 | 6/1999 |
| WO | WO 99/34833 A1 | 7/1999 |
| WO | WO 99/37779 A1 | 7/1999 |
| WO | WO 99/45964 A1 | 9/1999 |
| WO | WO 99/48515 A1 | 9/1999 |
| WO | WO 99/54342 A1 | 10/1999 |
| WO | WO 99/55376 A1 | 11/1999 |
| WO | WO 00/23114 | 4/2000 |
| WO | WO 00/26354 A1 | 5/2000 |
| WO | WO 00/29558 A1 | 5/2000 |
| WO | WO 00/29603 A2 | 5/2000 |
| WO | WO 00/44785 A1 | 8/2000 |
| WO | WO 00/46379 A1 | 8/2000 |
| WO | WO 00/65087 | 11/2000 |
| WO | WO 01/02017 A2 | 1/2001 |
| WO | WO 01/05434 A2 | 1/2001 |
| WO | WO 01/19955 A2 | 3/2001 |
| WO | WO 01/39788 A2 | 6/2001 |
| WO | WO 01/49830 A1 | 7/2001 |
| WO | WO 01/51510 A2 | 7/2001 |
| WO | WO 01/58493 A1 | 8/2001 |
| WO | WO 01/58935 A2 | 8/2001 |
| WO | WO 01/60411 A1 | 8/2001 |
| WO | WO 01/76640 A2 | 10/2001 |
| WO | WO 01/83725 A1 | 11/2001 |
| WO | WO 01/87329 A1 | 11/2001 |
| WO | WO 01/87925 A2 | 11/2001 |
| WO | WO 01/88117 A2 | 11/2001 |
| WO | WO 02/02597 A2 | 1/2002 |
| WO | WO 02/13843 A2 | 2/2002 |
| WO | WO 02/13873 A1 | 2/2002 |
| WO | WO 02/29025 A2 | 4/2002 |
| WO | WO 02/44196 A1 | 6/2002 |
| WO | WO 02/49673 A2 | 6/2002 |
| WO | WO 02/50099 A2 | 6/2002 |
| WO | WO 02/053580 A2 | 7/2002 |

(56) References Cited

FOREIGN PATENT DOCUMENTS

| | | |
|---|---|---|
| WO | WO 02/74806 A2 | 9/2002 |
| WO | WO 02/02764 A2 | 10/2002 |
| WO | WO 02/077218 A1 | 10/2002 |
| WO | WO 02/092619 A2 | 11/2002 |
| WO | WO 03/006501 A2 | 1/2003 |
| WO | WO 03/011879 A1 | 2/2003 |
| WO | WO 03/017949 A2 | 3/2003 |
| WO | WO 03/029291 A2 | 4/2003 |
| WO | WO 03/031464 A2 | 4/2003 |
| WO | WO 03/045980 A2 | 6/2003 |
| WO | WO 03/046150 A2 | 6/2003 |
| WO | WO 03/093448 A2 | 11/2003 |
| WO | WO 2004/000366 A1 | 12/2003 |
| WO | WO 2004/009838 A2 | 1/2004 |
| WO | WO 2004/010327 A2 | 1/2004 |
| WO | WO 2004/014417 A2 | 2/2004 |
| WO | WO 2004/022004 A2 | 3/2004 |
| WO | WO 2004/029090 A1 | 4/2004 |
| WO | WO 2004/029091 A2 | 4/2004 |
| WO | WO 2004/083259 A2 | 4/2004 |
| WO | WO 2004/046222 A1 | 6/2004 |
| WO | WO 2004/047858 A1 | 6/2004 |
| WO | WO 2004/067566 A1 | 8/2004 |
| WO | WO 2004/033651 A2 | 9/2004 |
| WO | WO 2004/075923 A2 | 9/2004 |
| WO | WO 2004/083258 A2 | 9/2004 |
| WO | WO 2004/091499 A2 | 10/2004 |
| WO | WO 2004/093823 A2 | 11/2004 |
| WO | WO 2004/096148 A2 | 11/2004 |
| WO | WO 2004/099231 A2 | 11/2004 |
| WO | WO 2004/101597 A2 | 11/2004 |
| WO | WO 2004/101740 A2 | 11/2004 |
| WO | WO 2004/103275 | 12/2004 |
| WO | WO 2004/106373 A1 | 12/2004 |
| WO | WO 2005/001025 A2 | 1/2005 |
| WO | WO 2005/003171 A2 | 1/2005 |
| WO | WO 2005/012484 A2 | 2/2005 |
| WO | WO 2005/014024 A2 | 2/2005 |
| WO | WO 2005/014035 A2 | 2/2005 |
| WO | WO 2005/025606 A1 | 3/2005 |
| WO | WO 2005/051327 A2 | 6/2005 |
| WO | WO 2005/055946 A2 | 6/2005 |
| WO | WO 2005/055950 A2 | 6/2005 |
| WO | WO 2005/056760 A2 | 6/2005 |
| WO | WO 2005/067601 A2 | 7/2005 |
| WO | WO 2005/070138 A2 | 8/2005 |
| WO | WO 2005/072371 A2 | 8/2005 |
| WO | WO 2005/079363 A2 | 9/2005 |
| WO | WO 2005/091944 A2 | 10/2005 |
| WO | WO 2005/121331 A2 | 12/2005 |
| WO | WO 2006/005058 A2 | 1/2006 |
| WO | WO 2006/010143 A2 | 1/2006 |
| WO | WO 2006/011839 A1 | 2/2006 |
| WO | WO 2006/013202 A2 | 2/2006 |
| WO | WO 2006/014349 A2 | 2/2006 |
| WO | WO 2006/014466 A2 | 2/2006 |
| WO | WO 2006/018204 A1 | 2/2006 |
| WO | WO 2006/020372 A2 | 2/2006 |
| WO | WO 2006/031811 A2 | 3/2006 |
| WO | WO 2006/035057 A1 | 4/2006 |
| WO | WO 2006/050247 A2 | 5/2006 |
| WO | WO 2006/053299 A2 | 5/2006 |
| WO | WO 2006/074279 A1 | 7/2006 |
| WO | WO 2006/074467 A2 | 7/2006 |
| WO | WO 2006/078645 A2 | 7/2006 |
| WO | WO 2006/082517 A1 | 8/2006 |
| WO | WO 2006/103298 A2 | 10/2006 |
| WO | WO 2006/105426 A2 | 10/2006 |
| WO | WO 2006/119987 A2 | 11/2006 |
| WO | WO 2006/121569 A2 | 11/2006 |
| WO | WO 2006/127910 A2 | 11/2006 |
| WO | WO 2006/134173 A2 | 12/2006 |
| WO | WO 2007/022512 A2 | 2/2007 |
| WO | WO 2007/056191 A2 | 5/2007 |
| WO | WO 2007/135182 A2 | 11/2007 |
| WO | WO 2008/011633 A2 | 1/2008 |
| WO | WO 2008/057683 A2 | 5/2008 |
| WO | WO 2008/060780 A2 | 5/2008 |
| WO | WO 2008/073620 A2 | 6/2008 |
| WO | WO 2008/124406 A2 | 10/2008 |
| WO | WO 2008/151258 A2 | 12/2008 |
| WO | WO 2008/154639 A2 | 12/2008 |
| WO | WO 2009/089396 A2 | 7/2009 |

OTHER PUBLICATIONS

Boissel et al., 1993, J. Biol. Chem. 268:15983-15993.
Bouizar et al., 1986, Eur. J. Biochem. 155:141-147.
Boyd et al., 1995, Mol. Immunol. 32:1311-1318.
Browning et al., 1989, J. Immunol. 143:1859-1867.
Bückmann et al., 1981, Makromol. Chem.182:1379-1384.
Burns et al., 2002, Blood 99:4400-4405.
Busterbosch et al., 1996, Eur. J. Biochem. 237:344-349.
Butnev et al., 1998, Biology of Reproduction 58:458-469.
Byun et al., 1992, ASAIO Journal M649-M653.
Casares et al., 2001, Nature Biotech 19:142-147.
Chaffee et al., 1992, J. Clin. Invest 89:1643-1651.
Charter et al., 2000, Glycobiology 10:1049-1056.
Chern et al., 1991, Eur. J. Biochem. 202:225-229.
Chiba et al., 1995, Biochem J. 308:405-409.
Chrisey et al., 1996, Nucleic Acids Res. 24:3031-3039.
Clark, et al., 1996, J. Biol. Chem,271(36)21969-21977.
Cointe, et al., 2000, Glycobiology, 10(5):511-519.
Conradt et al., 1987, J. Biol. Chem. 262:14600-14605.
Cope et al., 1991, Molecular Microbiology 5(5):1113-1124.
Copeland, Robert A., 2000, Enzymes, Second Edition, 146-150.
Crout et al., 1998, Curr. Opin. Chem. Biol. 2:98-111.
DeFrees, 2006, Glycobiology 16:833-843.
Delgado et al., 1992, Critical Reviews in Therapeutic 9:249-304.
Delgaldo et al., 1990, Biotechnol. Appl. Biochem. 12:119-128.
Detty et al., 1982, J. Org. Chem. 47:5416-5418.
Douglas, et al., 1991, J. Am. Chem. Soc., 113:5095-5097.
Dunn et al., 1991, Eds. Polymeric Drugs and Drug Delivery Systems, ACS Symposium Series vol. 469, American Chemical Society, Washington D.C.
Durieux, et al., 2001, Tetrahedron Letters, 42:2297-2299.
Dwek et al., 1995, J. Anat. 187:279-292.
Eavarone et al., 2000, J. Biomed Mater. Res. 51:10-14.
Fan et al., 1997, J. Biol. Chem. 272(43):27058-27064.
Fibi et al., 1995, Cells Blood 85:1229-1236.
Fischer et al., 1998, Thrombosis Research 89:147-150.
Flynn et al., 2000, Curr. Opin. Oncol. 12:574-581.
Garnett et al., 2002, Advanced Drug Delivery Reviews 53:171-216.
Gatot, et al., 1998, J. Biol. Chem., 273(21):12870-12880.
Gillis et al., 1988, Behring Inst. Mitt. August 83:1-7.
Ginns, Dr. Edward, PEG Glucocerebrosidase, Internet page from www.gaucher.org.uk/peg2.prg, printed Jun. 21, 2002.
Gotschlich, Emil C., 1994, J. Exp. Med., Coden: Jemeav; ISSN: 0022-1007, 180(6):2181-90.
Grabenhorst, et al., 1993, Euro. J. Biochem., 215:189-197.
Grodberg et al., 1993, Eur. J. Biochem. 218:597-601.
Gross, H.J., 1992, Eur. J. Biochem. 203(1-2):269-275.
Hall et al., 2001, Methods in Molecular Biology 166:139-154.
Haneda et al., Carbohydr. Res. 292:61-70.
Hang et al., 2001, J. Am. Chem. Soc. 123:1242-1243.
Harris, 1985, Macronol. Chem. Phys. C25: 325-373.
Harris et al., 2003, Nature Reviews Drug Discovery, 2:214-221.
Hayes et al., 1993, J. Biol. Chem. 268(22):16170-16178.
Hellstrom et al., 2001, Methods in Molecular Biology 166:3-16.
Hermanson et al., 1992, Immobilized Affinity Ligand Techniques, Academic Press.
Hermanson, 1996, Bioconjugate Techniques, Academic Press, San Diego.
Hermentin, et al., 1996, Glycobiology 6(2):217-230.
Hills et al., 2002, American Biotechnology Laboratory, 20(11):30.
Hollister et al., 2001, Glycobiology 11:1-19.
Hounsell et al., 1996, Glycoconj. J. 13:19-26.
Ichikawa et al., 1992, J. Am. Chem. Soc. 114:9283-9298.
Inoue et al., 1995, Biotechnology Annual Review 1:297-313.
Ito et al., 1993, Pure & Appl. Chem. 65(4):753-762.

(56) References Cited

OTHER PUBLICATIONS

Jackson et al., 1987, Anal. Biochem.165:114-127.
Jarvis et al., 1998, Curr. Opin. Biotechnol. 9:528-533.
Joppich et al., 1979, Makromol Chem. 180:1381-1384.
Joshi et al., 1990, J. Biol. Chem. 265:14518-14525.
Jung et al., 1983, Biochem. Biophys. Acta, 761:152-162.
Kalsner et al., 1995, Glycoconj. J. 12:360-370.
Kasina et al., 1998 Bioconjugate Chem., 9:108-117.
Katre et al., 1987, Proc. Natl. Acad. Sci. U.S.A. 84:1487-1491.
Keppler et al., 2001, Glycobiology 11:11R-18R.
Kitamura et al., 1990, Biochem. Biophys. Res. Commun. 28:1387-1394.
Kitamura et al., 1991, Cancer Res. 51:4310-4315.
Kodama et al., 1993, Tetrahedron Lett. 34:6419-6422.
Koeller et al., 2000, Nature Biotechnology 18: 835-841.
Koeller et al., 2001, Nature, 409:232-240.
Koide et al., 1983, Biochem Biophys. Res. Commun. 111:659-667.
Kreitmann 2001, Current Pharmaceutical Biotechnology 2:313-325.
Kuhn, et al., 1995, J. Biol. Chem. 270(49):29493-29497.
Lai et al, 1986, J. Biol. Chem. 261:3116-3121.
Lee-Huang et al., 1984, Proc. Natl. Acad. Sci. U.S.A. 81:2708-2712.
Lee et al., 1989, Biochemistry 28:1856-1861.
Leung, S., 1995, J. Immunology, 154:5919-5926.
Li et al., 2002, Trends in Pharmacological Sciences 23:206-209.
Li et al., 2002, Medicinal Research Reviews 22:225-250.
Liu et al., 2002, 1996, Chem. Eur. J. 2:1359-1362.
Long et al., 2006, Experimental Hematology 34:697-704.
Lord et al., 2001, Clin. Cancer Res. 7:2085-2090.
Lougheed et al., 1999, J. Biol. Chem. 274:37717-37722.
Luckow et al., 1993, Curr. Opin. Biotechnol 4:564-572.
Lund et al., 1995, FASEB J. 9:115-119.
Lund et al., 1996, J. Immunol. 157:4963-4969.
Mahal et al., 1997, Science 276:1125-1128.
Maranga et al., 2003, Biotechnology and Bioengineering 84(2):245-253.
Maras et al., 2000, Molecular cloning and enzymatic characterization of a Trichoderma reesei , 2-α-D-mannosidase, 77:255-263.
Miller et al., 1993, Curr. Opin. Genet. Dev. 3:97-101.
Min et al., 1996, Endocr. J. 43:585-593.
Mistry et al., 1996, Lancet 348:1555-1559.
Morimoto et al., 1996, Glycoconjugate J. 13:1013-1020.
NCBI—Accession No. NCAA26095 (2 pgs.).
NCBI—Accession No. NP_999299 (2 pgs.).
NCBI—Accession No. NP_058697 (3 pgs.).
NCBI Database hits for erythropoietin protein sequences (3 pgs.).
Nilsson et al., 1984, Methods Enzymol. 104:56-69.
O'Connell et al., 1992, J. Biol. Chem. 267:25010-25018.
Oetke, et al., 2002, J. Biol. Chem 277(8):6688-6695.
Olson et al., 1999, J. Biol. Chem. 274:29889-29896.
Palacpac et al., 1999, PNAS USA 96:4692-4697.
Park et al., 1986, J. Biol Chem. 261:205-210.
Paulson et al., 1997, J. Biol. Chem. 252:8624-8628.
Plummer et al., 1995, J. Biol. Chem. 270(22):13192-13196.
PNGase-F Amidase Sequence from F. Meningosepticum (Registry Nos. 128688-70-0).
PNGase-F Amidase Sequence from F. Meningosepticum (Registry Nos. 128688-71-1).
Pyatak et al., 1980, Res. Commun. Chem. Pathol Pharmacol 29:113-127.
Rabouille et al., 1999, J. Cell. Biol. 112:3319-3330.
Reff et al., 2002, Cancer Control 9:152-166.
Rosenthal, et al., 1994, Methods Enzymol. 235:253-285.
Sadler et al., 1982, Methods in Enzymology 83:458-514.
Saneyoshi et al., 2001, Biology of Reproduction 65:1686-1690.
Saxon et al., 2000, Science 287:2007-2010.
Schwientek et al., 1994, Gene 145:299-303.
Scouten 1987, Methods in Enzymology 135:30-65.
Shah et al., 1996, J. Pharm. Sci. 85:1306-1311.
Shapiro et al., 2005, B. Biochemistry 105:518-525.
Singh et al., 1996, Chem. Commun. 1996:993-994.
Sinha et al., 1980, Infection and Immunity 29(3):914-925.
Song et al., 2002, J. Pharmacol. Exp. Ther. 301:605-610.
Srinivasachar et al., 1989, Biochemistry 28:2501-2509.
Stephens et al., 1983, European J. of Biochem., 135(3):519-27.
Stephens et al., 1983, European J. of Biochem., 133(3):481-9.
Stephens et al., 1983, European J. of Biochem., 133(1):155-62.
Takane et al., 2000, J. Pharmacology and Experimental Therapeutics 294:746-752.
Takeda et al., 1995, Trends Biochem. Sci. 20:367-371.
Takeuchi, et al., 1990, The Journal of Biological Chemistry, 265(21): 12127-12130.
Tanner et al., 1987, Biochim. Biophys. Acta., 906:81-91.
Taylor et al., 1991, Protein Immobilization Fundamentals and Applications, Manual.
Thotakura et al., 1987, Meth Enzymol 138: 350-359.
Tsuboi et al., 2000 Archives of Biochemistry and Biophysics 374:100-106.
Tuddenham, E., 2002, Nature 419:23-24.
Udenfriend et al., 1995, Ann. Rev. Biochem. 64:563-591.
Ulloa-Aguirre et al., 1999, Role of Glycosylation in Function of Follicle-Stimulating Hormone, Endocrine 11:205-215.
Uludag et al., 2002, Biotechnol. Prog. 18:604-611.
Urdal et al, 1984, J. Chromatog, 296:171-179.
Van Berkel et al., 1996, Biochem J. 319:117-122.
Veronese et al., 1985, Appl. Biochem. Biotech. 11:141-152.
Vocadlo et al., 2000, In Carbohydrate Chemistry and Biology, vol. 2.
Vyas et al., 2001, Crit. Rev. Ther. Drug Carrier Syst. 18:1-76.
Wang et al., 1996, Tetrahedron Lett. 37:1975-1978.
Wang, M., 1998, Protein Engineering 11(12):1277-1283.
Wellhoner et al., 1991, J. Biol. Chem. 226:4309-4314.
Witte K. et al., 1997, J. Am. Chem. Soc. 119:2114-2118.
Woghiren et al., 1993, Bioconjugate Chem. 4:314-318.
Wong et al., 1992, Enzyme Microb.Technol. 14:866-874.
Wong et al., 1996, Biotechnology and Bioengineering 49:659-666.
Woods et al., 1989, Eur. J. Cell. Biol. 50:132-143.
Wright et al., 1998, J. Immunol. 160:3393-3402.
Wu et al., 2002, J. Drug targeting 10:239-245.
Xing et al., 1998, Biochem. J. 336:667-673.
Yamamoto et al., 1998, Carbohydr. Res. 305:415-422.
Yarema et al., 1998, J. Biol. Chem. 47:31168-31179.
Yoshida et al., 1999, Glycobiology 9:53-58.
Yoshitake et al., 1985, Biochemistry 24:3736-3750.
Zalipsky 1995, Bioconjugate Chem. 6:150-165.
Zalipsky et al., 1992, Poly (ethylene glycol) Chemistry: Biotechnical and Biomedical Applications 347-370.
Zheng et al., 1999, Biotechnology and Bioengineering 65(5):600-604.
Zhou, et al., 1994, Mol. Microbiol. 14(4):609-618.
Alam, et al., 1998, *J. Biotechnology*, 65:183-190.
Wells, 1990, *Biochemistry* 29(37):8509-8517.
Ngo, et al., 1994, *The Protein Folding Problem and Tertiary Structure Prediction, Chapter 14: Computational Complexity Protein Structure Prediction, and the Levinthal Paradox*, 433-440 and 492-495.
Bork, 2000, *Genome Research*, 10:398-400.
Stolnick, et al., 2000, *Trends in Biotech.*, 18(1):34-39.
Doerks et al., 1998, *Trends in Genetics*, 14(6):248-250.
Smith et al., 1997, *Nature Biotechnology*, 15:1222-1223.
Brenner, 1999, *Trends in Genetics*, 15(4):132-133.
Bork, et al., 1996, *Trends in Genetics*, 12(10):425-427.
Kornfeld, et al., "Assembly of Asparagine-linked Oligosaccharides," *Ann Rev Biochem* 54:631-664 (1985).
Kukuruzinska, et al., "Proetin Glycosylation in Yeast: Transcript Heterogeneity of the *ALG7* Gene," *Proc Natl Acad Sci USA*, 84:2145-2149 (Apr. 1987).
Herscovics, et al., "Glycoprotein Biosynthesis in Yeast," *FASEB J*, 7:540-550 (1993).
Orlean, "Biogenesis of Yeast Wall and Surface Components," *Saccharomyces*, 3:229-362 (1996).
Stemmer, "DNA Shuffling by Random Fragmentation and Reassembly: In vitro Recombination for Molecular Evolution," *Proc Natl Acad Sci USA*, 91:10747-10751 (Oct. 1994).
Stemmer, "Rapid Evolution of a Protein In vitro by DNA Shuffling," Letters to Nature, 370:389-391 (1994).

(56) References Cited

OTHER PUBLICATIONS

Hakimuddin, et al., "A Chemical Method for the Deglycosylation of Proteins," *Arch Biochem Biophys*, 259:52-57 (1987).
Edge, et al., "Deglycosylation of Glycoproteins by Trifluoromethanesculfonic Acid," *Anal Biochem*, 118:131-137 (1981).
Abuchowski et al., *J. Biol. Chem.*, 252(11): 3582-3586 (1977).
Barrios et al., *J. Mol. Recognit.*, 17(4):332-338 (2004).
Bedard et al., *Cytotechnology*, 15(1-3): 129-138 (1994).
Bennett et al., *J. Biol. Chem.*, 273(46): 30472-30481 (1998).
Bennett et al., *FEBS Lett.*, 460(2): 226-230 (1999).
Boime et al., *Recent Prog. Horm. Res.*, 54: 271-289 (1999).
Cohn et al., *J. Biomed. Mater. Res,*. 22(11): 993-1009 (1988).
Copeland, "Enzymes: A Practical Introduction to Structure, Mechanism and Data Analysis" 2nd ed., Wiley-VCH, New York, p. 146-150 (2000).
Felix et al., *J. Peptide Res.*, 63: 85-90 (2004).
Fritz et al., *Proc. Natl. Acad. Sci. USA*, 101(43): 15307-15312 (2004).
Fritz et al., *J. Biol. Chem.*, 281(13): 8613-8619 (2006).
Gervais et al., *Glycobiology*, 13(3): 179-189 (2003).
Gilbert et al., *Cytotechnology*, 22(1-3): 211-216 (1996).
Gross et al., *Biochemistry*, 28(18): 7386-7392 (1989).
Hagen et al., *J. Biol. Chem.*, 274(10): 6797-6803 (1999).
Hagen et al., *J. Biol. Chem.*, 276(20): 17395-17404 (2001).
Harris et al., *Abstracts of Papers of the American Chemical Society*, 201(4), P 64-POLY, 154-155 (1991).
Harris (ed.), "Poly(Ethylene Glycol) Chemistry: Biotechnical and Biomedical Applications", Plenum Press, New York (1992).
Harris et al. (eds.), "Poly(ethylene glycol): Chemistry and Biological Applications," ACS Symposium Series, vol. 680, American Chemical Society (1997).
Hassan et al., *Carbohydrates in Chemistry and Biology*, Part II, 3: 273-292 (2000).
Hassan et al., *J. Biol. Chem.*, 275(49): 38197-38205 (2000).
Hink et al., *Biotechnol. Prog.*, 7(1): 9-14 (1991).
Ikonomou et al., *In Vitro Cell. Dev. Biol. Anim.*, 37(9): 549-559 (1991).
Inlow et al., *J. Tissue Cult. Methods*, 12(1): 13-16 (1989).
Kajihara et al., *Carbohydr. Res.*, 315(1-2): 137-141 (1999).
Katre et al., *Proc. Natl. Acad. Sci. USA*, 84(6): 1487-1491 (1987).
Kawasaki et al., *Anal. Biochem.*, 285: 82-91 (2000).
Keana et al., *J. Org. Chem.*, 55(11): 3640-3647 (1990).
Keppler et al., *Glycobiol.*, 11(2): 11R-18R (2001).
Kobayashi et al., *Eur. J. Nucl. Med.*, 27(9):1334-1339 (2000).
Langer, *Science*, 249(4976): 1527-1533 (1990).
Lau et al., *J. Biotechnol.*, 75(2-3): 105-115 (1999).
Licari et al., *Biotechnol. Bioeng.*, 39(4): 432-441 (1992).
Licari et al., *Biotechnol. Bioeng.*, 39(9): 932-944 (1992).
Min et al., *Endocr. J.*, 43(5): 585-593 (1996).
Muller et al., *J. Biol. Chem.*, 272(40): 24780-24793 (1997).
Muller et al., *J. Biol. Chem.*, 274(26): 18165-18172 (1999).
Rudikoff et al., *Proc. Natl. Acad. Sci. USA*, 79(6):1979-1983 (1982).
Sandberg et al., *Semin. Hematol.*, 38(2 Suppl. 4): 4-12 (2001).
Schlaeger, *Cytotechnology*, 20(1-3): 57-70 (1996).
Schwientek et al., *J. Biol. Chem.*, 277(25): 22623-22638 (2002).
Seely et al., *J. Chromatog.*, 908: 235-241 (2001).
Seitz, *Chembiochem.*, 1(4): 214-246 (2000).
Shen et al., *Biochem. Biophys. Res. Commun.*, 102(3): 1048-1054 (1981).
Srinivasachar et al., *Biochemistry*, 28(6): 2501-2509 (1989).
Taniguchi et al., *Proteomics*, 1(2): 239-247 (2001).
Ten Hagen et al., *J. Biol. Chem.*, 274(39): 27867-27874 (1999).
Urdal et al, *J. Chromatogr.*, 296: 171-179 (1984).
Van Reis et al., *Biotechnol. Bioeng.*, 38(4): 413-422 (1991).
Vitetta et al., *Science*, 313: 308-309 (2006).
Wang et al., *Protein Eng.*, 11(12): 1277-1283 (1998).
Witte et al., *J. Am. Chem. Soc.*, 119(9): 2114-2118 (1997).
Witte et al., *Cancer and Metastasis Rev.*, 17: 155-161 (1998).
Wu et al., *J. Drug Target.*, 10(3): 239-245 (2002).
Yamada et al., *Biochemistry*, 20(17): 4836-4842 (1981).
Younes et al., *J. Biomed. Mater. Res.*, 21(11): 1301-1316 (1987).
Zarling et al., *J. Immunol.*, 124(2): 913-920 (1980).
Office Action dated Feb. 15, 2011 in U.S. Appl. No. 12/496,595.
Office Action dated Feb. 22, 2011 in U.S. Appl. No. 12/820,926.
Office Action dated Feb. 23, 2011 in U.S. Appl. No. 12/092,563.
Office Action dated Mar. 2, 2011 in U.S. Appl. No. 12/201,705.
Office Action dated Mar. 11, 2011 in U.S. Appl. No. 11/982,273.
Office Action dated Mar. 16, 2011 in U.S. Appl. No. 11/665,908.
Office Action dated Mar. 17, 2011 in U.S. Appl. No. 11/597,258.
Office Action dated May 31, 2011 in U.S. Appl. No. 11/144,223.
Office Action dated Jun. 9, 2011 in U.S. Appl. No. 11/597,258.
Office Action dated Jul. 8, 2011 in U.S. Appl. No. 11/632,005.
Office Action dated Jul. 21, 2011 in U.S. Appl. No. 11/665,908.
Office Action dated Aug. 17, 2011 in U.S. Appl. No. 11/632,005.
Office Action dated Aug. 22, 2011 in U.S. Appl. No. 11/659,942.
Office Action dated Sep. 22, 2011 in U.S. Appl. No. 12/820,926.
Office Action dated Oct. 6, 2011 in U.S. Appl. No. 12/663,748.
Office Action dated Nov. 2, 2011 in U.S. Appl. No. 12/201,705.
Office Action dated Nov. 17, 2011 in U.S. Appl. No. 12/443,428.
Office Action dated Dec. 1, 2011 in U.S. Appl. No. 11/794,560.
Office Action dated Dec. 22, 2011 in U.S. Appl. No. 12/858,247.
Office Action dated Jan. 3, 2012 in U.S. Appl. No. 11/632,005.
Office Action dated Feb. 29, 2012 in U.S. Appl. No. 12/858,247.
Office Action dated Mar. 21, 2012 in U.S. Appl. No. 11/794,560.
Office Action dated Mar. 29, 2012 in U.S. Appl. No. 12/594,326.
Office Action dated Apr. 18, 2012 in U.S. Appl. No. 12/663,748.
Office Action dated Apr. 19, 2012 in U.S. Appl. No. 13/215,439.
Office Action dated Aug. 8, 2012 in U.S. Appl. No. 13/157,575.
Office Action dated Aug. 17, 2012 in U.S. Appl. No. 12/594,326.
Office Action dated Sep. 21, 2012 in U.S. Appl. No. 12/663,748.
Office Action dated Sep. 24, 2012 in U.S. Appl. No. 12/784,323.
Office Action dated Sep. 25, 2012 in U.S. Appl. No. 13/186,726.
Espuelas et al., *Bioorg. Med. Chem. Lett.*, 13(15): 2557-2560 (2003).
Hu et al., *Mol. Cell. Biol.*, 18(10): 6063-6074 (1998).
Natsuka et al., *J. Biol. Chem.*, 269(24): 16789-16794 (1994).
R & D Systems, Fibroblast Growth Factors (FGFs), Internet page from www.rndsystems.com/mini_review_detail_objectname_MR01_FGFs.aspx, 2001, printed Mar. 10, 2011.
Saxon et al., *J. Am. Chem. Soc.*, 124(50): 14893-14902 (2002).
Weston et al., *J. Biol. Chem.*, 267(6): 4152-4160 (1992).
Arslan et al., *Transf. Apher. Sci.*, 37: 179-185 (2007).
Broxmeyer et al., *J. Exp. Med.*, 201(8): 1307-1318 (2005).
Brumeanu et al., *J. Immunol. Meth.*, 183: 185-197 (1995).
Capoccia et al., *Blood*, 108(7): 2438-2445 (2006).
Cashen et al., *Bone Marrow Trans.*, 39: 577-588 (2007).
Deacon, *Diabetes*, 54: 2181-2189 (2004).
Flomenberg et al., *Blood*, 106(5): 1867-1874 (2005).
GE Healthcare, "Ion Exchange Chromatography & Chromatofocusing: Principles and Methods," Edition AA, Amersham Biosciences, pp. 7, 11-12, 16-17, 21-23, 26-36, 41, 89, 156, 160, 161 (2004).
Gross et al., *Eur. J. Biochem*,. 177(3): 583-589 (1988).
Guo et al., *Appl. Biochem. Biotechnol.*, 68(1-2): 1-20 (1997).
Haneda et al., *Carbohydr. Res.*, 292: 61-70 (1996).
Hällgren et al., *J. Carb. Chem.*, 14(4-5): 453-464 (1995).
Hill et al., *Biol. Blood Marrow Trans.*, 12: 603-607 (2006).
Hübel et al., *Ann. Hematol.*, 82: 207-213 (2003).
Kennedy, "Hydrophobic-Interaction Chromatography," in *Current Protocols in Protein Science*, pp. 8.4.1-8.4.21, Wiley (1995).
Kroschinsky et al., *Trans. Apher. Sci.*, 38: 237-244 (2008).
Krystal et al., *Blood*, 67(1): 71-99 (1986).
Liles et al., *Transfusion*, 45: 295-300 (2005).
Liu et al., *Chem. Eur. J.*, 2(11): 1359-1362 (1996).
NCBI—Accession No. NCAA26095 (2 pgs.) (2006).
NCBI—Accession No. NP_058697 (3 pgs.) (2007).
NCBI—Accession No. NP_999299 (2 pgs.) (2007).
NCBI Database hits for erythropoietin protein sequences (3 pgs.) (2007).
O'Shannessy et al., *J. Appl. Biochem.*, 7: 347-355 (1985).
PNGase-F Amidase Sequence from F. Meningosepticum (RN 128688-70-0) (2007).
PNGase-F Amidase Sequence from F. Meningosepticum (RN 128688-71-1) (2007).
Quelle et al., *Blood*, 74(2): 652-657 (1989).

(56) References Cited

OTHER PUBLICATIONS

Rathnam et al., *Biochim. Biophys. Acta*, 624(2): 436-442 (1980).
Schwarz et al., *Nucl. Med. Biol.*, 26(4):383-388 (1999).
Srivastava et al., *J. Biol. Chem.*, 267(31): 22356-22361 (1992).
Tom et al., *AAPS Journal*, 9(2): E227-E234 (2007).
Uptima, Detergents: Solubilization of Biomolecules, Internet page from www.interchim.com/interchim/bio/produits_uptima/product_line/p1p_detergents.htm, 2001, printed Nov. 14, 2011.
Veronese, *Biomaterials*, 22(5): 405-417 (2001).
Yin et al., *Pharm. Res.*, 21(12): 2377-2383 (2004).
Office Action dated Sep. 20, 1994 in U.S. Appl. No. 08/215,727.
Office Action dated May 4, 1995 in U.S. Appl. No. 08/102,385.
Office Action dated Jun. 7, 1995 in U.S. Appl. No. 08/215,727.
Office Action dated Apr. 5, 1996 in U.S. Appl. No. 08/102,385.
Office Action dated Jun. 23, 1996 in U.S. Appl. No. 08/447,435.
Office Action dated Jun. 28, 1996 in U.S. Appl. No. 08/447,783.
Office Action dated Aug. 28, 1996 in U.S. Appl. No. 08/478,140.
Office Action dated Oct. 15, 1996 in U.S. Appl. No. 08/102,385.
Office Action dated Feb. 24, 1997 in U.S. Appl. No. 08/447,435.
Office Action dated Feb. 24, 1997 in U.S. Appl. No. 08/447,783.
Office Action dated Apr. 12, 1997 in U.S. Appl. No. 08/215,727.
Office Action dated Jul. 23, 1997 in U.S. Appl. No. 08/102,385.
Office Action dated Aug. 8, 1997 in U.S. Appl. No. 08/745,840.
Office Action dated Oct. 9, 1997 in U.S. Appl. No. 08/478,140.
Office Action dated Dec. 1, 1997 in U.S. Appl. No. 08/446,875.
Office Action dated Jan. 2, 1998 in U.S. Appl. No. 08/878,360.
Office Action dated Mar. 30, 1998 in U.S. Appl. No. 08/745,840.
Office Action dated Jun. 19, 1998 in U.S. Appl. No. 08/478,140.
Office Action dated Oct. 29, 1998 in U.S. Appl. No. 08/745,840.
Office Action dated Feb. 4, 1999 in U.S. Appl. No. 08/478,140.
Office Action dated Apr. 1, 1999 in U.S. Appl. No. 08/745,840.
Office Action dated Oct. 23, 1999 in U.S. Appl. No. 08/102,385.
Office Action dated Oct. 4, 2000 in U.S. Appl. No. 09/333,412.
Office Action dated Jan. 30, 2001 in U.S. Appl. No. 09/338,943.
Office Action dated Jun. 4, 2002 in U.S. Appl. No. 09/855,320.
Office Action dated Sep. 27, 2002 in U.S. Appl. No. 09/855,320.
Office Action dated Dec. 9, 2002 in U.S. Appl. No. 10/007,267.
Office Action dated Jun. 2, 2003 in U.S. Appl. No. 10/007,267.
Office Action dated Aug. 26, 2003 in U.S. Appl. No. 10/109,498.
Office Action dated Nov. 5, 2003 in U.S. Appl. No. 10/007,267.
Office Action dated Nov. 17, 2003 in U.S. Appl. No. 09/855,320.
Office Action dated Dec. 16, 2003 in U.S. Appl. No. 10/109,498.
Office Action dated Jun. 9, 2004 in U.S. Appl. No. 09/855,320.
Office Action dated Oct. 20, 2004 in U.S. Appl. No. 10/198,806.
Office Action dated Nov. 12, 2004 in U.S. Appl. No. 10/219,197.
Office Action dated Jan. 12, 2005 in U.S. Appl. No. 10/198,806.
Office Action dated Mar. 4, 2005 in U.S. Appl. No. 10/410,945.
Office Action dated Mar. 7, 2005 in U.S. Appl. No. 10/287,994.
Office Action dated Mar. 14, 2005 in U.S. Appl. No. 09/855,320.
Office Action dated Jun. 2, 2005 in U.S. Appl. No. 10/654,528.
Office Action dated Jun. 9, 2005 in U.S. Appl. No. 10/109,498.
Office Action dated Jun. 29, 2005 in U.S. Appl. No. 10/287,994.
Office Action dated Jul. 21, 2005 in U.S. Appl. No. 10/198,806.
Office Action dated Aug. 10, 2005 in U.S. Appl. No. 10/410,945.
Office Action dated Sep. 21, 2005 in U.S. Appl. No. 10/391,035.
Office Action dated Sep. 28, 2005 in U.S. Appl. No. 10/410,897.
Office Action dated Sep. 28, 2005 in U.S. Appl. No. 10/410,913.
Office Action dated Sep. 28, 2005 in U.S. Appl. No. 10/410,930.
Office Action dated Sep. 28, 2005 in U.S. Appl. No. 10/410,962.
Office Action dated Sep. 28, 2005 in U.S. Appl. No. 10/410,980.
Office Action dated Sep. 28, 2005 in U.S. Appl. No. 10/410,997.
Office Action dated Sep. 28, 2005 in U.S. Appl. No. 10/411,012.
Office Action dated Sep. 28, 2005 in U.S. Appl. No. 10/411,037.
Office Action dated Sep. 28, 2005 in U.S. Appl. No. 10/411,043.
Office Action dated Sep. 28, 2005 in U.S. Appl. No. 10/411,044.
Office Action dated Sep. 28, 2005 in U.S. Appl. No. 10/411,049.
Office Action dated Oct. 6, 2005 in U.S. Appl. No. 10/411,026.
Office Action dated Oct. 19, 2005 in U.S. Appl. No. 10/997,405.
Office Action dated Nov. 14, 2005 in U.S. Appl. No. 10/410,897.
Office Action dated Nov. 14, 2005 in U.S. Appl. No. 10/410,997.
Office Action dated Nov. 15, 2005 in U.S. Appl. No. 10/287,994.
Office Action dated Nov. 30, 2005 in U.S. Appl. No. 10/654,528.
Office Action dated Dec. 7, 2005 in U.S. Appl. No. 10/609,701.
Office Action dated Dec. 8, 2005 in U.S. Appl. No. 10/391,035.
Office Action dated Dec. 13, 2005 in U.S. Appl. No. 11/033,365.
Office Action dated Dec. 29, 2005 in U.S. Appl. No. 09/855,320.
Office Action dated Jan. 24, 2006 in U.S. Appl. No. 10/410,930.
Office Action dated Jan. 26, 2006 in U.S. Appl. No. 10/410,913.
Office Action dated Jan. 26, 2006 in U.S. Appl. No. 10/411,012.
Office Action dated Jan. 27, 2006 in U.S. Appl. No. 10/410,945.
Office Action dated Jan. 31, 2006 in U.S. Appl. No. 10/410,962.
Office Action dated Feb. 7, 2006 in U.S. Appl. No. 10/410,980.
Office Action dated Feb. 7, 2006 in U.S. Appl. No. 10/411,043.
Office Action dated Feb. 7, 2006 in U.S. Appl. No. 10/997,405.
Office Action dated Mar. 3, 2006 in U.S. Appl. No. 10/391,035.
Office Action dated Mar. 15, 2006 in U.S. Appl. No. 10/198,806.
Office Action dated Mar. 22, 2006 in U.S. Appl. No. 10/411,049.
Office Action dated Apr. 4, 2006 in U.S. Appl. No. 10/410,897.
Office Action dated Apr. 4, 2006 in U.S. Appl. No. 10/410,997.
Office Action dated Apr. 4, 2006 in U.S. Appl. No. 10/411,026.
Office Action dated Apr. 6, 2006 in U.S. Appl. No. 11/102,497.
Office Action dated May 2, 2006 in U.S. Appl. No. 11/144,223.
Office Action dated Jul. 28, 2006 in U.S. Appl. No. 10/109,498.
Office Action dated Aug. 24, 2006 in U.S. Appl. No. 10/492,261.
Office Action dated Aug. 30, 2006 in U.S. Appl. No. 11/102,497.
Office Action dated Oct. 6, 2006 in U.S. Appl. No. 10/497,284.
Office Action dated Oct. 17, 2006 in U.S. Appl. No. 11/339,752.
Office Action dated Nov. 1, 2006 in U.S. Appl. No. 11/183,205.
Office Action dated Nov. 1, 2006 in U.S. Appl. No. 11/183,218.
Office Action dated Nov. 15, 2006 in U.S. Appl. No. 10/411,026.
Office Action dated Nov. 28, 2006 in U.S. Appl. No. 11/144,223.
Office Action dated Dec. 8, 2006 in U.S. Appl. No. 10/997,405.
Office Action dated Dec. 13, 2006 in U.S. Appl. No. 10/410,980.
Office Action dated Dec. 13, 2006 in U.S. Appl. No. 10/411,043.
Office Action dated Dec. 13, 2006 in U.S. Appl. No. 10/497,284.
Office Action dated Dec. 18, 2006 in U.S. Appl. No. 09/855,320.
Office Action dated Dec. 21, 2006 in U.S. Appl. No. 11/183,205.
Office Action dated Dec. 21, 2006 in U.S. Appl. No. 11/183,218.
Office Action dated Dec. 29, 2006 in U.S. Appl. No. 11/033,365.
Office Action dated Jan. 22, 2007 in U.S. Appl. No. 10/198,806.
Office Action dated Jan. 24, 2007 in U.S. Appl. No. 11/404,266.
Office Action dated Jan. 31, 2007 in U.S. Appl. No. 10/497,283.
Office Action dated Feb. 27, 2007 in U.S. Appl. No. 10/609,701.
Office Action dated Feb. 28, 2007 in U.S. Appl. No. 10/492,261.
Office Action dated Apr. 5, 2007 in U.S. Appl. No. 10/485,892.
Office Action dated Apr. 6, 2007 in U.S. Appl. No. 11/339,752.
Office Action dated Apr. 12, 2007 in U.S. Appl. No. 10/497,283.
Office Action dated Apr. 16, 2007 in U.S. Appl. No. 10/410,980.
Office Action dated Apr. 26, 2007 in U.S. Appl. No. 11/033,365.
Office Action dated Apr. 27, 2007 in U.S. Appl. No. 11/183,205.
Office Action dated Apr. 30, 2007 in U.S. Appl. No. 11/183,218.
Office Action dated May 15, 2007 in U.S. Appl. No. 11/144,223.
Office Action dated May 31, 2007 in U.S. Appl. No. 11/395,784.
Office Action dated Jun. 1, 2007 in U.S. Appl. No. 11/102,497.
Office Action dated Jun. 11, 2007 in U.S. Appl. No. 11/514,484.
Office Action dated Jun. 25, 2007 in U.S. Appl. No. 10/411,043.
Office Action dated Jun. 26, 2007 in U.S. Appl. No. 10/411,026.
Office Action dated Jul. 13, 2007 in U.S. Appl. No. 11/440,839.
Office Action dated Jul. 26, 2007 in U.S. Appl. No. 11/395,784.
Office Action dated Aug. 16, 2007 in U.S. Appl. No. 10/497,283.
Office Action dated Aug. 17, 2007 in U.S. Appl. No. 10/492,261.
Office Action dated Aug. 30, 2007 in U.S. Appl. No. 10/497,284.
Office Action dated Sep. 4, 2007 in U.S. Appl. No. 11/144,223.
Office Action dated Sep. 18, 2007 in U.S. Appl. No. 09/855,320.
Office Action dated Oct. 1, 2007 in U.S. Appl. No. 10/411,043.
Office Action dated Oct. 2, 2007 in U.S. Appl. No. 11/166,028.
Office Action dated Oct. 3, 2007 in U.S. Appl. No. 11/514,484.
Office Action dated Oct. 16, 2007 in U.S. Appl. No. 11/183,205.
Office Action dated Oct. 16, 2007 in U.S. Appl. No. 11/183,218.
Office Action dated Oct. 30, 2007 in U.S. Appl. No. 11/580,669.
Office Action dated Nov. 1, 2007 in U.S. Appl. No. 11/339,752.
Office Action dated Nov. 15, 2007 in U.S. Appl. No. 11/166,404.
Office Action dated Nov. 28, 2007 in U.S. Appl. No. 11/102,497.

(56) References Cited

OTHER PUBLICATIONS

Office Action dated Dec. 7, 2007 in U.S. Appl. No. 10/530,972.
Office Action dated Dec. 11, 2007 in U.S. Appl. No. 11/440,839.
Office Action dated Dec. 17, 2007 in U.S. Appl. No. 10/497,284.
Office Action dated Dec. 27, 2007 in U.S. Appl. No. 11/396,215.
Office Action dated Dec. 28, 2007 in U.S. Appl. No. 11/402,105.
Office Action dated Dec. 28, 2007 in U.S. Appl. No. 10/565,331.
Office Action dated Jan. 3, 2008 in U.S. Appl. No. 10/549,528.
Office Action dated Jan. 9, 2008 in U.S. Appl. No. 11/144,223.
Office Action dated Jan. 11, 2008 in U.S. Appl. No. 10/485,892.
Office Action dated Jan. 30, 2008 in U.S. Appl. No. 10/411,043.
Office Action dated Feb. 6, 2008 in U.S. Appl. No. 11/395,784.
Office Action dated Mar. 3, 2008 in U.S. Appl. No. 11/166,404.
Office Action dated Mar. 4, 2008 in U.S. Appl. No. 09/855,320.
Office Action dated Mar. 7, 2008 in U.S. Appl. No. 11/580,669.
Office Action dated Mar. 10, 2008 in U.S. Appl. No. 10/497,284.
Office Action dated Mar. 13, 2008 in U.S. Appl. No. 10/411,026.
Office Action dated Mar. 20, 2008 in U.S. Appl. No. 10/411,044.
Office Action dated Mar. 31, 2008 in U.S. Appl. No. 10/549,528.
Office Action dated Apr. 3, 2008 in U.S. Appl. No. 11/166,028.
Office Action dated Apr. 7, 2008 in U.S. Appl. No. 11/344,767.
Office Action dated Apr. 28, 2008 in U.S. Appl. No. 11/402,105.
Office Action dated Apr. 29, 2008 in U.S. Appl. No. 10/565,331.
Office Action dated May 12, 2008 in U.S. Appl. No. 10/485,892.
Office Action dated Jun. 9, 2008 in U.S. Appl. No. 09/855,320.
Office Action dated Jun. 30, 2008 in U.S. Appl. No. 11/396,215.
Office Action dated Jul. 10, 2008 in U.S. Appl. No. 11/514,484.
Office Action dated Jul. 22, 2008 in U.S. Appl. No. 11/102,497.
Office Action dated Jul. 24, 2008 in U.S. Appl. No. 11/344,767.
Office Action dated Aug. 15, 2008 in U.S. Appl. No. 11/845,175.
Office Action dated Aug. 21, 2008 in U.S. Appl. No. 10/411,044.
Office Action dated Aug. 26, 2008 in U.S. Appl. No. 11/580,669.
Office Action dated Sep. 16, 2008 in U.S. Appl. No. 11/440,839.
Office Action dated Sep. 22, 2008 in U.S. Appl. No. 10/556,094.
Office Action dated Oct. 21, 2008 in U.S. Appl. No. 10/530,972.
Office Action dated Oct. 30, 2008 in U.S. Appl. No. 10/411,026.
Office Action dated Oct. 31, 2008 in U.S. Appl. No. 11/166,404.
Office Action dated Nov. 12, 2008 in U.S. Appl. No. 11/144,223.
Office Action dated Nov. 18, 2008 in U.S. Appl. No. 10/497,284.
Office Action dated Dec. 24, 2008 in U.S. Appl. No. 11/396,215.
Office Action dated Jan. 6, 2009 in U.S. Appl. No. 10/549,528.
Office Action dated Jan. 21, 2009 in U.S. Appl. No. 10/565,331.
Office Action dated Feb. 9, 2009 in U.S. Appl. No. 09/855,320.
Office Action dated Feb. 10, 2009 in U.S. Appl. No. 11/166,404.
Office Action dated Mar. 4, 2009 in U.S. Appl. No. 11/580,669.
Office Action dated Mar. 12, 2009 in U.S. Appl. No. 11/102,497.
Office Action dated Mar. 12, 2009 in U.S. Appl. No. 11/514,484.
Office Action dated Mar. 17, 2009 in U.S. Appl. No. 10/411,026.
Office Action dated Apr. 1, 2009 in U.S. Appl. No. 10/552,896.
Office Action dated Apr. 16, 2009 in U.S. Appl. No. 10/576,506.
Office Action dated May 11, 2009 in U.S. Appl. No. 10/411,044.
Office Action dated May 14, 2009 in U.S. Appl. No. 11/910,958.
Office Action dated May 22, 2009 in U.S. Appl. No. 11/166,404.
Office Action dated Jun. 1, 2009 in U.S. Appl. No. 12/201,705.
Office Action dated Jun. 3, 2009 in U.S. Appl. No. 10/549,520.
Office Action dated Jun. 17, 2009 in U.S. Appl. No. 11/934,700.
Office Action dated Jul. 2, 2009 in U.S. Appl. No. 10/497,284.
Office Action dated Jul. 21, 2009 in U.S. Appl. No. 11/440,839.
Office Action dated Jul. 21, 2009 in U.S. Appl. No. 10/549,528.
Office Action dated Aug. 7, 2009 in U.S. Appl. No. 10/556,094.
Office Action dated Aug. 7, 2009 in U.S. Appl. No. 10/579,621.
Office Action dated Aug. 11, 2009 in U.S. Appl. No. 10/549,445.
Office Action dated Aug. 13, 2009 in U.S. Appl. No. 09/855,320.
Office Action dated Aug. 17, 2009 in U.S. Appl. No. 10/581,538.
Office Action dated Sep. 18, 2009 in U.S. Appl. No. 11/652,467.
Office Action dated Sep. 23, 2009 in U.S. Appl. No. 12/201,705.
Office Action dated Sep. 28, 2009 in U.S. Appl. No. 11/910,958.
Office Action dated Sep. 29, 2009 in U.S. Appl. No. 11/645,839.
Office Action dated Sep. 29, 2009 in U.S. Appl. No. 11/714,874.
Office Action dated Oct. 2, 2009 in U.S. Appl. No. 11/781,900.
Office Action dated Oct. 2, 2009 in U.S. Appl. No. 11/781,902.
Office Action dated Oct. 14, 2009 in U.S. Appl. No. 10/549,528.
Office Action dated Oct. 14, 2009 in U.S. Appl. No. 10/565,331.
Office Action dated Oct. 23, 2009 in U.S. Appl. No. 11/396,215.
Office Action dated Oct. 27, 2009 in U.S. Appl. No. 11/402,105.
Office Action dated Nov. 2, 2009 in U.S. Appl. No. 11/659,942.
Office Action dated Nov. 2, 2009 in U.S. Appl. No. 11/866,969.
Office Action dated Nov. 4, 2009 in U.S. Appl. No. 10/549,445.
Office Action dated Nov. 20, 2009 in U.S. Appl. No. 11/580,669.
Office Action dated Nov. 24, 2009 in U.S. Appl. No. 11/781,888.
Office Action dated Nov. 27, 2009 in U.S. Appl. No. 11/781,885.
Office Action dated Dec. 10, 2009 in U.S. Appl. No. 11/144,223.
Office Action dated Dec. 12, 2009 in U.S. Appl. No. 12/418,530.
Office Action dated Dec. 14, 2009 in U.S. Appl. No. 11/102,497.
Office Action dated Dec. 17, 2009 in U.S. Appl. No. 10/581,538.
Office Action dated Dec. 17, 2009 in U.S. Appl. No. 11/781,896.
Office Action dated Dec. 22, 2009 in U.S. Appl. No. 09/855,320.
Office Action dated Dec. 28, 2009 in U.S. Appl. No. 12/371,156.
Office Action dated Jan. 6, 2010 in U.S. Appl. No. 11/656,643.
Office Action dated Jan. 19, 2010 in U.S. Appl. No. 11/597,258.
Office Action dated Jan. 26, 2010 in U.S. Appl. No. 11/166,404.
Office Action dated Jan. 27, 2010 in U.S. Appl. No. 11/440,839.
Office Action dated Feb. 4, 2010 in U.S. Appl. No. 12/201,705.
Office Action dated Feb. 5, 2010 in U.S. Appl. No. 11/584,743.
Office Action dated Feb. 5, 2010 in U.S. Appl. No. 11/657,441.
Office Action dated Feb. 8, 2010 in U.S. Appl. No. 12/184,956.
Office Action dated Feb. 19, 2010 in U.S. Appl. No. 11/981,483.
Office Action dated Feb. 19, 2010 in U.S. Appl. No. 11/982,273.
Office Action dated Mar. 3, 2010 in U.S. Appl. No. 10/579,620.
Office Action dated Mar. 3, 2010 in U.S. Appl. No. 11/917,772.
Office Action dated Mar. 4, 2010 in U.S. Appl. No. 09/855,320.
Office Action dated Mar. 8, 2010 in U.S. Appl. No. 11/652,467.
Office Action dated Mar. 11, 2010 in U.S. Appl. No. 12/101,389.
Office Action dated Mar. 15, 2010 in U.S. Appl. No. 10/497,284.
Office Action dated Mar. 29, 2010 in U.S. Appl. No. 11/514,484.
Office Action dated Mar. 30, 2010 in U.S. Appl. No. 12/496,595.
Office Action dated Apr. 2, 2010 in U.S. Appl. No. 11/701,949.
Office Action dated Apr. 5, 2010 in U.S. Appl. No. 10/556,094.
Office Action dated Apr. 5, 2010 in U.S. Appl. No. 10/579,621.
Office Action dated May 3, 2010 in U.S. Appl. No. 12/276,885.
Office Action dated May 13, 2010 in U.S. Appl. No. 11/781,888.
Office Action dated May 14, 2010 in U.S. Appl. No. 11/781,885.
Office Action dated May 24, 2010 in U.S. Appl. No. 10/581,538.
Office Action dated May 26, 2010 in U.S. Appl. No. 11/144,223.
Office Action dated May 26, 2010 in U.S. Appl. No. 11/659,942.
Office Action dated May 26, 2010 in U.S. Appl. No. 11/866,969.
Office Action dated May 27, 2010 in U.S. Appl. No. 10/565,331.
Office Action dated Jun. 16, 2010 in U.S. Appl. No. 11/843,588.
Office Action dated Jul. 1, 2010 in U.S. Appl. No. 11/981,483.
Office Action dated Jul. 2, 2010 in U.S. Appl. No. 11/632,005.
Office Action dated Jul. 6, 2010 in U.S. Appl. No. 10/579,620.
Office Action dated Jul. 6, 2010 in U.S. Appl. No. 11/917,772.
Office Action dated Jul. 8, 2010 in U.S. Appl. No. 11/867,553.
Office Action dated Jul. 15, 2010 in U.S. Appl. No. 11/664,199.
Office Action dated Jul. 15, 2010 in U.S. Appl. No. 11/701,949.
Office Action dated Jul. 20, 2010 in U.S. Appl. No. 11/652,467.
Office Action dated Jul. 22, 2010 in U.S. Appl. No. 12/201,705.
Office Action dated Jul. 27, 2010 in U.S. Appl. No. 11/656,643.
Office Action dated Aug. 5, 2010 in U.S. Appl. No. 12/496,595.
Office Action dated Aug. 17, 2010 in U.S. Appl. No. 11/632,005.
Office Action dated Aug. 19, 2010 in U.S. Appl. No. 11/665,908.
Office Action dated Aug. 20, 2010 in U.S. Appl. No. 11/144,223.
Office Action dated Sep. 10, 2010 in U.S. Appl. No. 11/867,553.
Office Action dated Sep. 14, 2010 in U.S. Appl. No. 12/371,156.
Office Action dated Sep. 22, 2010 in U.S. Appl. No. 11/982,273.
Office Action dated Oct. 1, 2010 in U.S. Appl. No. 11/166,404.
Office Action dated Oct. 1, 2010 in U.S. Appl. No. 11/597,258.
Office Action dated Oct. 1, 2010 in U.S. Appl. No. 11/644,014.
Office Action dated Oct. 1, 2010 in U.S. Appl. No. 11/910,958.
Office Action dated Oct. 4, 2010 in U.S. Appl. No. 12/302,167.
Office Action dated Oct. 5, 2010 in U.S. Appl. No. 11/579,401.
Office Action dated Oct. 12, 2010 in U.S. Appl. No. 12/066,619.
Office Action dated Oct. 13, 2010 in U.S. Appl. No. 11/792,610.

(56) References Cited

OTHER PUBLICATIONS

Office Action dated Oct. 14, 2010 in U.S. Appl. No. 11/781,885.
Office Action dated Oct. 15, 2010 in U.S. Appl. No. 11/664,199.
Office Action dated Oct. 15, 2010 in U.S. Appl. No. 11/781,888.
Office Action dated Nov. 24, 2010 in U.S. Appl. No. 11/866,969.
Office Action dated Nov. 26, 2010 in U.S. Appl. No. 11/981,483.
Office Action dated Dec. 16, 2010 in U.S. Appl. No. 10/579,620.
Office Action dated Dec. 16, 2010 in U.S. Appl. No. 11/701,949.
Office Action dated Dec. 17, 2010 in U.S. Appl. No. 11/658,218.
Office Action dated Dec. 21, 2010 in U.S. Appl. No. 11/632,005.
Office Action dated Dec. 27, 2010 in U.S. Appl. No. 11/144,223.
Office Action dated Jan. 10, 2011 in U.S. Appl. No. 11/659,942.
Office Action dated Jan. 18, 2011 in U.S. Appl. No. 12/444,380.
Office Action dated Jan. 20, 2011 in U.S. Appl. No. 10/586,166.
Office Action dated Jan. 21, 2011 in U.S. Appl. No. 11/843,588.
Office Action dated Feb. 1, 2011 in U.S. Appl. No. 11/867,553.
Office Action dated Feb. 3, 2011 in U.S. Appl. No. 11/794,555.
Office Action dated Feb. 3, 2011 in U.S. Appl. No. 11/914,104.
Office Action dated Feb. 3, 2011 in U.S. Appl. No. 12/443,428.
Office Action dated Feb. 4, 2011 in U.S. Appl. No. 11/794,560.
Adelhorst et al., *J. Biol. Chem.*, 269(9): 6275-6278 (1994).
Amersham Pharmacia Biotech, "Hydrophobic Interaction Chromatography: Principles and Methods," 104 pp. (2000).
Brockhausen et al., *Acta Anatomica*, 161: 36-78 (1998).
Brockhausen et al., *Glycoconj. J.*, 15: 595-603 (1998).
Broun et al., *Science*, 282(5392): 1315-1317 (1998).
Cantin et al., *Am. J. Respir. Cell Mol. Biol.*, 27(6): 659-665 (2002).
Costa et al., *J. Biol. Chem.*, 272(17): 11613-11621 (1997).
Culajay et al., *Biochem.*, 39: 7153-7158 (2000).
De Vries et al, *J. Biol. Chem.*, 270(15): 8712-8722 (1995).
De Vries et al., *Glycobiology*, 7(7): 921-927 (1997).
Dinter et al., *Biotechnol. Lett.*, 22(1): 25-30 (2000).
Dubé et al., *J. Biol. Chem.*, 263(33): 17516-17521 (1988).
Dumas et al., *Bioorg. Med. Chem. Lett.*, 1(8): 425-428 (1991).
Elhalabi et al., *Curr. Med. Chem.*, 6(2): 93-116 (1999).
Fairhall et al., *Endocrinology*, 131(4): 1963-1969 (1992).
Feldman et al., *Proc. Natl. Acad. Sci. USA*, 102(8): 3016-3021 (2005).
Francis et al., *Intl. J. Hematol.*, 68(1): 1-18 (1998).
Ge et al., *J. Biol. Chem.*, 272(34): 21357-21363 (1997).
Gombotz et al., "PEGylation: A Tool for Enhanced Protein Delivery," in *Controlled Drug Delivery*, Park et al. (eds.), Chapter 12, pp. 110-123, ACS Symposium Series, American Chemical Society, Washington D.C. (2000).
Grabenhorst et al., *J. Biol. Chem.*, 274(51): 36107-36116 (1999).
Hansen et al., *Biochem J.*, 308: 801-813 (1995).
Haro et al., *Biochem. Biophys. Res. Comm.*, 228(2): 549-556 (1996).
Höglund, *Med. Oncol.*, 15(4): 229-233 (1998).
Jezek et al., *J. Peptide Sci.*, 5: 46-55 (1999).
Kaneko et al., *Cytogenet. Cell Genet.*, 86(3-4): 329-330 (1999).
Kaneko et al., *FEBS Lett.*, 452(3): 237-242 (1999).
Keene et al., *J. Biol. Chem.*, 264(9): 4769-4775 (1989).
Kimura et al., *Proc. Natl. Acad. Sci. USA*, 96(8): 4530-4535 (1999).
Kisselev, *Structure*, 10(1): 8-9 (2002).
Kukowska-Latallo et al., *Genes Dev.*, 4(8): 1288-1303 (1990).
Legault et al., *J. Biol. Chem.*, 270(36): 20987-20996 (1995).
Leist et al., *Science*, 305: 239-242 (2004).
Leiter et al., *J. Biol. Chem.*, 274(31): 21830-21839 (1999).
Lewis et al., *Endocr. J.*, 47(Suppl.): S1-S8 (2000).
Lin et al., *Proc. Natl. Acad. Sci. USA*, 82: 7580-7584 (1985).
Lönnberg, *Curr. Org. Synth.*, 6(4): 400-425 (2009).
Malissard et al., *Biochem. Biophys. Res. Commun.*, 267(1): 169-173 (2000).
Meynial-Salles et al., *J. Biotechnol.*, 46(1): 1-14 (1996).
Mollicone et al., *Eur. J. Biochem.*, 191(1): 169-176 (1990).
Monaco et al., *Gene*, 180: 145-150 (1996).
Nagata et al., *EMBO J.*, 5(3): 575-581 (1986).
Nunez et al., *Can. J. Chem.*, 59(14): 2086-2095 (1981).
Oh-Eda et al., *J. Biol. Chem.*, 265: 11432-11435 (1990).
Orskov et al., *J. Biol. Chem.*, 264(22): 12826-12829 (1989).
Palcic et al., *Carbohydr. Res.*, 190(1): 1-11 (1989).
Prati et al., *Biotech and Bioeng.*, 79(5): 580-585 (2002).
Prieels et al., *J. Biol. Chem.*, 256(20): 10456-10463 (1981).
Rasko et al., *J. Biol. Chem.*, 275(7): 4988-4994 (2000).
Rotondaro et al., *Mol. Biotech.*, 11: 117-128 (1999).
Sasaki et al., *J. Biol. Chem.*, 262(25): 12059-12076 (1987).
Sasaki et al., *J.Biol. Chem.*, 269: 14730-14737 (1994).
Seffernick et al., *J. Bacteriol.*, 183(8): 2405-2410 (2001).
Shinkai et al., *Prot. Exp. Purif.*, 10: 379-385 (1997).
Sinclair et al., *J. Pharm. Sci.*, 94: 1626-1635 (2005).
Snider et al., *J. Chromatogr.*, A 599(1-2): 141-155 (1992).
Staudacher, *Trends Glycosci. Glycotechnol.*, 8(44): 391-408 (1996).
Strausberg et al., *Proc Natl Acad Sci USA*, 99(26): 16899-16903 (2002).
Tenno et al., *J. Biol. Chem.*, 277(49): 47088-47096 (2002).
Trottein et al., *Mol. Biochem. Parasitol.*, 107(2): 279-287 (2000).
Tsunoda et al., *J. Pharmacol. Exp. Ther.*, 209(1): 368-372 (1999).
Van Tetering et al., *FEBS Lett.*, 461(3): 311-314 (1999).
Wang et al., *Glycobiology*, 6(8): 837-842 (1996).
Wang et al., *Microbiol.*, 145(Pt. 11): 3245-3253 (1999).
Weston et al., *J. Biol. Chem.*, 267(34): 24575-24584 (1992).
White et al., *J. Biol. Chem.*, 270(41): 24156-24165 (1995).
Wishart et al., *J. Biol. Chem.*, 270(45): 26782-26785 (1995).
Witkowski at al., *Biochemistry*, 38(36): 11643-11650 (1999).
Zhang et al., *Biochim. Biophys. Acta*, 1425: 441-452 (1998).
Ajisaka et al., *Biosci. Biotechnol. Biochem.*, 65(5): 1240-1243 (2001).
Andree et al., *Biochim. Biophys. Acta*, 544(3): 489-495 (1978).
Apicella et al., *Infect. Immun.*, 55(8): 1755-1761 (1987).
Arsequell et al., *Tetrahedron: Asymmetry*, 10(16): 3045-3094 (1999).
ATCC Catalog of Bacteria and Bacteriophages, 17th ed., p. 150-151 (1989).
Auge et al., *Carbohydr. Res.*, 151: 147-156 (1986).
Auge et al., *Carbohydr. Res.*, 200: 257-268 (1990).
Avigad et al., *J. Biol. Chem.*, 237(9): 2736-2743 (1962).
Barker et al., *J. Biol. Chem.*, 247(22): 7135-7147 (1972).
Bayer et al., *Glycobiology*, 13(11): 890-891 (2003).
Bertozzi et al., *J. Am. Chem. Soc.*, 114(26): 10639-10641 (1992).
Biemann et al., *Science*, 237(4818): 992-998 (1987).
Binder et al., *Tetrahedron*, 50(35): 10407-10418 (1994).
Bishop et al., *Endocrinology*, 136(6): 2635-2640 (1995).
Bocci, *Adv. Drug Deliv. Rev.*, 4(2): 149-169 (1989).
Borman, *Chem. Eng. News*, 84(36): 13-22 (2006).
Breton et al., *Curr. Opin. Struct. Biol.*, 9(5): 563-571 (1999).
Breton et al., *Biochimie*, 83(8): 713-718 (2001).
Brinkman-Van Der Linden et al., *J. Biol. Chem.*, 271(24): 14492-14495 (1996).
Broquet et al., *Eur. J. Biochem.* 123(1): 9-13 (1982).
Burczak et al., *Biochim. Biophys. Acta*, 804(4): 442-449 (1984).
Burns et al., *J. Org. Chem.*, 56(8): 2648-2650 (1991).
Calvet, *Pediatr. Nephrol.*, 5(6): 751-757 (1991).
Carlson et al., *J. Biol. Chem.*, 248(16): 5742-5750 (1973).
Chang et al, *Biotechnol. Bioprocess Eng.*, 3(1): 40-43 (1998).
Chang et al., *Biochemistry*, 38(34): 10940-10948 (1999).
Clogston et al., *J. Chromatogr. A*, 637(1): 55-62 (1993).
Corfield, "Analysis of Sugar Sequences in Glycoproteins by Glycosidase Digestion and Gel Filtration," *Methods in Molecular Biology*, 19: 269-286 (1993).
Dabkowski et al., *Transplant Proc.*, 25(5): 2921 (1993).
Danaher et al., *J. Bacteriol.*, 177(24): 7275-7279 (1995).
Datta et al., *J. Biol. Chem.*, 270(4): 1497-1500 (1995).
David et al., *Pure Appl. Chem.*, 59(11): 1501-1508 (1987).
Davis et al., *Synlett* 1999, (9): 1495-1507 (1999).
De Rosa et al., *Phytochemistry*, 42(4): 1031-1034 (1996).
DeAngelis et al., *Biochemistry*, 33(31): 9033-9039 (1994).
DeLuca et al., *J. Am. Chem. Soc.*, 117(21): 5869-5870 (1995).
Dennis et al., *J. Biol. Chem.*, 277(38): 35035-35043 (2002).
Dickinson et al., *Proc. Natl. Acad. Sci. USA*, 93(25): 14379-14384 (1996).
Dreyfus et al., *Anal. Biochem.*, 249(1): 67-78 (1997).
Drucker et al., "Glucagon Gene Expression in Vertebrate Brain," *J. Biol. Chem.*, 263(27): 13475-13478 (1988).
Dudas et al., *Infect. Immun.*, 56(2): 499-504 (1988).

(56) References Cited

OTHER PUBLICATIONS

Dudziak et al., *Tetrahedron*, 56(32): 5865-5869 (2000).
Edano et al., *Biol. Pharm. Bull.*, 21(4): 382-385 (1998).
Ellis, "Vaccines" Plotkin et al. (eds.), Chapter 29, W.B. Saunders Co., Philadelphia, pp. 568-575 (1988).
EMBL Accession No. M80599 and M86935, pp. 1-6 (Jan. 23, 1992).
EMBL Accession No. S56361, pp. 1-4 (May 4, 1993).
EMBL Accession No. 000039, pp. 1-137 (Jun. 2, 1994).
Ernst et al., *Glycoconj. J.*, 16(2): 161-170 (1999).
Fu et al., *Bioconjug. Chem.*, 12(2): 271-279 (2001).
Fujita et al., *Biochim. Biophys. Acta*, 1528(1): 9-14 (2001).
GE Healthcare, Instructions 28-9064-05 AA, pp. 1-32 (2006).
GE Healthcare, Instructions 28-9064-05 AC, pp. 1-40 (2006).
Genbank Accession No. AAA98726, "Factor IX," pp. 1-3 (Apr. 14, 2009).
Genbank Accession No. CAA01607, "Factor IX of Homo sapiens," pp. 1-2 (Apr. 14, 2009).
Genbank Accession No. D49915, pp. 1-3 (Sep. 1, 1995).
Genbank Accession No. U02304, p. 1 (Mar. 8, 1994).
Genbank Accession No. U18918, p. 1 (Oct. 1, 1995).
Gibson et al., *J. Bacteriol.*, 175(9): 2702-2712 (1993).
Gilbert, "Methods in Enzymology" Packer (ed.), 2(251): 8-28, Biothiols Part A, Elsevier (1995).
Gilbert et al., "The Synthesis of Sialylated Oligosaccharides Using a CMP-Neu5Ac Synthetase/Sialyltransferase Fusion," *Nature Biotechnology*, 16: 769-772 (1998).
Gillespie et al., *FASEB Journal*, 4(7): A2068 [Abstract No. 2173] (1990).
Gillespie et al., *J. Biol. Chem.*, 267(29): 21004-21010 (1992).
Goodson et al., *Biotechnology (N.Y.)*, 8(4): 343-346 (1990).
Greenwell et al., *Blood Group A Synthesising Activity of the Blood Group B Gene Specified .alpha.-3-D-Galactosyl Transferase*, p. 268-269 (1979).
Greenwell et al., *Carbohydr. Res.*, 149(1): 149-170 (1986).
Gross et al., *Eur. J. Biochem.*, 168(3): 595-602 (1987).
Grundmann et al., *Nucleic Acids Res.*, 18(3): 667 (1990).
Gu et al., *FEBS Lett.*, 275(1-2): 83-86 (1990).
Guivisdalsky et al., *J. Med. Chem.*, 33(9): 2614-2621 (1990).
Hakomori et al., "Methods in Enzymology," Fleischer et al. (eds.), 33(32): 345-367, Biomembranes Part B, Elsevier USA (1974).
Hedner et al., "Recombinant Activated Factor VII in the Treatment of Bleeding Episodes in Patients With Inherited and Acquired Bleeding Disorders," *Transfusion Medicine Reviews*, VII(2): 78-83 (1993).
Heimgartner et al., "Reversible and Irreversible Cross-Linking of Immunoglobulin Heavy Chains Through Their Carbohydrate Residues," *Biochem. J.*, 267: 585-591 (1990).
Helling et al., *Cancer Res.*, 54(1): 197-203 (1994).
Higa et al., *J. Biol. Chem.*, 260(15): 8838-8849 (1985).
Higashi et al., *J. Biol. Chem.*, 272(41): 25724-25730 (1997).
High et al., *Mol. Microbiol.*, 9(6): 1275-1282 (1993).
Hoffman et al., *Thromb. Haemost.*, 85(6): 958-965 (2001).
Ichikawa et al., *J. Am. Chem. Soc.*, 113(12): 4698-4700 (1991).
Ichikawa et al., *J. Am. Chem. Soc.*, 113(16): 6300-6302 (1991).
Ito et al., *J. Am. Chem. Soc.*, 115(4): 1603-1605 (1993).
Japanese Biochemical Society, "New Course in Biochemistry Experiments 3, Sugars I, Glycoproteins (top)," Tokyo Kagaku Dojin K.K., First Edition, p. 340 (1990).
Jennemann et al., *J. Biochem.*, 115(6): 1047-1052 (1994).
Jennings et al., *Mol. Microbiol.*, 10(2): 361-369 (1993).
John et al., *J. Biol. Chem.*, 266(29): 19303-19311 (1991).
Jonsson et al., *EMBO J.*, 10(2): 477-488 (1991).
Joziasse et al., *J. Biol. Chem.*, 260(8): 4941-4951 (1985).
Joziasse et al., *J. Biol. Chem.*, 264(24): 14290-14297 (1989).
Kawai et al., *J. Lipid Res.*, 26(3): 338-343 (1985).
Kerwood et al., *Biochemistry*, 31(51): 12760-12768 (1992).
Khidekel et al., *J. Am. Chem. Soc.*, 125(52): 16162-16163 (2003).
Kitagawa et al., *Biochem. Biophys. Res. Commun.*, 194(1): 375-382 (1993).
Kitagawa et al., *J. Biol. Chem.*, 269(27): 17872-17878 (1994).
Knight et al., *Mol. Microbiol.*, 6(11): 1565-1573 (1992).

Koeller et al., "Complex Carbohydrate Synthesis Tools for Glycobiologists: Enzyme-Based Approach and Programmable One-Pot Strategies," *Glycobiology*, 10(11): 1157-1169 (2000).
Kogan, *Synth. Commun.*, 22(16): 2417-2424 (1992).
Koike et al., *Carbohydr. Res.*, 162(2): 237-246 (1987).
Kurosawa et al., *Eur. J. Biochem.*, 219(1-2): 375-381 (1994).
Larsen et al, *Proc. Natl. Acad. Sci. USA*, 86(21): 8227-8231 (1989).
Lee et al., *Science*, 239(4845): 1288-1291 (1988).
Lidholt et al, *Biochem. J.*, 261(3): 999-1007 (1989).
Livingston et al., *J. Biol. Chem.*, 268(16): 11504-11507 (1993).
Lundstrom-Ljung et al., *J. Biol. Chem.*, 270(14): 7822-7828 (1995).
Luo et al., "Spontaneous Calcification of Arteries and Cartilage in Mice Lacking Matrix GLA Protein," *Nature*, 386: 78-81 (1997).
Maccioni et al., *Biochim Biophys Acta.*, 1437(2): 101-118 (1999).
Mackenzie et al., *J. Am. Chem. Soc.*, 120(22): 5583-5584 (1998).
Madnick et al., *Arch. Biochem. Biophys.*, 212(2): 432-442 (1981).
Mandrell et al., *J. Exp. Med.*, 168(1): 107-126 (1988).
Mandrell et al., *J. Exp. Med.*, 171(5): 1649-1664 (1990).
Mandrell et al., *J. Bacteriol.*, 173(9): 2823-2832 (1991).
Mandrell, *Infect. Immun.*, 60(7): 3017-3020 (1992).
Manfioletti et al., "The Protein Encoded by a Growth Arrest-Specific Gene (*gas6*) Is a New Member of the Vitamin K-Dependent Proteins Related to Protein S, a Negative Coregulator in the Blood Coagulation Cascade," *Mol. Cell. Bio.*, 13(8): 4976-4985 (1993).
Marinier et al., *J. Med. Chem.*, 40(20): 3234-3247 (1997).
Mathews et al., *J. Biol. Chem.*, 262(16): 7537-7545 (1987).
Mizuguchi et al., *Thromb. Haemost.*, Abstract 1474: 466, Suppl. (Aug. 1999).
Monfardini et al., "A Branched Monomethoxypoly (ethylene glycol) for Protein Modification," *Bioconjug. Chem.*, 6(1): 62-69 (1995).
Moscatelli et al., *J. Biol. Chem.*, 236(11): 2858-2862 (1961).
Muramatsu et al., *Comprehensive Research on Clinical Organ Xenotransplantation by Genetic Regulation*, p. 10-12. (1997) English Translation.
Nelsestuen et al., "Vitamin K-Dependent Proteins," *Vitamins and Hormones*, 58: 355-389 (2000).
Nemansky et al., *FEBS Lett.*, 312(1): 31-36 (1992).
Nilsson, *Trends Biotechnol.*, 6(10): 256-264 (1988).
Nucci et al., *Adv. Drug Deliv. Rev.*, 6(2): 133-151 (1991).
Nunez et al., *Biochemistry*, 15(17): 3843-3847 (1976).
Palcic et al., *Glycobiology*, 1(2): 205-209 (1991).
Parsons et al., *Microb. Pathog.*, 7(1): 63-72 (1989).
Patra et al., *Protein Expr. Purif.*, 18(2): 182-192 (2000).
Paulson et al., *Chemical Abstracts*, 86(25): 213 [Abstract No. 185016b] (1977).
Paulson et al., *J. Biol. Chem.*, 252(7): 2356-2362 (1977).
Paulson et al., *J. Biol. Chem.*, 264(19):10931-10934 (1989).
Perrin et al., "Common Physical Techniques Used in Purification," in *Purification of Laboratory Chemicals*, pp. 30-31, Pergamon (1980).
Pfaffli et al., *Carbohydr. Res.*, 23(2): 195-206 (1972).
Pradel et al., *J. Bacteriol.*, 174(14): 4736-4745 (1992).
Preuss et al., *J. Biol. Chem.*, 268(35): 26273-26278 (1993).
Probert et al., *Tetrahedron Lett.*, 38(33): 5861-5864 (1997).
Rabina et al., "Analysis of Nucleotide Sugars from Cell Lysates by Ion-Pair Solid-Phase Extraction and Reversed-Phase High-Performance Liquid Chromatography," *Glycoconj. J.*, 18(10): 799-805 (2001).
Raju et al., "Glycoengineering of Therapeutic Glycoproteins: In Vitro Galactosylation and Sialylation of Glycoproteins with Terminal N-Acetylglucosamine and Galactose Residues," *Biochemistry*, 40(30): 8868-8876 (2001).
Rao et al., *Protein Sci.*, 8(11): 2338-2346 (1999).
Rearick et al., *J. Biol. Chem.*, 254(11): 4444-4451 (1979).
Rice et al., *J. Biol. Chem.*, 265(30): 18423-18428 (1990).
Robertson et al., *Mol. Microbiol.*, 8(5): 891-901 (1993).
Rosevear et al., *Biochemistry*, 21(6): 1421-1431 (1982).
Sadler et al., *J. Biol. Chem.*, 254(11): 4434-4442 (1979).
Sadler et al., *J. Biol. Chem.*, 254(13): 5934-5941 (1979).
Saenko et al., *Haemophilia*, 12(suppl. 3): 42-51 (2006).
Sambrook et al., "Molecular Cloning: A Laboratory Manual" 2nd ed., Cold Spring Harbor Laboratory Press, Cold Spring Harbor, New York, pp. 9.50-9.51 (1989).
Sandlin et al., *J. Bacteriol.*, 176(10): 2930-2937 (1994).

(56) References Cited

OTHER PUBLICATIONS

Schmidt et al., *Trends Cardiovasc. Med.*, 13(1): 39-45 (2003).
Schneider et al., *Infect. Immun.*, 56(4): 942-946 (1988).
Schneider et al., *J. Exp. Med.*, 174(6): 1601-1605 (1991).
Schram et al., *Biochim. Biophys. Acta*, 482(1): 138-144 (1977).
Sears et al., *Science*, 291(5512): 2344-2350 (2001).
Shames et al., *Glycobiology*, 1(2): 187-191 (1991).
Shao et al., *Glycobiology*, 12(11): 763-770 (2002).
Simon et al., *J. Am. Chem. Soc.*, 110(21): 7159-7163 (1988).
Sogin et al., *Biochemistry* 19(23): 5417-5420 (1980).
Song et al., "Reassembled Biosynthetic Pathway for a Large-Scale Synthesis of CMP-Neu5Ac," *Mar. Drugs*, 1: 34-45 (2003).
Sorensen et al., "Incorporation of an Active Site Inhibitor in Factor VIIa Alters the Affinity for Tissue Factor," *J. Biol. Chem.*, 272(18): 11863-11868 (1997).
Stamenkovic et al., *J. Exp. Med.*, 172(2): 641-643 (1990).
Stennicke et al., *Anal. Biochem.*, 248(1): 141-148 (1997).
Stephens et al., *Infect Immun.*, 62(7): 2947-2952 (1994).
Stoolmiller et al., *J. Biol. Chem.*, 244(2): 236-246 (1969).
Suzuki et al., *J. Biol. Chem.*, 260(3): 1362-1365 (1985).
Swiss-Prot Accession No. P19817, p. 1 (Feb. 1, 1991).
Swiss-Prot Accession No. P25740, pp. 1-6 (May 1, 1992).
Swiss-Prot Accession No. P27129, pp. 1-5 (Aug. 1, 1992).
Takegawa et al., *J. Biol. Chem.*, 270(7): 3094-3099 (1995).
Takeya et al., *J. Biol. Chem.*, 263(29): 14868-14877 (1988).
Takeya et al., *Jpn. J. Med. Sci. Biol.*, 46(1): 1-15 (1993).
Tarui et al., *J. Biosci. Bioeng.*, 90(5): 508-514 (2000).
Toone et al., *Tetrahedron*, 45(17): 5365-5422 (1989).
Tsai et al., *Infect. Immun.*, 59(10): 3604-3609 (1991).
Tsuboi et al., "6'-Sulfo Sialyl Le$^x$ but Not 6-Sulfo Sialyl Le$^x$ Expressed on the Cell Surface Supports L-selectin-mediated Adhesion," *J. Biol. Chem.*, 271(44): 27213-27216 (1996).
Tsuji, "Molecular Cloning and Functional Analysis of Sialyltransferases," *J. Biochemistry*, 120: 1-13 (1996).
Tsujihara et al., *Chem. Pharm. Bull.*, (Tokyo) 29(11): 3262-3273 (1981).
Van Den Eijnden et al., *J. Biol. Chem.*, 256(7): 3159-3162 (1981).
Van Den Eijnden et al., *J. Biol. Chem.*, 258(6): 3435-3437 (1983).
Van Putten et al., *EMBO J.*, 12(11): 4043-4051 (1993).
Van Roey et al., *Biochemistry*, 33(47): 13989-13996 (1994).
Vann et al., *J Biol Chem.*, 262(36): 17556-17562 (1987).
Verheul et al., *Microbiol. Rev.*, 57(1): 34-49 (1993).
Vijay et al., *J. Biol. Chem.*, 250(1): 164-170 (1975).
Waddling et al., *Biochemistry*, 39(27): 7878-7885 (2000).
Wakarchuk et al., *J. Biol. Chem.*, 271(32): 19166-19173 (1996).
Wang et al., *Protein Eng.*, 10(4): 405-411 (1997).
Webster et al., *J. Biol. Chem.*, 258(17): 10637-10641 (1983).
Weerapana et al., "Investigating Bacterial N-Linked Glycosylation: Synthesis and Glycosyl Acceptor Activity of the Undecaprenyl Pyrophosphate-Linked Bacillosamine," *J. Am. Chem. Soc.*, 127(40): 13766-13767 (2005).
Weinstein et al., *J. Biol. Chem.*, 257(22): 13835-13844 (1982).
Weinstein et al., *J. Biol. Chem.*, 257(22): 13845-13853 (1982).
Wen et al., *FASEB Journal*, 6(1): A231 [abstract No. 1329] (1992).
Wen et al., *J. Biol. Chem.*, 267(29): 21011-21019 (1992).
Whisstock et al., *Q. Rev. Biophys.*, 36(3): 307-340 (2003).
Wikipedia, Image:Ceramide.svg, http://en.wikipedia.org/wiki/Ceramide, pp. 1-2 (2007).
Wong et al., *J. Org. Chem.*, 57(16): 4343-4344 (1992).
Xiao et al., *J. Biol. Chem.*, 280(22): 21099-21106 (2005).
Yamamoto et al., *J. Biol. Chem.*, 265(31): 19257-19262 (1990).
Yamamoto et al., *Nature*, 345(6272): 229-233 (1990).
Yamasaki et al., *J. Bacteriol.*, 175(14): 4565-4568 (1993).
Yoshikawa et al., *Phytochemistry*, 34(5): 1431-1433 (1993).
Zalipsky et al., *Polymer Prepr.*, 27(1): 1-2 (1986).
Zalipsky et al., *Int. J. Pept. Protein Res.*, 30(6): 740-783 (1987).
Zapata et al., *J. Biol. Chem.*, 264(25): 14769-14774 (1989).
Zhou et al., *J. Biol. Chem.*, 269(15): 11162-11169 (1994).

FIGURE 2

GH-N (O-Glycosylation)

→ ptt f pttp lsrlfdnam lrahrlhqla fdtyqefeea yipkeqkysf lqnpqtslcf sesiptpsnr
→ ptts
eetqqksnle llrislliq swlepvqflr svfanslvyg asdsnvydll kdleegiqtl mgrledgs
→ ptttt
ptt qifk ttts kfdtnshndd allknyglly cfrkdmdkve tflrivqcrs vegscgf
→ ptt lcf sesi ptttt GH-N (pituit

FIGURE 3

```
                              50
hGH O-linked 134   (1)   ---FPTIPLSRLFDNAMLRAHRLHQLAFDTYQEFEEAYIPKEQKYSFLQN
hGH O-linked 5'    (1)   PTTFPTIPLSRLFDNAMLRAHRLHQLAFDTYQEFEEAYIPKEQKYSFLQN
hGH-N1 mature      (1)   ---FPTIPLSRLFDNAMLRAHRLHQLAFDTYQEFEEAYIPKEQKYSFLQN
Consensus          (1)      FPTIPLSRLFDNAMLRAHRLHQLAFDTYQEFEEAYIPKEQKYSFLQN
                         51                                               100
hGH O-linked 134  (48)   PQTSLCFSESIPTPSNREETQQKSNLELLRISLLLIQSWLEPVQFLRSVF
hGH O-linked 5'   (51)   PQTSLCFSESIPTPSNREETQQKSNLELLRISLLLIQSWLEPVQFLRSVF
hGH-N1 mature     (48)   PQTSLCFSESIPTPSNREETQQKSNLELLRISLLLIQSWLEPVQFLRSVF
Consensus         (51)   PQTSLCFSESIPTPSNREETQQKSNLELLRISLLLIQSWLEPVQFLRSVF
                         101                                              150
hGH O-linked 134  (98)   ANSLVYGASDSNVYDLLKDLEEGIQTLMGRLEDGSPTTTQIFKQTYSKFD
hGH O-linked 5'  (101)   ANSLVYGASDSNVYDLLKDLEEGIQTLMGRLEDGSPRTGQIFKQTYSKFD
hGH-N1 mature     (98)   ANSLVYGASDSNVYDLLKDLEEGIQTLMGRLEDGSPRTGQIFKQTYSKFD
Consensus        (101)   ANSLVYGASDSNVYDLLKDLEEGIQTLMGRLEDGSPRTGQIFKQTYSKFD
                         151                                    194
hGH O-linked 134 (148)   TNSHNDDALLKNYGLLLYCFRKDMDKVETFLRIVQCRSVEGSCGF
hGH O-linked 5'  (151)   TNSHNDDALLKNYGLLLYCFRKDMDKVETFLRIVQCRSVEGSCGF
hGH-N1 mature    (148)   TNSHNDDALLKNYGLLLYCFRKDMDKVETFLRIVQCRSVEGSCGF
Consensus        (151)   TNSHNDDALLKNYGLLLYCFRKDMDKVETFLRIVQCRSVEGSCGF
```

FIGURE 4

```
hGH O-linked 134    (1)   ---FPTIPLSRLFDNAMLRAHRLHQLAFDTYQEFEEAYIPKEQKYSFLQN
hGH O-linked 5'     (1)   -MVTPTIPLSRLFDNAMLRAHRLHQLAFDTYQEFEEAYIPKEQKYSFLQN
hGH-N1 mature       (1)   ---FPTIPLSRLFDNAMLRAHRLHQLAFDTYQEFEEAYIPKEQKYSFLQN
Consensus           (1)      FPTIPLSRLFDNAMLRAHRLHQLAFDTYQEFEEAYIPKEQKYSFLQN
                                                                              50 hGH O-linked 134   (48)   PQTSLCFSESIPTPSNREETQQKSNLELLRISLLLIQSWLEPVQFLRSVF
hGH O-linked 5'    (51)   PQTSLCFSESIPTPSNREETQQKSNLELLRISLLLIQSWLEPVQFLRSVF
hGH-N1 mature      (48)   PQTSLCFSESIPTPSNREETQQKSNLELLRISLLLIQSWLEPVQFLRSVF
Consensus          (51)   PQTSLCFSESIPTPSNREETQQKSNLELLRISLLLIQSWLEPVQFLRSVF
                                                                             100 hGH O-linked 134   (98)   ANSLVYGASDSNVYDLLKDLEEGIQTLMGRLEDGSPTTGQIFKQTYSKFD
hGH O-linked 5'   (101)   ANSLVYGASDSNVYDLLKDLEEGIQTLMGRLEDGSPRTGQIFKQTYSKFD
hGH-N1 mature      (98)   ANSLVYGASDSNVYDLLKDLEEGIQTLMGRLEDGSPRTGQIFKQTYSKFD
Consensus         (101)   ANSLVYGASDSNVYDLLKDLEEGIQTLMGRLEDGSPRTGQIFKQTYSKFD
                                                                             150 hGH O-linked 134  (148)   TNSHNDDALLKNYGLLYCFRKDMDKVETFLRIVQCRSVEGSCGF
hGH O-linked 5'   (151)   TNSHNDDALLKNYGLLYCFRKDMDKVETFLRIVQCRSVEGSCGF
hGH-N1 mature     (148)   TNSHNDDALLKNYGLLYCFRKDMDKVETFLRIVQCRSVEGSCGF
Consensus         (151)   TNSHNDDALLKNYGLLYCFRKDMDKVETFLRIVQCRSVEGSCGF
                                                                 194
```

FPTIPLSRLFDNAMLRAHRLHQLAFDTYQEFEEAYIPKEQKYSFLQNPQTSLCFSE
SIPTPSNREETQQKSNLELLRISLLLIQSWLEPVQFLRSVFANSLVYGASDSNVYDL
LKDLEEGIQTLMGRLEDGSPRTGQIFKQTYSKFDTNSHNDDALLKNYGLLYCFRK
DMDKVETFLRIVQCRSVEGSCGF

FIG. 5A

FPTIPLSRLFDNAMLRARRLYQLAYDTYQEFEEAYILKEQKYSFLQNPQTSLCFSE
SIPTPSNRVKTQQKSNLELLRISLLLIQSWLEPVQLLRSVFANSLVYGASDSNVYR
HLKDLEEGIQTLMWRLEDGSPRTGQIFNQSYSKFDTKSHNDDALLKNYGLLYCF
RKDMDKVETFLRIVQCRSVEGSCGF

FIG. 5B

FPTIPLSRLFDNAMLRAHRLHQLAFDTYQEFEEAYIPKEQKYSFLQNPQTSLCFSE
SIPTPSNREETQQKSNLELLRISLLLIQSWLEPVQFLRSVFANSLVYGASDSNVYDL
LKDLEEGIQTLMGRLEDGSPTTTQIFKQTYSKFDTNSHNDDALLKNYGLLYCFRK
DMDKVETFLRIVQCRSVEGSCGF

FIG. 5C

PTTFPTIPLSRLFDNAMLRAHRLHQLAFDTYQEFEEAYIPKEQKYSFLQNPQTSLC
FSESIPTPSNREETQQKSNLELLRISLLLIQSWLEPVQFLRSVFANSLVYGASDSNV
YDLLKDLEEGIQTLMGRLEDGSPRTGQIFKQTYSKFDTNSHNDDALLKNYGLLY
CFRKDMDKVETFLRIVQCRSVEGSCGF

FIG. 5D

FPTIPLSRLFDNAMLRAHRLHQLAFDTYQEFEEAYIPKEQKYSFLQNPQTSLCFSE
SIPTPSNREETQQKSNLELLRISLLLIQSWLEPVQFLRSVFANSLVYGASDSNVYDL
LKDLEEGIQTLMGRLEDGSPTTGQIFKQTYSKFDTNSHNDDALLKNYGLLYCFRK
DMDKVETFLRIVQCRSVEGSCGF

FIG. 5E

MVTPTIPLSRLFDNAMLRAHRLHQLAFDTYQEFEEAYIPKEQKYSFLQNPQTSLCF
SESIPTPSNREETQQKSNLELLRISLLLIQSWLEPVQFLRSVFANSLVYGASDSNVY
DLLKDLEEGIQTLMGRLEDGSPRTGQIFKQTYSKFDTNSHNDDALLKNYGLLYCF
RKDMDKVETFLRIVQCRSVEGSCGF

FIG. 5F

MVTPTIPLSRLFDNAMLRAHRLHQLAFDTYQEFEEAYIPKEQKYSFLQNPQTSLCF
SESIPTPSNREETQQKSNLELLRISLLLIQSWLEPVQFLRSVFANSLVYGASDSNVY
DLLKDLEEGIQTLMGRLEDGSPRTGQIFKQTYSKFDTNSHNDDALLKNYGLLYCF
RKDMDKVETFLRIVQCRSVEGSCGF

FIG. 5G

MFPTIPLSRLFDNAMLRAHRLHQLAFDTYQEFEEAYIPKEQKYSFLQNPQTSLCFS
ESIPTPSNREETQQKSNLELLRISLLLIQSWLEPVQFLRSVFANSLVYGASDSNVYD
LLKDLEEGIQTLMGRLEDGSPTVGQIFKQTYSKFDTNSHNDDALLKNYGLLYCFR
KDMDKVETFLRIVQCRSVEGSCGF

FIG. 5H

MFPTIPLSRLFDNAMLRAHRLHQLAFDTYQEFEEAYIPKEQKYSFLQNPQTSLCFS
ESIPTPSNREETQQKSNLELLRISLLLIQSWLEPVQFLRSVFANSLVYGASDSNVYD
LLKDLEEGIQTLMGRLEDGSPTTQIFKQTYSKFDTNSHNDDALLKNYGLLYCFR
KDMDKVETFLRIVQCRSVEGSCGF

FIG. 5I

Human Growth Hormone Glycosylation Mutants (in larger non-italicized bold font) with and without proteolysis mutations (larger italicized bold font).

P214

MFPT*E*IPLSRLFDNAMLRAHRLHQLAFDTYQEFEEAYIPKEQKYSFLQNPQTSL
CFSESIPTPSNREETQQKSNLELLRISLLLIQSWLEPVQFLRSVFANSLVYGASD
SNVYDLLKDLEEGIQTLMGRLEDGSPRTGQIFKQTYSKFDTNSHNDDALLKNYG
LLYCFRKDMDKVETFLRIVQCRSVEGSCGF          (SEQ ID NO: 80)

MFPTIPLSRLFDNAMLRAHRLHQLAFDTYQEFEEAYIPKEQKYSFLQNPQTSLC
FSESIPTPSNREETQQKSNLELLRISLLLIQSWLEPVQFLRSVHANSLVYGASDS
NVYDLLKDLEEGIQTLMGRLEDGSPTTVSIFKQTYSKFDTNSHNDDALLKNYGL
LYCFRKDMDKVETFLRIVQCRSVEGSCGF          (SEQ ID NO: 81)

MFPTIPLSRLFDNAMLRAHRLHQLAFDTYQEFEEAYIPKEQKYSFLQNPQTSLC
FSESIPTPSNREETQQKSNLELLRISLLLIQSWLEPVQFLRSVFANSLVYGASDS
NVYDLLKDLEEGIQTLMGRLEDGSPRTGQIPTQ*A*YSKFDTNSHNDDALLKNYG
LLYCFRKDMDKVETFLRIVQCRSVEGSCGF          (SEQ ID NO: 82)

MFPTIPLSRLFDNAMLRAHRLHQLAFDTYQEFEEAYIPKEQKYSFLQNPQTSLC
ESESIPTPSNREETQQKSNLELLRISLLLIQSWLERVQFLRSVFANSLVYGASDS
NVYDLLKDLEEGIQTLMGRLEDGSPTINTIFKQTYSKFDTNSHNDDALLKNYGL
LYCFRKDMDKVETFLRIVQCRSVEGSCGF          (SEQ ID NO: 83)

MFPTIPLSRLFDNAMLRAHRLHQLAFDTYQEFEEAYIPKEQKASFLQNPQTSLC
FSESIPTPSNREETQQKSNLELLRISLLLIQSWLEPVQFLRSVFANSLVYGASDS
NVYDLLKDLEEGIQTLMGRLEDGSPTINTIFKQTYSKFDTNSHNDDALLKNYGL
LYCFRKDMDKVETFLRIVQCRSVEGSCGF          (SEQ ID NO: 84)

MFPTIPLSRLFDNAMLRAHRLHQLAFDTYQEFEEAYIPKEQKASFLQNPQTSLC
FSESIPTPSNREETQQKSNLELLRISLLLIQSWLEPVQFLRSVFANSLVYGASDS
NVYDLLKDLEEGIQTLMGRLEDGSPTINTIFKQTASKFDTNSHNDDALLKNYGL
LYCFRKDMDKVETFLRIVQCRSVEGSCGF          (SEQ ID NO: 85)

MFPTIPLSRLFDNAMLRAHRLHQLAFDTYQEFEEAYIPKEQKASFLQNPQTSLC
FSESIPTPSNREETQQKSNLELLRISLLLIQSWLEPVQFLRSVFANSLVYGASDS
NVYDLLKDLEEGIQTLMGRLEDGSPTINTIANQTASKFDTNSHNDDALLKNYG
LLYCFRKDMDKVETFLRIVQCRSVEGSCGF          (SEQ ID NO: 86)

MFPTIPLSRLFDNAMLRAHRLHQLAFDTYQEFEEAYIPKEQKASFLQNPQTSLC
FSESIPTPSNREETQQKSNLELLRISLLLIQSWLEPVQFLRSVFANSLVYGASDS
NVYDLLKDLEEGIQTLMGRLEDGSPRTGQIPTQAYSKFDTNSHNDDALLKNYG
LLYCFRKDMDKVETFLRIVQCRSVEGSCGF          (SEQ ID NO: 87)

FIG. 6H

Glycosylation/GlycoPEGylation mutants that are chemically PEGylated to reduce proteolysis. Larger, encircled bold font indicates the potential sites of chemical PEGylation. The underlined sequences are the regions of the hGH that are most susceptible to proteases.

P218

(M)FPTIPLSRLFDNAMLRAHRLHQLAFDTYQEFEEAYIP(K)E(Q)(K)YSFLQNPQTSLCFSESIPTP SNREETQQ(K)SNLELLRISLLLIQSWLEPVQFLRSVFANSLVYGASDSNVYDL(K)DLEEGIQTL MGRLEDGSPTTVSIF(K)QTY(S)(K)FDTNSHNDDAL(K)NYGLLYCFR(K)DMD(K)VETFLRIVQC RSVEGSCGF (SEQ ID NO: 88)

(M)FPTIPLSRLFDNAMLRAHRLHQLAFDTYQEFEEAYIP(K)E(Q)(K)YSFLQNPQTSLCFSESIPTP SNREETQQ(K)SNLELLRISLLLIQSWLEPVQFLRSVFANSLVYGASDSNVYDL(K)DLEEGIQTL MGRLEDGSPTINTIF(K)QTY(S)(K)FDTNSHNDDAL(K)NYGLLYCFR(K)DMD(K)VETFLRIVQC RSVEGSCGF (SEQ ID NO: 89)

FIG. 6J

Human Growth Hormone Glycosylation Mutants (as deduced from the specification and sequences above) with proteolysis mutation sites (designated in larger, italicized font) (X to A). One or more of these mutations can be added to the glycosylation/glycoPEGylation mutants.

MFPTIPLSRL*FD*NAMLRAHRLHQ*LA*F*DT*YQE*F*EEAYIPKEQK*YSFL*QNPQTSLCFSESIPT PSNREETQQKSNLELLRISLLLIQSWLEPVQFLRSVFANSLV*Y*GASDSNVYDLLKDLEEGIQTL MGRLEDGSPRTGQI*FK*QT*Y*SK*F*DTN*SH*NDDALLKNYGLLYCFRKDMDKVETFLRIVQCR SVEGSCGF (SEQ ID NO: 95)

Nb2-11 Cell Proliferation Assay

| ID Number | AA sequence | Cell Proliferation Assay (Nb2-11) | |
|---|---|---|---|
| | | % activity vs Control | % Specific Activity maximal response vs Control |
| AA | LEDGSP$^{134}$RTGQIFKQTYS | 100 % | 100 % |
| AB | LEDGSP$^{134}$RTGQIFNQSYS | NT | NT |
| AC | LEDGSP$^{134}$TQGAMFKQTYS | 48% | ND |
| AD | LEDGSP$^{134}$TTTQIFKQTYS | 33% | ND |
| AE | M$^1$FPTEIPLSRL | 170 % | 91 % |
| AF | M$^1$FPTVLPLSRL | 209 % | 96 % |
| AG | LEDGSP$^{134}$RTGQIPTQAYS | 57 % | 95 % |
| AH | LEDGSP$^{134}$TTVSIFKQTYS | 80 % | 79 % |
| AI | LEDGSP$^{134}$TQGAMFKQTYS | 64 % | 98 % |
| AJ | LEDGSP$^{134}$TINTIFKQTYS | 74 % | 90 % |
| AK | Y43A; LEDGSP$^{134}$TINTIFKQTYS | 46 % | ND |
| AL | Y43A; Y144A; LEDGSP$^{134}$TINTIFKQTYS | 24 % | ND |
| AM | Y43A; Y144A; FK140,141AN LEDGSP$^{134}$TINTIFKQTYS | 38 % | ND |
| AN | Y43A; LEDGSP$^{134}$RTGQIPTQAYS | 51 % | ND |

AA is Norditropin

FIGURE 12

Cell Proliferation Assay - Nb2-11

| Test Articles | Source | AA sequence | GlycoPEGylated Product | Nb2-11 Relative Activity |
|---|---|---|---|---|
| AA | Norditropin | natural | none | 100% |
| AS | Neose | P[134]TINTIF | GalNAc-Gal-SA-Cys-PEG-40 kDa | 17% |
| AQ | Neose | P[134]RTGQIPTQAYS | GalNAc-Gal-SA-Cys-PEG-40 kDa | 9% |
| AT | Neose | P[134]TQGAMF | GalNAc-Gal-SA-Cys-PEG-40 kDa | 3% |
| AP | Neose | Y43A; P[134]TINTIF | GalNAc-Gal-SA-Cys-PEG-40 kDa | 3% |
| AU | Neose | Y43A; Y144A; P[134]TINTIF | GalNAc-Gal-SA-Cys-PEG-40 kDa | 4% |
| AO | Neose | Y43A; Y144A; FK140,141AN; P[134]TINTIAN | GalNAc-Gal-SA-Cys-PEG-40 kDa | 6% |
| AR | Neose | Y43A; P[134]RTGQIPTQAYS | GalNAc-Gal-SA-Cys-PEG-40 kDa | 6% |

FIGURE 25

Cell Proliferation Data (Nb2-11)

| Test Articles | AA sequence | GlycoPEGylated Product | Nb2-11 Relative Activity | Nb2-11 Maximal Response |
|---|---|---|---|---|
| AA | natural | none | 100% | 100% |
| BA | p¹³⁴TTVS ~5-PEGs (2 kDa) | GalNAc-Gal-SA-PEG-30 kDa | 0.1% | 89% |
| AS | p¹³⁴TINT | GalNAc-Gal-SA-Cys-PEG-40 kDa | 17% | 90% |
| BB | p¹³⁴TINT ~4-PEGs (2 kDa) | GalNAc-Gal-SA-Cys-PEG-40 kDa | 0.2% | 91% |
| AY | p¹³⁴TINT ~5-PEGs (2 kDa) | GalNAc-Gal-SA-Cys-PEG-40 kDa | 0.1% | 81% |
| BC | p¹³⁴TINT ~7-PEGs (2 kDa) | GalNAc-Gal-SA-Cys-PEG-40 kDa | 0.03% | 89% |
| AZ | p¹³⁴TINT Y43A; Y144A; FK140,141AN | GalNAc-Gal-SA-Glycerol-PEG-40 kDa | 3% | 74% |
| AO | p¹³⁴TINT Y43A; Y144A; FK140,141AN | GalNAc-Gal-SA-Cys-PEG-40 kDa | 3% | 83% |

Fig. 26

GH-N (pituitary)

fpti plsrlfdnam lrahrlhqla fdtyqefeea yipkeqkysf lqnpqtslcf sesiptpsnr eetqqksnle llrislliq swlepvqflr svfanslvyg asdsnvydll kdleegiqtl mgrledgspr tgqifkqtys kfdtnshndd allknyglly cfrkdmdkve tflrivqcrs vegscgf

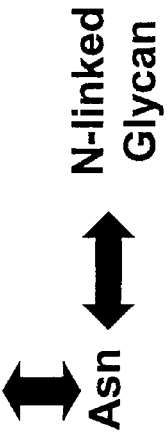

Asn — N-linked Glycan

GH-V (placenta)

fpti plsrlfdnam lrarrlyqla ydtyqefeea yilkeqkysf lqnpqtslcf sesiptpsnr vktqqksnle llrislliq swlepvqllr svfanslvyg asdsnvyrhl kdleegiqtl mwrledgspr tgqifnqsys kfdtkshndd allknyglly cfrkdmdkve tflrivqcrs vegscgf

N-linked Glycan

SDS-PAGE analysis of hGH mutant expression

← hGH mutant

Lane 1, Protein molecular weight marker;
Lane 2, P134TTGQIF;    Lane 3, P134TQGAMF;
Lane 4, P134TQGQIF;    Lane 5, P134TTAQIF;
Lane 6, P134TTVSIF;    Lane 7, L129ETETPRT;
Lane 8, P134TQGAIF;    Lane 9, I139PTQAYS;
Lane 10, P134TATQIF;

SDS-PAGE analysis of inclusion bodies for hGH mutants

Lane 1, Protein MW marker;
Lane 2, P134TINTIF;
Lane 3, P134TTVSIF;
Lane 4, I139PTQAYS;
Lane 5, P134TQGAMF;
Lane 6, M1FPTEIP;
Lane 7, M1FPTVLP;

← hGH mutants

SDS-PAGE analysis of pre- and post-refolding IBs for an hGH mutant

← P134TINTIF

1, MW marker;
2, Inclusion bodies (IBs);
3, Solubilized IBs in basic urea;
4, refolded IBs;
5, refolded IBs after filtration

COMPOSITIONS AND METHODS FOR THE PREPARATION OF PROTEASE RESISTANT HUMAN GROWTH HORMONE GLYCOSYLATION MUTANTS

CROSS-REFERENCE TO RELATED APPLICATIONS

The present application is a U.S. National Phase of PCT Application No. PCT/US06/13903 filed Apr. 10, 2006, which claims the benefit of U.S. Provisional Patent Application No. 60/669,736 filed Apr. 8, 2005, U.S. Provisional Patent Application No. 60/710,401 filed Aug. 22, 2005 and U.S. Provisional Patent Application No. 60/720,030 filed Sep. 23, 2005, which are incorporated herein by reference in their entirety for all purposes.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: One 127,188 Byte ASCII (Text) file named "705720-RevisedST25.TXT," created on Dec. 17, 2014.

BACKGROUND OF THE INVENTION

Human growth hormone (hGH) and agonist variants thereof are members of a family of recombinant proteins, described in U.S. Pat. Nos. 4,658,021 and 5,633,352. Their recombinant production and methods of use are detailed in U.S. Pat. Nos. 4,342,832, 4,601,980; 4,898,830; 5,424,199; and 5,795,745. Human growth hormone participates in various aspects of the regulation of normal human growth and development. Through interaction with its receptors, this 22 kDa pituitary hormone modulates a multitude of biological effects, such as linear growth (somatogenesis), lactation, activation of macrophages, and insulin-like and diabetogenic effects. Chawla, *Annu. Rev. Med.,* 34: 519 (1983); Edwards et al., *Science,* 239: 769 (1988); Isaksson et al., *Annu. Rev. Physiol.,* 47: 483 (1985); Thomer and Vance, *J. Clin. Invest.,* 82: 745 (1988); Hughes and Friesen, *Annu. Rev. Physiol.,* 47: 469 (1985).

The administration of glycosylated and non-glycosylated peptides for engendering a particular physiological response is well known in the medicinal arts. Both purified and recombinant hGH have been used for treating conditions and diseases due to hGH deficiency, e.g., dwarfism in children. A principal factor that has limited the use of therapeutic peptides is the immunogenic nature of most peptides. In a patient, an immunogenic response to an administered peptide can neutralize the peptide and/or lead to the development of an allergic response in the patient. Other deficiencies of therapeutic glycopeptides include suboptimal potency and rapid clearance rates. The problems inherent in peptide therapeutics are recognized in the art, and various methods of eliminating the problems have been investigated. For example, to provide soluble peptide therapeutics, synthetic polymers have been attached to the peptide backbone.

The attachment of synthetic polymers to the peptide backbone to improve the pharmacokinetic properties of glycoprotein therapeutics is known in the art. An exemplary polymer that has been conjugated to peptides is poly(ethylene glycol) ("PEG"). The use of PEG to derivatize peptide therapeutics has been demonstrated to reduce the immunogenicity of the peptides. For example, U.S. Pat. No. 4,179,337 (Davis et al.) discloses non-immunogenic polypeptides such as enzymes and peptide hormones coupled to polyethylene glycol (PEG) or polypropylene glycol. Between 10 and 100 moles of polymer are used per mole of polypeptide and at least 15% of the physiological activity is maintained. In addition to reduced immunogenicity, the clearance time in circulation is prolonged due to the increased size of the PEG-conjugate of the polypeptides in question.

The principal mode of attachment of PEG, and its derivatives, to peptides is a non-specific bonding through a peptide amino acid residue (see e.g., U.S. Pat. Nos. 4,088,538 4,496,689, 4,414,147, 4,055,635, and PCT WO 87/00056). Another mode of PEG-to-peptide attachment is through the non-specific oxidation of glycosyl residues on a glycopeptide (see e.g., WO 94/05332).

In many chemical PEGylation methods, poly(ethyleneglycol) is added in a random, non-specific manner to reactive residues on a peptide backbone. The random addition of PEG molecules has its inherent disadvantages, including, e.g. the lack of homogeneity in the final product and potential for reduction in the biological or enzymatic activity of the peptide. Therefore, a derivitization strategy that results in the formation of a specifically labeled, readily characterizable, essentially homogeneous product is far superior in the context of therapeutic peptide production. Such methods have been developed.

Specifically labeled, homogeneous peptide therapeutics can be produced in vitro through the action of enzymes. Unlike the typical non-specific methods for attaching a synthetic polymer or other label to a peptide, enzyme-based syntheses have the advantages of regioselectivity and stereoselectivity. Two principal classes of enzymes that can be employed in the synthesis of labeled peptides are glycosyltransferases (e.g., sialyltransferases, oligosaccharyltransferases, N-acetylglucosaminyltransferases) and glycosidases. These enzymes can be used for the specific attachment of sugars which can be subsequently modified to comprise a therapeutic moiety. Alternatively, glycosyltransferases and modified glycosidases can be used to directly transfer modified sugars to a peptide backbone (see e.g., U.S. Pat. No. 6,399,336, and U.S. Patent Application Publications 20030040037, 20040132640, 20040137557, 20040126838, and 20040142856). Methods combining both chemical and enzymatic synthetic elements are also known (see e.g., Yamamoto et al. *Carbohydr. Res.* 305: 415-422 (1998) and U.S. Patent Application Publication 20040137557).

In response to the need for improved therapeutic hGH, the present invention provides a glycopegylated hGH that is therapeutically active and which has pharmacokinetic parameters and properties that are improved relative to an identical, or closely analogous, hGH peptide that is not glycopegylated. Furthermore, the present invention provides cost-effective methods by which improved hGH peptides can be produced on an industrial scale.

Glycosyl residues have also been modified to bear ketone groups. For example, Mahal and co-workers (*Science* 276: 1125 (1997)) have prepared N-levulinoyl mannosamine ("ManLev"), which has a ketone functionality at the position normally occupied by the acetyl group in the natural substrate. Cells were treated with the ManLev, thereby incorporating a ketone group onto the cell surface. See, also Saxon et al., *Science* 287: 2007 (2000); Hang et al., *J. Am. Chem. Soc.* 123: 1242 (2001); Yarema et al., *J. Biol. Chem.* 273: 31168 (1998); and Charter et al., *Glycobiology* 10: 1049 (2000).

Carbohydrates are attached to glycopeptides in several ways of which N-linked to asparagine and mucin-type O-linked to serine and threonine are the most relevant for recombinant glycoprotein therapeutics. A determining factor for initiation of glycosylation of a protein is the primary sequence context, although clearly other factors including protein region and conformation have their roles. N-linked glycosylation occurs at the consensus sequence NXS/T, where X can be any amino acid but proline.

As previously mentioned, rapid in vivo degradation and clearance rate are other well-known problems that interfere with the optimal desired physiological effects of administered polypeptides. Soon after injection, polypeptides such as human growth hormone are readily proteolyzed by numerous proteases in the blood and lymphatic system. These proteases cleave the human growth hormone in both the amino internal and carboxy terminal regions, thereby fragmenting the protein and reducing the growth effects of hGH. The proteolysis also facilitates clearance of the degraded protein, dramatically reducing the residence time in the body after injection. In light of the above, there is a need for polypeptides with protease resistance and method of producing such polypeptides.

The methods discussed above do not provide access to industrially relevant quantities of modified peptides that substantially retain the pharmacological activity of their unmodified analogues and possess protease resistance.

The present invention answers these needs by providing hGH mutants that contain newly introduced O-linked glycosylation sites, providing flexibility in glycosylation and/or glycoconjugation, e.g., glycoPEGylation of these recombinant hGH mutants. The O-glycosylation mutants optionally further include one or more proteolysis resistant mutation or sites for chemical PEGylation of region(s) most susceptible to proteases. Moreover, the invention provides an industrially practical method for the modification of N- or O-linked mutant hGH peptides with modifying groups such as water-soluble polymers, therapeutic moieties, biomolecules, and the like. Of particular interest are methods in which the modified mutant hGH has improved properties, which enhance its use as a therapeutic or diagnostic agent.

SUMMARY OF THE INVENTION

The present invention provides for hGH mutants with N-linked or O-linked glycosylation sites not found in wild-type hGH. Exemplary embodiments of the invention include N- or O-linked glycosylated hGH mutants having one or more characteristics selected from the following: glycoPEGylation, protease resistance, and chemically PEGylation. Through the controlled modification of hGH, the present invention yields novel hGH derivatives with pharmacokinetic properties that are improved relative to the corresponding native hGH.

In a first aspect, the present invention provides an isolated nucleic acid comprising a polynucleotide sequence encoding a mutant human growth hormone. The mutant human growth hormone comprises an N-linked or O-linked glycosylation site and/or proteolysis resistant mutation(s) that are not present in wild-type human growth hormone. In exemplary embodiments, the wild-type human growth hormones have the amino acid sequence of pituitary-derived GH-N (SEQ ID NO:1) or placenta-derived GH-V (SEQ ID NO:2). In some preferred embodiments, the mutant human growth hormone includes the amino acid sequence of SEQ ID NO:3, 4, 5, 6, 7, 8, 9, 80, 81, 82, 83, 84, 85, 86, 87, and 88.

In another aspect, the present invention provides an expression cassette or a cell that comprises a nucleic acid, e.g., an isolated nucleic acid, including a polynucleotide sequence encoding a mutant human growth hormone. The mutant human growth hormone includes an N-linked or O-linked glycosylation site and/or proteolysis inhibiting mutation(s) that are not present in the wild-type human growth hormone.

In still another aspect, the present invention provides a mutant glycoPEGylated human growth hormone that includes one or more N-linked or O-linked glycosylation site not present in the wild-type human growth hormone. In some embodiments, the wild-type human growth hormone has the amino acid sequence of SEQ ID NO:1 or SEQ ID NO:2. In some preferred embodiments, the mutant human growth hormone comprises the amino acid sequence of SEQ ID NO:3, 4, 5, 6, 7, 8, 9, 80, 81, 82, 83, 84, 85, 86, 87, and 88.

In still another aspect, the present invention provides a mutant human growth hormone that includes one or more N-linked or O-linked glycosylation site not present in the wild-type human growth hormone and one or more proteolysis resistant mutations(s) not present in the wild-type human growth hormone. In some embodiments, the wild-type human growth hormone has the amino acid sequence of SEQ ID NO:1 or SEQ ID NO:2. In some preferred embodiments, the mutant human growth hormone comprises the amino acid sequence of SEQ ID NO:3, 4, 5, 6, 7, 8, 9, 80, 81, 82, 83, 84, 85, 86, 87, and 88.

In still another aspect, the present invention provides a chemically PEGylated mutant human growth hormone that includes one or more N-linked or O-linked glycosylation site not present in the wild-type human growth hormone. In some embodiments, the wild-type human growth hormone has the amino acid sequence of SEQ ID NO:1 or SEQ ID NO:2. In some preferred embodiments, the mutant human growth hormone comprises the amino acid sequence of SEQ ID NO:3, 4, 5, 6, 7, 8, 9, 80, 81, 82, 83, 84, 85, 86, 87, and 88.

In another aspect, the present invention provides a glycoPEGylated mutant human growth hormone that includes one or more N-linked or O-linked glycosylation site not present in the wild-type human growth hormone and one or more proteolysis resistant mutations(s) not present in the wild-type human growth hormone. In some embodiments, the wild-type human growth hormone has the amino acid sequence of SEQ ID NO:1 or SEQ ID NO:2. In some preferred embodiments, the mutant human growth hormone comprises the amino acid sequence of SEQ ID NO:3, 4, 5, 6, 7, 8, 9, 80, 81, 82, 83, 84, 85, 86, 87, and 88.

In another aspect, the present invention provides a chemically PEGylated mutant human growth hormone that includes one or more N-linked or O-linked glycosylation site not present in the wild-type human growth hormone and one or more proteolysis resistant mutations(s) not present in the wild-type human growth hormone. In some embodiments, the wild-type human growth hormone has the amino acid sequence of SEQ ID NO:1 or SEQ ID NO:2. In some preferred embodiments, the mutant human growth hormone comprises the amino acid sequence of SEQ ID NO:3, 4, 5, 6, 7, 8, 9, 80, 81, 82, 83, 84, 85, 86, 87, and 88.

In another aspect, the present invention provides a glycoPEGylated and chemically PEGylated mutant human growth hormone that includes one or more N-linked or O-linked glycosylation site not present in the wild-type human growth hormone. In some embodiments, the wild-type human growth hormone has the amino acid sequence of SEQ ID NO:1 or SEQ ID NO:2. In some preferred embodiments, the mutant human growth hormone comprises the amino acid sequence of SEQ ID NO:3, 4, 5, 6, 7, 8, 9, 80, 81, 82, 83, 84, 85, 86, 87, and 88.

In another aspect, the present invention provides a glycoPEGylated and chemically PEGylated mutant human growth hormone that includes one or more N-linked or O-linked glycosylation site not present in the wild-type human growth hormone and one or more proteolysis resistant mutations(s) not present in the wild-type human growth hormone. In some embodiments, the wild-type human growth hormone has the amino acid sequence of SEQ ID NO:1 or SEQ ID NO:2. In some preferred embodiments, the mutant human growth hormone comprises the amino acid sequence of SEQ ID NO:3, 4, 5, 6, 7, 8, 9, 80, 81, 82, 83, 84, 85, 86, 87, and 88.

In another aspect, the present invention provides a method for making a mutant human growth hormone that includes an N-linked or O-linked glycosylation site and/or proteolysis inhibiting mutation(s) that are not present in the wild-type human growth hormone. This method includes the steps of recombinantly producing the mutant human growth hormone, and glycosylating the mutant human growth hormone at the new glycosylation site. In some embodiments, the wild-type human growth hormone has the amino acid sequence of SEQ ID NO:1 or SEQ ID NO:2. In some preferred embodiments, the mutant human growth hormone comprises the amino acid sequence of SEQ ID NO:3, 4, 5, 6, 7, 8, 9, 80, 81, 82, 83, 84, 85, 86, 87, and 88.

In still a further aspect, the present invention provides a pharmaceutical composition having a therapeutically effective amount of a mutant human growth hormone that includes an N-linked or O-linked glycosylation site and/or proteolysis inhibiting mutation(s) not present in the wild-type human growth hormone. In some embodiments, the wild-type human growth hormone has the amino acid sequence of SEQ ID NO:1 or SEQ ID NO:2. In some preferred embodiments, the mutant human growth hormone comprises the amino acid sequence of SEQ ID NO:3, 4, 5, 6, 7, 8, 9, 80, 81, 82, 83, 84, 85, 86, 87, and 88.

In another aspect, the present invention provides a method for treating human growth hormone deficiency in a subject. The method includes administering to the subject an amount of a mutant human growth hormone effective to treat or ameliorate the growth hormone deficiency. The mutant human growth hormone used in this method comprises an N-linked or O-linked glycosylation site and/or proteolysis inhibiting mutation(s) that do not exist in the corresponding wild-type human growth hormone. In some embodiments, the corresponding wild-type human growth hormone has the amino acid sequence of SEQ ID NO:1 or SEQ ID NO:2. In some preferred embodiments, the mutant human growth hormone comprises the amino acid sequence of SEQ ID NO:3, 4, 5, 6, 7, 8, 9, 80, 81, 82, 83, 84, 85, 86, 87, and 88.

In each of the aspects described above, the mutant human growth hormone is optionally conjugated to one or more modifying groups, preferably via glycoconjugation, giving rise to a glycosyl linking group between the glycosylation site and the modifying group. An exemplary modifying group is poly(ethylene glycol), otherwise known as PEG.

In exemplary embodiments of the present invention, "glycopegylated" hGH molecules are produced by the enzyme-mediated formation of a conjugate between a glycosylated or non-glycosylated hGH peptide and an enzymatically transferable saccharyl moiety that includes one or more poly(ethylene glycol) moieties within its structure The PEG moiety is attached to the saccharyl moiety directly (i.e., through a single group formed by the reaction of two reactive groups) or through a linker moiety, e.g., substituted or unsubstituted alkyl, substituted or unsubstituted heteroalkyl, etc.

Other objects, aspects, and advantages of the present invention will be apparent from the detailed description that follows.

BRIEF DESCRIPTION OF THE DRAWINGS

FIG. 2 shows a pituitary derived hGH (GH-N) sequence into which six (6) different exemplary O-linked glycosylation sites have been introduced (SEQ ID NO:90). The wild-type amino acid sequence for GH-N (SEQ ID NO:1) is also shown for comparison. The arrows indicate the threonine residue of the GH-N glycan mutant on which O-linked glycosylation will occur.

FIG. 3 includes the alignment of amino acid sequences for hGH O-linked GH-N mutant 134(rtg)→ttt (SEQ ID NO:91) and hGH O-linked 5' GH-N mutant (SEQ ID NO:92) in which amino acids −3 to −1 (ptt) are inserted at the amino terminus, resulting in a 194 amino acid hGH polypeptide, with the native amino acid sequence of mature hGH-N1 (SEQ ID NO: 1).

FIG. 4 includes the amino acid sequences of hGH O-linked GH-N mutant 134(rtg)→ttg (SEQ ID NO:93) and hGH O-linked 5' GH-N mutant (SEQ ID NO:94) in which amino acids −3 to −1 (mvt) are inserted at the amino terminus, resulting in a 194 amino acid hGH polypeptide, with the native amino acid sequence of mature hGH-N1 (SEQ ID NO:1).

FIG. 5A depicts the amino acid sequence of mature pituitary-derived human growth hormone (GH-N) (SEQ ID NO:1). FIG. 5B depicts the amino acid sequence of mature placenta-derived human growth hormone (GH-V) (SEQ ID NO:2). FIG. 5C depicts the amino acid sequence of human growth hormone mutant 1 (SEQ ID NO:3). FIG. 5D depicts the amino acid sequence of human growth hormone mutant 2 (SEQ ID NO:4). FIG. 5E depicts the amino acid sequence of human growth hormone mutant 3 (SEQ ID NO:5). FIG. 5F depicts the amino acid sequence of human growth hormone mutant 4 (SEQ ID NO:6). FIG. 5G depicts the amino acid sequence of human growth hormone mutant 5 (SEQ ID NO:7). FIG. 5H depicts the amino acid sequence of human growth hormone mutant 6 (SEQ ID NO:8). FIG. 5I depicts the amino acid sequence of human growth hormone mutant 7 (SEQ ID NO:9).

FIG. 6A depicts the amino acid sequence of human growth hormone mutant 8 (SEQ ID NO:80). FIG. 6B depicts the amino acid sequence of human growth hormone mutant 9 (SEQ ID NO:81). FIG. 6C depicts the amino acid sequence of human growth hormone mutant 10 (SEQ ID NO:82). FIG. 6D depicts the amino acid sequence of human growth hormone mutant 11 (SEQ ID NO:83). FIG. 6E depicts the amino acid sequence of human growth hormone mutant 12 (SEQ ID NO:84). FIG. 6F depicts the amino acid sequence of human growth hormone mutant 13 (SEQ ID NO:85). FIG. 6G depicts the amino acid sequence of human growth hormone mutant 14 (SEQ ID NO:86). FIG. 6H depicts the amino acid sequence of human growth hormone mutant 15 (SEQ ID NO:87). FIG. 6I depicts the amino acid sequence of human growth hormone mutant 16 (SEQ ID NO:88). FIG. 6J depicts the amino acid sequence of human growth hormone mutant 17 (SEQ ID NO: 89). FIG. 6K depicts the amino acid sequence of mature human growth hormone (GH-N) with the various proteolysis inhibiting mutation sites in bold (SEQ ID NO:95).

FIG. 7 shows data for various hGH mutants with proteolysis inhibiting mutations from an Nb2-11 cell proliferation assay.

FIG. 12 shows the results of an Nb2-11 cell proliferation assay for seven hGH-PEG mutants relative to wild-type hGH.

FIG. 25 shows the results of an Nb2-11 cell proliferation assay for seven hGH-PEG mutants relative to wild-type hGH.

FIG. 26 is the amino acid sequences of GH-N (pituitary derived hGH) and GH-V (placental derived hGH). The arrows indicate the amino acid position for a mutational introduction of (GH-N) or a naturally existing (GH-V) N-linked glycosylation site.

DETAILED DESCRIPTION OF THE INVENTION

Abbreviations

Figure 1:
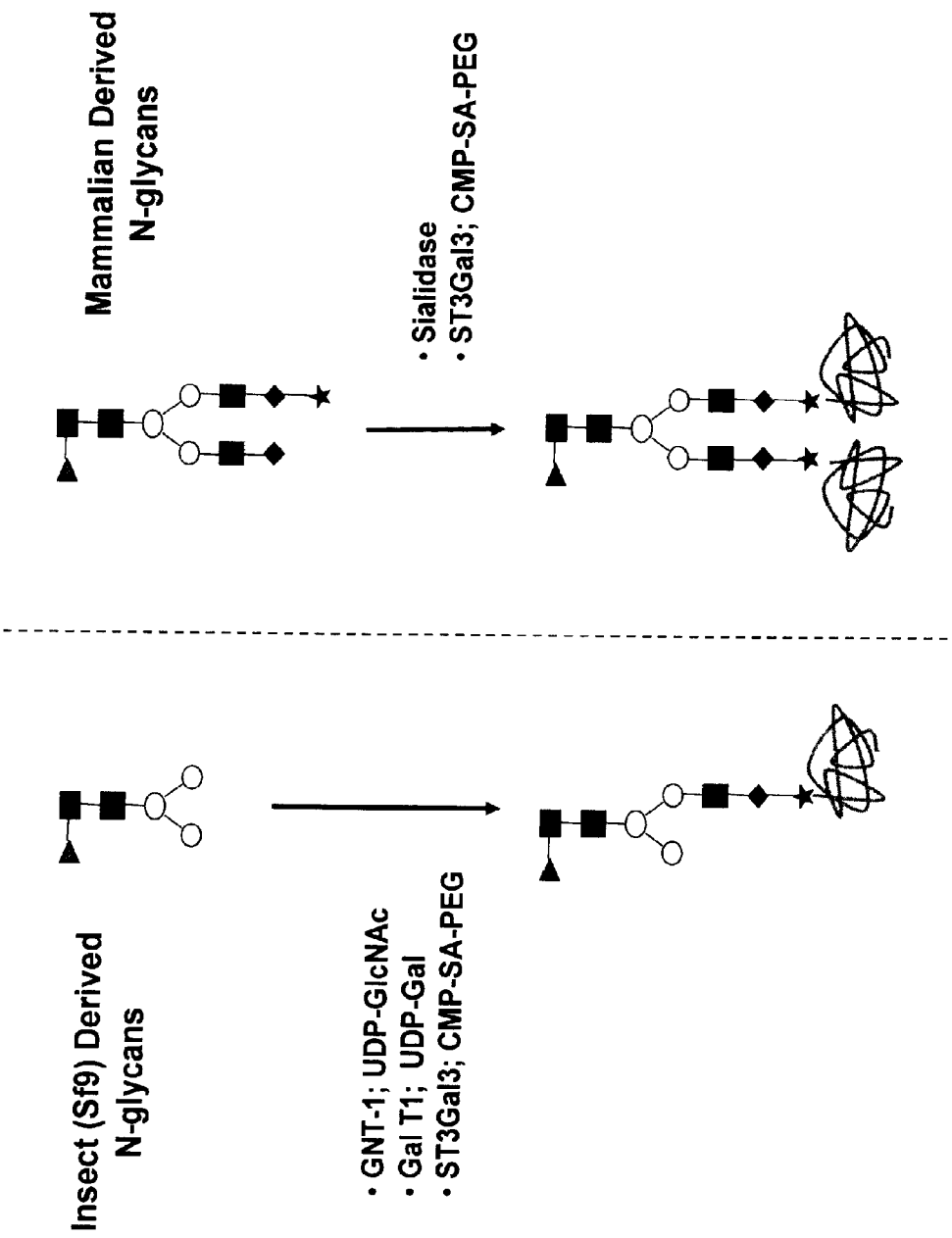
FIG. 1 are glycoPEGylation schemes for insect cell and mammalian cell produced hGH N-linked glycan mutants.
Figure 8:
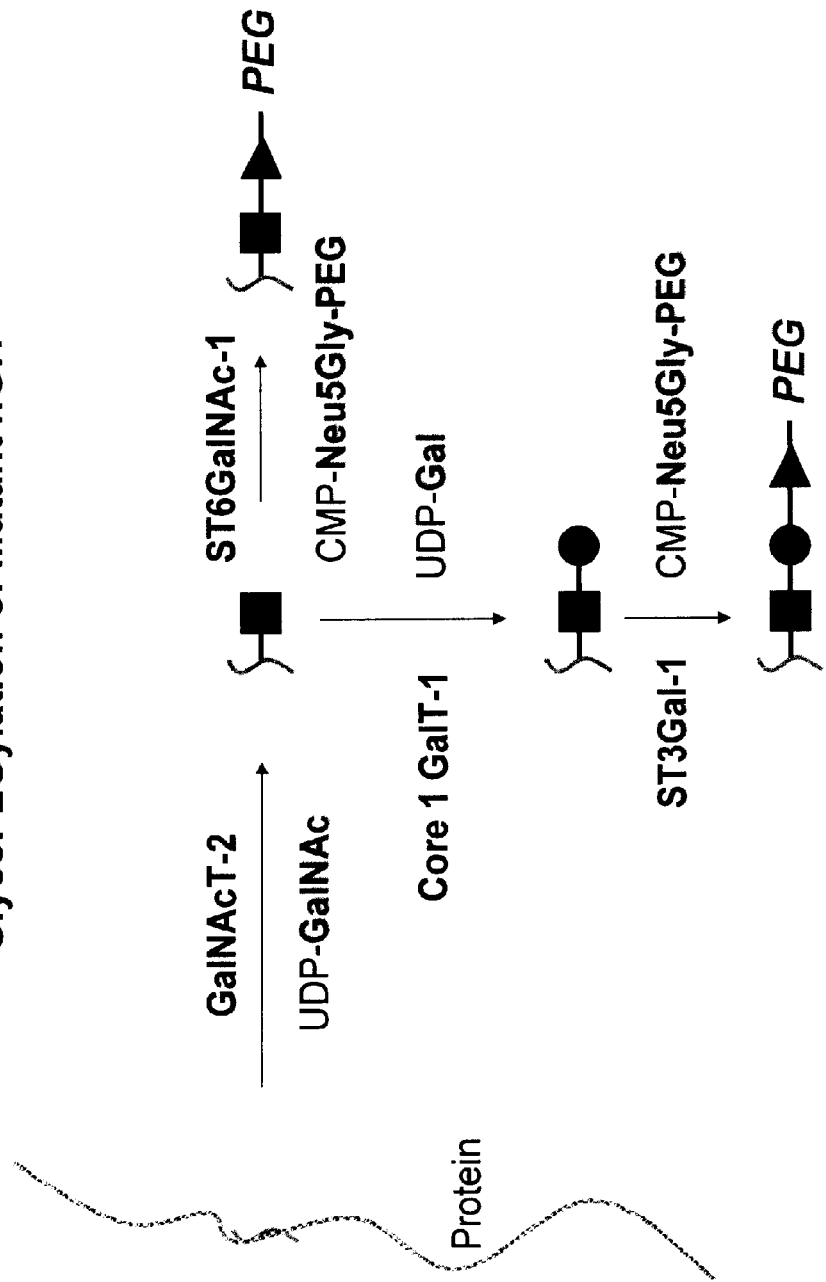
FIG. 8 depicts exemplary reactions through which glycoPEGylation of mutant hGH can be achieved.
Figure 9:
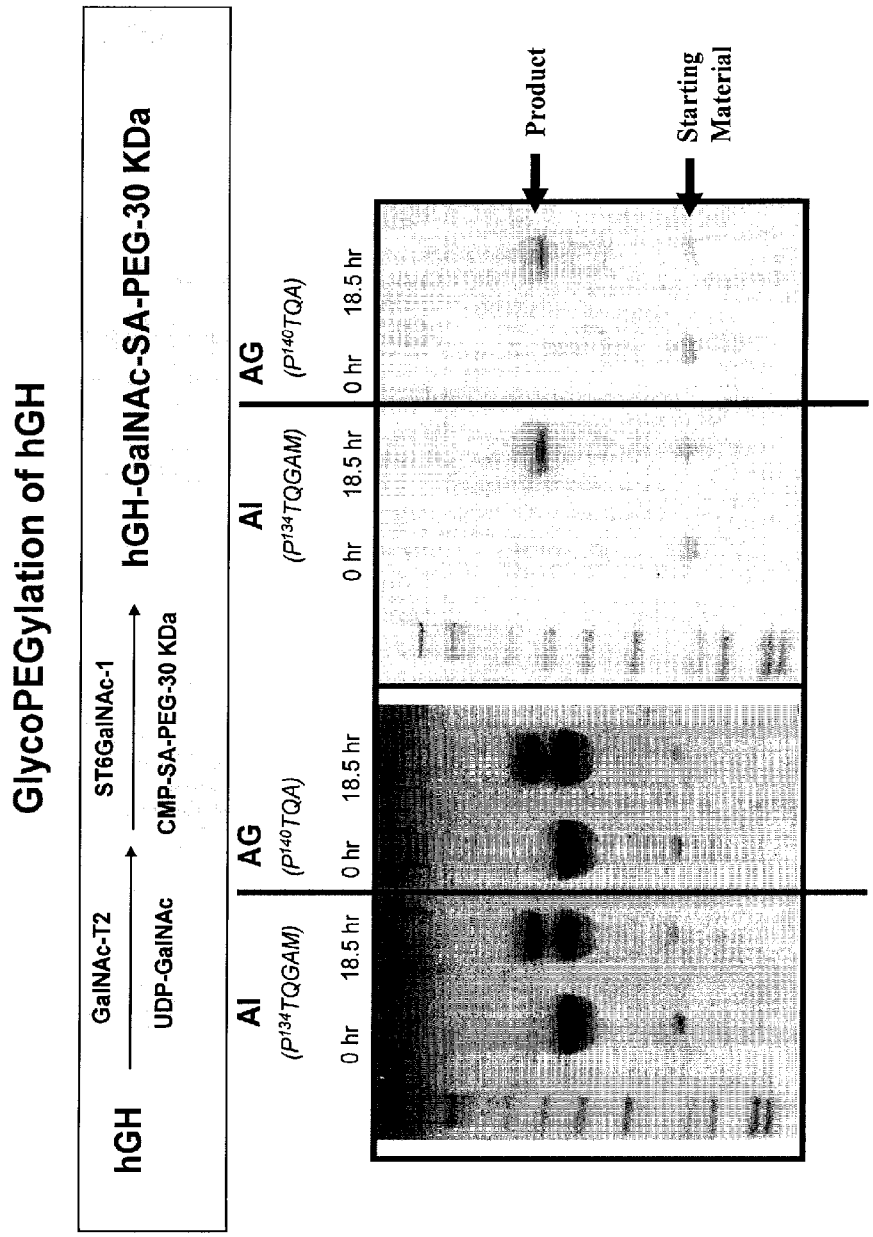
FIG. 9 shows the gel runs for the starting material and product in the glycoPEGylation of hGH mutants ID# AI and AG ($P^{134}$TQGAM and $P^{140}$TQA).
Figure 10:
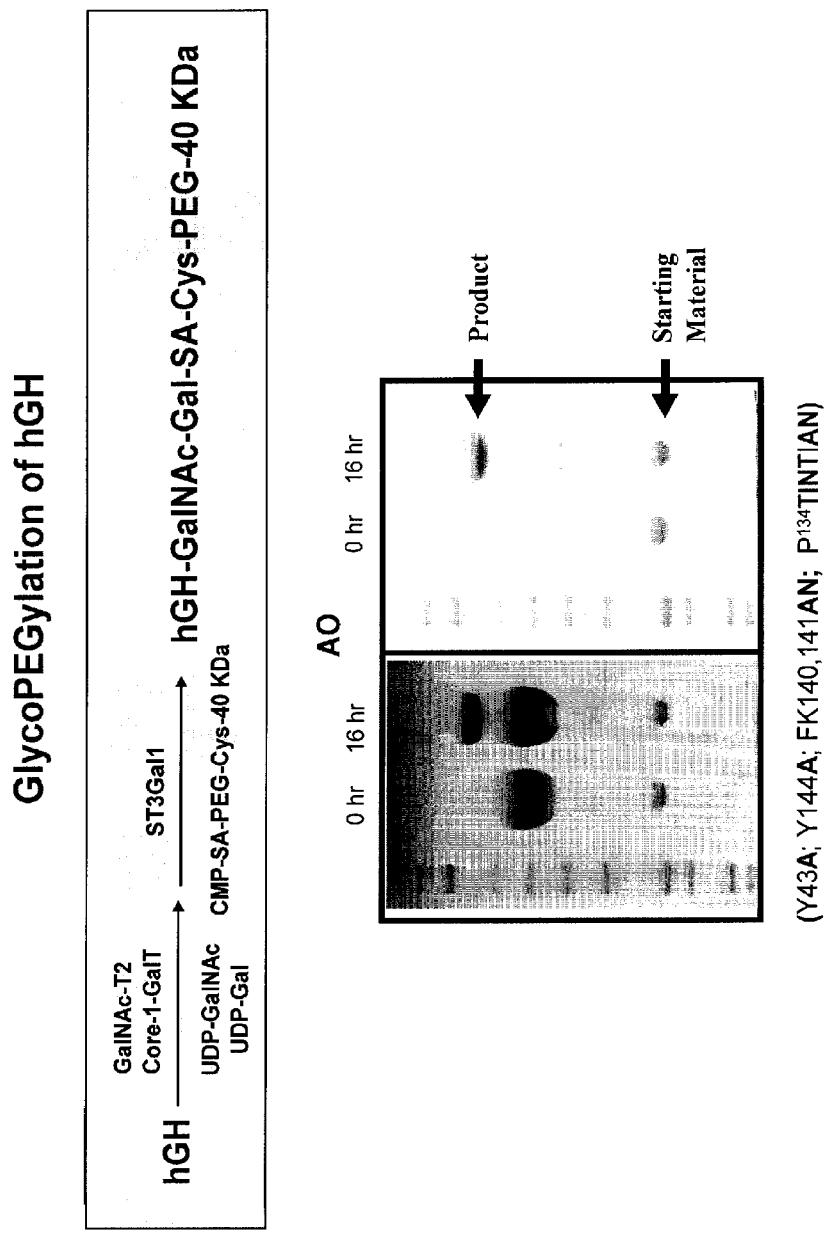
FIG. 10 shows the gel runs for the starting material and product in the glycoPEGylation of hGH mutant ID# AO ($P^{134}$TINTIAN).
Figure 11:
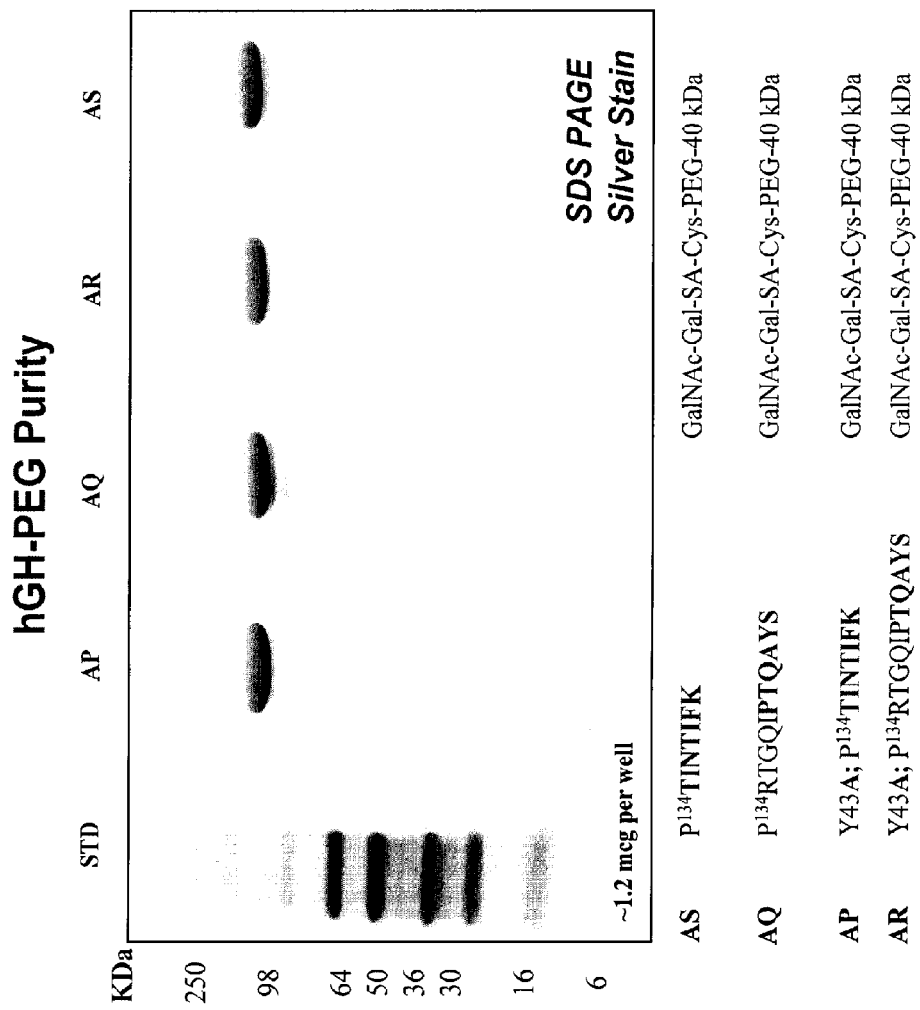
FIG. 11 shows the results of an SDS PAGE silver stain to demonstrate the purity of four exemplary hGH-PEG conjugates.
Figure 13:
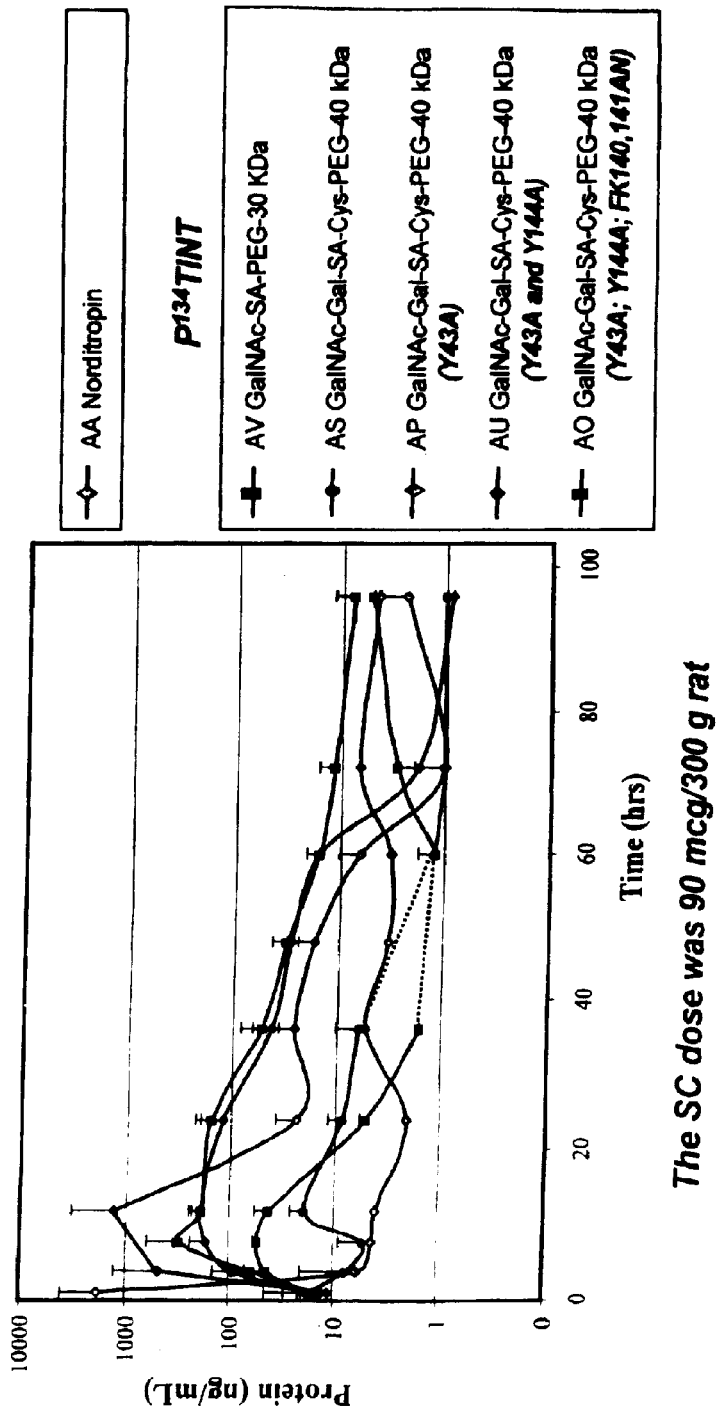
FIG. 13 shows the respective pharmacokinetic data in rats given subcutaneous administration of five hGH-PEG mutants ($P^{134}$TINT).
Figure 14:
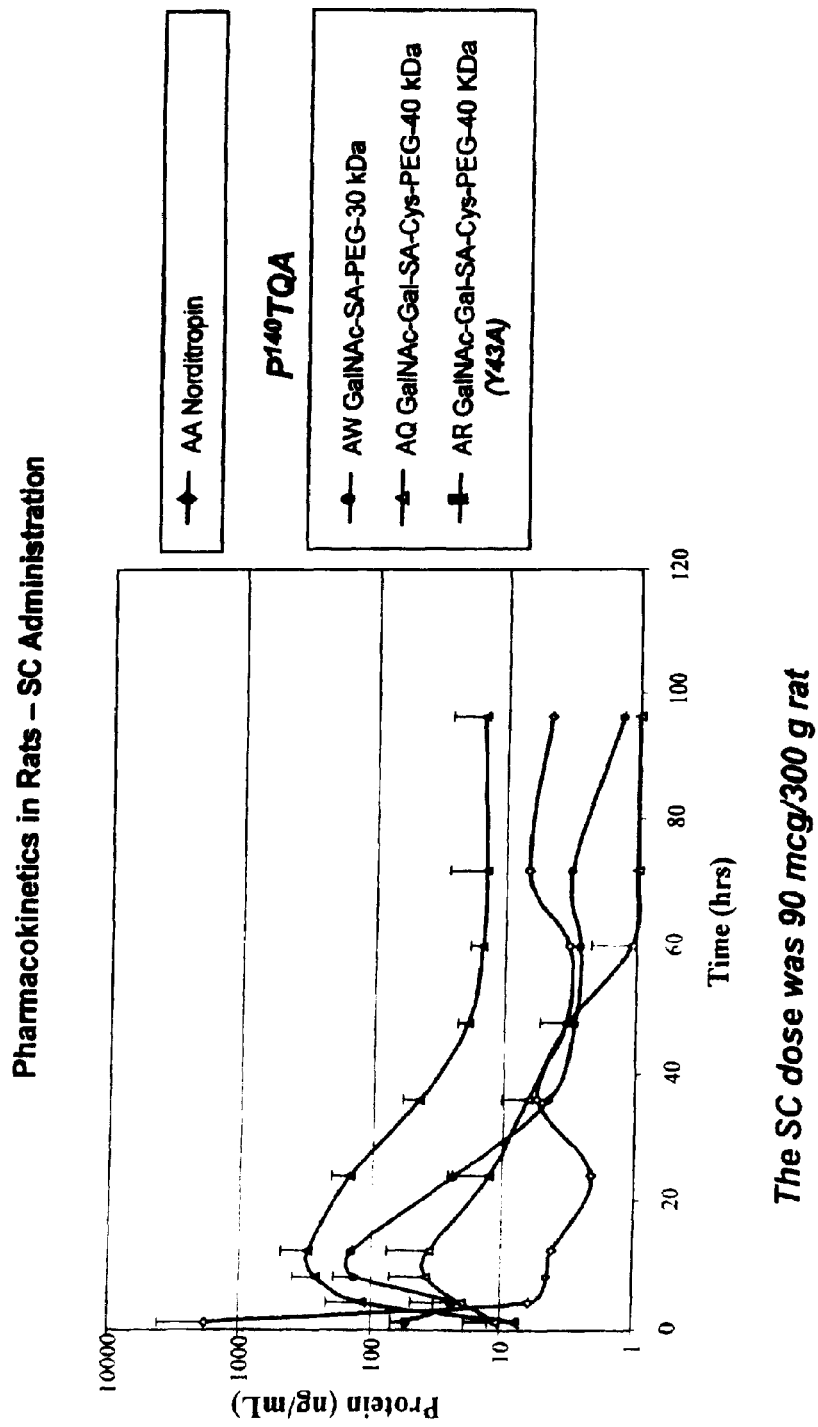
FIG. 14 shows the respective pharmacokinetic data in rats given subcutaneous administration of three hGH-PEG mutants ($P^{140}$TQA).
Figure 15:
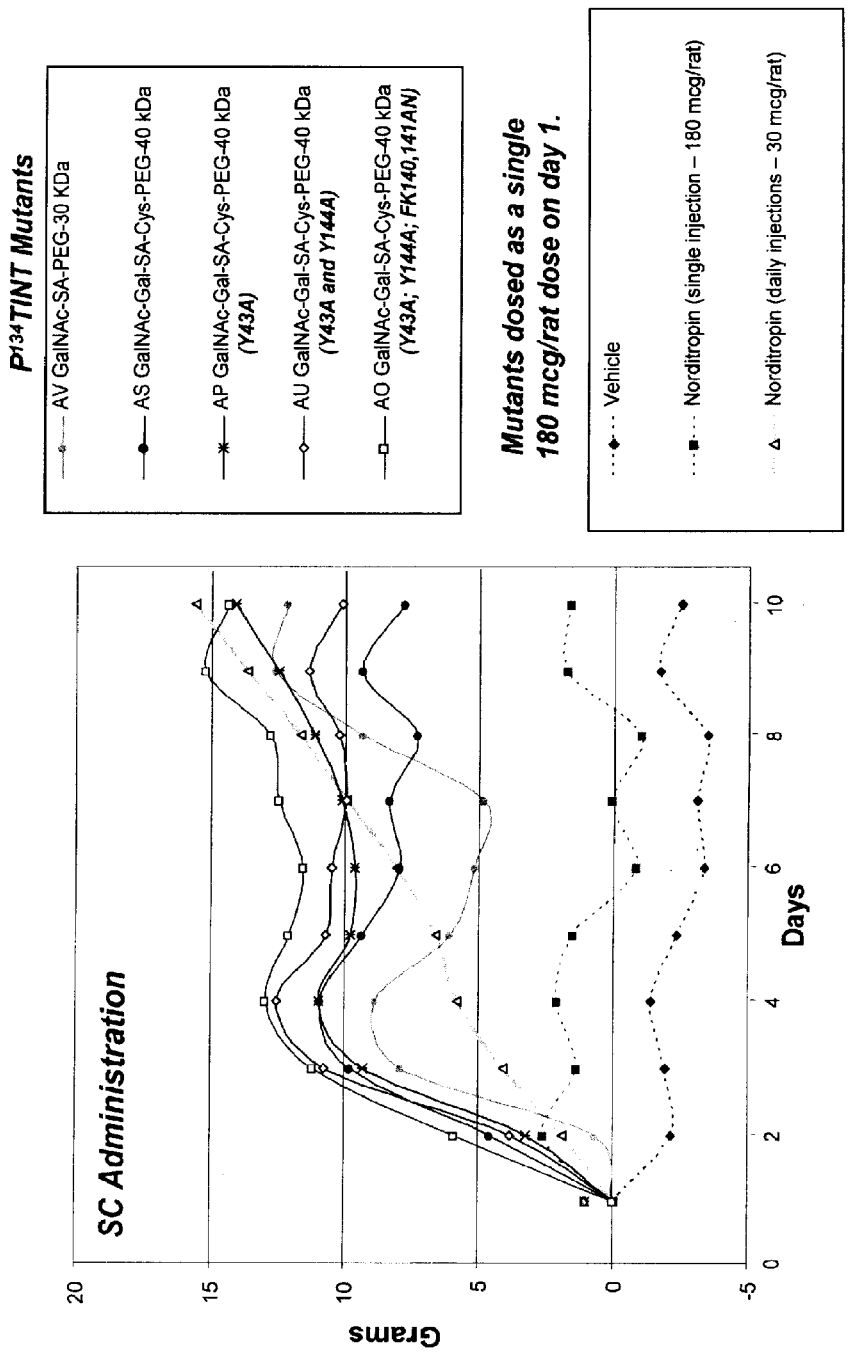
FIG. 15 shows the respective amount of weight gained by hypophysectomized rats given subcutaneous administration of five hGH-PEG mutants ($P^{134}$TINT).
Figure 16:
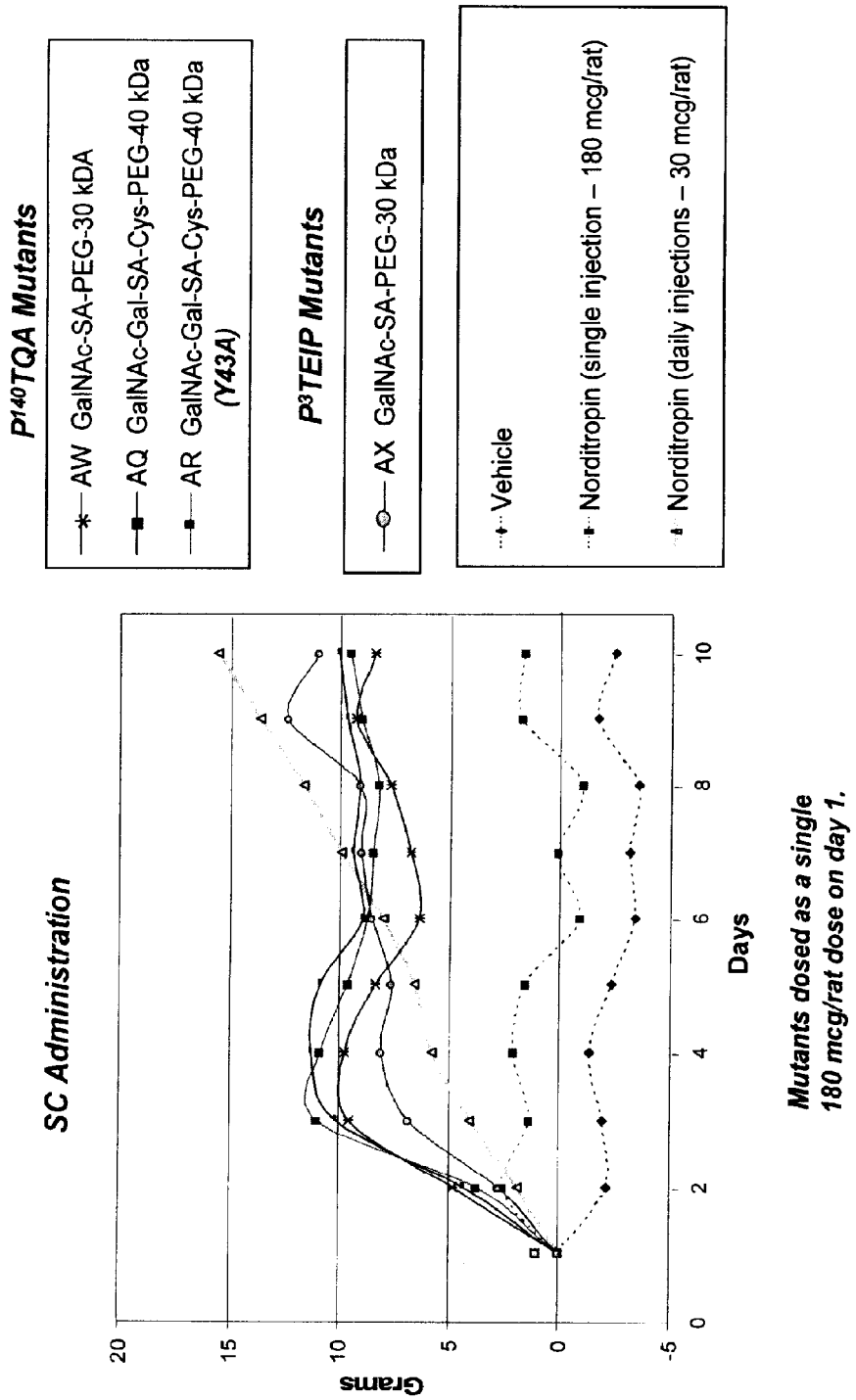
FIG. 16 shows the respective amount of weight gained by hypophysectomized rats given subcutaneous administration of three hGH-PEG mutants with the $P^{140}$TQA mutation motif and 1 hGH-PEG mutant with a $P^{3}$TEIP mutation motif.
Figure 17:
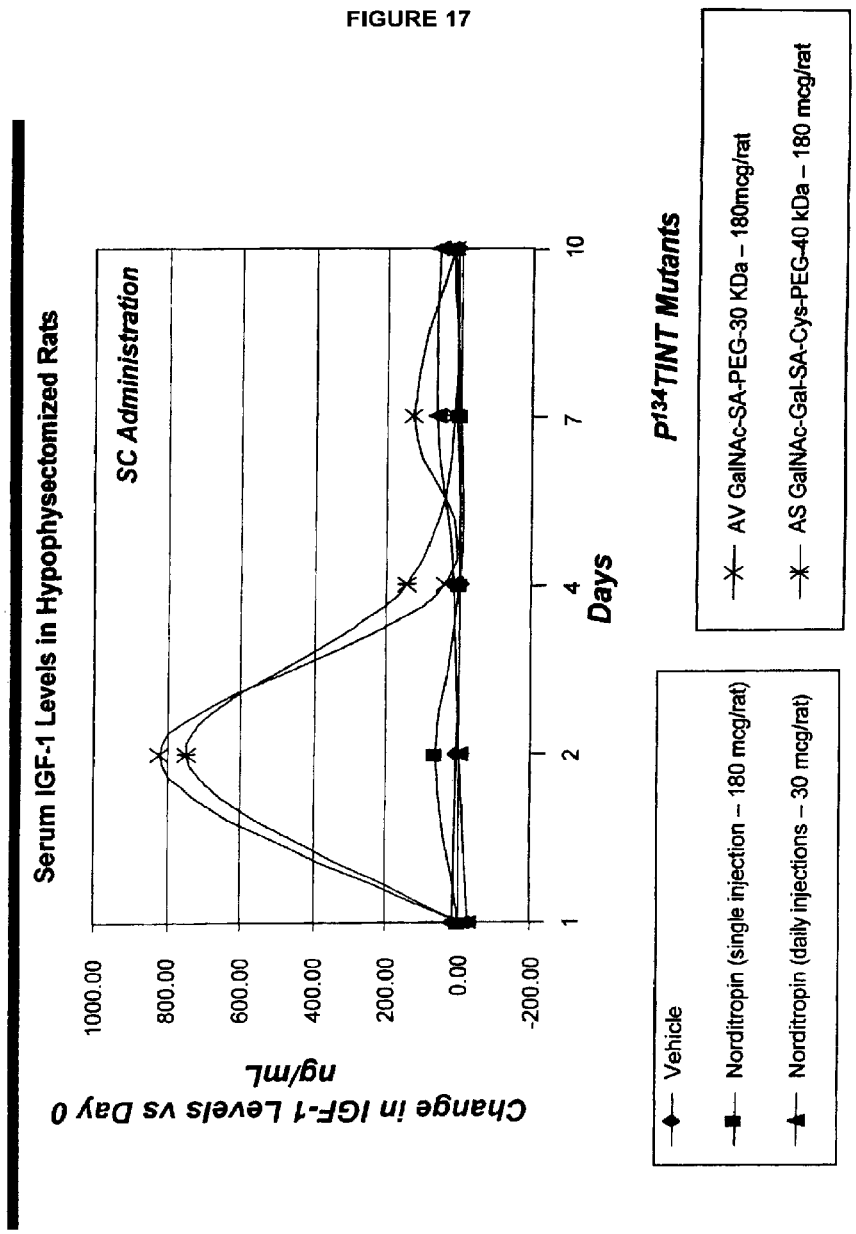
FIG. 17 shows the respective serum IGF-1 levels in hypophysectomized rats given subcutaneous administration of two hGH-PEG mutants ($P^{134}$TINT).
Figure 18:
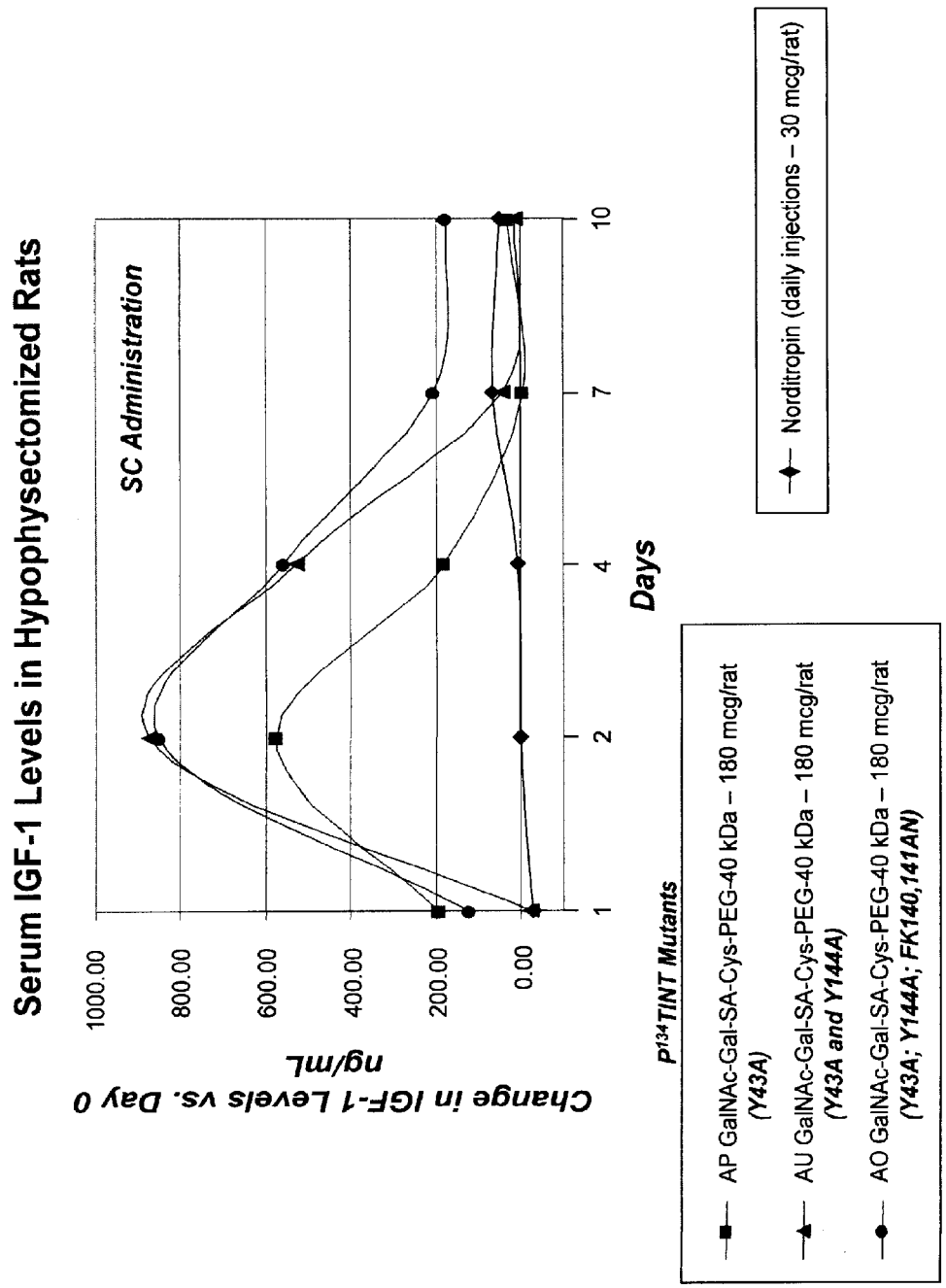
FIG. 18 shows the respective serum IGF-1 levels in hypophysectomized rats given subcutaneous administration of three hGH-PEG mutants ($P^{134}$TINT).
Figure 19:
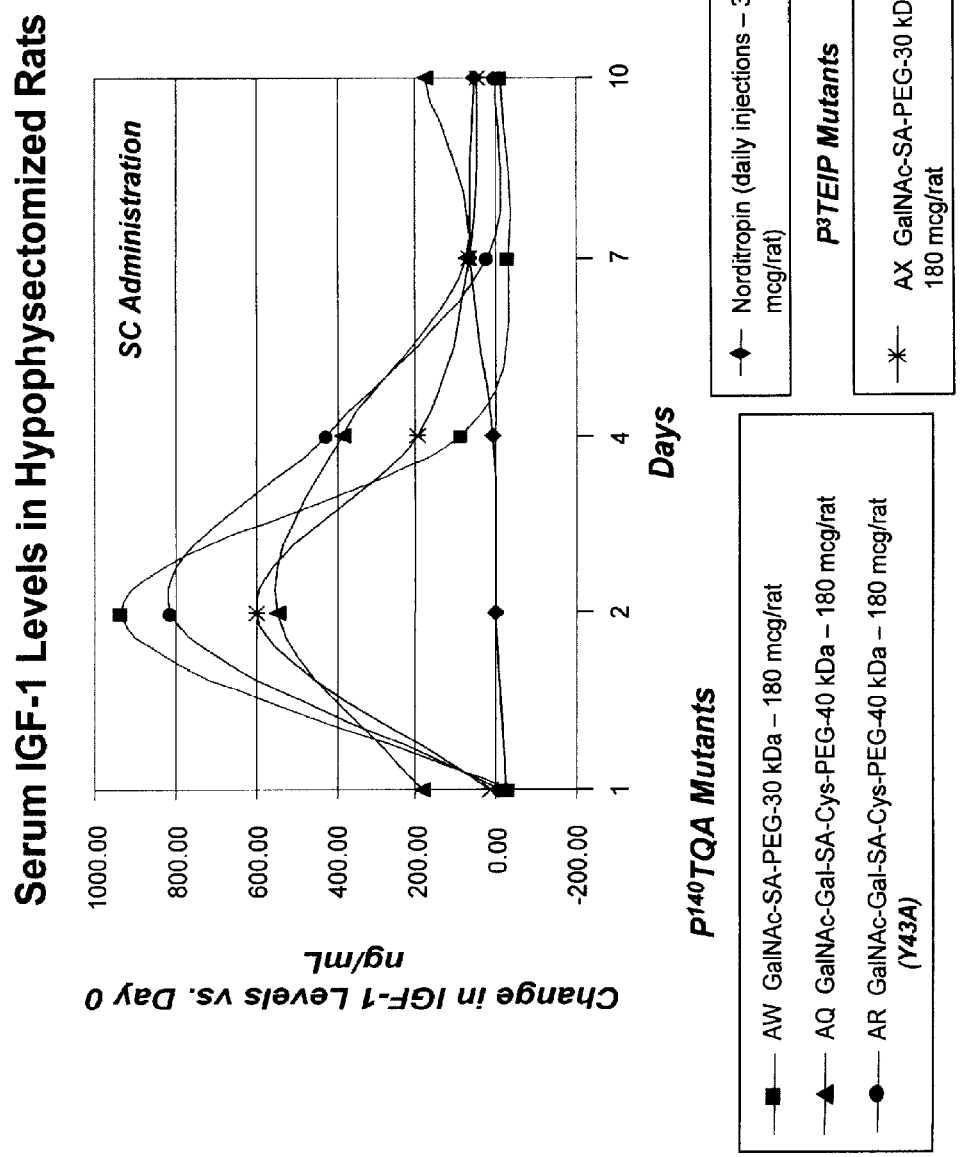
FIG. 19 shows the respective serum IGF-1 levels in hypophysectomized rats given subcutaneous administration of three hGH-PEG mutants with the $P^{140}$TQA mutation motif and 1 hGH-PEG mutant with a $P^{3}$TEIP mutation motif.
Figure 20:
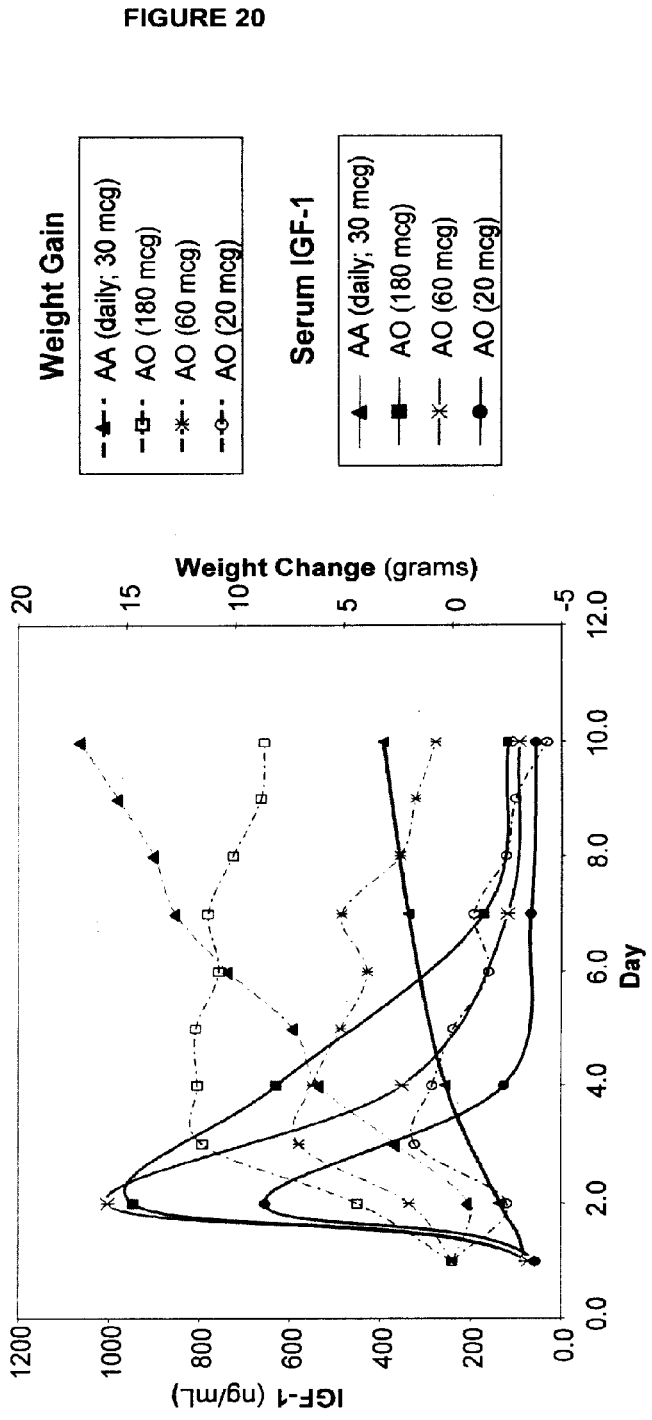
FIG. 20 shows the respective weight gain and respective serum IGF-1 levels over time in hypophysectomized rats that were administered a recombinant wild-type hGH and an exemplary hGH mutant at varying dosages.
Figure 21:
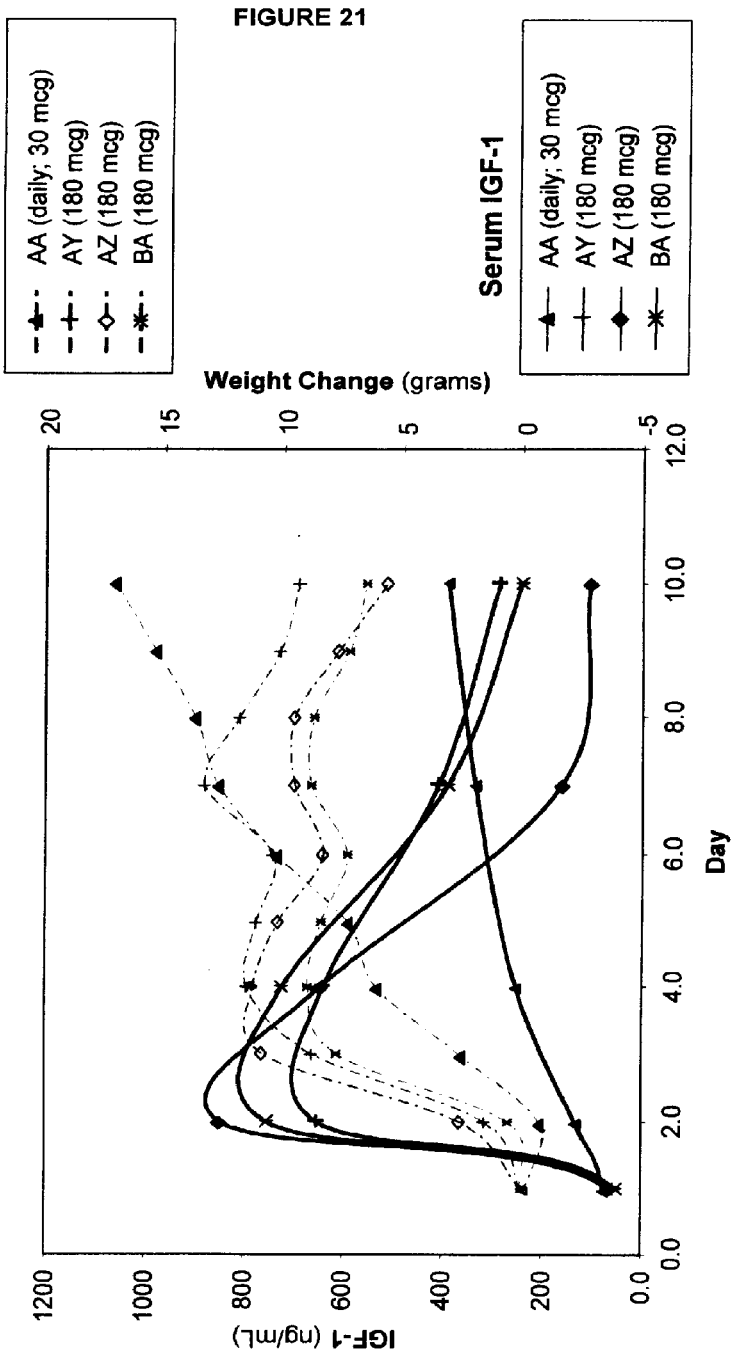
FIG. 21 shows the respective weight gain and respective serum IGF-1 levels over time in hypophysectomized rats that were administered a recombinant wild-type hGH and various exemplary hGH mutants.
Figure 22:
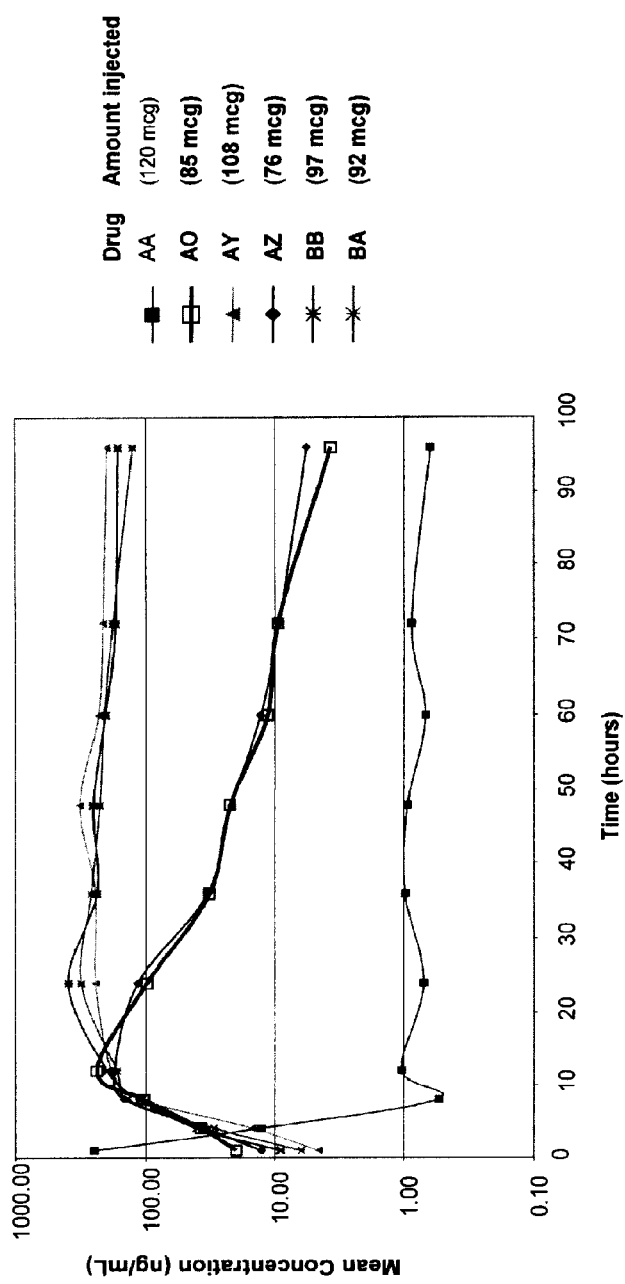
FIG. 22 shows the respective mean hGH concentration levels over time in rats that were administered single subcutaneous injections of a recombinant wild-type hGH and various exemplary hGH mutants.
Figure 23:
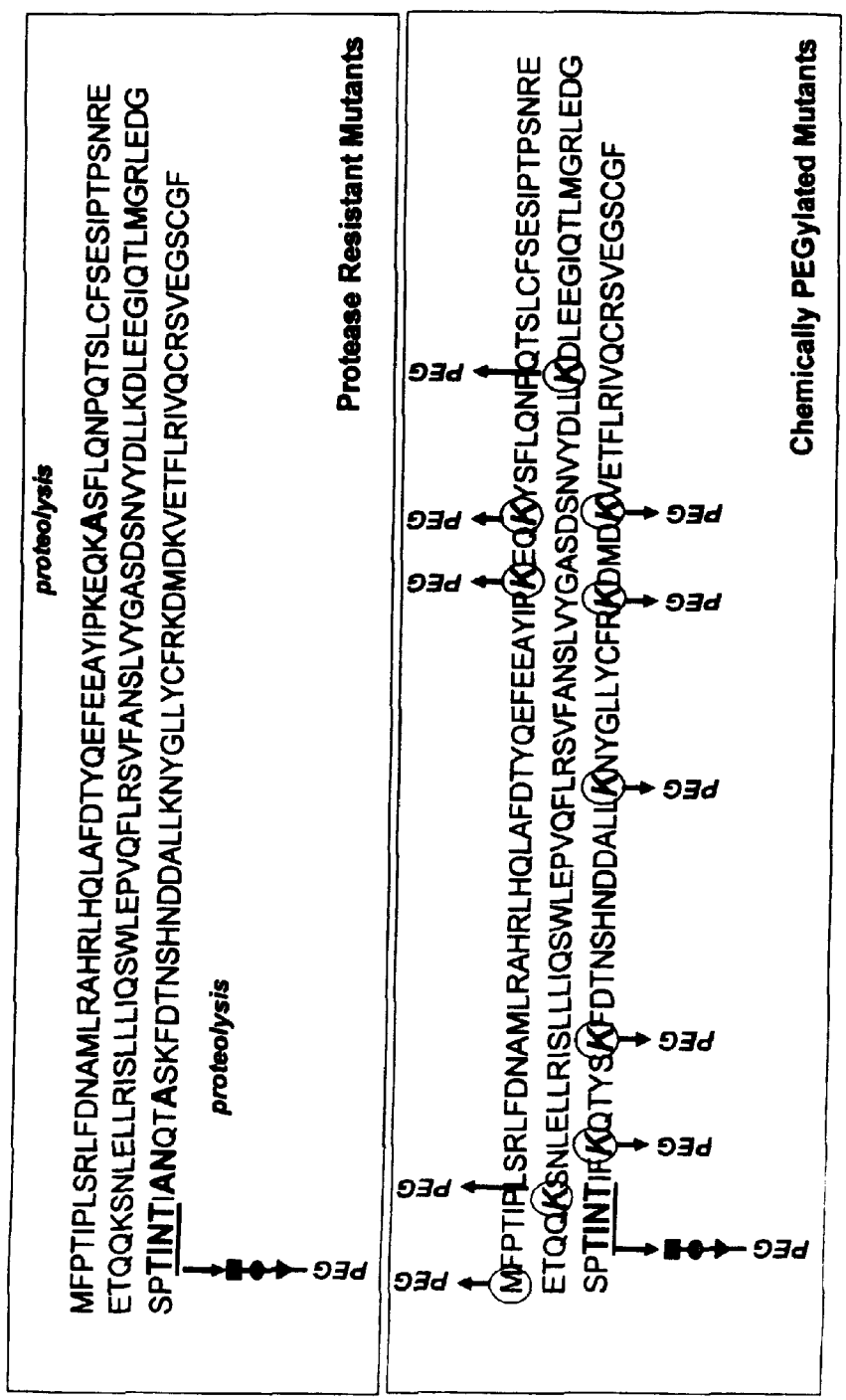
FIG. 23 shows an exemplary hGH mutant construct (SEQ ID NO: 86) with exemplary mutations indicated in bold underlined lettering and exemplary proteolysis mutations indicated in bold lettering in the upper panel. In the lower panel, mutations in an exemplary hGH mutant construct (SEQ ID NO:89) are indicated in bold underlined lettering and exemplary sites for chemical PEGylation are indicated in bold, encircled lettering.
Figure 24:
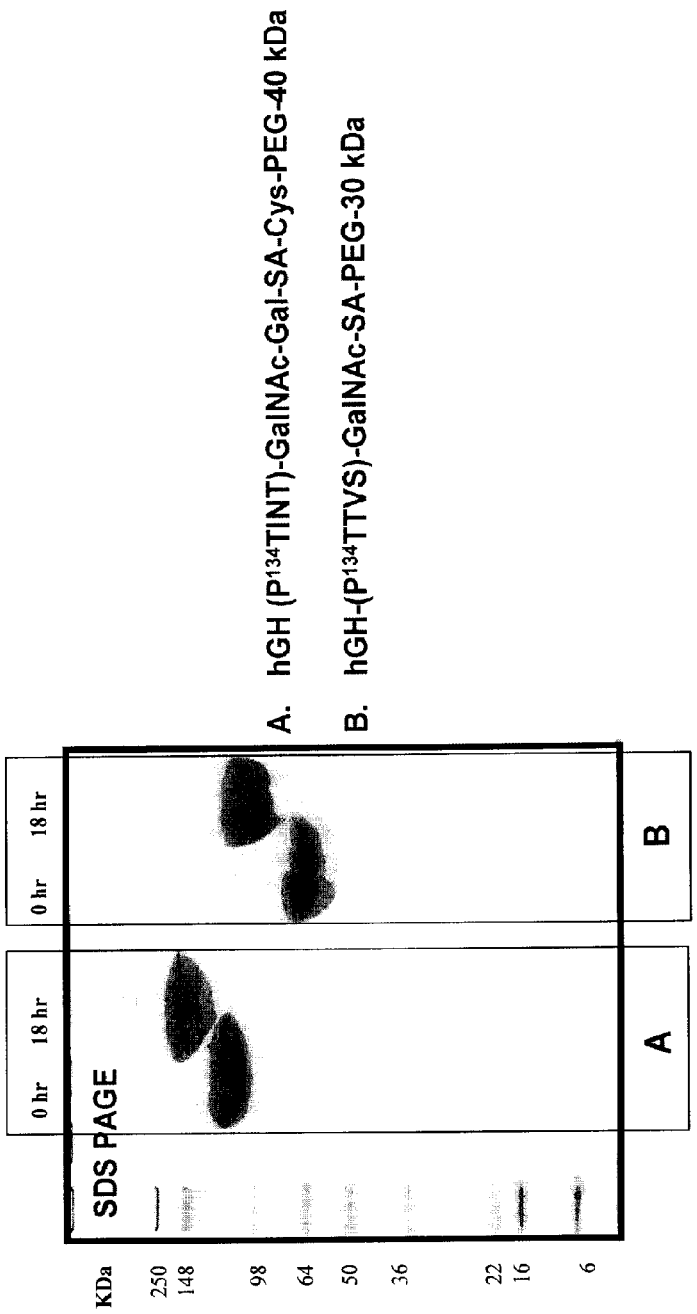
FIG. 24 are SDS-PAGE analysis results for two exemplary glycoPEGylated hGH, illustrating the extent to which two exemplary glycoPEGylated hGH mutants are chemically PEGylated over 18 hours.

PEG, poly(ethylene glycol), e.g. monomethoxy poly(ethyleneglycol) (m-PEG); PPG, poly(propyleneglycol); Ara, arabinosyl; Fru, fructosyl; Fuc, fucosyl; Gal, galactosyl; GalNAc, N-acetylgalactosaminyl; Glc, glucosyl; GlcNAc, N-acetylglucosaminyl; Man, mannosyl; ManAc, N-acetylmannosaminyl; Xyl, xylosyl; NeuAc, sialyl or N-acetylneuraminyl; Sia, sialyl or N-acetylneuraminyl, and derivatives and analogues thereof.

Definitions

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry and nucleic acid chemistry and hybridization are those well known and commonly employed in the art. Standard techniques are used for nucleic acid and peptide synthesis. The techniques and procedures are generally performed according to conventional methods in the art and various general references (see generally, Sambrook et al. MOLECULAR CLONING: A LABORATORY MANUAL, 2d ed. (1989) Cold Spring Harbor Laboratory Press, Cold Spring Harbor, N.Y., which is incorporated herein by reference), which are provided throughout this document. The nomenclature used herein and the laboratory procedures in analytical chemistry, and organic synthetic described below are those well known and commonly employed in the art. Standard techniques, or modifications thereof, are used for chemical syntheses and chemical analyses.

The term "nucleic acid" or "polynucleotide" refers to deoxyribonucleic acids (DNA) or ribonucleic acids (RNA) and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); and Rossolini et al., *Mol. Cell. Probes* 8:91-98 (1994)). The term nucleic acid is used interchangeably with gene, cDNA, and mRNA encoded by a gene.

The term "gene" means the segment of DNA involved in producing a polypeptide chain. It may include regions preceding and following the coding region (leader and trailer) as well as intervening sequences (introns) between individual coding segments (exons).

The term "isolated," when applied to a nucleic acid or protein, denotes that the nucleic acid or protein is essentially free of other cellular components with which it is associated in the natural state. It is preferably in a homogeneous state although it can be in either a dry or aqueous solution. Purity and homogeneity are typically determined using analytical chemistry techniques such as polyacrylamide gel electrophoresis or high performance liquid chromatography. A protein that is the predominant species present in a preparation is substantially purified. In particular, an isolated gene is separated from open reading frames that flank the gene and encode a protein other than the gene of interest. The term "purified" denotes that a nucleic acid or protein gives rise to essentially one band in an electrophoretic gel. Particularly, it means that the nucleic acid or protein is at least 85% pure, more preferably at least 95% pure, and most preferably at least 99% pure.

The term "proximate," when not used in reference to a proline residue, describes an amino acid having five or few amino acids removed from the C terminal end or N terminal end of the protease recognition site.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds having a structure that is different from the general chemical structure of an amino acid, but that functions in a manner similar to a naturally occurring amino acid. As used herein, "amino acid," whether it is in a linker or a component of a peptide sequence refers to both the D- and L-isomer of the amino acid as well as mixtures of these two isomers.

There are various known methods in the art that permit the incorporation of an unnatural amino acid derivative or analog into a polypeptide chain in a site-specific manner, see, e.g., WO 02/086075.

"Conservatively modified variants" applies to both amino acid and nucleic acid sequences. With respect to particular nucleic acid sequences, "conservatively modified variants" refers to those nucleic acids that encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein that encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another:
Alanine (A), Glycine (G);
Aspartic acid (D), Glutamic acid (E);
Asparagine (N), Glutamine (Q);
Arginine (R), Lysine (K);
Isoleucine (I), Leucine (L), Methionine (M), Valine (V);
Phenylalanine (F), Tyrosine (Y), Tryptophan (W);
Serine (S), Threonine (T); and
Cysteine (C), Methionine (M)
(see, e.g., Creighton, *Proteins* (1984)).

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

In the present application, amino acid residues are numbered according to their relative positions from the left most residue, which is numbered 1, in an unmodified wild-type polypeptide sequence.

"Proximate a proline residue," as used herein refers to an amino acid that is less than about 10 amino acids removed from a proline residue, preferably, less than about 9, 8, 7, 6 or 5 amino acids removed from a proline residue, more preferably, less than about 4, 3, 2 or 1 residues removed from a proline residue. The amino acid "proximate a proline residue" may be on the C- or N-terminal side of the proline residue.

The term "sialic acid" refers to any member of a family of nine-carbon carboxylated sugars. The most common member of the sialic acid family is N-acetyl-neuraminic acid (2-keto-5-acetamido-3,5-dideoxy-D-glycero-D-galactononulopyranos-1-onic acid (often abbreviated as Neu5Ac, NeuAc, or NANA). A second member of the family is N-glycolyl-neuraminic acid (Neu5Gc or NeuGc), in which the N-acetyl group of NeuAc is hydroxylated. A third sialic acid family member is 2-keto-3-deoxy-nonulosonic acid (KDN) (Nadano et al. (1986) *J. Biol. Chem.* 261: 11550-11557; Kanamori et al., *J. Biol. Chem.* 265: 21811-21819 (1990)). Also included are 9-substituted sialic acids such as a 9-O—$C_1$-$C_6$ acyl-Neu5Ac like 9-O-lactyl-Neu5Ac or 9-O-acetyl-Neu5Ac, 9-deoxy-9-fluoro-Neu5Ac and 9-azido-9-deoxy-Neu5Ac. For review of the sialic acid family, see, e.g., Varki, *Glycobiology* 2: 25-40 (1992); *Sialic Acids: Chemistry, Metabolism and Function*, R. Schauer, Ed. (Springer-Verlag, New York (1992)). The synthesis and use of sialic acid compounds in a sialylation procedure is disclosed in international application WO 92/16640, published Oct. 1, 1992.

"Peptide" refers to a polymer in which the monomers are amino acids and are joined together through amide bonds, alternatively referred to as a polypeptide or a protein. Additionally, unnatural amino acids, for example, β-alamine, phenylglycine and homoarginine are also included. Amino acids that are not gene-encoded may also be used in the present invention. Furthermore, amino acids that have been modified to include reactive groups, glycosylation sites, polymers, therapeutic moieties, biomolecules and the like may also be used in the invention. All of the amino acids used in the present invention may be either the d- or l-isomer. The l-isomer is generally preferred. In addition, other peptidomimetics are also useful in the present invention. As used herein, "peptide" refers to both glycosylated and unglycosylated peptides. Also included are peptides that are incompletely glycosylated by a system that expresses the peptide. For a general review, see, Spatola, A. F., in Chemistry and Biochemistry of Amino Acids, Peptides and Proteins, B. Weinstein, eds., Marcel Dekker, New York, p. 267 (1983). The numbering of the amino acid residues in the peptides of the invention is based on the initial unmodified sequence in which the left most residue, methionine, is numbered as position 1.

The term "peptide conjugate," refers to species of the invention in which a peptide is conjugated with a modified sugar as set forth herein.

hGH peptides of the invention comprise sequences with additional amino acids. These amino acids can be inserted into the middle of the sequence, as shown in U.S. patent application Ser. No. 10/585,385, entitled "O-linked Glycosylation of Peptides", filed Jan. 10, 2005. Additional amino acids, both natural and unnatural, can also be attached at the beginning or end of the amino acid sequence.

As used herein, the term "proteolysis resistant mutant" or "protease resistant mutant" refers to a hGH mutant that is proteolyzed more slowly than the corresponding wild-type hGH. In preferred embodiments, the protease resistant mutant of the invention is proteolyzed at a rate of 90% or less relative to the corresponding wild-type hGH. More preferably, the protease resistant mutant of the invention is proteolyzed at a rate of 70% or less relative to the corresponding wild-type hGH. Even more preferably, the protease resistant mutant of the invention is proteolyzed at a rate of 50% or less relative to the corresponding wild-type hGH.

The term "mutating" or "mutation," as used in the context of introducing additional N- or O-linked glycosylation site(s) into a wild-type human growth hormone, refers to the deletion, insertion, or substitution of any nucleotide or amino acid residue, by chemical, enzymatic, or any other means, in a polynucleotide sequence encoding a wild-type human growth hormone or the amino acid sequence of a wild-type human growth hormone, respectively, such that the amino acid sequence of the resulting human growth hormone comprises at least one N- or O-linked glycosylation site that does not exist in the corresponding wild-type human growth hormone. In the case of amino acid substitution, both conservative and non-conservative substitutions may be used to create a hGH mutant that contains a new N- or O-linked glycosylation site.

The site for a mutation introducing a new N- or O-linked glycosylation site may be located anywhere in the polypeptide. Exemplary amino acid sequences for human growth hormone mutants are depicted in SEQ ID NOs:3-9, and 80-89. A "mutant human growth hormone" of this invention thus comprises at least one mutated amino acid residue. On the other hand, the wild-type human growth hormone whose coding sequence is modified to generate a mutant human growth hormone is referred to in this application as "the corresponding wild-type human growth hormone." For example, SEQ ID NO:1 is the amino acid sequence of the corresponding wild-type human growth hormone for mutant human growth hormones having the amino acid sequences of SEQ ID NOs:3-9, and 80-89.

As used herein, the term "modified sugar," refers to a naturally- or non-naturally-occurring carbohydrate that is enzymatically added onto an amino acid or a glycosyl residue of a peptide in a process of the invention. The modified sugar is selected from a number of enzyme substrates including, but not limited to sugar nucleotides (mono-, di-, and tri-phosphates), activated sugars (e.g., glycosyl halides, glycosyl mesylates) and sugars that are neither activated nor nucleotides. In some embodiments, the "modified sugar" can be covalently functionalized with a "modifying group."

As used herein, the term "modifying group" refers to a component of the hGH conjugate that is covalently attached to a glycosyl linking group. A modifying group can be a component of the modified sugar that is subsequently attached to the hGH peptide. A modifying group can also be attached directly to a sugar moiety that is already attached to the hGH peptide. Useful modifying groups include, but are not limited to, water-soluble polymer moieties such as PEG, water-insoluble polymer moieties, therapeutic moieties, diagnostic moieties, biomolecules, and the like. The modifying group also includes reactive functional groups, such as levulinic acid. These reactive functional groups can serve as the locus of attachment for water-soluble polymers such as PEG moieties, therapeutic moieties, diagnostic moieties, biomolecules, and the like. These reactive functional groups can also comprise protecting groups which can be removed at appropriate times to facilitate proper functionalization. Reactive functional groups with protecting groups are alternatively known as masked reactive functional groups. The modifying group is preferably not a naturally occurring, or an unmodified carbohydrate. The locus of functionalization with the modifying group is selected such that it does not prevent the "modified sugar" from being added enzymatically to a peptide.

The term "water-soluble" refers to moieties that have some detectable degree of solubility in water. Methods to detect and/or quantify water solubility are well known in the art. Exemplary water-soluble polymers include peptides, saccharides, poly(ethers), poly(amines), poly(carboxylic acids) and the like. Peptides can have mixed sequences or be composed of a single amino acid, e.g., poly(lysine). An exemplary polysaccharide is poly(sialic acid). An exemplary poly(ether) is poly(ethylene glycol). Poly(ethylene imine) is an exemplary polyamine, and poly(acrylic) acid is a representative poly(carboxylic acid).

The polymer backbone of the water-soluble polymer can be poly(ethylene glycol) (i.e. PEG). However, it should be understood that other related polymers are also suitable for use in the practice of this invention and that the use of the term PEG or poly(ethylene glycol) is intended to be inclusive and not exclusive in this respect. The term PEG includes poly (ethylene glycol) in any of its forms, including alkoxy PEG, difunctional PEG, multiarmed PEG, forked PEG, branched PEG, pendent PEG (i.e. PEG or related polymers having one or more functional groups pendent to the polymer backbone), or PEG with degradable linkages therein.

The polymer backbone can be linear or branched. Branched polymer backbones are generally known in the art. Typically, a branched polymer has a central branch core moiety and a plurality of linear polymer chains linked to the central branch core. PEG is commonly used in branched forms that can be prepared by addition of ethylene oxide to various polyols, such as glycerol, pentaerythritol and sorbitol.

The central branch moiety can also be derived from several amino acids, such as lysine. The branched poly(ethylene glycol) can be represented in general form as R(-PEG-OH)$_m$ in which R represents the core moiety, such as glycerol or pentaerythritol, and m represents the number of arms. Multiarmed PEG molecules, such as those described in U.S. Pat. No. 5,932,462, which is incorporated by reference herein in its entirety, can also be used as the polymer backbone.

Many other polymers are also suitable for the invention. Polymer backbones that are non-peptidic and water-soluble, with from 2 to about 300 termini, are particularly useful in the invention. Examples of suitable polymers include, but are not limited to, other poly(alkylene glycols), such as poly(propylene glycol) ("PPG"), copolymers of ethylene glycol and propylene glycol and the like, poly(oxyethylated polyol), poly(olefinic alcohol), poly(vinylpyrrolidone), poly(hydroxypropylmethacrylamide), poly(α-hydroxy acid), poly(vinyl alcohol), polyphosphazene, polyoxazoline, poly(N-acryloylmorpholine), such as described in U.S. Pat. No. 5,629,384, which is incorporated by reference herein in its entirety, and copolymers, terpolymers, and mixtures thereof. Although the molecular weight of each chain of the polymer backbone can vary, it is typically in the range of from about 100 Da to about 100,000 Da, often from about 6,000 Da to about 80,000 Da.

The "area under the curve" or "AUC", as used herein in the context of administering a peptide drug to a patient, is defined as total area under the curve that describes the concentration of drug in systemic circulation in the patient as a function of time from zero to infinity.

The term "half-life" or "t½", as used herein in the context of administering a peptide drug to a patient, is defined as the time required for plasma concentration of a drug in a patient to be reduced by one half. There may be more than one half-life associated with the peptide drug depending on multiple clearance mechanisms, redistribution, and other mechanisms well known in the art. Usually, alpha and beta half-lives are defined such that the alpha phase is associated with redistribution, and the beta phase is associated with clearance. However, with protein drugs that are, for the most part, confined to the bloodstream, there can be at least two clearance half-lives. For some glycosylated peptides, rapid beta phase clearance may be mediated via receptors on macrophages, or endothelial cells that recognize terminal galactose, N-acetylgalactosamine, N-acetylglucosamine, mannose, or fucose. Slower beta phase clearance may occur via renal glomerular filtration for molecules with an effective radius <2 nm (approximately 68 kD) and/or specific or non-specific uptake and metabolism in tissues. GlycoPEGylation may cap terminal sugars (e.g., galactose or N-acetylgalactosamine) and thereby block rapid alpha phase clearance via receptors that recognize these sugars. It may also confer a larger effective radius and thereby decrease the volume of distribution and tissue uptake, thereby prolonging the late beta phase. Thus, the precise impact of glycoPEGylation on alpha phase and beta phase half-lives will vary depending upon the size, state of glycosylation, and other parameters, as is well known in the art. Further explanation of "half-life" is found in Pharmaceutical Biotechnology (1997, D F A Crommelin and R D Sindelar, eds., Harwood Publishers, Amsterdam, pp 101-120).

The term "glycoconjugation," as used herein, refers to the enzymatically mediated conjugation of a modified sugar species to an amino acid or glycosyl residue of a polypeptide, e.g., a mutant human growth hormone of the present invention. A subgenus of "glycoconjugation" is "glycoPEGylation," in which the modifying group of the modified sugar is poly(ethylene glycol), and alkyl derivative (e.g., m-PEG) or reactive derivative (e.g., H2N-PEG, HOOC-PEG) thereof.

Exemplary methods of glycoconjugation are described in PCT/US02/32263, U.S. application Ser. No. 10/411,012.

The terms "large-scale" and "industrial-scale" are used interchangeably and refer to a reaction cycle that produces at least about 250 mg, preferably at least about 500 mg, and more preferably at least about 1 gram of glycoconjugate at the completion of a single reaction cycle.

The term, "glycosyl linking group," as used herein refers to a glycosyl residue to which a modifying group (e.g., PEG moiety, therapeutic moiety, biomolecule) is covalently attached; the glycosyl linking group joins the modifying group to the remainder of the conjugate. In the methods of the invention, the "glycosyl linking group" becomes covalently attached to a glycosylated or unglycosylated peptide, thereby linking the agent to an amino acid and/or glycosyl residue on the peptide. A "glycosyl linking group" is generally derived from a "modified sugar" by the enzymatic attachment of the "modified sugar" to an amino acid and/or glycosyl residue of the peptide. The glycosyl linking group can be a saccharide-derived structure that is degraded during formation of modifying group-modified sugar cassette (e.g., oxidation→Schiff base formation→reduction), or the glycosyl linking group may be intact. An "intact glycosyl linking group" refers to a linking group that is derived from a glycosyl moiety in which the saccharide monomer that links the modifying group to the remainder of the conjugate is not degraded, e.g., oxidized by sodium metaperiodate. "Intact glycosyl linking groups" of the invention may be derived from a naturally occurring oligosaccharide by addition of glycosyl unit(s) or removal of one or more glycosyl unit from a parent saccharide structure.

The term "targeting moiety," as used herein, refers to species that will selectively localize in a particular tissue or region of the body. The localization is mediated by specific recognition of molecular determinants, molecular size of the targeting agent or conjugate, ionic interactions, hydrophobic interactions and the like. Other mechanisms of targeting an agent to a particular tissue or region are known to those of skill in the art. Exemplary targeting moieties include antibodies, antibody fragments, transferrin, HS-glycoprotein, coagulation factors, serum proteins, β-glycoprotein, hGH, GM-CSF, M-CSF, EPO and the like.

As used herein, "therapeutic moiety" means any agent useful for therapy including, but not limited to, antibiotics, anti-inflammatory agents, anti-tumor drugs, cytotoxins, and radioactive agents. "Therapeutic moiety" includes prodrugs of bioactive agents, constructs in which more than one therapeutic moiety is bound to a carrier, e.g., multivalent agents. Therapeutic moiety also includes proteins and constructs that include proteins. Exemplary proteins include, but are not limited to, Erythropoietin (EPO), Granulocyte Colony Stimulating Factor (G-CSF), Granulocyte Macrophage Colony Stimulating Factor (GMCSF), Interferon (e.g., Interferon-α, -β, -γ), Interleukin (e.g., Interleukin II), serum proteins (e.g., Factors VII, VIIa, VIII, IX, and X), Human Chorionic Gonadotropin (HCG), Follicle Stimulating Hormone (FSH) and Lutenizing Hormone (LH) and antibody fusion proteins (e.g. Tumor Necrosis Factor Receptor ((TNFR)/Fc domain fusion protein)).

As used herein, "a radioactive agent" includes any radioisotope that is effective in diagnosing or destroying a tumor. Examples include, but are not limited to, indium-111, cobalt-60. Additionally, naturally occurring radioactive elements such as uranium, radium, and thorium, which typically represent mixtures of radioisotopes, are suitable examples of a radioactive agent. The metal ions are typically chelated with an organic chelating moiety.

Many useful chelating groups, crown ethers, cryptands and the like are known in the art and can be incorporated into the compounds of the invention (e.g., EDTA, DTPA, DOTA, NTA, HDTA, etc. and their phosphonate analogs such as DTPP, EDTP, HDTP, NTP, etc). See, for example, Pitt et al., "The Design of Chelating Agents for the Treatment of Iron Overload," In, INORGANIC CHEMISTRY IN BIOLOGY AND MEDICINE; Martell, Ed.; American Chemical Society, Washington, D.C., 1980, pp. 279-312; Lindoy, THE CHEMISTRY OF MACROCYCLIC LIGAND COMPLEXES; Cambridge University Press, Cambridge, 1989; Dugas, BIOORGANIC CHEMISTRY; Springer-Verlag, New York, 1989, and references contained therein.

Additionally, a manifold of routes allowing the attachment of chelating agents, crown ethers and cyclodextrins to other molecules is available to those of skill in the art. See, for example, Meares et al., "Properties of In vivo Chelate-Tagged Proteins and Polypeptides." In, MODIFICATION OF PROTEINS: FOOD, NUTRITIONAL, AND PHARMACOLOGICAL ASPECTS;" Feeney, et al., Eds., American Chemical Society, Washington, D.C., 1982, pp. 370-387; Kasina et al., Bioconjugate Chem., 9: 108-117 (1998); Song et al., Bioconjugate Chem., 8: 249-255 (1997).

As used herein, "pharmaceutically acceptable carrier" includes any material, which when combined with the conjugate retains the conjugate's activity and is non-reactive with the subject's immune systems. Examples include, but are not limited to, any of the standard pharmaceutical carriers such as a phosphate buffered saline solution, water, emulsions such as oil/water emulsion, and various types of wetting agents. Other carriers may also include sterile solutions, tablets including coated tablets and capsules. Typically such carriers contain excipients such as starch, milk, sugar, certain types of clay, gelatin, stearic acid or salts thereof, magnesium or calcium stearate, talc, vegetable fats or oils, gums, glycols, or other known excipients. Such carriers may also include flavor and color additives or other ingredients. Compositions comprising such carriers are formulated by well known conventional methods.

As used herein, "administering," means oral administration, inhalation, administration as a suppository, topical contact, intravenous, intraperitoneal, intramuscular, intralesional, intranasal or subcutaneous administration, or the implantation of a slow-release device e.g., a mini-osmotic pump, to the subject. Administration is by any route including parenteral, and transmucosal (e.g., oral, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc.

The term "ameliorating" or "ameliorate" refers to any indicia of success in the treatment of a pathology or condition, including any objective or subjective parameter such as abatement, remission or diminishing of symptoms or an improvement in a patient's physical or mental well-being. Amelioration of symptoms can be based on objective or subjective parameters, including the results of a physical examination and/or a psychiatric evaluation.

The term "therapy" refers to "treating" or "treatment" of a disease or condition including preventing the disease or condition from occurring in an animal that may be predisposed to the disease but does not yet experience or exhibit symptoms of the disease (prophylactic treatment), inhibiting the disease (slowing or arresting its development), providing relief from the symptoms or side-effects of the disease (including palliative treatment), and relieving the disease (causing regression of the disease).

The term "effective amount," as used herein, refers to an amount that produces therapeutic effects for which a substance is administered. The effects include the prevention, correction, or inhibition of progression of the symptoms of a disease/condition and related complications to any detectable extent. The exact amount will depend on the purpose of the treatment, and will be ascertainable by one skilled in the art using known techniques (see, e.g., Lieberman, Pharmaceutical Dosage Forms (vols. 1-3, 1992); Lloyd, The Art, Science and Technology of Pharmaceutical Compounding (1999); and Pickar, Dosage Calculations (1999)).

The term "isolated" refers to a material that is substantially or essentially free from components, which are used to produce the material. For peptide conjugates of the invention, the term "isolated" refers to material that is substantially or essentially free from components, which normally accompany the material in the mixture used to prepare the peptide conjugate. "Isolated" and "pure" are used interchangeably. Typically, isolated peptide conjugates of the invention have a level of purity preferably expressed as a range. The lower end of the range of purity for the peptide conjugates is about 60%, about 70% or about 80% and the upper end of the range of purity is about 70%, about 80%, about 90% or more than about 90%.

When the peptide conjugates are more than about 90% pure, their purities are also preferably expressed as a range. The lower end of the range of purity is about 90%, about 92%, about 94%, about 96% or about 98%. The upper end of the range of purity is about 92%, about 94%, about 96%, about 98% or about 100% purity.

Purity is determined by any art-recognized method of analysis (e.g., band intensity on a silver stained gel, polyacrylamide gel electrophoresis, HPLC, or a similar means).

"Essentially each member of the population," as used herein, describes a characteristic of a population of peptide conjugates of the invention in which a selected percentage of the modified sugars added to a peptide are added to multiple, identical acceptor sites on the peptide. "Essentially each member of the population" speaks to the "homogeneity" of the sites on the peptide conjugated to a modified sugar and refers to conjugates of the invention, which are at least about 80%, preferably at least about 90% and more preferably at least about 95% homogenous.

"Homogeneity," refers to the structural consistency across a population of acceptor moieties to which the modified sugars are conjugated. Thus, in a peptide conjugate of the invention in which each modified sugar moiety is conjugated to an acceptor site having the same structure as the acceptor site to which every other modified sugar is conjugated, the peptide conjugate is said to be about 100% homogeneous. Homogeneity is typically expressed as a range. The lower end of the range of homogeneity for the peptide conjugates is about 60%, about 70% or about 80% and the upper end of the range of purity is about 70%, about 80%, about 90% or more than about 90%.

When the peptide conjugates are more than or equal to about 90% homogeneous, their homogeneity is also preferably expressed as a range. The lower end of the range of homogeneity is about 90%, about 92%, about 94%, about 96% or about 98%. The upper end of the range of purity is about 92%, about 94%, about 96%, about 98% or about 100% homogeneity. The purity of the peptide conjugates is typically determined by one or more methods known to those of skill in the art, e.g., liquid chromatography-mass spectrometry (LC- MS), matrix assisted laser desorption mass time of flight spectrometry (MALDITOF), capillary electrophoresis, and the like.

"Substantially uniform glycoform" or a "substantially uniform glycosylation pattern," when referring to a glycopeptide species, refers to the percentage of acceptor moieties that are glycosylated by the glycosyltransferase of interest (e.g., fucosyltransferase). For example, in the case of a α1,2 fucosyltransferase, a substantially uniform fucosylation pattern exists if substantially all of the Galβ1,4-GlcNAc-R and sialylated analogues thereof are fucosylated in a peptide conjugate of the invention. In the fucosylated structures set forth herein, the Fuc-GlcNAc linkage is generally α1,6 or α1,3, with α1,6 generally preferred. It will be understood by one of skill in the art, that the starting material may contain glycosylated acceptor moieties (e.g., fucosylated Galβ1,4-GlcNAc-R moieties). Thus, the calculated percent glycosylation will include acceptor moieties that are glycosylated by the methods of the invention, as well as those acceptor moieties already glycosylated in the starting material.

The term "substantially" in the above definitions of "substantially uniform" generally means at least about 40%, at least about 70%, at least about 80%, or more preferably at least about 90%, and still more preferably at least about 95% of the acceptor moieties for a particular glycosyltransferase are glycosylated.

Where substituent groups are specified by their conventional chemical formulae, written from left to right, they equally encompass the chemically identical substituents, which would result from writing the structure from right to left, e.g., —$CH_2O$— is intended to also recite —$OCH_2$—.

The term "alkyl," by itself or as part of another substituent means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e. $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1, 4-pentadienyl), ethynyl, 1- and 3-propynyl, 3-butynyl, and the higher homologs and isomers. The term "alkyl," unless otherwise noted, is also meant to include those derivatives of alkyl defined in more detail below, such as "heteroalkyl." Alkyl groups that are limited to hydrocarbon groups are termed "homoalkyl".

The term "alkylene" by itself or as part of another substituent means a divalent radical derived from an alkane, as exemplified, but not limited, by —$CH_2CH_2CH_2CH_2$—, and further includes those groups described below as "heteroalkylene." Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and at least one heteroatom selected from the group consisting of O, N, Si and S, and wherein the nitrogen and sulfur atoms may optionally be oxidized and the nitrogen heteroatom may optionally be quaternized. The heteroatom(s) O, N and S and Si may be placed at any interior position of the heteroalkyl group or at the position at which the alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$,—S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, and —CH=CH—N($CH_3$)—$CH_3$. Up to two heteroatoms may be consecutive, such as, for example, —$CH_2$—NH—$OCH_3$ and —$CH_2$—O—Si(CH3)$_3$. Similarly, the term "heteroalkylene" by itself or as part of another substituent means a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —$C(O)_2$R'— represents both —$C(O)_2$R'— and —R'$C(O)_2$—.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo(C1-C4)alkyl" is mean to include, but not be limited to, trifluoromethyl, 2,2,2-trifluoroethyl, 4-chlorobutyl, 3-bromopropyl, and the like.

The term "aryl" means, unless otherwise stated, a polyunsaturated, aromatic, substituent that can be a single ring or multiple rings (preferably from 1 to 3 rings), which are fused together or linked covalently. The term "heteroaryl" refers to aryl groups (or rings) that contain from one to four heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, tetrazolyl, benzo[b]furanyl, benzo[b]thienyl, 2,3-dihydrobenzo[1,4]dioxin-6-yl, benzo [1,3]dioxol-5-yl and 6-quinolyl. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") is meant to include both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) are generically referred to as "alkyl group substituents," and they can be one or more of a variety of groups selected from, but not limited to: —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —CN and —NO$_2$ in a number ranging from zero to (2 m'+1), where m' is the total number of carbon atoms in such radical. R', R", R'" and R"" each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R'" and R"" groups when more than one of these groups is present. When R' and R" are attached to the same nitrogen atom, they can be combined with the nitrogen atom to form a 5-, 6-, or 7-membered ring. For example, —NR'R" is meant to include, but not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are generically referred to as "aryl group substituents." The substituents are selected from, for example: halogen, —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —CN and —NO$_2$, —R', —N$_3$, —CH(Ph)$_2$, fluoro(C$_1$-C$_4$)alkoxy, and fluoro(C$_1$-C$_4$)alkyl, in a number ranging from zero to the total number of open valences on the aromatic ring system; and where R', R", R'" and R"" are preferably independently selected from hydrogen, substituted or unsubstituted alkyl, substituted or unsubstituted heteroalkyl, substituted or unsubstituted aryl and substituted or unsubstituted heteroaryl. When a compound of the invention includes more than one R group, for example, each of the R groups is independently selected as are each R', R", R'" and R"" groups when more than one of these groups is present. In the schemes that follow, the symbol X represents "R" as described above.

Two of the substituents on adjacent atoms of the aryl or heteroaryl ring may optionally be replaced with a substituent of the formula -T-C(O)—(CRR')q-U—, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula -A-(CH$_2$)r-B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')s-X—(CR"R'")d-, where s and d are independently integers of from 0 to 3, and X is —O—, —NR'—, —S—, —S(O)—, —S(O)$_2$—, or —S(O)$_2$NR'—. The substituents R, R', R" and R'" are preferably independently selected from hydrogen or substituted or unsubstituted (C1-C6)alkyl.

As used herein, the term "heteroatom" is meant to include oxygen (O), nitrogen (N), sulfur (S) and silicon (Si).

Introduction

To improve the effectiveness of recombinant human growth hormone (rhGH) used for therapeutic purposes, the present invention provides genetically engineered mutants of human growth hormone that contain N-linked and/or O-linked glycosylation sites not present in naturally occurring human growth hormone. To further minimize in vivo degradation and lower the clearance rate of recombinant human growth hormone in the body, some of the mutants contain a proteolysis resistant mutation(s) and/or potential sites for chemical PEGylation in regions susceptible to proteases. FIGS. 6A-6K illustrate exemplary proteolysis resistant mutation sites. While hGH mutants of the invention also substantially retain the biological activity of the wild-type hormone, the newly introduced glycosylation sites allow the recombinantly produced hGH mutants to be selectively glycosylated in a large variety of patterns. Moreover, the non-natural glycosylation sites provide loci for selective glycoconjugation of modifying groups to the peptide at one or more sites. An exemplary modifying group is a water-soluble polymer, such as poly(ethylene glycol), e.g., PEG (e.g., m-PEG), PPG (e.g., m-PPG). Modification of the hGH mutants improve the stability and in vivo retention time of the recombinant hGH, reduces the peptides' antigenicity, and enhances the peptides' ability to target a specific tissue in need of treatment.

The Mutants

Glycosylation Mutants

The present invention provides mutants of hGH that include one or more O- or N-linked glycosylation sites that are not found in the wild type peptide. In all cases, the N-terminal Met may be present or absent on any hGH mutant. The mutants are substrates for enzymatic glycosylation and/or glycoPEGylation at one or more sites that would not normally be glycosylated, or would be poorly glycosylated, in the wild type peptide. These mutants allow the position of a glycosyl residue or a glycosyl linking group to be engineered to obtain a peptide having selected desirable properties. In addition to the position and number of glycosyl residues or glycosyl linking groups, other properties that can be varied using the mutants and methods of the invention include pharmacokinetics, pharmacodynamics, resistance to proteolysis, immunogenicity, recognition by the reticuloendothelial system, tissue distribution and the like.

Exemplary glycosylation mutants include the following:

P134TTGQIF = Mutant BD:
(SEQ ID NO: 96)
MFPTIPLSRLFDNAMLRAHRLHQLAFDTYQEFEEAYIPKEQKYSFLQNPQTSLCFSESIPTPSNREETQQ
KSNLELLRISLLLIQSWLEPVQFLRSVFANSLVYGASDSNVYDLLKDLEEGIQTLMGRLFDGSPTTGQIF
KQTYSKFDTNSHNDDALLKNYGLLYCFRKDMDKVETFLRIVQCRSVEGSCGF P134TTAQIF = Mutant BE:

(SEQ ID NO: 97)
MFPTIPLSRLFDNAMLRAHRLHQLAFDTYQEFEEAYIPKEQKYSFLQNPQTSLCFSESIPTPSNREETQQ
KSNLELLRISLLLIQSWLEPVQFLRSVFANSLVYGASDSNVYDLLKDLEEGIQTLMGRLEDGSPTTAQIF
KQTYSKFDTNSHNDDALLKNYGLLYCFRKDMDKVETFLRIVQCRSVEGSCGF

P134TATQIF = Mutant BF:

(SEQ ID NO: 98)
MFPTIPLSRLFDNAMLRAHRLHQLAFDTYQEFEEAYIPKEQKYSFLQNPQTSLCFSFSIPTPSNREETQQ
KSNLELLRISLLLIQSWLEPVQFLRSVFANSLVYGASDSNVYDLLKDLEEGIQTLMGRLEDGSPTATQIF
KQTYSKFDTNSHNDDALLKNYGLLYCFRKDMDKVETFLRIVQCRSVEGSCGF

P134TQGAMF = Mutant AI:

(SEQ ID NO: 99)
MFPTIPLSRLFDNAMLRAHRLHQLAFDTYQEFEEAYIPKEQKYSFLQNPQTSLCFSESIPTPSNREETQQKSNLELLRI
SLLLIQSWLEPVQFLRSVFANSLVYGASDSNVYDLLKDLEEGIQTLMGRLEDGSPTQGAMFKQTYSKFDTNSHNDD
ALLKNYGLLYCFRKDMDKVETFLRIVQCRSVEGSCGF

P134TQGAIF = Mutant BG:

(SEQ ID NO: 100)
MFPTIPLSRLFDNAMLRAHRLHQLAFDTYQEFEEAYIPKEQKYSFLQNPQTSLCFSESIPTPSNREETQQ
KSNLELLRISLLLIQSWLEPVQFLRSVFANSLVYGASDSNVYDLLKDLEEGIQTLMGRLEDGSPTQGAIF
KQTYSKFDTNSHNDDALLKNYGLLYCFRKDMDKVETFLRIVQCRSVEGSCGF

P134TQGQIF = Mutant BH:

(SEQ ID NO: 101)
MFPTIPLSRLFDNAMLRAHRLHQLAFDTYQEFEEAYIPKEQKYSFLQNPQTSLCFSESIPTPSNREETQQ
KSNLELLRISLLLIQSWLEPVQFLRSVFANSLVYGASDSNVYDLLKDLEEGIQTLMGRLEDGSPTQGQIF
KQTYSKFDTNSHNDDALLKNYGLLYCFRKDMDKVETFLRIVQCRSVEGSCGF

P134TTLYVF = Mutant BI:

(SEQ ID NO: 102)
MFPTIPLSRLFDNAMLRAHRLHQLAFDTYQEFEEAYIPKEQKYSFLQNPQTSLCFSESIPTPSNREETQQ
KSNLELLRISLLLIQSWLEPVQFLRSVFANSLVYGASDSNVYDLLKDLEEGIQTLMGRLEDGSPTTLYVF
KQTYSKFDTNSHNDDALLKNYGLLYCFRKDMDKVETFLRIVQCRSVEGSCGF

P134TINTIF = Mutant AJ:

(SEQ ID NO: 103)
MFPTIPLSRLFDNAMLRAHRLHQLAFDTYQEFEEAYIPKEQKYSFLQNPQTSLCFSESIPTPSNREETQQKSNLELLRI
SLLLIQSWLEPVQFLRSVFANSLVYGASDSNVYDLLKDLEEGIQTLMGRLEDGSPTINTIFKQTYSKFDTNSHNDDA
LLKNYGLLYCFRKDMDKVETFLRIVQCRSVEGSCGF

P134TTVSIF = Mutant AH:

(SEQ ID NO: 104)
MFPTIPLSRLFDNAMLRAHRLHQLAFDTYQEFEEAYIPKEQKYSFLQNPQTSLCFSESIPTPSNREETQQ
KSNLELLRISLLLIQSWLEPVQFLRSVFANSLVYGASDSNVYDLLKDLEEGIQTLMGRLEDGSPTTVSIF
KQTYSKFDTNSHNDDALLKNYGLLYCFRKDMDKVETFLRIVQCRSVEGSCGF

I139PTQTYS = Mutant BJ:

(SEQ ID NO: 105)
MFPTIPLSRLFDNAMLRAHRLHQLAFDTYQEFEEAYIPKEQKYSFLQNPQTSLCFSESIPTPSNREETQQ
KSNLELLRISLLLIQSWLEPVQFLRSVFANSLVYGASDSNVYDLLKDLEEGIQTLMGRLEDGSPRTGQIP
TQTYSKFDTNSHNDDALLKNYGLLYCFRKDMDKVETFLRIVQCRSVEGSCGF

I139PTQAYS = Mutant AG:

(SEQ ID NO: 106)
MFPTIPLSRLFDNAMLRAHRLHQLAFDTYQEFEEAYIPKEQKYSFLQNPQTSLCFSESIPTPSNREETQQKSNLELLRI
SLLLIQSWLEPVQFLRSVFANSLVYGASDSNVYDLLKDLEEGIQTLMGRLEDGSPRTGQIPTQAYSKFDTNSHNDDA
LLKNYGLLYCFRKDMDKVETFLRIVQCRSVEGSCGF

P134TTLQIF = Mutant BK:

(SEQ ID NO: 107)
MFPTIPLSRLFDNAMLRAHRLHQLAFDTYQEFEEAYIPKEQKYSFLQNPQTSLCFSESIPTPSNREETQQ
KSNLELLRISLLLIQSWLEPVQFLRSVFANSLVYGASDSNVYDLLKDLEEGIQTLMGRLEDGSPTTLQIF
KQTYSKFDTNSHNDDALLKNYGLLYCFRKDMDKVETFLRIVQCRSVEGSCGF

P134TTVQIF = Mutant BL:

(SEQ ID NO: 108)
MFPTIPLSRLFDNAMLRAHRLHQLAFDTYQEFEEAYIPKEQKYSFLQNPQTSLCFSESIPTPSNREETQQ
KSNLELLRISLLLIQSWLEPVQFLRSVFANSLVYGASDSNVYDLLKDLEEGIQTLMGRLEDGSPTTVQIF
KQTYSKFDTNSHNDDALLKNYGLLYCFRKDMDKVETFLRIVQCRSVEGSCGF

P134TTNQIf = Mutant BM:

(SEQ ID NO: 109)

MFPTIPLSRLFDNAMLRAHRLHQLAFDTYQEFEEAYIPKEQKYSFLQNPQTSLCFSESIPTPSNREETQQ
KSNLELLRISLLLIQSWLEPVQFLRSVFANSLVYGASDSNVYDLLKDLEEGIQTLMGRLEDGSPTTNQIF
KQTYSKFDTNSHNDDALLKNYGLLYCFRKDMDKVETFLRIVQCRSVEGSCGF

P134TTQQIF = Mutant BN:

(SEQ ID NO: 110)

MFPTIPLSRLFDNAMLRAHRLHQLAFDTYQEFEEAYIPKEQKYSFLQNPQTSLCFSESIPTPSNREETQQ
KSNLELLRISLLLIQSWLEPVQFLRSVFANSLVYGASDSNVYDLLKDLEEGIQTLMGRLEDGSPTTQQIF
KQTYSKFDTNSHNDDALLKNYGLLYCFRKDMDKVETFLRIVQCRSVEGSCGF

P134TIGQIF = Mutant BO:

(SEQ ID NO: 111)

MFPTIPLSRLFDNAMLRAHRLHQLAFDTYQEFEEAYIPKEQKYSFLQNPQTSLCFSESIPTPSNREETQQ
KSNLELLRISLLLIQSWLEPVQFLRSVFANSLVYGASDSNVYDLLKDLEEGIQTLMGRLEDGSPTIGQIF
KQTYSKFDTNSHNDDALLKNYGLLYCFRKDMDKVETFLRIVQCRSVEGSCGF

P134TILQHF = Mutant BP:

(SEQ ID NO: 112)

MFPTIPLSRLFDNAMLRAHRLHQLAFDTYQEFEEAYIPKEQKYSFLQNPQTSLCFSESIPTPSNREETQQ
KSNLELLRISLLLIQSWLEPVQFLRSVFANSLVYGASDSNVYDLLKDLEEGIQTLMGRLEDGSPTILQIF
KQTYSKFDTNSHNDDALLKNYGLLYCFRKDMDKVETFLRIVQCRSVEGSCGF

P134TIVQIF = Mutant BQ:

(SEQ ID NO: 113)

MFPTIPLSRLFDNAMLRAHRLHQLAFDTYQEFEEAYIPKEQKYSFLQNPQTSLCFSESIPTPSNREETQQ
KSNLELLRISLLLIQSWLEPVQFLRSVFANSLVYGASDSNVYDLLKDLEEGIQTLMGRLEDGSPTIVQIF
KQTYSKFDTNSHNDDALLKNYGLLYCFRKDMDKVETFLRIVQCRSVEGSCGF

P134TINQIF = Mutant BR:

(SEQ ID NO: 114)

MFPTIPLSRLFDNAMLRAHRLHQLAFDTYQEFEEAYIPKEQKYSFLQNPQTSLCFSESIPTPSNREETQQ
KSNLELLRISLLLIQSWLEPVQFLRSVFANSLVYGASDSNVYDLLKDLEEGIQTLMGRLEDGSPTINQIF
KQTYSKFDTNSHNDDALLKNYGLLYCFRKDMDKVETFLRIVQCRSVEGSCGF

P134TIQQIF = Mutant BS:

(SEQ ID NO: 115)

MFPTIPLSRLFDNAMLRAHRLHQLAFDTYQEFEEAYIPKEQKYSFLQNPQTSLCFSESIPTPSNREETQQ
KSNLELLRISLLLIQSWLEPVQFLRSVFANSLVYGASDSNVYDLLKDLEEGIQTLMGRLEDGSPTIQQIF
KQTYSKFDTNSHNDDALLKNYGLLYCFRKDMDKVETFLRIVQCRSVEGSCGF

P134TIAQIF = Mutant BT:

(SEQ ID NO: 116)

MFPTIPLSRLFDNAMLRAHRLHQLAFDTYQEFEEAYIPKEQKYSFLQNPQTSLCFSESIPTPSNREETQQ
KSNLELLRISLLLIQSWLEPVQFLRSVFANSLVYGASDSNVYDLLKDLEEGIQTLMGRLEDGSPTIAQIF
KQTYSKFDTNSHNDDALLKNYGLLYCFRKDMDKVETFLRIVQCRSVEGSCGF

L129ETETPRT = Mutant BU:

(SEQ ID NO: 117)

MFPTIPLSRLFDNAMLRAHRLHQLAFDTYQEFEEAYIPKEQKYSFLQNPQTSLCFSESIPTPSNREETQQ
KSNLELLRISLLLIQSWLEPVQFLRSVFANSLVYGASDSNVYDLLKDLEEGIQTLMGRLETETPRTGQIF
KQTYSKFDTNSHNDDALLKNYGLLYCFRKDMDKVETFLRIVQCRSVEGSCGF

L129VTETPRT = Mutant BY:

(SEQ ID NO: 118)

MFPTIPLSRLFDNAMLRAHRLHQLAFDTYQEFEEAYIPKEQKYSFLQNPQTSLCFSESIPTPSNREETQQ
KSNLELLRISLLLIQSWLEPVQFLRSVFANSLVYGASDSNVYDLLKDLEEGIQTLMGRLVTETPRTGQIF
KQTYSKFDTNSHNDDALLKNYGLLYCFRKDMDKVETFLRIVQCRSVEGSCGF

L129ETQSPRT = Mutant BW:

(SEQ ID NO: 119)

MFPTIPLSRLFDNAMLRAHRLHQLAFDTYQEFEEAYIPKEQKYSFLQNPQTSLCFSESIPTPSNREETQQ
KSNLELLRISLLLIQSWLEPVQFLRSVFANSLVYGASDSNVYDLLKDLEEGIQTLMGRLETQSPRTGQIF
KQTYSKFDTNSHNDDALLKNYGLLYCFRKDMDKVETFLRIVQCRSVEGSCGF

L129VTQSPRT = Mutant BX:

(SEQ ID NO: 120)

MFPTIPLSRLFDNAMLRAHRLHQLAFDTYQEFEEAYIPKEQKYSFLQNPQTSLCFSESIPTPSNREETQQ
KSNLELLRISLLLIQSWLEPVQFLRSVFANSLVYGASDSNVYDLLKDLEEGIQTLMGRLVTQSPRTGQIF
KQTYSKFDTNSHNDDALLKNYGLLYCFRKDMDKVETFLRIVQCRSVEGSCGF

L129VTETPAT = Mutant BY:

(SEQ ID NO: 121)

MFPTIPLSRLFDNAMLRAHRLHQLAFDTYQEFEEAYIPKEQKYSFLQNPQTSLCFSESIPTPSNREETQQ
KSNLELLRISLLLIQSWLEPVQFLRSVFANSLVYGASDSNVYDLLKDLEEGIQTLMGRLVTETPATGQIF
KQTYSKFDTNSHNDDALLKNYGLLYCFRKDMDKVETFLRIVQCRSVEGSCGF

-continued

L129ETETPAT = Mutant BZ:

(SEQ ID NO: 122)
MFPTIPLSRLFDNAMLRAHRLHQLAFDTYQEFEEAYIPKEQKYSFLQNPQTSLCFSESIPTPSNREETQQ
KSNLELLRISLLLIQSWLEPVQFLRSVFANSLVYGASDSNVYDLLKDLEEGIQTLMGRLETETPATGQIF
KQTYSKFDTNSHNDDALLKNYGLLYCFRKDMDKVETFLRIVQCRSVEGSCGF

L129ATGSPRT = Mutant CA:

(SEQ ID NO: 123)
MFPTIPLSRLFDNAMLRAHRLHQLAFDTYQEFEEAYIPKEQKYSFLQNPQTSLCFSESIPTPSNREETQQ
KSNLELLRISLLLIQSWLEPVQFLRSVFANSLVYGASDSNVYDLLKDLEEGIQTLMGRLATGSPRTGQIF
KQTYSKFDTNSHNDDALLKNYGLLYCFRKDMDKVETFLRIVQCRSVEGSCGF

L129ETQSPST = Mutant CB:

(SEQ ID NO: 124)
MFPTIPLSRLFDNAMLRAHRLHQLAFDTYQEFEEAYIPKEQKYSFLQNPQTSLCFSESIPTPSNREETQQ
KSNLELLRISLLLIQSWLEPVQFLRSVFANSLVYGASDSNVYDLLKDLEEGIQTLMGRLETQSPSTGQIF
KQTYSKFDTNSHNDDALLKNYGLLYCFRKDMDKVETFLRIVQCRSVEGSCGF

L129ETQSPAT = Mutant CC:

(SEQ ID NO: 125)
MFPTIPLSRLFDNAMLRAHRLHQLAFDTYQEFEEAYIPKEQKYSFLQNPQTSLCFSESIPTPSNREETQQ
KSNLELLRISLLLIQSWLEPVQFLRSVFANSLVYGASDSNVYDLLKDLEEGIQTLMGRLETQSPATGQIF
KQTYSKFDTNSHNDDALLKNYGLLYCFRKDMDKVETFLRIVQCRSVEGSCGF

L129ETQSPLT = Mutant CD:

(SEQ ID NO: 126)
MFPTIPLSRLFDNAMLRAHRLHQLAFDTYQEFEEAYIPKEQKYSFLQNPQTSLCFSESIPTPSNREETQQ
KSNLELLRISLLLIQSWLEPVQFLRSVFANSLVYGASDSNVYDLLKDLEEGIQTLMGRLETQSPLTGQIF
KQTYSKFDTNSHNDDALLKNYGLLYCFRKDMDKVETFLRIVQCRSVEGSCGF

Y43change to A; P134TINTFKQTYS = Mutant CE:

(SEQ ID NO: 127)
MFPTIPLSRLFDNAMLRAHRLHQLAFDTYQEFEEAYIPKEQASFLQNPQTSLCFSESIPTPSNREETQQKSNLELLRI
SLLLIQSWLEPVQFLRSVFANSLVYGASDSNVYDLLKDLEEGIQTLMGRLEDGSPTINTIFKQTYSKFDTNSHNDDA
LLKNYGLLYCFRKDMDKVETFLRIVQCRSVEGSCGF

Y43 change to A; Y144 change to A; P134TINTIFKQTA = Mutant CF:

(SEQ ID NO: 128)
MFPTIPLSRLFDNAMLRAHRLHQLAFDTYQEFEEAYIPKEQASFLQNPQTSLCFSESIPTPSNREETQQKSNLELLRI
SLLLIQSWLEPVQFLRSVFANSLVYGASDSNVYDLLKDLEEGIQTLMGRLEDGSPTINTIFKQTASKFDTNSHNDDA
LLKNYGLLYCFRKDMDKVETFLRIVQCRSVEGSCGF

Y43 change to A; Y144 change to A; F140 change to A;
K141 change to N; P134TINTIANQTA = Mutant CG:

(SEQ ID NO: 129)
MFPTIPLSRLFDNAMLRAHRLHQLAFDTYQEFEEAYIPKEQASFLQNPQTSLCFSESIPTPSNREETQQKSNLELLRI
SLLLIQSWLEPVQFLRSVFANSLVYGASDSNVYDLLKDLEEGIQTLMGRLEDGSPTINTIANQTASKFDTNSHNDDA
LLKNYGLLYCFRKDMDKVETFLRIVQCRSVEGSCGF

Y43 change to A; I139PTQAYS = Mutant CH:

(SEQ ID NO: 130)
MFPTIPLSRLFDNAMLRAHRLHQLAFDTYQEFEEAYIPKEQASFLQNPQTSLCFSESIPTPSNREETQQKSNLELLRI
SLLLIQSWLEPVQFLRSVFANSLVYGASDSNVYDLLKDLEEGIQTLMGRLEDGSPRTGQIPTQAYSKFDTNSHNDDA
LLKNYGLLYCFRKDMDKVETFLRIVQCRSVEGSCGF

V1TPT = Mutant CI:

(SEQ ID NO: 131)
VTPTIPLSRLFDNAMLRAHRLHQLAFDTYQEFEEAYIPKEQKYSFLQNPQTSLCFSESIPTPSNREETQQKSNLELLRI
SLLLIQSWLEPVQFLRSVFANSLVYGASDSNVYDLLKDLEEGIQTLMGRLEDGSPRTGQIFKQTYSKFDTNSHNDDA
LLKNYGLLYCFRKDMDKVETFLRIVQCRSVEGSCGF

P134TQGAMP = Mutant CJ:

(SEQ ID NO: 132)
MFPTIPLSRLFDNAMLRAHRLHQLAFDTYQEFEEAYIPKEQKYSFLQNPQTSLCFSESIPTPSNREETQQKSNLELLRI
SLLLIQSWLEPVQFLRSVFANSLVYGASDSNVYDLLKDLEEGIQTLMGRLEDGSPTQGAMPKQTYSKFDTNSHNDD
ALLKNYGLLYCFRKDMDKVETFLRIVQCRSVEGSCGF

P134TTTQIF = Mutant CK:

(SEQ ID NO: 133)
MFPTIPLSRLFDNAMLRAHRLHQLAFDTYQEFEEAYIPKEQKYSFLQNPQTSLCFSESIPTPSNREETQQKSNLELLRI
SLLLIQSWLEPVQFLRSVFANSLVYGASDSNVYDLLKDLEEGIQTLMGRLEDGSPTTTQIFKQTYSKFDTNSHNDDA
LLKNYGLLYCFRKDMDKVETFLRIVQCRSVEGSCGF

P134NTGQIF = Mutant CL:

(SEQ ID NO: 134)
MFPTIPLSRLFDNAMLRAHRLHQLAFDTYQEFEEAYIPKEQKYSFLQNPQTSLCFSESIPTPSNREETQQKSNLELLRI
SLLLIQSWLEPVQFLRSVFANSLVYGASDSNVYDLLKDLEEGIQTLMGRLEDGSPNTGQIFKQTYSKFDTNSHNDDA
LLKNYGLLYCFRKDMDKVETFLRIVQCRSVEGSCGF

-continued

```
M1FPTEIP = Mutant CM:
                                                                    (SEQ ID NO: 135)
MFPTEIPLSRLFDNAMLRAHRLHQLAFDTYQEFEEAYIPKEQKYSFLQNPQTSLCFSESIPTPSNREETQQKSNLELLR
ISLLLIQSWLEPVQFLRSVFANSLVYGASDSNVYDLLKDLEEGIQTLMGRLEDGSPRTGQIFKQTYSKFDTNSHNDD
ALLKNYGLLYCFRKDMDKVETFLRIVQCRSVEGSCGF M1FPTVLP = Mutant CN:
                                                                    (SEQ ID NO: 136)
MFPTVLPLSRLFDNAMLRAHRLHQLAFDTYQEFEEAYIPKFQKYSFLQNPQTSLCFSFSIPTPSNREETQQKSNLELL
RISLLLIQSWLEPVQFLRSVFANSLVYGASDSNVYDLLKDLEEGIQTLMGRLEDGSPRTGQIFKQTYSKFDTNSHND
DALLKNYGLLYCFRKDMDKVETFLRIVQCRSVEGSCGF
```

A. GlycoPEGylated rhGH Mutants

The present invention provides glycoPEGylated mutants of hGH that include one or more O- or N-linked glycosylation sites that are not found in the wild type peptide. In all cases, the N-terminal Met may be present or absent on any hGH mutant. In addition to the position and number of glycosyl residues or glycosyl linking groups, other properties that can be varied using the mutants and methods of the invention include pharmacokinetics, pharmacodynamics, resistance to proteolysis, immunogenicity, recognition by the reticuloendothelial system, tissue distribution and the like.

B. Proteolysis Resistant Mutants

The present invention also provides mutants of hGH with mutations that impart resistance towards degradation of the peptide by proteolytic enzymes. In all cases, the N-terminal Met may be present or absent on any hGH mutant. Protease resistance is achieved by modifying, substituting, inserting or deleting one or more amino acids within the protease recognition or cleavage sites in rhGH. Exemplary mutant motifs include, but is not limited to the following:

-$P^{134}$TINT-  -$P^{134}$TQGAMP-  -$P^{134}$TTVS-  -$P^{134}$TQGAM-  -$P^{140}$TQA-

 ← amino acids insertion mutants wherein horizontal lines on both sides of the various motifs represent amino acid sequences which precede and follow it in the corresponding native hGH amino acid sequence. For purpose of illustration, examples of the $P^{134}$ TINT motif have been provided in FIGS. 6D, 6E, 6F, 6G, and 6J. In each of these five mutants, the native $R^{135}$TGQ sequence has been replaced by TINT.

Examples of the $P^{140}$TQA motif are provided in FIGS. 6C and 6H, and examples of the $P^{134}$TTVS motif in FIGS. 6B and 6I. In FIGS. 6C and 6H, the native FKQT motif has been replaced by PTQA. In FIGS. 6B and 6I, the native $R^{135}$TGQ sequence has been replaced by $T^{135}$TVS. An exemplary insertion mutant can be found in FIG. 6A, where a glutamic acid has been inserted between the threonine at the 4th position and isoleucine at the 5th position of the native hGH sequence.

In addition to what is provided in FIGS. 6A to 6J, FIG. 6K shows other possible sites for the proteolysis resistant mutations, as indicated on the native hGH amino acid sequence. Protease resistant mutations can be the sole mutation type or the mutant peptide can also include one or more glycosylation mutation to form a protease resistant conjugate that can also serve as substrates for enzymatic glycosylation and/or glycoPEGylation. FIGS. 6A-6J depict various exemplary mutant hGH amino acid sequences containing both a glycosylation site and at least one type of the proteolysis inhibiting mutations mentioned above.

C. Chemically PEGylated rhGH

The present invention further provides wild-type hGH peptides and hGH mutants that are substrates for chemical PEGylation.

Protease resistance can also be achieved through a mechanism other than the proteolysis resistant mutations described above. Since many of the lysine residues in hGH are present in regions most susceptible to proteases, chemical PEGylation of one or more of these lysines has the effect of blocking the proteolytic cleavage or binding site, which thereby reduces in vivo degradation of the polypeptide. The amino terminus and histidine residues in hGH are other useful sites for chemical PEGylation. Exemplary chemical PEGylation sites of the invention are indicated by larger, highlighted, bold font in FIG. 6I and FIG. 6J.

Mixed Modalities

While chemical PEGylation can be used alone, combining glycoPEGylation with chemical PEGylation or protease resistant mutation(s) creates a protein superior to what is known in the art. These mutants have the dual advantage of extended serum/blood half-life and increased resistance to proteolysis. Extended residence time in the body is achieved through the introduction of a PEG at the glycoPEGylation site whereas reduced susceptibility to proteolysis is promoted either through chemical PEGylation or a protease resistant mutation. Exemplary amino acid sequences of mutants that can be employed in this twofold approach are shown in FIGS. 6I and 6J. For illustrative purposes, the methionine residue at the N-terminus and lysine residues have been highlighted to show exemplary sites for chemical PEGylation.

The present invention also provides for chemically PEGylated hGH mutants containing protease resistant mutations. In these conjugates, the combined use of chemical PEGylation of residues near or in the protease cleavage/recognition site and protease resistant mutations provides a two-pronged method of blocking proteolytic activity. In addition, proteolysis inhibiting mutations can be selectively introduced so as to provide amino-containing side chains, which can be used as additional substrates for chemical PEGylation. exemplary sites for chemical PEGylation.

Moreover, chemical PEGylation, glycoPEGylation, and proteolysis inhibiting mutations can all be used in conjunction, as exemplified by FIGS. 6A-6K. Each of these amino acid sequences contains proteolysis inhibiting mutations and glycosylation sites according to the present invention. Preferably, though not necessary to practice this aspect of the invention, glycosylation site mutations and proteolysis inhibiting mutations are introduced in such a manner as to retain at least one lysine or histidine residue within the mutant amino acid sequence.

The present invention provides for hGH mutants with N-linked or O-linked glycosylation sites not found in wild-type hGH. Exemplary embodiments of the invention include N- or O-linked glycosylated hGH mutants having one or more characteristics selected from the following: glycoPEGylation, protease resistance, and chemically PEGylation. Through the controlled modification of hGH, the present invention yields novel hGH derivatives with pharmacokinetic properties that are improved relative to the corresponding native hGH.

In a first aspect, the present invention provides an isolated nucleic acid comprising a polynucleotide sequence encoding a mutant human growth hormone. The mutant human growth hormone comprises an N-linked or O-linked glycosylation site and/or proteolysis resistant mutation(s) that are not present in wild-type human growth hormone. In exemplary embodiments, the wild-type human growth hormones have the amino acid sequence of pituitary-derived GH-N (SEQ ID NO:1) or placenta-derived GH-V (SEQ ID NO:2). In some preferred embodiments, the mutant human growth hormone includes the amino acid sequence of SEQ ID NO:3, 4, 5, 6, 7, 8, 9, 80, 81, 82, 83, 84, 85, 86, 87, and 88.

In another aspect, the present invention provides an expression cassette or a cell that comprises a nucleic acid, e.g., an isolated nucleic acid, including a polynucleotide sequence encoding a mutant human growth hormone. The mutant human growth hormone includes an N-linked or O-linked glycosylation site and/or proteolysis inhibiting mutation(s) that are not present in the wild-type human growth hormone.

In still another aspect, the present invention provides a mutant glycoPEGylated human growth hormone that includes one or more N-linked or O-linked glycosylation site not present in the wild-type human growth hormone. In some embodiments, the wild-type human growth hormone has the amino acid sequence of SEQ ID NO:1 or SEQ ID NO:2. In some preferred embodiments, the mutant human growth hormone comprises the amino acid sequence of SEQ ID NO:3, 4, 5, 6, 7, 8, 9, 80, 81, 82, 83, 84, 85, 86, 87, and 88.

In still another aspect, the present invention provides a mutant human growth hormone that includes one or more N-linked or O-linked glycosylation site not present in the wild-type human growth hormone and one or more proteolysis resistant mutations(s) not present in the wild-type human growth hormone. In some embodiments, the wild-type human growth hormone has the amino acid sequence of SEQ ID NO:1 or SEQ ID NO:2. In some preferred embodiments, the mutant human growth hormone comprises the amino acid sequence of SEQ ID NO:3, 4, 5, 6, 7, 8, 9, 80, 81, 82, 83, 84, 85, 86, 87, and 88.

In still another aspect, the present invention provides a chemically PEGylated mutant human growth hormone that includes one or more N-linked or O-linked glycosylation site not present in the wild-type human growth hormone. In some embodiments, the wild-type human growth hormone has the amino acid sequence of SEQ ID NO:1 or SEQ ID NO:2. In some preferred embodiments, the mutant human growth hormone comprises the amino acid sequence of SEQ ID NO:3, 4, 5, 6, 7, 8, 9, 80, 81, 82, 83, 84, 85, 86, 87, and 88.

In another aspect, the present invention provides a glycoPEGylated mutant human growth hormone that includes one or more N-linked or O-linked glycosylation site not present in the wild-type human growth hormone and one or more proteolysis resistant mutations(s) not present in the wild-type human growth hormone. In some embodiments, the wild-type human growth hormone has the amino acid sequence of SEQ ID NO:1 or SEQ ID NO:2. In some preferred embodiments, the mutant human growth hormone comprises the amino acid sequence of SEQ ID NO:3, 4, 5, 6, 7, 8, 9, 80, 81, 82, 83, 84, 85, 86, 87, and 88.

In another aspect, the present invention provides a chemically PEGylated mutant human growth hormone that includes one or more N-linked or O-linked glycosylation site not present in the wild-type human growth hormone and one or more proteolysis resistant mutations(s) not present in the wild-type human growth hormone. In some embodiments, the wild-type human growth hormone has the amino acid sequence of SEQ ID NO:1 or SEQ ID NO:2. In some preferred embodiments, the mutant human growth hormone comprises the amino acid sequence of SEQ ID NO:3, 4, 5, 6, 7, 8, 9, 80, 81, 82, 83, 84, 85, 86, 87, and 88.

In another aspect, the present invention provides a glycoPEGylated and chemically PEGylated mutant human growth hormone that includes one or more N-linked or O-linked glycosylation site not present in the wild-type human growth hormone. In some embodiments, the wild-type human growth hormone has the amino acid sequence of SEQ ID NO:1 or SEQ ID NO:2. In some preferred embodiments, the mutant human growth hormone comprises the amino acid sequence of SEQ ID NO:3, 4, 5, 6, 7, 8, 9, 80, 81, 82, 83, 84, 85, 86, 87, and 88.

In another aspect, the present invention provides a glycoPEGylated and chemically PEGylated mutant human growth hormone that includes one or more N-linked or O-linked glycosylation site not present in the wild-type human growth hormone and one or more proteolysis resistant mutations(s) not present in the wild-type human growth hormone. In some embodiments, the wild-type human growth hormone has the amino acid sequence of SEQ ID NO:1 or SEQ ID NO:2. In some preferred embodiments, the mutant human growth hormone comprises the amino acid sequence of SEQ ID NO:3, 4, 5, 6, 7, 8, 9, 80, 81, 82, 83, 84, 85, 86, 87, and 88.

In another aspect, the present invention provides a method for making a mutant human growth hormone that includes an N-linked or O-linked glycosylation site and/or proteolysis inhibiting mutation(s) that are not present in the wild-type human growth hormone. This method includes the steps of recombinantly producing the mutant human growth hormone, and glycosylating the mutant human growth hormone at the new glycosylation site. In some embodiments, the wild-type human growth hormone has the amino acid sequence of SEQ ID NO:1 or SEQ ID NO:2. In some preferred embodiments, the mutant human growth hormone comprises the amino acid sequence of SEQ ID NO:3, 4, 5, 6, 7, 8, 9, 80, 81, 82, 83, 84, 85, 86, 87, and 88.

In still a further aspect, the present invention provides a pharmaceutical composition having a therapeutically effective amount of a mutant human growth hormone that includes an N-linked or O-linked glycosylation site and/or proteolysis inhibiting mutation(s) not present in the wild-type human growth hormone. In some embodiments, the wild-type human growth hormone has the amino acid sequence of SEQ ID NO:1 or SEQ ID NO:2. In some preferred embodiments, the mutant human growth hormone comprises the amino acid sequence of SEQ ID NO:3, 4, 5, 6, 7, 8, 9, 80, 81, 82, 83, 84, 85, 86, 87, and 88.

In another aspect, the present invention provides a method for treating human growth hormone deficiency in a subject. The method includes administering to the subject an amount of a mutant human growth hormone effective to treat or ameliorate the growth hormone deficiency. The mutant human growth hormone used in this method comprises an N-linked or O-linked glycosylation site and/or proteolysis inhibiting mutation(s) that do not exist in the corresponding wild-type human growth hormone. In some embodiments, the corresponding wild-type human growth hormone has the amino acid sequence of SEQ ID NO:1 or SEQ ID NO:2. In some preferred embodiments, the mutant human growth hormone comprises the amino acid sequence of SEQ ID NO:3, 4, 5, 6, 7, 8, 9, 80, 81, 82, 83, 84, 85, 86, 87, and 88.

Acquisition of hGH Coding Sequences

General Recombinant Technology

This invention relies on routine techniques in the field of recombinant genetics. Basic texts disclosing the general methods of use in this invention include Sambrook and Russell, *Molecular Cloning, A Laboratory Manual* (3rd ed. 2001); Kriegler, *Gene Transfer and Expression: A Laboratory Manual* (1990); and Ausubel et al., eds., *Current Protocols in Molecular Biology* (1994).

A number of polynucleotide sequences encoding a wild-type human growth hormone, e.g., GenBank Accession Nos. NM 000515, NM 002059, NM 022556, NM 022557, NM 022558, NM 022559, NM 022560, NM 022561, and NM 022562, have been determined and can be obtained from a commercial supplier.

Introducing Mutations into an hGH Sequence

From an encoding polynucleotide sequence, the amino acid sequence of a wild-type human growth hormone, e.g., SEQ ID NO:1 or SEQ ID NO:2, can be determined. Subsequently, this amino acid sequence may be modified to introduce proteolysis inhibiting mutations and/or alter the protein's glycosylation pattern, by introducing additional glycosylation site(s) at various locations in the amino acid sequence.

Several types of protein glycosylation sites are well known in the art. For instance, in eukaryotes, N-linked glycosylation occurs on the asparagine of the consensus sequence Asn-$X_{aa}$-Ser/Thr, in which $X_{aa}$ is any amino acid except proline (Kornfeld et al., *Ann Rev Biochem* 54:631-664 (1985); Kukuruzinska et al., *Proc. Natl. Acad. Sci. USA* 84:2145-2149 (1987); Herscovics et al., *FASEB J* 7:540-550 (1993); and Orlean, *Saccharomyces* Vol. 3 (1996)). O-linked glycosylation takes place at serine or threonine residues (Tanner et al., *Biochim. Biophys. Acta.* 906:81-91 (1987); and Hounsell et al., *Glycoconj. J.* 13:19-26 (1996)). Other glycosylation patterns are formed by linking glycosylphosphatidylinositol to the carboxyl-terminal carboxyl group of the protein (Takeda et al., *Trends Biochem. Sci.* 20:367-371 (1995); and Udenfriend et al., *Ann. Rev. Biochem.* 64:593-591 (1995). Based on this knowledge, suitable mutations can thus be introduced into a wild-type human growth hormone sequence to form new glycosylation sites.

Although direct modification of an amino acid residue within a human growth hormone polypeptide sequence may be feasible to introduce a new N-linked or O-linked glycosylation site, more frequently, introduction of a new glycosylation site is accomplished by mutating the polynucleotide sequence encoding a human growth hormone. This can be achieved by using any of known mutagenesis methods, some of which are discussed below. Exemplary modifications to human growth hormone include those illustrated in SEQ ID NOS: 3-9, and 80-89.

A variety of mutation-generating protocols are established and described in the art. See, e.g., Zhang et al., *Proc. Natl. Acad. Sci. USA,* 94: 4504-4509 (1997); and Stemmer, *Nature,* 370: 389-391 (1994). The procedures can be used separately or in combination to produce variants of a set of nucleic acids, and hence variants of encoded polypeptides. Kits for mutagenesis, library construction, and other diversity-generating methods are commercially available.

Mutational methods of generating diversity include, for example, site-directed mutagenesis (Botstein and Shortle, *Science,* 229: 1193-1201 (1985)), mutagenesis using uracil-containing templates (Kunkel, *Proc. Natl. Acad. Sci. USA,* 82: 488-492 (1985)), oligonucleotide-directed mutagenesis (Zoller and Smith, *Nucl. Acids Res.,* 10: 6487-6500 (1982)), phosphorothioate-modified DNA mutagenesis (Taylor et al., *Nucl. Acids Res.,* 13: 8749-8764 and 8765-8787 (1985)), and mutagenesis using gapped duplex DNA (Kramer et al., *Nucl. Acids Res.,* 12: 9441-9456 (1984)).

Other possible methods for generating mutations include point mismatch repair (Kramer et al, *Cell,* 38: 879-887 (1984)), mutagenesis using repair-deficient host strains (Carter et al., *Nucl. Acids Res.,* 13: 4431-4443 (1985)), deletion mutagenesis (Eghtedarzadeh and Henikoff, *Nucl. Acids Res.,* 14: 5115 (1986)), restriction-selection and restriction-purification (Wells et al., *Phil. Trans. R. Soc. Lond. A,* 317: 415-423 (1986)), mutagenesis by total gene synthesis (Nambiar et al., *Science,* 223: 1299-1301 (1984)), double-strand break repair (Mandecki, *Proc. Natl. Acad. Sci. USA,* 83: 7177-7181 (1986)), mutagenesis by polynucleotide chain termination methods (U.S. Pat. No. 5,965,408), and error-prone PCR (Leung et al., *Biotechniques,* 1: 11-15 (1989)).

Following sequence verification, the mutant human growth hormone of the present invention can be produced using routine techniques in the field of recombinant genetics, relying on the polynucleotide sequences encoding the polypeptide disclosed herein.

To obtain high level expression of a nucleic acid encoding a mutant human growth hormone of the present invention, one typically subclones a polynucleotide encoding the mutant human growth hormone into an expression vector that contains a strong promoter to direct transcription, a transcription/translation terminator and a ribosome binding site for translational initiation. Suitable bacterial promoters are well known in the art and described, e.g., in Sambrook and Russell, supra, and Ausubel et al., supra. Bacterial expression systems for expressing the wild-type or mutant human growth hormone are available in, e.g., *E. coli, Bacillus* sp., *Salmonella,* and *Caulobacter.* Kits for such expression systems are commercially available. Eukaryotic expression systems for mammalian cells, yeast, and insect cells are well known in the art and are also commercially available.

When periplasmic expression of a recombinant protein (e.g., a hGH mutant of the present invention) is desired, the expression vector further comprises a sequence encoding a secretion signal, such as the *E. coli* OppA (Periplasmic Oligopeptide Binding Protein) secretion signal or a modified version thereof, which is directly connected to 5' of the coding sequence of the protein to be expressed. This signal sequence directs the recombinant protein produced in cytoplasm through the cell membrane into the periplasmic space. The expression vector may further comprise a coding sequence for signal peptidase 1, which is capable of enzymatically cleaving the signal sequence when the recombinant protein is entering the periplasmic space. More detailed description for periplasmic production of a recombinant protein can be found in, e.g., Gray et al., *Gene* 39: 247-254 (1985), U.S. Pat. Nos. 6,160,089 and 6,436,674.

As discussed above, a person skilled in the art will recognize that various conservative substitutions can be made to any wild-type or mutant human growth hormone or its coding sequence while still retaining the biological activity of the human growth hormone. Moreover, modifications of a polynucleotide coding sequence may also be made to accommodate preferred codon usage in a particular expression host without altering the resulting amino acid sequence.

Standard transfection methods are used to produce bacterial, mammalian, yeast, insect, or plant cell lines that express large quantities of the mutant human growth hormone, which are then purified using standard techniques (see, e.g., Colley et al., *J. Biol. Chem.* 264: 17619-17622 (1989); *Guide to*

*Protein Purification*, in *Methods in Enzymology*, vol. 182 (Deutscher, ed., 1990)). Transformation of eukaryotic and prokaryotic cells are performed according to standard techniques (see, e.g., Morrison, *J. Bact.* 132: 349-351 (1977); Clark-Curtiss & Curtiss, *Methods in Enzymology* 101: 347-362 (Wu et al., eds, 1983).

Any of the well known procedures for introducing foreign nucleotide sequences into host cells may be used. These include the use of calcium phosphate transfection, polybrene, protoplast fusion, electroporation, liposomes, microinjection, plasma vectors, viral vectors and any of the other well known methods for introducing cloned genomic DNA, cDNA, synthetic DNA, or other foreign genetic material into a host cell (see, e.g., Sambrook and Russell, supra). It is only necessary that the particular genetic engineering procedure used be capable of successfully introducing at least one gene into the host cell capable of expressing the mutant human growth hormone.

After the expression vector is introduced into appropriate host cells, the transfected cells are cultured under conditions favoring expression of the mutant human growth hormone. The cells are then screened for the expression of the recombinant polypeptide, which is subsequently recovered from the culture using standard techniques (see, e.g., Scopes, *Protein Purification: Principles and Practice* (1982); U.S. Pat. No. 4,673,641; Ausubel et al., supra; and Sambrook and Russell, supra).

Several general methods for screening gene expression are well known among those skilled in the art. First, gene expression can be detected at the nucleic acid level. A variety of methods of specific DNA and RNA measurement using nucleic acid hybridization techniques are commonly used (e.g., Sambrook and Russell, supra). Some methods involve an electrophoretic separation (e.g., Southern blot for detecting DNA and Northern blot for detecting RNA), but detection of DNA or RNA can be carried out without electrophoresis as well (such as by dot blot). The presence of nucleic acid encoding a mutant human growth hormone in transfected cells can also be detected by PCR or RT-PCR using sequence-specific primers.

Second, gene expression can be detected at the polypeptide level. Various immunological assays are routinely used by those skilled in the art to measure the level of a gene product, particularly using polyclonal or monoclonal antibodies that react specifically with a mutant human growth hormone of the present invention, such as a polypeptide having the amino acid sequence of SEQ ID NO:3, 4, or 5, (e.g., Harlow and Lane, *Antibodies, A Laboratory Manual, Chapter* 14, Cold Spring Harbor, 1988; Kohler and Milstein, *Nature,* 256: 495-497 (1975)). Such techniques require antibody preparation by selecting antibodies with high specificity against the mutant human growth hormone or an antigenic portion thereof. The methods of raising polyclonal and monoclonal antibodies are well established and their descriptions can be found in the literature, see, e.g., Harlow and Lane, supra; Kohler and Milstein, *Eur. J. Immunol.,* 6: 511-519 (1976). More detailed descriptions of preparing antibody against the mutant human growth hormone of the present invention and conducting immunological assays detecting the mutant human growth hormone are provided in a later section.

Purification of Recombinantly Produced Mutant hGH

In one exemplary embodiment, art-recognized methods for purifying bacterially-expressed peptides are utilized. For example, when the mutant human growth hormones of the present invention are produced recombinantly by transformed bacteria in large amounts, typically after promoter induction, although expression can be constitutive, the proteins may form insoluble aggregates. There are several protocols that are suitable for purification of protein inclusion bodies. Purification of aggregate proteins (hereinafter referred to as inclusion bodies) typically involves the extraction, separation and/or purification of inclusion bodies by disruption of bacterial cells, e.g., by incubation in a buffer of about 100-150 µg/ml lysozyme and 0.1% Nonidet P40, a non-ionic detergent. The cell suspension can be ground using a Polytron grinder (Brinkman Instruments, Westbury, N.Y.). Alternatively, the cells can be sonicated on ice. Alternate methods of lysing bacteria are described in Ausubel et al. and Sambrook and Russell, both supra, and will be apparent to those of skill in the art.

The cell suspension is generally centrifuged and the pellet containing the inclusion bodies resuspended in buffer which does not dissolve but washes the inclusion bodies, e.g., 20 mM Tris-HCl (pH 7.2), 1 mM EDTA, 150 mM NaCl and 2% Triton-X 100, a non-ionic detergent. It may be necessary to repeat the wash step to remove as much cellular debris as possible. The remaining pellet of inclusion bodies may be resuspended in an appropriate buffer (e.g., 20 mM sodium phosphate, pH 6.8, 150 mM NaCl). Other appropriate buffers will be apparent to those of skill in the art.

Following the washing step, the inclusion bodies are solubilized by the addition of a solvent that is both a strong hydrogen acceptor and a strong hydrogen donor (or a combination of solvents each having one of these properties). The proteins that formed the inclusion bodies may then be renatured by dilution or dialysis with a compatible buffer. Suitable solvents include, but are not limited to, urea (from about 4 M to about 8 M), formamide (at least about 80%, volume/volume basis), and guanidine hydrochloride (from about 4 M to about 8 M). Some solvents that are capable of solubilizing aggregate-forming proteins, such as SDS (sodium dodecyl sulfate) and 70% formic acid, may be inappropriate for use in this procedure due to the possibility of irreversible denaturation of the proteins, accompanied by a lack of immunogenicity and/or activity. Although guanidine hydrochloride and similar agents are denaturants, this denaturation is not irreversible and renaturation may occur upon removal (by dialysis, for example) or dilution of the denaturant, allowing reformation of the immunologically and/or biologically active protein of interest. After solubilization, the protein can be separated from other bacterial proteins by standard separation techniques. For further description of purifying recombinant human growth hormone from bacterial inclusion body, see, e.g., Patra et al., *Protein Expression and Purification* 18: 182-190 (2000).

Alternatively, it is possible to purify recombinant polypeptides, e.g., a mutant human growth hormone, from bacterial periplasm. Where the recombinant protein is exported into the periplasm of the bacteria, the periplasmic fraction of the bacteria can be isolated by cold osmotic shock in addition to other methods known to those of skill in the art (see e.g., Ausubel et al., supra). To isolate recombinant proteins from the periplasm, the bacterial cells are centrifuged to form a pellet. The pellet is resuspended in a buffer containing 20% sucrose. To lyse the cells, the bacteria are centrifuged and the pellet is resuspended in ice-cold 5 mM $MgSO_4$ and kept in an ice bath for approximately 10 minutes. The cell suspension is centrifuged and the supernatant decanted and saved. The recombinant proteins present in the supernatant can be separated from the host proteins by standard separation techniques well known to those of skill in the art.

Standard Protein Separation Techniques for Purification

When a recombinant polypeptide, e.g., the mutant human growth hormone of the present invention, is expressed in host cells in a soluble form, its purification can follow the standard protein purification procedure described below.

Solubility Fractionation

Often as an initial step, and if the protein mixture is complex, an initial salt fractionation can separate many of the unwanted host cell proteins (or proteins derived from the cell culture media) from the recombinant protein of interest, e.g., a mutant human growth hormone of the present invention. The preferred salt is ammonium sulfate. Ammonium sulfate precipitates proteins by effectively reducing the amount of water in the protein mixture. Proteins then precipitate on the basis of their solubility. The more hydrophobic a protein is, the more likely it is to precipitate at lower ammonium sulfate concentrations. A typical protocol is to add saturated ammonium sulfate to a protein solution so that the resultant ammonium sulfate concentration is between 20-30%. This will precipitate the most hydrophobic proteins. The precipitate is discarded (unless the protein of interest is hydrophobic) and ammonium sulfate is added to the supernatant to a concentration known to precipitate the protein of interest. The precipitate is then solubilized in buffer and the excess salt removed if necessary, through either dialysis or diafiltration. Other methods that rely on solubility of proteins, such as cold ethanol precipitation, are well known to those of skill in the art and can be used to fractionate complex protein mixtures.

Size Differential Filtration

Based on a calculated molecular weight, a protein of greater and lesser size can be isolated using ultrafiltration through membranes of different pore sizes (for example, Amicon or Millipore membranes). As a first step, the protein mixture is ultrafiltered through a membrane with a pore size that has a lower molecular weight cut-off than the molecular weight of a protein of interest, e.g., a mutant human growth hormone. The retentate of the ultrafiltration is then ultrafiltered against a membrane with a molecular cut off greater than the molecular weight of the protein of interest. The recombinant protein will pass through the membrane into the filtrate. The filtrate can then be chromatographed as described below.

Column Chromatography

The proteins of interest (such as the mutant human growth hormone of the present invention) can also be separated from other proteins on the basis of their size, net surface charge, hydrophobicity, or affinity for ligands. In addition, antibodies raised against human growth hormone can be conjugated to column matrices and the human growth hormone immunopurified. All of these methods are well known in the art.

It will be apparent to one of skill that chromatographic techniques can be performed at any scale and using equipment from many different manufacturers (e.g., Pharmacia Biotech).

Immunoassays for Detection of Mutant hGH Expression

To confirm the production of a recombinant mutant human growth hormone, immunological assays may be useful to detect in a sample the expression of the polypeptide. Immunological assays are also useful for quantifying the expression level of the recombinant hormone. Antibodies against a mutant human growth hormone are necessary for carrying out these immunological assays.

Methods for producing polyclonal and monoclonal antibodies that react specifically with an immunogen of interest are known to those of skill in the art (see, e.g., Coligan, *Current Protocols in Immunology* Wiley/Greene, N.Y., 1991; Harlow and Lane, *Antibodies: A Laboratory Manual* Cold Spring Harbor Press, NY, 1989; Stites et al. (eds.) *Basic and Clinical Immunology* (4th ed.) Lange Medical Publications, Los Altos, Calif., and references cited therein; Goding, *Monoclonal Antibodies: Principles and Practice* (2d ed.) Academic Press, New York, N.Y., 1986; and Kohler and Milstein *Nature* 256: 495-497, 1975). Such techniques include antibody preparation by selection of antibodies from libraries of recombinant antibodies in phage or similar vectors (see, Huse et al., *Science* 246: 1275-1281, 1989; and Ward et al., *Nature* 341: 544-546, 1989).

Immunoassays for Detecting Mutant hGH Expression

Once antibodies specific for a mutant human growth hormone of the present invention are available, the amount of the polypeptide in a sample, e.g., a cell lysate, can be measured by a variety of immunoassay methods providing qualitative and quantitative results to a skilled artisan. For a review of immunological and immunoassay procedures in general see, e.g., Stites, supra; U.S. Pat. Nos. 4,366,241; 4,376,110; 4,517,288; and 4,837,168.

Glycosylation and Glycoconjugation of the Mutant hGH

Glycosylation and Glycoconjugation by Enzymatic Methods

Post-expression in vitro modification of peptides is an attractive strategy to remedy the deficiencies of methods that rely on controlling glycosylation by engineering expression systems, including both modification of glycan structures or introduction of glycans at novel sites. A comprehensive arsenal of enzymes that transfer saccharide donor moieties is becoming available, making in vitro enzymatic synthesis of glycoconjugates with custom designed glycosylation patterns and glycosyl structures possible. See, for example, U.S. Pat. Nos. 5,876,980; 6,030,815; 5,728,554; 5,922,577; and published patent applications WO 98/31826; WO 01/88117; WO 03/031464; WO 03/046150; WO 03/045980; WO 03/093448; WO 04/009838; US2002/142370; US2003/040037; US2003/180835; US2004/063911; US2003/207406; and US2003/124645.

The invention provides methods for preparing conjugates of glycosylated and unglycosylated mutant human growth hormones, which have new glycosylation sites that do not exist in the corresponding wild-type hGH. Such conjugation may take place directly on the appropriate sugar units of a glycosylated mutant hGH, or following the removal (i.e., "trimming back") of any undesired sugar units. The conjugates are formed between peptides and diverse species such as water-soluble polymers, therapeutic moieties, diagnostic moieties, targeting moieties and the like. Also provided are conjugates that include two or more peptides linked together through a linker arm, i.e., multifunctional conjugates. The multi-functional conjugates of the invention can include two or more copies of the same peptide or a collection of diverse peptides with different structures, and/or properties.

The conjugates of the invention are formed by the enzymatic attachment of a modified sugar to the glycosylated or unglycosylated peptide. The modified sugar, when interposed between the peptide and the modifying group on the sugar becomes what is referred to herein as "a glycosyl linking group," e.g., an intact glycosyl linking group. Using the exquisite selectivity of enzymes, such as glycosyltransferases, the present method provides peptides that bear a desired group at one or more specific locations. Thus, according to the present invention, a modified sugar is attached directly to a selected locus on the peptide chain or, alternatively, the modified sugar is appended onto a carbohydrate moiety of a glycopeptide. Peptides in which modified sugars are bound to both a glycopeptide carbohydrate and directly to an amino acid residue of the peptide backbone are also within the scope of the present invention.

In contrast to known chemical and enzymatic peptide elaboration strategies, the methods of the invention make it possible to assemble peptides and glycopeptides that have a substantially homogeneous derivatization pattern; the enzymes used in the invention are generally selective for a particular amino acid residue or combination of amino acid residues of the peptide. The methods are also practical for large-scale production of modified peptides and glycopeptides. Thus, the methods of the invention provide a practical means for large-scale preparation of glycopeptides having preselected uniform derivatization patterns. The methods are particularly well suited for modification of therapeutic peptides, including but not limited to, glycopeptides that are incompletely glycosylated during production in cell culture cells (e.g., mammalian cells, insect cells, plant cells, fungal cells, yeast cells, or prokaryotic cells) or transgenic plants or animals.

The present invention also provides conjugates of glycosylated and unglycosylated peptides with increased therapeutic half-life due to, for example, resistance to proteolysis, reduced clearance rate, or reduced rate of uptake by the immune or reticuloendothelial system (RES), etc. Moreover, the methods of the invention provide a means for masking antigenic determinants on peptides, thus reducing or eliminating a host immune response against the peptide. Selective attachment of targeting agents can also be used to target a peptide to a particular tissue or cell surface receptor that is specific for the particular targeting agent.

The Conjugates

In a first aspect, the present invention provides a conjugate between one or more selected modifying groups, e.g. PEG, and a peptide that has an in vivo activity similar or otherwise analogous to art-recognized hGH. The modifying group(s) may be attached at a mutant glycosylation site or at a site that is present in the wild type peptide.

As discussed herein, the selected modifying moiety is essentially any species that can be attached to a saccharide unit, resulting in a modified sugar that is recognized by an appropriate transferase enzyme, which appends the modified sugar onto the peptide, or a glycosyl residue attached thereto. The saccharide component of the modified sugar, when interposed between the peptide and a selected moiety, becomes a "glycosyl linking group," e.g., an "intact glycosyl linking group." The glycosyl linking group is formed from any mono- or oligo-saccharide that, after modification with the modifying group, is a substrate for an enzyme that adds the modified sugar to an amino acid or glycosyl residue of a peptide.

In some exemplary embodiments of the invention, the hGH peptide is conjugated to one or more polymeric modifying moieties through a glycosyl linking group. The polymeric modifying moiety can be attached at any position of a glycosyl moiety of hGH. Moreover, the polymeric modifying moiety can be bound to a glycosyl residue at any position of a wild type or mutant hGH amino acid sequence. Those of ordinary skill in the art will therefore appreciate that an hGH peptide can be conjugated to a plurality of the same or different polymeric modifying moieties via a single glycosyl linking group or via multiple glycosyl linking groups.

Exemplary hGH peptide conjugates include a glycosyl linking group having a formula selected from:

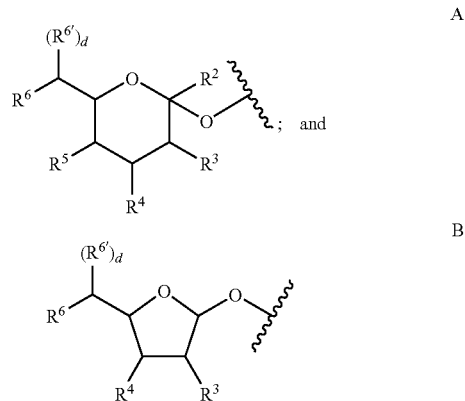

In Formulae A and B, $R^2$ is H, $CH_2OR^7$, $COOR^7$, $COO^-M^+$ or $OR^7$, in which $R^7$ represents H, substituted or unsubstituted alkyl or substituted or unsubstituted heteroalkyl. When $COOR^7$ is a carboxylic acid or carboxylate, both forms are represented by the designation of the single structure $COO^-$ or COOH. The symbols $R^3$, $R^4$, $R^5$, $R^6$ and $R^{6'}$ independently represent H, substituted or unsubstituted alkyl, $OR^8$, $NHC(O)R^9$. $M^+$ is a metal. The index d is 0 or 1. $R^8$ and $R^9$ are independently selected from H, substituted or unsubstituted alkyl, substituted or unsubstituted heteroalkyl, sialic acid or polysialic acid. At least one of $R^3$, $R^4$, $R^5$, $R^6$ or $R^{6'}$ includes a polymeric modifying moiety e.g., PEG. In an exemplary embodiment, $R^6$ and $R^{6'}$, together with the carbon to which they are attached are components of the pyruvyl side chain of sialic acid. In a further exemplary embodiment, this side chain is functionalized with the polymeric modifying moiety. In another exemplary embodiment, $R^6$ and $R^{6'}$, together with the carbon to which they are attached are components of the side chain of sialic acid and the polymeric modifying moiety is a component of $R^5$.

In exemplary embodiments of the present invention, the polymeric modifying moiety is bound to the glycosyl linking group, generally through a heteroatom on the glycosyl core (e.g., N, O), through a linker, L, as shown below:

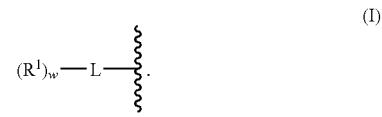

$R^1$ is the polymeric modifying group and L is selected from a bond and a linking group. The index w represents an integer selected from 1-6, preferably 1-3 and more preferably 1-2. Exemplary linking groups include substituted or unsubstituted alkyl, substituted or unsubstituted heteroalkyl moieties and sialic acid. An exemplary component of the linker is an acyl moiety. Another exemplary linking group is an amino acid residue (e.g., cysteine, serine, lysine, and short oligopeptides, e.g., Lys-Lys, Lys-Lys-Lys, Cys-Lys, Ser-Lys, etc.)

When L is a bond, it is formed by reaction of a reactive functional group on a precursor of $R^1$ and a reactive functional group of complementary reactivity on a precursor of the glycosyl linking group. When L is a non-zero order linking group, L can be in place on the glycosyl moiety prior to reaction with the $R^1$ precursor. Alternatively, the precursors of $R^1$ and L can be incorporated into a preformed cassette that is subsequently attached to the glycosyl moiety.

An exemplary compound according to the invention has a structure according to Formulae A or B, in which at least one of $R^2$, $R^3$, $R^4$, $R^5$, $R^6$ or $R^{6'}$ has the formula:

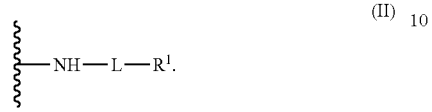
(II)

In another example according to this embodiment at least one of $R^2$, $R^3$, $R^4$, $R^5$, $R^6$ or $R^{6'}$ has the formula:

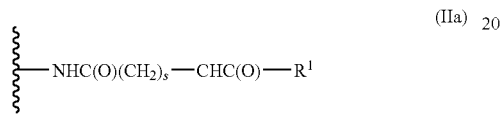
(IIa)

in which s is an integer from 0 to 20 and $R^1$ is a linear polymeric modifying moiety.

In an exemplary embodiment, the polymeric modifying moiety-linker construct is a branched structure that includes two or more polymeric chains attached to central moiety. In this embodiment, the construct has a structure according to Formula I.

When L is a bond it is formed between a reactive functional group on a precursor of $R^1$ and a reactive functional group of complementary reactivity on the saccharyl core. When L is a non-zero order linker, a precursor of L can be in place on the glycosyl moiety prior to reaction with the $R^1$ precursor. Alternatively, the precursors of $R^1$ and L can be incorporated into a preformed cassette that is subsequently attached to the glycosyl moiety. As set forth herein, the selection and preparation of precursors with appropriate reactive functional groups is within the ability of those skilled in the art. Moreover, coupling the precursors proceeds by chemistry that is well understood in the art.

In an exemplary embodiment, L is a linking group that is formed from an amino acid, or small peptide (e.g., 1-4 amino acid residues) providing a modified sugar in which the polymeric modifying moiety is attached through a substituted alkyl linker. Exemplary linkers include glycine, lysine, serine and cysteine. The PEG moiety can be attached to the amine moiety of the linker through an amide or urethane bond. The PEG is linked to the sulfur or oxygen atoms of cysteine and serine through thioether or ether bonds, respectively.

In an exemplary embodiment, $R^5$ includes the polymeric modifying moiety. In another exemplary embodiment, $R^5$ includes both the polymeric modifying moiety and a linker, L, joining the modifying moiety to the remainder of the molecule. As discussed above, L can be a linear or branched structure. Similarly, the polymeric modifying moiety can be branched or linear.

In an exemplary embodiment, Formula I has a structure according to the following formula:

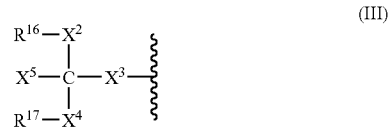
(III)

in which the moiety:

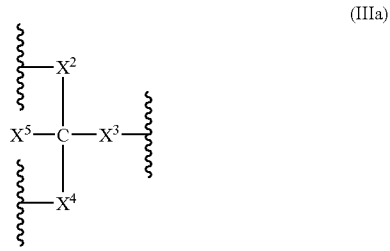
(IIIa)

is the linker arm, L, and $R^{16}$ and $R^{17}$ are $R^1$. $R^{16}$ and $R^{17}$ are independently selected polymeric modifying moieties. C is carbon. $X^5$ is preferably a non-reactive group (e.g., H, unsubstituted alkyl, unsubstituted heteroalkyl), and can be a polymeric arm. $X^2$ and $X^4$ are linkage fragments that are preferably essentially non-reactive under physiological conditions, which may be the same or different. An exemplary linker includes neither aromatic nor ester moieties. Alternatively, these linkages can include one or more moiety that is designed to degrade under physiologically relevant conditions, e.g., esters, disulfides, etc. $X^2$ and $X^4$ join polymeric arms $R^{16}$ and $R^{17}$ to C. Exemplary linkage fragments for $X^2$, $X^3$ and $X^4$ are independently selected and include S, SC(O)NH, HNC(O)S, SC(O)O, O, NH, NHC(O), (O)CNH and NHC(O)O, and OC(O)NH, $CH_2S$, $CH_2O$, $CH_2CH_2O$, $CH_2CH_2S$, $(CH_2)_oO$, $(CH_2)_oS$ or $(CH_2)_oY'$-PEG wherein, Y' is S, NH, NHC(O), C(O)NH, NHC(O)O, OC(O)NH, or O and o is an integer from 1 to 50. In an exemplary embodiment, the linkage fragments $X^2$ and $X^4$ are different linkage fragments.

In an exemplary embodiment, Formula I has a structure according to the following formula:

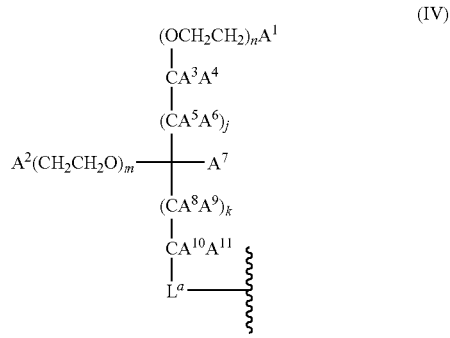
(IV)

the indices m and n are integers independently selected from 0 to 5000. $A^1$, $A^2$, $A^3$, $A^4$, $A^5$, $A^6$, $A^7$, $A^8$, $A^9$, $A^{10}$ and $A^{11}$ are members independently selected from H, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, —NA$^{12}$A$^{13}$, —OA$^{12}$ and —SiA$^{12}$A$^{13}$. The indices j and k are integers independently selected from 0 to 20. A$^{12}$ and A$^{13}$ are members independently selected from substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

In an exemplary embodiment, Formula IV has a structure according to the following formula:

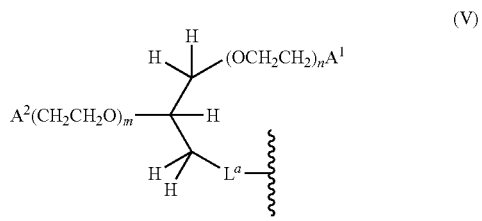

(V)

In an exemplary embodiment, A$^1$ and A$^2$ are each —OCH$_3$ or H.

In one embodiment, the present invention provides an hGH peptide comprising the moiety:

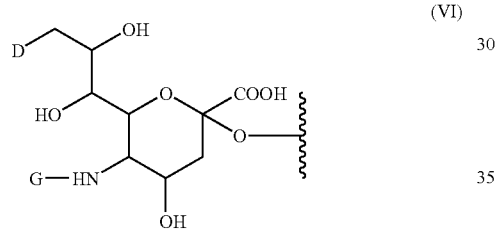

(VI)

wherein D is a member selected from —OH and R$^1$-L-HN—; G is a member selected from H and R$^1$-L- and —C(O)(C$_1$-C$_6$)alkyl; R$^1$ is a moiety comprising a straight-chain or branched poly(ethylene glycol) residue; and L is a linker, e.g., a bond ("zero order"), substituted or unsubstituted alkyl and substituted or unsubstituted heteroalkyl. In exemplary embodiments, when D is OH, G is R$^1$-L-, and when G is —C(O)(C$_1$-C$_6$)alkyl, D is R$^1$-L-NH—.

As set forth herein, the selection and preparation of precursors with appropriate reactive functional groups is within the ability of those skilled in the art. Moreover, coupling of the precursors proceeds by chemistry that is well understood in the art.

In an exemplary embodiment, the selected modifying moiety is a water-soluble polymer, e.g., m-PEG. The PEG moiety is attached directly to a glycosyl linker, preferably an intact glycosyl linker, or via a non-glycosyl linker, e.g., substituted or unsubstituted alkyl, substituted or unsubstituted heteroalkyl. The glycosyl linker is covalently attached to an amino acid residue or a glycosyl residue of the peptide. The invention also provides conjugates in which an amino acid residue and a glycosyl residue are modified with a glycosyl linker.

An exemplary water-soluble polymer is poly(ethylene glycol), e.g., methoxy-poly(ethylene glycol). The poly(ethylene glycol) used in the present invention is not restricted to any particular form or molecular weight range. As discussed herein, the PEG of use in the conjugates of the invention can be linear or branched. For unbranched poly(ethylene glycol) molecules, the molecular weight preferably ranges from about 500 to 100,000. A molecular weight of 2000-60,000 is preferably used and preferably of from 5,000 to about 30,000. More preferably, the molecular weight is from about 5,000 to about 30,000.

In another embodiment the poly(ethylene glycol) is a branched PEG having more than one PEG moiety attached. Examples of branched PEGs are described in U.S. Pat. Nos. 5,932,462; 5,342,940; 5,643,575; 5,919,455; 6,113,906; 5,183,660; WO 02/09766; Kodera Y., *Bioconjugate Chemistry* 5: 283-288 (1994); and Yamasaki et al., *Agric. Biol. Chem.*, 52: 2125-2127, 1998. In preferred embodiments of the present invention, the molecular weight of each poly (ethylene glycol) of the branched PEG is less than or equal to 40,000 daltons.

An exemplary precursor of use to form the branched PEG containing peptide conjugates according to this embodiment of the invention has the formula:

(IIIb)

The branched polymer species according to this formula are essentially pure water-soluble polymers. X$^{3'}$ is a moiety that includes an ionizable (e.g., OH, COOH, H$_2$PO$_4$, HSO$_3$, NH$_2$, and salts thereof, etc.) or other reactive functional group, e.g., infra. C is carbon. X$^5$, R$^{16}$ and R$^{17}$ are independently selected from non-reactive groups (e.g., H, unsubstituted alkyl, unsubstituted heteroalkyl) and polymeric arms (e.g., PEG). X$^2$ and X$^4$ are linkage fragments that are preferably essentially non-reactive under physiological conditions, which may be the same or different. An exemplary linker includes neither aromatic nor ester moieties. Alternatively, these linkages can include one or more moieties that are designed to degrade under physiologically relevant conditions, e.g., esters, disulfides, etc. X$^2$ and X$^4$ join polymeric arms R$^{16}$ and R$^{17}$ to C. When X$^{3'}$ is reacted with a reactive functional group of complementary reactivity on a linker, sugar or linker-sugar cassette, X$^{3'}$ is converted to a component of linkage fragment X$^3$.

With respect to the glycosyl linking group, it can be, or can include, a saccharide moiety that is degradatively modified before or during the addition of the modifying group. For example, the glycosyl linking group can be derived from a saccharide residue that is produced by oxidative degradation of an intact saccharide to the corresponding aldehyde, e.g., via the action of metaperiodate, and subsequently converted to a Schiff base with an appropriate amine, which is then reduced to the corresponding amine. Exemplary intact glycosyl linking groups include sialic acid moieties that are derivatized with PEG.

Exemplary conjugates of the present invention can be characterized by the general structure:

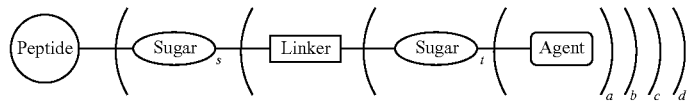

in which the symbols a, b, c, and d represent a positive, non-zero integer and s and t are either 0 or a positive integer. The "agent" is a therapeutic agent, a bioactive agent, a detectable label, water-soluble moiety (e.g., PEG, m-PEG, PPG, and m-PPG) or the like. The "agent" can be a peptide, e.g., enzyme, antibody, antigen, etc. The linker can be any of a wide array of linking groups, infra. Alternatively, the linker may be a single bond or a "zero order linker."

In addition to providing conjugates that are formed through an enzymatically added glycosyl linking group, the present invention provides conjugates that are highly homogenous in their substitution patterns. Using the methods of the invention, it is possible to form peptide conjugates in which essentially all of the modified sugar moieties across a population of conjugates of the invention are attached to multiple copies of a structurally identical amino acid or glycosyl residue. Thus, in a second aspect, the invention provides a peptide conjugate having a population of water-soluble polymer moieties, which are covalently bound to the peptide through a glycosyl linking group, e.g. an intact glycosyl linking group. In a preferred conjugate of the invention, essentially each member of the population is bound via the glycosyl linking group to a glycosyl residue of the peptide, and each glycosyl residue of the peptide to which the glycosyl linking group is attached has the same structure.

Also provided is a peptide conjugate having a population of water-soluble polymer moieties covalently bound thereto through a glycosyl linking group. In a preferred embodiment, essentially every member of the population of water soluble polymer moieties is bound to an amino acid residue of the peptide via a glycosyl linking group, and each amino acid residue having a glycosyl linking group attached thereto has the same structure.

The present invention also provides conjugates analogous to those described above in which the peptide is conjugated to a therapeutic moiety, diagnostic moiety, targeting moiety, toxin moiety or the like via an intact glycosyl linking group. Each of the above-recited moieties can be a small molecule, natural polymer (e.g., polypeptide) or synthetic polymer.

The peptides of the invention include at least one N-, or O-linked glycosylation site, which is glycosylated with a glycosyl residue that includes a polymeric modifying moiety, e.g. a PEG moiety. In exemplary embodiments, the PEG is covalently attached to the peptide via an intact glycosyl linking group. The glycosyl linking group is covalently attached to either an amino acid residue or a glycosyl residue of the peptide. Alternatively, the glycosyl linking group is attached to one or more glycosyl units of a glycopeptide. The invention also provides conjugates in which a glycosyl linking group is attached to both an amino acid residue and a glycosyl residue.

In an exemplary embodiment, mutant human growth hormone is conjugated to transferrin via a bifunctional linker that includes an intact glycosyl linking group at each terminus of the PEG moiety. For example, one terminus of the PEG linker is functionalized with an intact sialic acid linker that is attached to transferrin and the other is functionalized with an intact GalNAc linker that is attached to the mutant hGH.

The conjugates of the invention can include intact glycosyl linking groups that are mono- or multi-valent (e.g., antennary structures). Thus, conjugates of the invention include both species in which a selected moiety is attached to a peptide via a monovalent glycosyl linking group. Also included within the invention are conjugates in which more than one selected moiety is attached to a peptide via a multivalent linking group.

In a still further embodiment, the invention provides conjugates that localize selectively in a particular tissue due to the presence of a targeting agent as a component of the conjugate. In an exemplary embodiment, the targeting agent is a protein. Exemplary proteins include transferrin (brain, blood pool), HS-glycoprotein (bone, brain, blood pool), antibodies (brain, tissue with antibody-specific antigen, blood pool), coagulation factors V-XII (damaged tissue, clots, cancer, blood pool), serum proteins, e.g., α-acid glycoprotein, fetuin, α-fetal protein (brain, blood pool), β2-glycoprotein (liver, atherosclerosis plaques, brain, blood pool), hGH, GM-CSF, M-CSF, and EPO (immune stimulation, cancers, blood pool, red blood cell overproduction, neuroprotection), albumin (increase in half-life), and lipoprotein E.

The Methods

In addition to the conjugates discussed above, the present invention provides methods for preparing these and other conjugates. Thus, in a further aspect, the invention provides a method of forming a covalent conjugate between a selected moiety and a peptide. Additionally, the invention provides methods for targeting conjugates of the invention to a particular tissue or region of the body. Furthermore, the present invention provides a method for preventing, curing, or ameliorating a disease state by administering a conjugate of the invention to a subject at risk of developing the disease or a subject that has the disease.

In exemplary embodiments, the conjugate is formed between a polymeric modifying moiety, a therapeutic moiety, targeting moiety or a biomolecule, and a glycosylated or non-glycosylated peptide. The polymer, therapeutic moiety or biomolecule is conjugated to the peptide via a glycosyl linking group (or glycosyl residue), which is interposed between, and covalently linked to both the peptide and the modifying group (e.g., water-soluble polymer). The method includes contacting the peptide with a mixture containing a modified sugar and an enzyme, e.g. glycosyltransferase, that conjugates the modified sugar to the substrate. The reaction is conducted under conditions sufficient to form a covalent bond between the modified sugar and the peptide. The sugar moiety of the modified sugar is preferably selected from nucleotide sugars, activated sugars, and sugars that are neither nucleotides nor activated.

The acceptor hGH peptide (glycosylated or non-glycosylated) is typically synthesized de novo, or recombinantly expressed in a prokaryotic cell (e.g., bacterial cell, such as *E. coli*) or in a eukaryotic cell such as a mammalian, yeast, insect, fungal or plant cell. The peptide can be either a full-length protein or a fragment. Moreover, the peptide can be a wild type or mutated peptide. In an exemplary embodiment, the peptide includes a mutation that adds one or more O- or N-linked glycosylation sites to the hGH peptide sequence.

The method of the invention also provides for modification of incompletely glycosylated peptides that are produced recombinantly. Many recombinantly produced glycoproteins are incompletely glycosylated, exposing carbohydrate residues that may have undesirable properties, e.g., immunogenicity, recognition by the RES. Employing a modified sugar in a method of the invention, the peptide can be simultaneously further glycosylated and derivatized with, e.g., a water-soluble polymer, therapeutic agent, or the like. The sugar moiety of the modified sugar can be the residue that would properly be conjugated to the acceptor in a fully glycosylated peptide, or another sugar moiety with desirable properties.

Peptides modified by the methods of the invention can be synthetic or wild-type peptides or they can be mutated peptides, produced by methods known in the art, such as site-directed mutagenesis. Glycosylation of peptides is typically either N-linked or O-linked. An exemplary N-linkage is the attachment of the modified sugar to the side chain of an asparagine residue. The tripeptide sequences asparagine-X-serine and asparagine-X-threonine, where X is any amino acid except proline, are the recognition sequences for enzymatic attachment of a carbohydrate moiety to the asparagine side chain. Thus, the presence of either of these tripeptide sequences in a polypeptide creates a potential glycosylation site. O-linked glycosylation refers to the attachment of one sugar (e.g., N-aceylgalactosamine, galactose, mannose, GlcNAc, glucose, fucose or xylose) to the hydroxy side chain of a hydroxyamino acid, preferably serine or threonine, although 5-hydroxyproline or 5-hydroxylysine may also be used.

Addition of glycosylation sites to a peptide or other structure is conveniently accomplished by altering the amino acid sequence such that it contains one or more glycosylation sites. The addition may also be made by the incorporation of one or more species presenting an —OH group, preferably serine or threonine residues, within the sequence of the peptide (for O-linked glycosylation sites). The addition may be made by mutation or by full chemical synthesis of the peptide. The peptide amino acid sequence is preferably altered through changes at the DNA level, particularly by mutating the DNA encoding the peptide at preselected bases such that codons are generated that will translate into the desired amino acids. The DNA mutation(s) are preferably made using methods known in the art.

In an exemplary embodiment, the glycosylation site is added by shuffling polynucleotides. Polynucleotides encoding a candidate peptide can be modulated with DNA shuffling protocols. DNA shuffling is a process of recursive recombination and mutation, performed by random fragmentation of a pool of related genes, followed by reassembly of the fragments by a polymerase chain reaction-like process. See, e.g., Stemmer, *Proc. Natl. Acad. Sci. USA* 91:10747-10751 (1994); Stemmer, *Nature* 370:389-391 (1994); and U.S. Pat. Nos. 5,605,793, 5,837,458, 5,830,721 and 5,811,238.

The present invention also provides means of adding (or removing) one or more selected glycosyl residues to a peptide, after which a modified sugar is conjugated to at least one of the selected glycosyl residues of the peptide. The present embodiment is useful, for example, when it is desired to conjugate the modified sugar to a selected glycosyl residue that is either not present on a peptide or is not present in a desired amount. Thus, prior to coupling a modified sugar to a peptide, the selected glycosyl residue is conjugated to the peptide by enzymatic or chemical coupling. In another embodiment, the glycosylation pattern of a glycopeptide is altered prior to the conjugation of the modified sugar by the removal of a carbohydrate residue from the glycopeptide. See, for example WO 98/31826.

Addition or removal of any carbohydrate moieties present on the glycopeptide is accomplished either chemically or enzymatically. Chemical deglycosylation is preferably brought about by exposure of the polypeptide variant to the compound trifluoromethanesulfonic acid, or an equivalent compound. This treatment results in the cleavage of most or all sugars except the linking sugar (N-acetylglucosamine or N-acetylgalactosamine), while leaving the peptide intact. Chemical deglycosylation is described by Hakimuddin et al., *Arch. Biochem. Biophys.* 259: 52 (1987) and by Edge et al., *Anal Biochem.* 118: 131 (1981). Enzymatic cleavage of carbohydrate moieties on polypeptide variants can be achieved by the use of a variety of endo- and exo-glycosidases as described by Thotakura et al., *Meth. Enzymol.* 138: 350 (1987).

Chemical addition of glycosyl moieties is carried out by any art-recognized method. Enzymatic addition of sugar moieties is preferably achieved using a modification of the methods set forth herein, substituting native glycosyl units for the modified sugars used in the invention. Other methods of adding sugar moieties are disclosed in U.S. Pat. Nos. 5,876,980, 6,030,815, 5,728,554, and 5,922,577.

Exemplary attachment points for selected glycosyl residue include, but are not limited to: (a) consensus sites for N-linked glycosylation and O-linked glycosylation; (b) terminal glycosyl moieties that are acceptors for a glycosyltransferase; (c) arginine, asparagine and histidine; (d) free carboxyl groups; (e) free sulfhydryl groups such as those of cysteine; (f) free hydroxyl groups such as those of serine, threonine, or hydroxyproline; (g) aromatic residues such as those of phenylalanine, tyrosine, or tryptophan; or (h) the amide group of glutamine. Exemplary methods of use in the present invention are described in WO 87/05330 published Sep. 11, 1987, and in Aplin and Wriston, CRC CRIT. REV. BIOCHEM., pp. 259-306 (1981).

In an exemplary embodiment, the modified sugar, such as those set forth above, is activated as the corresponding nucleotide sugars. Exemplary sugar nucleotides that are used in the present invention in their modified form include nucleotide mono-, di- or triphosphates or analogs thereof. In a preferred embodiment, the modified sugar nucleotide is selected from a UDP-glycoside, CMP-glycoside, or a GDP-glycoside. Even more preferably, the sugar nucleotide portion of the modified sugar nucleotide is selected from UDP-galactose, UDP-galactosamine, UDP-glucose, UDP-glucosamine, GDP-mannose, GDP-fucose, CMP-sialic acid, or CMP-NeuAc. In an exemplary embodiment, the nucleotide phosphate is attached to C-1.

Modified Sugars

The present invention uses modified sugars, such as modified sugar nucleotides, as reactants in the production of hGH conjugates. In the modified sugars of the invention, the sugar moiety is preferably a saccharide, a deoxy-saccharide, an amino-saccharide, or an N-acyl saccharide. The term "saccharide" and its equivalents, "saccharyl," "sugar," and "glycosyl" refer to monomers, dimers, oligomers and polymers.

The sugar moiety is also functionalized with a modifying group. The modifying group is conjugated to the sugar moiety, typically, through conjugation with an amine, sulfhydryl or hydroxyl, e.g., primary hydroxyl, moiety on the sugar. In an exemplary embodiment, the modifying group is attached through an amine moiety on the sugar, e.g., through an amide, a urethane or a urea that is formed through the reaction of the amine with a reactive derivative of the modifying group.

Any sugar can be utilized in the hGH conjugates of the invention. Exemplary sugars that are useful in the conjugates of the invention include, but are not limited to, glucose, galactose, mannose, fucose, and sialic acid. Other useful sugars include amino sugars such as glucosamine, galactosamine, mannosamine, the 5-amine analogue of sialic acid and the like. The sugar can be a structure found in nature or it can be modified to provide a site for conjugating the modifying group. For example, in one embodiment, the invention provides a sialic acid derivative in which the 9-hydroxy moiety is replaced with an amine. The amine is readily derivatized with an activated analogue of a modifying group.

In an exemplary embodiment, the invention utilizes a modified sugar amine that has the formula:

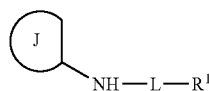

in which J is a glycosyl moiety (e.g. a nucleotide sugar), and L is a bond or a linker and $R^1$ is the modifying group, e.g. a polymeric modifying moiety. Exemplary bonds are those that are formed between an $NH_2$ moiety on the glycosyl moiety and a group of complementary reactivity on the modifying group. For example, when $R^1$ includes a carboxylic acid moiety, such moiety may be activated and coupled with the $NH_2$ moiety on the glycosyl residue, thereby affording a bond having the structure $NHC(O)R^1$. J is preferably a glycosyl moiety that is "intact," i.e. not having been degraded by exposure to conditions that cleave the pyranose or furanose structure, e.g. oxidative conditions, sodium periodate.

Exemplary linkers include alkyl and heteroalkyl moieties. The linkers include linking groups, such as acyl-based linking groups, e.g., —C(O)NH—, —OC(O)NH—, and the like. The linking groups are bonds formed between components of the species of the invention, e.g. between the glycosyl moiety and the linker (L), or between the linker and the modifying group ($R^1$). Other exemplary linking groups are ethers, thioethers and amines. For example, in one embodiment, the linker is an amino acid residue, such as a glycine residue. The carboxylic acid moiety of the glycine is converted to the corresponding amide by reaction with an amine on the glycosyl residue, and the amine of the glycine is converted to the corresponding amide or urethane by reaction with an activated carboxylic acid or carbonate on the rest of the modifying group.

Another exemplary linker is a PEG moiety, e.g. a PEG moiety that is functionalized with an amino acid residue. The PEG linker is conjugated to the glycosyl group through the amino acid residue at one PEG terminus and bound to $R^1$ through the other PEG terminus. Alternatively, the amino acid residue is bound to $R^1$ and the PEG terminus, which is not bound to the amino acid, is bound to the glycosyl group.

An exemplary species of NH-L-$R^1$ has the formula: —NH{C(O)(CH$_2$)$_a$NH}$_s${C(O)(CH$_2$)$_b$(OCH$_2$CH$_2$)$_c$O (CH$_2$)$_d$ NH}$_t$R$^1$, in which the indices s and t are independently 0 or 1. The indices a, b and d are independently integers from 0 to 20, and c is an integer from 1 to 2500. Other similar linkers are based on species in which an —NH moiety is replaced by another group, for example, —S, —O or —CH$_2$. As those of skill will appreciate, one or more of the bracketed moieties corresponding to indices s and t can be replaced with a substituted or unsubstituted alkyl or heteroalkyl moiety.

More particularly, the invention utilizes compounds in which NH-L$^5$-R$^1$ is: NHC(O)(CH$_2$)$_a$NHC(O)(CH$_2$)$_b$(OCH$_2$CH$_2$)$_c$O(CH$_2$)$_d$NHR$^1$, NHC(O)(CH$_2$)$_b$(OCH$_2$CH$_2$)$_c$O(CH$_2$)$_d$NHR$^1$, NHC(O)O(CH$_2$)$_b$(OCH$_2$CH$_2$)$_c$O(CH$_2$)$_d$NHR$^1$, NH(CH$_2$)$_a$NHC(O)(CH$_2$)$_b$(OCH$_2$CH$_2$)$_c$O(CH$_2$)$_d$NHR$^1$, NHC(O)(CH$_2$)$_a$NHR$^1$, NH(CH$_2$)$_a$NHR$^1$, and NHR$^1$. In these formulae, the indices a, b and d are independently selected from the integers from 0 to 20, preferably from 1 to 5. The index c is an integer from 1 to 2500.

In an exemplary embodiment, c is selected such that the PEG moiety is approximately 1 kDa, 2 kDa, 5 kDa, 10 kDa, 15 kDa, 20 kDa, 25 kDa, 30 kDa, 35 kDa, 40 kDa, 45 kDa, 50 kDa, 55 kDa, 60 kDa, 65 kDa, 70 kDa, 75 kDa or 80 kDa.

In the discussion that follows the invention is illustrated by reference to the use of selected derivatives of sialic acid. Those of skill in the art will recognize that the focus of the discussion is for clarity of illustration and that the structures and compositions set forth are generally applicable across the genus of saccharide groups, modified saccharide groups, activated modified saccharide groups and conjugates of modified saccharide groups.

In an exemplary embodiment, J is sialic acid and selected compounds of use in the invention have the formulae:

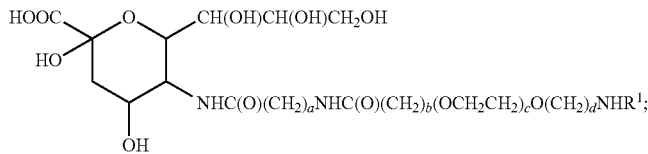
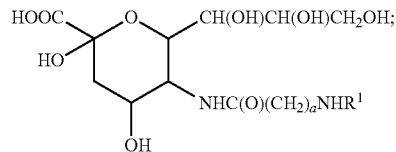
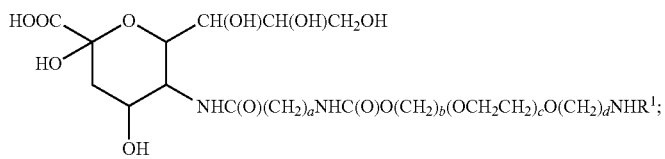
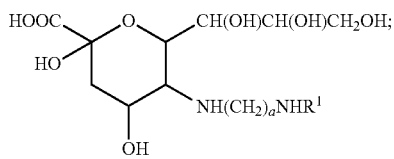

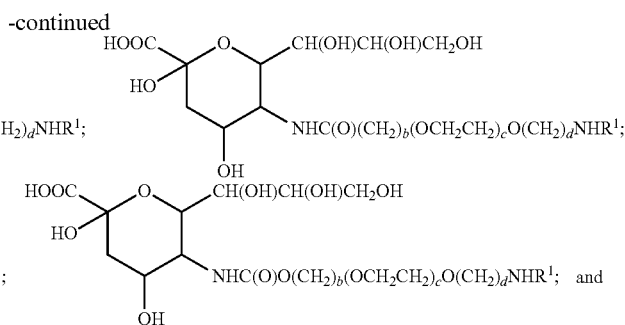
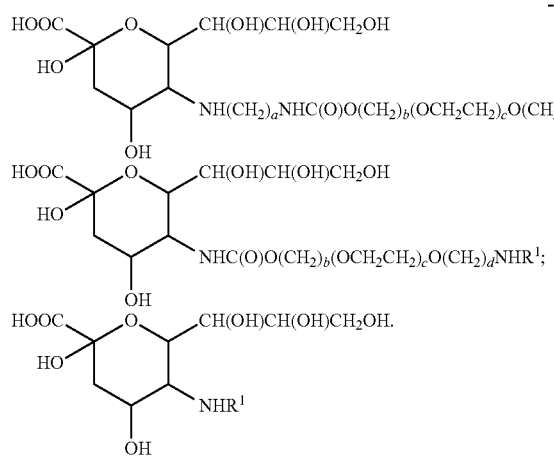

As those of skill in the art will appreciate, the sialic acid moiety in the exemplary compounds above can be replaced with any other amino-saccharide including, but not limited to, glucosamine, galactosamine, mannosamine, their N-acetyl derivatives, and the like.

In another illustrative embodiment, a primary hydroxyl moiety of the sugar is functionalized with a modifying group. For example, the 9-hydroxyl of sialic acid can be converted to the corresponding amine and functionalized to provide a modified sugar according to the invention. Formulae according to this embodiment include:

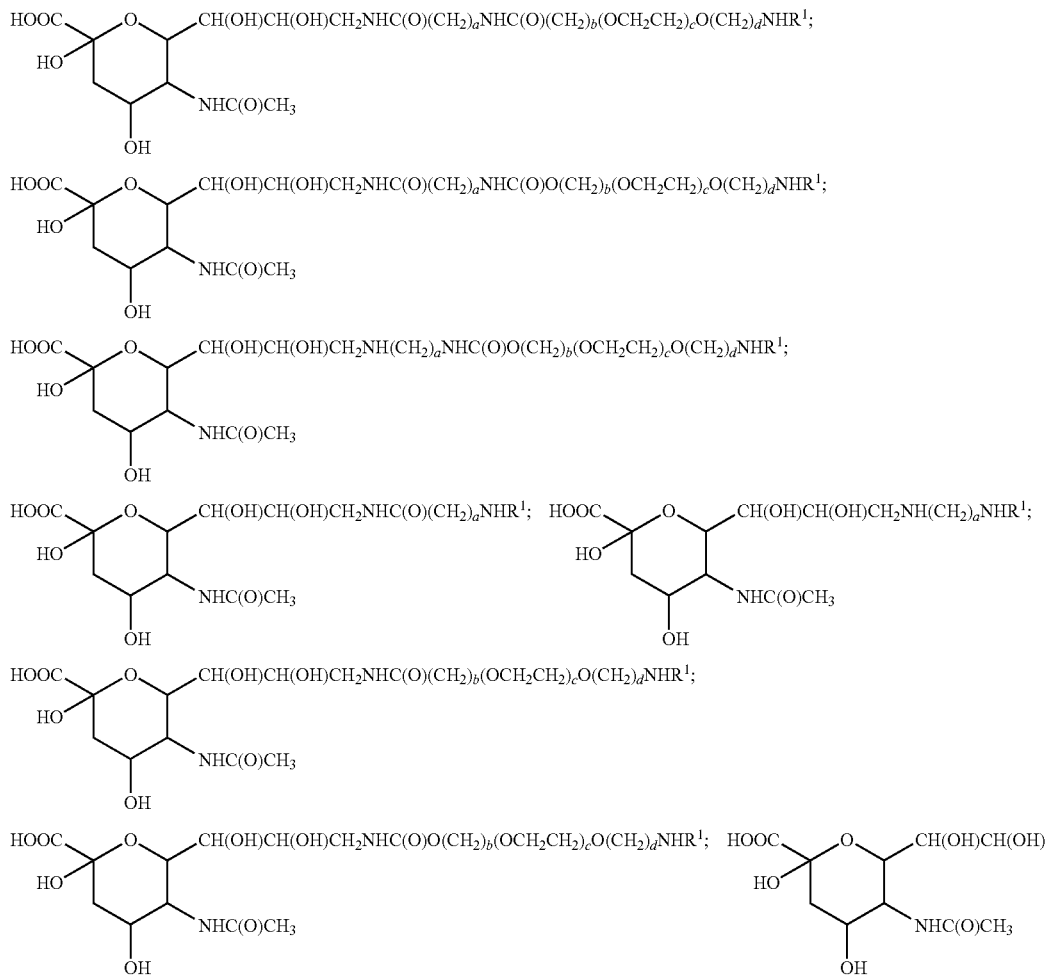

Thus, in an illustrative embodiment in which the glycosyl moiety is sialic acid, the method of the invention utilizes compounds having the formulae:

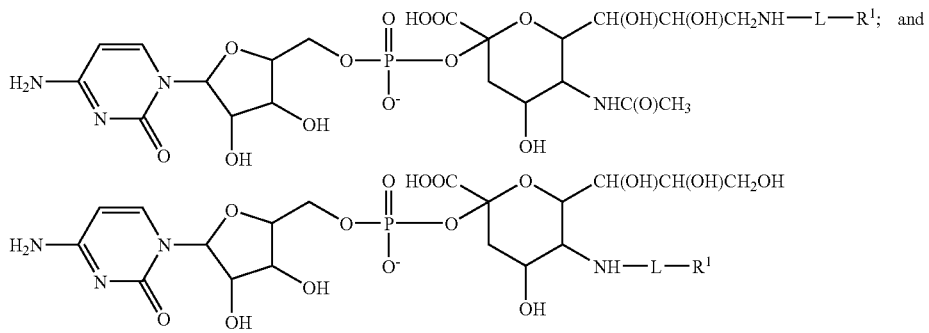

in which L-R$^1$ is as discussed above, and L$^1$-R$^1$ represents a linker bound to the modifying group. As with L, exemplary linker species according to L$^1$ include a bond, alkyl or heteroalkyl moieties.

Moreover, as discussed above, the present invention provides for the use of nucleotide sugars that are modified with a water-soluble polymer, which is either straight-chain or branched. For example, compounds having the formula shown below are of use to prepare conjugates within the scope of the present invention:

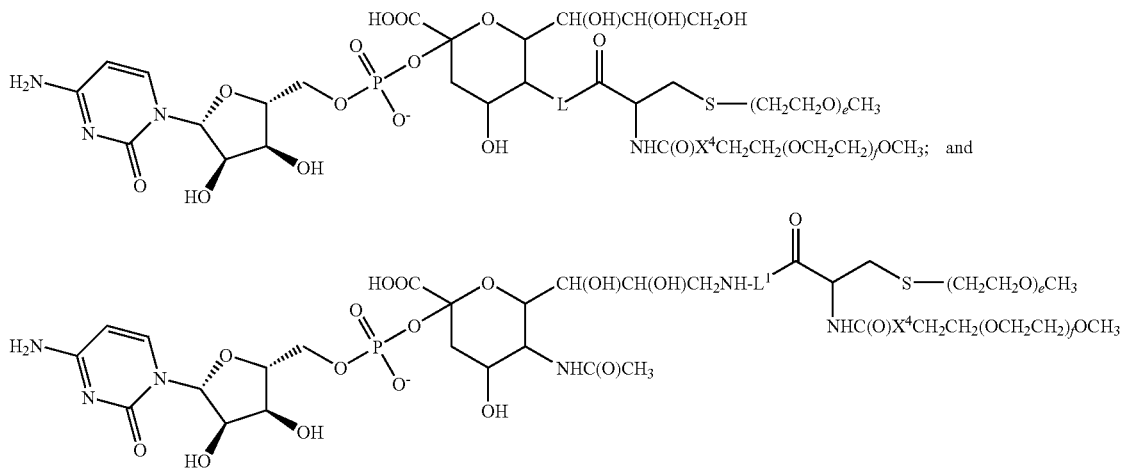

in which X$^4$ is O or a bond.

Selected conjugates according to this motif are based on mannose, galactose or glucose, or on species having the stereochemistry of mannose, galactose or glucose. The general formulae of these conjugates are:

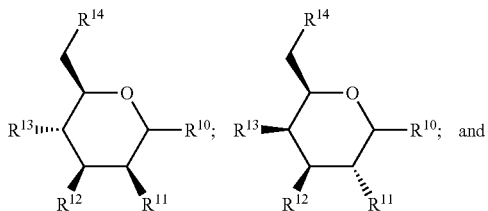

-continued

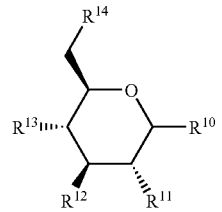

As discussed above, the invention provides saccharides bearing a modifying group, activated analogues of these species and conjugates formed between species such as peptides and lipids and a modified saccharide of the invention.

In another exemplary embodiment, the invention utilizes modified sugars as set forth above that are activated as the corresponding nucleotide sugars. Exemplary sugar nucleotides that are used in the present invention in their modified form include nucleotide mono-, di- or triphosphates or analogs thereof. In a preferred embodiment, the modified sugar nucleotide is selected from a UDP-glycoside, CMP-glycoside, or a GDP-glycoside. Even more preferably, the sugar nucleotide portion of the modified sugar nucleotide is selected from UDP-galactose, UDP-galactosamine, UDP-glucose, UDP-glucosamine, GDP-mannose, GDP-fucose, CMP-sialic acid, or CMP-NeuAc. In an exemplary embodiment, the nucleotide phosphate is attached to C-1.

The invention also provides for the use of sugar nucleotides modified with L-$R^1$ at the 6-carbon position. Exemplary species according to this embodiment include:

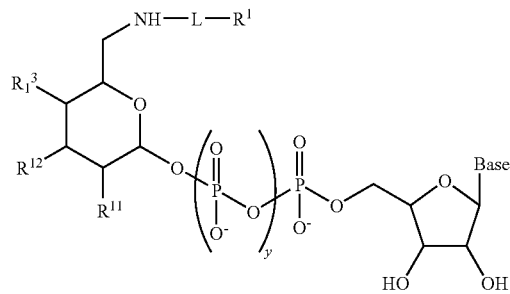

in which the R groups, and L, represent moieties as discussed above. The index "y" is 0, 1 or 2. In an exemplary embodiment, L is a bond between NH and $R^1$. The base is a nucleic acid base.

Exemplary nucleotide sugars of use in the invention in which the carbon at the 6-position is modified include species having the stereochemistry of GDP mannose, e.g.:

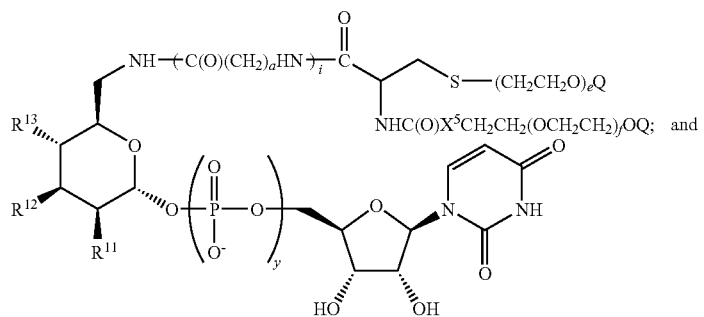

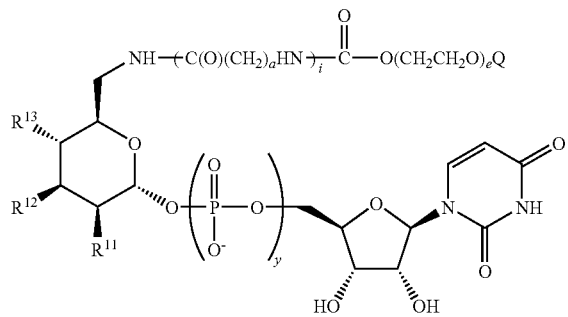

in which $X^5$ is a bond or O. The index i represents 0 or 1. The index a represents an integer from 1 to 20. The indices e and f independently represent integers from 1 to 2500. Q, as discussed above, is H or substituted or unsubstituted $C_1$-$C_6$ alkyl. As those of skill will appreciate, the serine derivative, in which S is replaced with O also falls within this general motif.

In a still further exemplary embodiment, the invention provides a conjugate in which the modified sugar is based on the stereochemistry of UDP galactose. An exemplary nucleotide sugar of use in this invention has the structure:

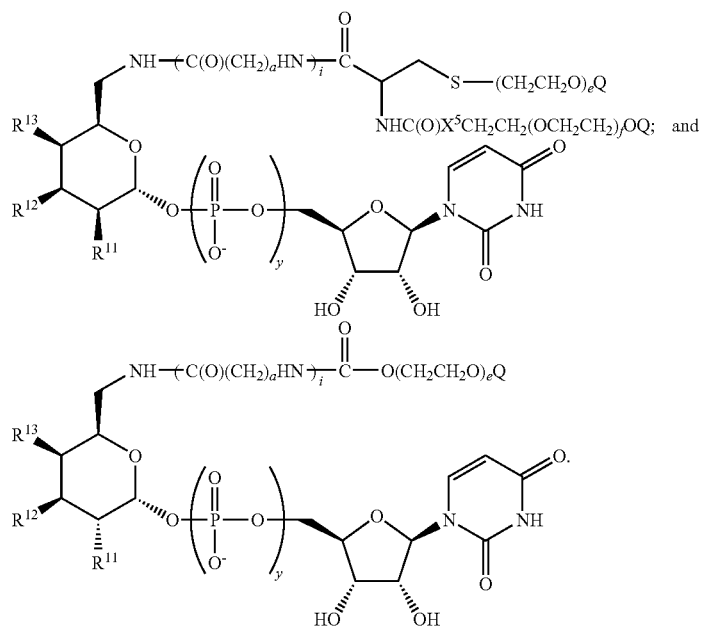

In another exemplary embodiment, the nucleotide sugar is based on the stereochemistry of glucose. Exemplary species according to this embodiment have the formulae:

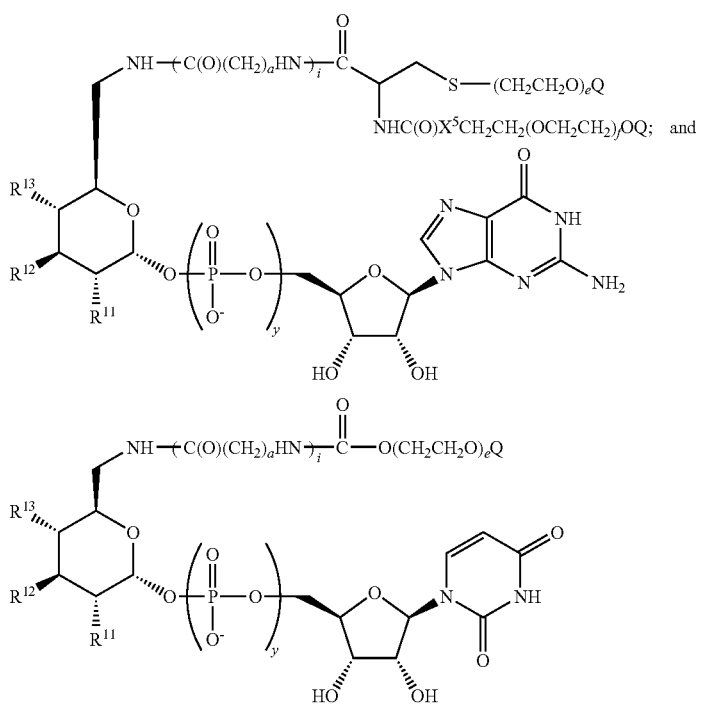

In one embodiment, the invention provides a method for linking hGH and one or more peptide through a linking group. The linking group is of any useful structure and may be selected from straight-chain and branched chain structures. Preferably, each terminus of the linker, which is attached to a peptide, includes a modified sugar (i.e., a nascent intact glycosyl linking group).

In an exemplary method of the invention, two peptides are linked together via a linker moiety that includes a PEG linker. The construct conforms to the general structure set forth in the cartoon above. As described herein, the construct of the invention includes two intact glycosyl linking groups (i.e., s+t=1). The focus on a PEG linker that includes two glycosyl groups is for purposes of clarity and should not be interpreted as limiting the identity of linker arms of use in this embodiment of the invention.

Thus, a PEG moiety is functionalized at a first terminus with a first glycosyl unit and at a second terminus with a second glycosyl unit. The first and second glycosyl units are preferably substrates for different transferases, allowing orthogonal attachment of the first and second peptides to the first and second glycosylunits, respectively. In practice, the (glycosyl)$^1$-PEG-(glycosyl)$^2$ linker is contacted with the first peptide and a first transferase for which the first glycosyl unit is a substrate, thereby forming (peptide)$^1$-(glycosyl)$^1$-PEG-(glycosyl)$^2$. Glycosyltransferase and/or unreacted peptide is then optionally removed from the reaction mixture. The second peptide and a second transferase for which the second glycosyl unit is a substrate are added to the (peptide)$^1$-(glycosyl)$^1$-PEG-(glycosyl)$^2$ conjugate, forming (peptide)$^1$-(glycosyl)$^1$-PEG-(glycosyl)$^2$-(peptide)$^2$. Those of skill in the art will appreciate that the method outlined above is also applicable to forming conjugates between more than two peptides by, for example, the use of a branched PEG, dendrimer, poly (amino acid), polsaccharide or the like.

In an exemplary embodiment, human growth hormone is conjugated to transferrin via a bifunctional linker that includes an intact glycosyl linking group at each terminus of the PEG moiety (Scheme 1). The hGH conjugate has an in vivo half-life that is increased over that of hGH alone by virtue of the greater molecular sized of the conjugate. Moreover, the conjugation of hGH to transferrin serves to selectively target the conjugate to the brain. For example, one terminus of the PEG linker is functionalized with a CMP sialic acid and the other is functionalized with an UDP GalNAc. The linker is combined with hGH in the presence of a GalNAc transferase, resulting in the attachment of the GalNAc of the linker arm to a serine and/or threonine residue on the hGH.

Scheme 1

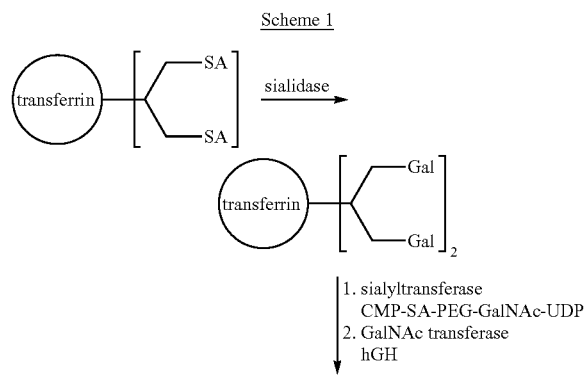

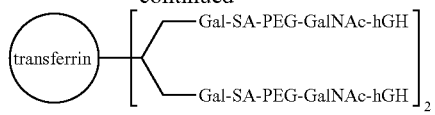

The processes described above can be carried through as many cycles as desired, and is not limited to forming a conjugate between two peptides with a single linker. Moreover, those of skill in the art will appreciate that the reactions functionalizing the intact glycosyl linking groups at the termini of the PEG (or other) linker with the peptide can occur simultaneously in the same reaction vessel, or they can be carried out in a step-wise fashion. When the reactions are carried out in a step-wise manner, the conjugate produced at each step is optionally purified from one or more reaction components (e.g., enzymes, peptides).

A still further exemplary embodiment is set forth in Scheme 2. Scheme 2 shows a method of preparing a conjugate that targets a selected protein, e.g., human growth hormone, to bone and increases the circulatory half-life of the selected protein.

Scheme 2

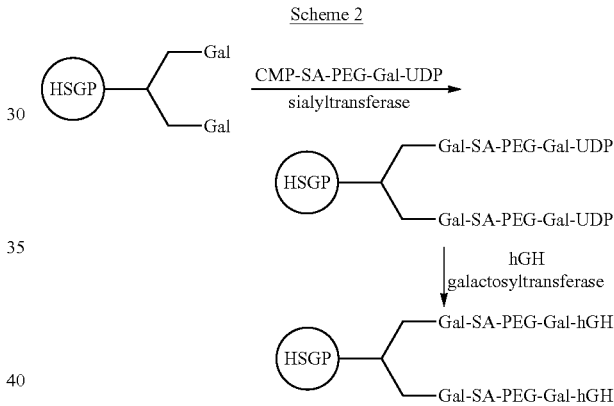

in which G is a glycosyl residue on an activated sugar moiety (e.g., sugar nucleotide), which is converted to an intact glycosyl linker group in the conjugate. When s is greater than 0, L is a saccharyl linking group such as GalNAc, or GalNAc-Gal.

The use of reactive derivatives of PEG (or other linkers) to attach one or more peptide moieties to the linker is within the scope of the present invention. The invention is not limited by the identity of the reactive PEG analogue. Many activated derivatives of poly(ethylene glycol) are available commercially and in the literature. It is well within the abilities of one of skill to choose, and synthesize if necessary, an appropriate activated PEG derivative with which to prepare a substrate useful in the present invention. See, Abuchowski et al. *Cancer Biochem. Biophys.,* 7: 175-186 (1984); Abuchowski et al., *J. Biol. Chem.,* 252: 3582-3586 (1977); Jackson et al., *Anal. Biochem.,* 165: 114-127 (1987); Koide et al., *Biochem Biophys. Res. Commun.,* 111: 659-667 (1983)), tresylate (Nilsson et al, *Methods Enzymol.,* 104: 56-69 (1984); Delgado et al., *Biotechnol. Appl. Biochem.,* 12: 119-128 (1990)); N-hydroxysuccinimide derived active esters (Buckmann et al., *Makromol. Chem.,* 182: 1379-1384 (1981); Joppich et al., *Makromol. Chem.,* 180: 1381-1384 (1979); Abuchowski et al., *Cancer Biochem. Biophys.,* 7: 175-186 (1984); Katre et al. *Proc. Natl. Acad. Sci. U.S.A.,* 84: 1487-1491 (1987); Kitamura et al., *Cancer Res.*, 51: 4310-4315 (1991); Boccui et al., *Z. Naturforsch.*, 38C: 94-99 (1983), carbonates (Zalipsky et al., POLY(ETHYLENE GLYCOL) CHEMISTRY: BIOTECHNICAL AND BIOMEDICAL APPLICATIONS, Harris, Ed., Plenum Press, New York, 1992, pp. 347-370; Zalipsky et al., *Biotechnol. Appl. Biochem.*, 15: 100-114 (1992); Veronese et al., *Appl. Biochem. Biotech.*, 11: 141-152 (1985)), imidazolyl formates (Beauchamp et al., *Anal. Biochem.*, 131: 25-33 (1983); Berger et al., *Blood*, 71: 1641-1647 (1988)), 4-dithiopyridines (Woghiren et al., *Bioconjugate Chem.*, 4: 314-318 (1993)), isocyanates (Byun et al., *ASAIO Journal*, M649-M-653 (1992)) and epoxides (U.S. Pat. No. 4,806,595, issued to Noishiki et al., (1989). Other linking groups include the urethane linkage between amino groups and activated PEG. See, Veronese, et al., *Appl. Biochem. Biotechnol.*, 11: 141-152 (1985).

In another exemplary embodiment, the invention provides a method for extending the blood-circulation half-life of a selected peptide, in essence targeting the peptide to the blood pool, by conjugating the peptide to a synthetic or natural polymer of a size sufficient to retard the filtration of the protein by the glomerulus (e.g., albumin). See, Scheme 3. This embodiment of the invention is illustrated in Scheme 3 in which hGH is conjugated to albumin via a PEG linker using a combination of chemical and enzymatic modification.

Scheme 3

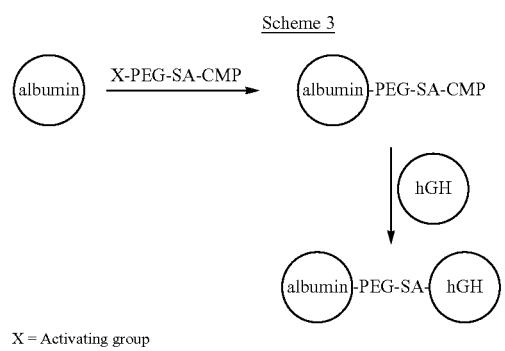

X = Activating group

Thus, as shown in Scheme 3, a residue (e.g., amino acid side chain) of albumin is modified with a reactive PEG derivative, such as X-PEG-(CMP-sialic acid), in which X is an activating group (e.g., active ester, isothiocyanate, etc). The PEG derivative and hGH are combined and contacted with a transferase for which CMP-sialic acid is a substrate. In a further illustrative embodiment, an ε-amine of lysine is reacted with the N-hydroxysuccinimide ester of the PEG-linker to form the albumin conjugate. The CMP-sialic acid of the linker is enzymatically conjugated to an appropriate residue on hGH, e.g., Gal or GalNAc, thereby forming the conjugate. Those of skill will appreciate that the above-described method is not limited to the reaction partners set forth. Moreover, the method can be practiced to form conjugates that include more than two protein moieties by, for example, utilizing a branched linker having more than two termini.

In other exemplary embodiments, the invention utilizes modified sugars in which the 6-hydroxyl position is converted to the corresponding amine moiety, which bears a modifying group such as those set forth above. Exemplary saccharyl groups that can be used as the core of these modified sugars include Gal, GalNAc, Glc, GlcNAc, Fuc, Xyl, Man, and the like. A representative modified sugar according to this embodiment has the formula:

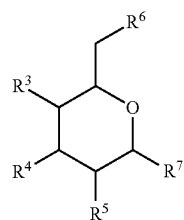

in which $R^3$-$R^6$ are members independently selected from H, OH, C(O)CH$_3$, NH, and NH C(O)CH$_3$. $R^7$ is a link to another glycosyl residue (—O-glycosyl) or to an amino acid of the hGH peptide. $R^6$ is $OR^1$, $NHR^1$ or $NH$-$L$-$R^1$, which is as described above.

Thus, in an illustrative embodiment in which the sugar moiety is sialic acid. In another exemplary embodiment, the modified sugar is based upon a 6-amino-N-acetyl-glycosyl moiety. As shown below for N-acetylgalactosamine, the 6-amino-sugar moiety is readily prepared by standard methods.

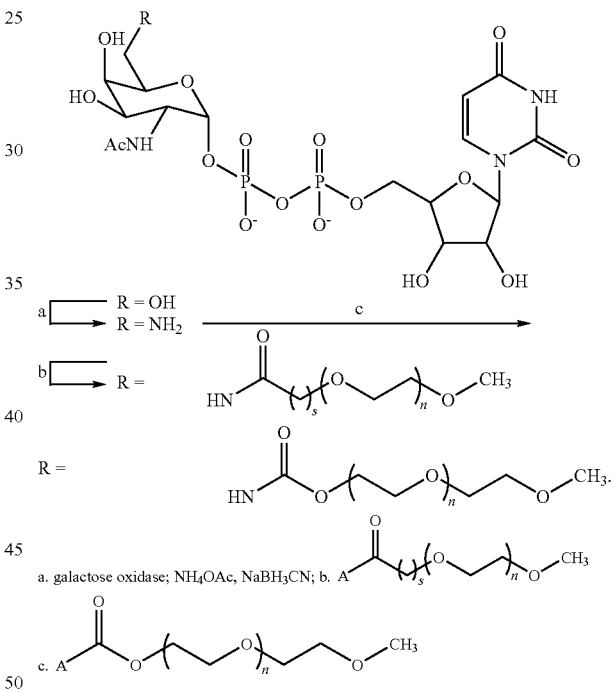

a. galactose oxidase; NH$_4$OAc, NaBH$_3$CN; b. c.

In the scheme above, the index n represents an integer from 1 to 2500, preferably from 10 to 1500, and more preferably from 10 to 1200. The symbol "A" represents an activating group, e.g., a halo, a component of an activated ester (e.g., a N-hydroxysuccinimide ester), a component of a carbonate (e.g., p-nitrophenyl carbonate) and the like. Preferred activated leaving groups, for use in the present invention, are those that do not significantly sterically encumber the enzymatic transfer of the glycoside to the acceptor. Those of skill in the art will appreciate that other PEG-amide nucleotide sugars are readily prepared by this and analogous methods.

In other exemplary embodiments, the amide moiety is replaced by a group such as a urethane or a urea.

Due to the versatility of the methods available for modifying glycosyl residues on a therapeutic peptide such as hGH, the glycosyl structures on the peptide conjugates of the invention can have substantially any structure. Moreover, the glycans can be O-linked or N-linked. As exemplified in the discussion below, each of the pyranose and furanose derivatives discussed above can be a component of a glycosyl moiety of a peptide.

Some embodiments of the invention provide a modified hGH peptide that includes a glycosyl group having the formula:

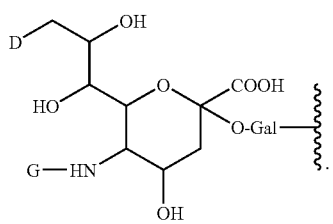

In other embodiments, the group has the formula:

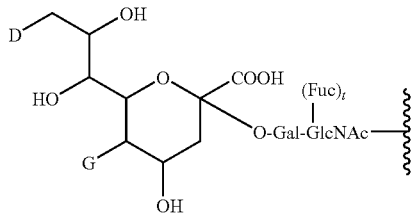

in which the index t is 0 or 1.

In a still further exemplary embodiment, the group has a structure which is a member selected from the following formulae:

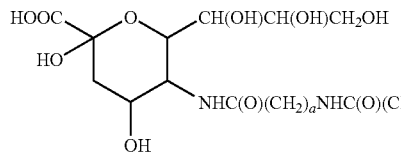 and 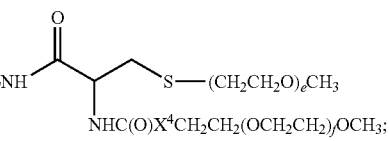

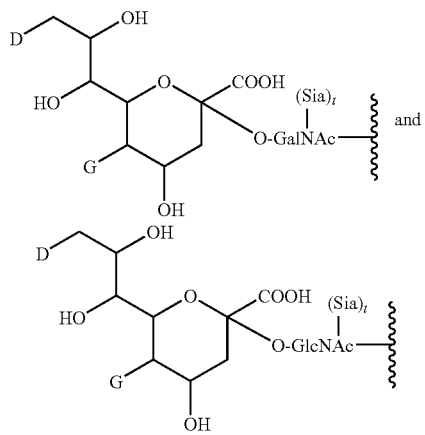

in which the index t is 0 or 1.

In yet another embodiment, the group has the formula:

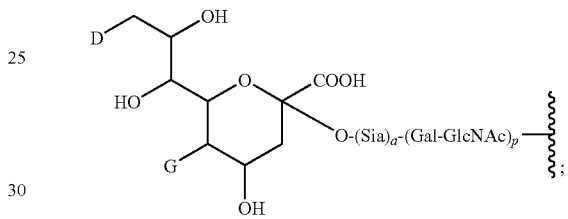

in which the index p represents and integer from 1 to 10; and a is either 0 or 1.

In still further embodiments, $R^1$ is a branched PEG, for example, one of those species set forth above. Illustrative compounds according to this embodiment include:

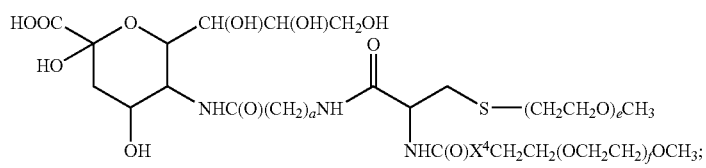

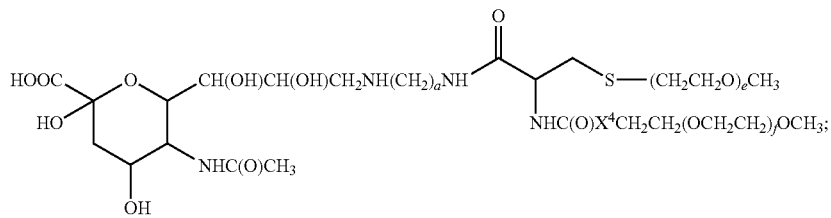

-continued

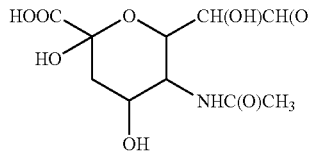
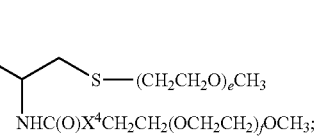

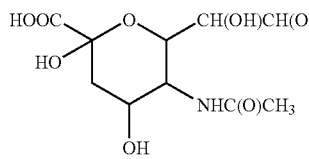
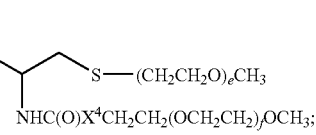

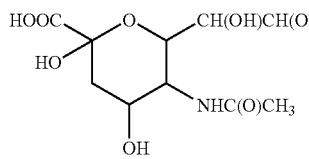
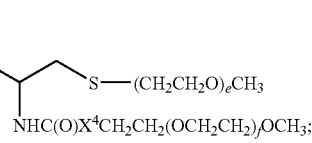

in which $X^4$ is a bond or O.

In other exemplary embodiments, the invention provides hGH peptide conjugates that includes a glycosyl linking group, such as those set forth above, that is covalently attached to an amino acid residue of the peptide. In one embodiment according to this motif, the glycosyl linking moiety is linked to a galactose residue through a Sia residue:

An exemplary species according to this motif is prepared by conjugating Sia-L-$R^1$ to a terminal sialic acid of a glycan using an enzyme that forms Sia-Sia bonds, e.g., CST-II, ST8Sia-II, ST8Sia-III and ST8Sia-IV.

In another exemplary embodiment, the sugar moiety is a sialic acid moiety that has been oxidized and conjugated to a polymeric modifying moiety, such as is described in commonly assigned U.S. Provisional Patent Application No. 60/641,956, filed Jan. 6, 2005.

In this embodiment, an exemplary linker is derived from a natural or unnatural amino acid, amino acid analogue or amino acid mimetic, or a small peptide formed from one or more such species. For example, certain branched polymers found in the compounds of the invention have the formula:

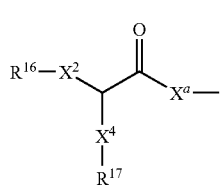
(IV)

$X^a$ is a linkage fragment that is formed by the reaction of a reactive functional group, e.g. $X^{3'}$, on a precursor of the branched polymeric modifying moiety and a reactive functional group on the sugar moiety, or a precursor to a linker. For example, when $X^{3'}$ is a carboxylic acid, it can be activated and bound directly to an amine group pendent from an aminosaccharide (e.g., Sia, GalNH$_2$, GlcNH$_2$, ManNH$_2$, etc.), forming an $X^a$ that is an amide. Additional exemplary reactive functional groups and activated precursors are described hereinbelow. The index c represents an integer from 1 to 10. The other symbols have the same identity as those discussed above.

In another exemplary embodiment, $X^a$ is a linking moiety formed with another linker:

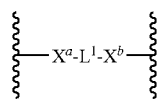

in which $X^b$ is a second linkage fragment and is independently selected from those groups set forth for $X^a$, and similar to L, $L^1$ is a bond, substituted or unsubstituted alkyl or substituted or unsubstituted heteroalkyl.

Exemplary species for $X^a$ and $X^b$ include S, SC(O)NH, HNC(O)S, SC(O)O, O, NH, NHC(O), C(O)NH and NHC(O)O, and OC(O)NH.

In another exemplary embodiment, $X^4$ is a peptide bond to $R^{17}$, which is an amino acid, di-peptide, e.g. Lys-Lys, or tri-peptide (e.g. Lys-Lys-Lys) in which the alpha-amine moiety(ies) and/or side chain heteroatom are modified with a polymeric modifying moiety.

In a further exemplary embodiment, the conjugates of the invention include a moiety, e.g. an $R^{15}$ moiety that has a formula that is selected from:

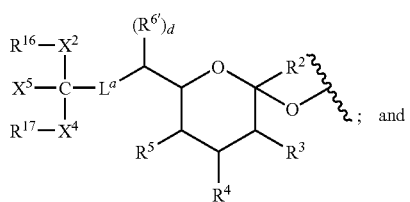

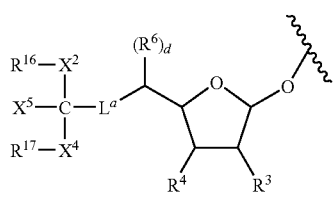

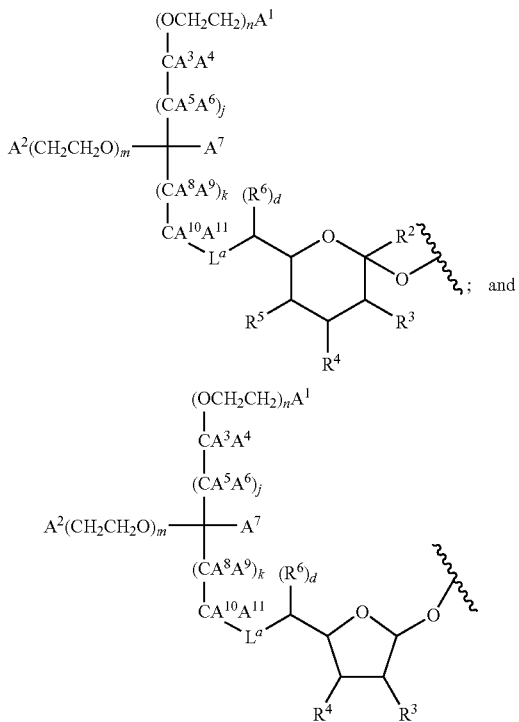

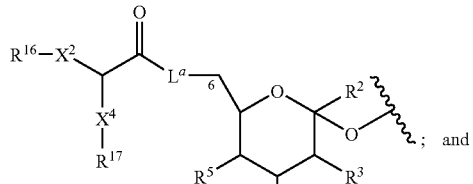

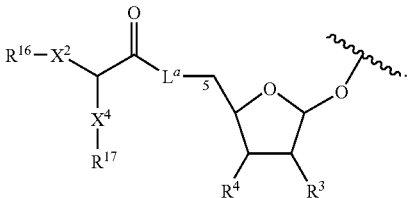

The identity of the radicals represented by the various symbols is the same as that discussed hereinabove. As those of skill will appreciate, the linker arm in Formulae VII and VIII is equally applicable to other modified sugars set forth herein. In exemplary embodiment, the species of Formulae VI and VII are the $R^{15}$ moieties attached to the glycan structures set forth herein.

In yet another exemplary embodiment, the hGH peptide includes an $R^{15}$ moiety with the formula:

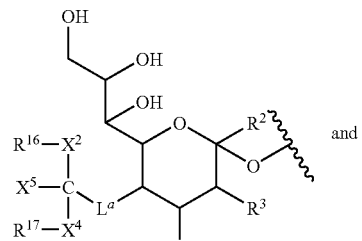

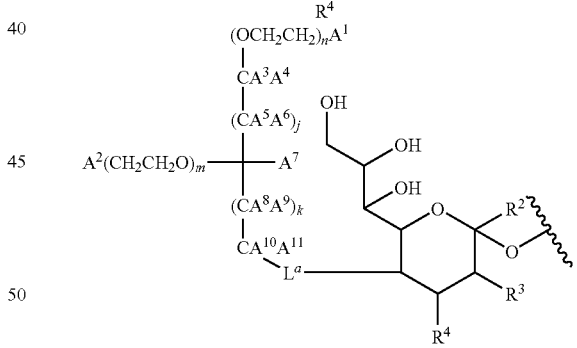

in which the identity of the radicals represented by the various symbols is the same as that discussed hereinabove. $L^a$ is a bond or a linker as discussed above for L and $L^1$, e.g. substituted or unsubstituted alkyl or substituted or unsubstituted heteroalkyl moiety. In an exemplary embodiment, $L^a$ is a moiety of the side chain of sialic acid that is functionalized with the polymeric modifying moiety as shown. Exemplary $L^a$ moieties include substituted or unsubstituted alkyl chains that include one or more OH or $NH_2$.

In yet another exemplary embodiment, the invention provides conjugates having a moiety, e.g. an $R^{15}$ moiety with formula:

in which the identities of the radicals are as discussed above. An exemplary species for $L^a$ is $-(CH_2)_jC(O)NH(CH_2)_hC(O)NH-$, in which the indices h and j are independently selected integers from 0 to 10. A further exemplary species is $-C(O)NH-$. The indices j and k are integers independently selected from 0 to 20. The indices m and n are integers independently selected from 0 to 5000. $A^1, A^2, A^3, A^4, A^5, A^6, A^7, A^8, A^9, A^{10}$ and $A^{11}$ are members independently selected from H, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, $-NA^{12}A^{13}$, $-OA^{12}$ and $-SiA^{12}A^{13}$. $A^{12}$ and $A^{13}$ are members independently selected from substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

In a further exemplary embodiment, the modified sugar is an oligosaccharide having an antennary structure. In a preferred embodiment, one or more of the termini of the antennae bear the modifying moiety. When more than one modifying moiety is attached to an oligosaccharide having an antennary structure, the oligosaccharide is useful to "amplify" the modifying moiety; each oligosaccharide unit conjugated to the peptide attaches multiple copies of the modifying group to the peptide. The general structure of a typical chelate of the invention as set forth in the drawing above, encompasses multivalent species resulting from preparing a conjugate of the invention utilizing an antennary structure. Many antennary saccharide structures are known in the art, and the present method can be practiced with them without limitation.

The embodiments of the invention set forth above are further exemplified by reference to species in which the polymer is a water-soluble polymer, particularly poly(ethylene glycol) ("PEG"), e.g., methoxy-poly(ethylene glycol). Those of skill will appreciate that the focus in the sections that follow is for clarity of illustration and the various motifs set forth using PEG as an exemplary polymer are equally applicable to species in which a polymer other than PEG is utilized.

PEG of any molecular weight, e.g., 1 kDa, 2 kDa, 5 kDa, 10 kDa, 15 kDa, 20 kDa, 25 kDa, 30 kDa, 35 kDa, 40 kDa, 45 kDa, 50 kDa, 55 kDa, 60 kDa, 65 kDa, 70 kDa, 75 kDa or 80 kDa can be used in the present invention.

In an exemplary embodiment, the $R^{15}$ moiety has a formula that is a member selected from the group:

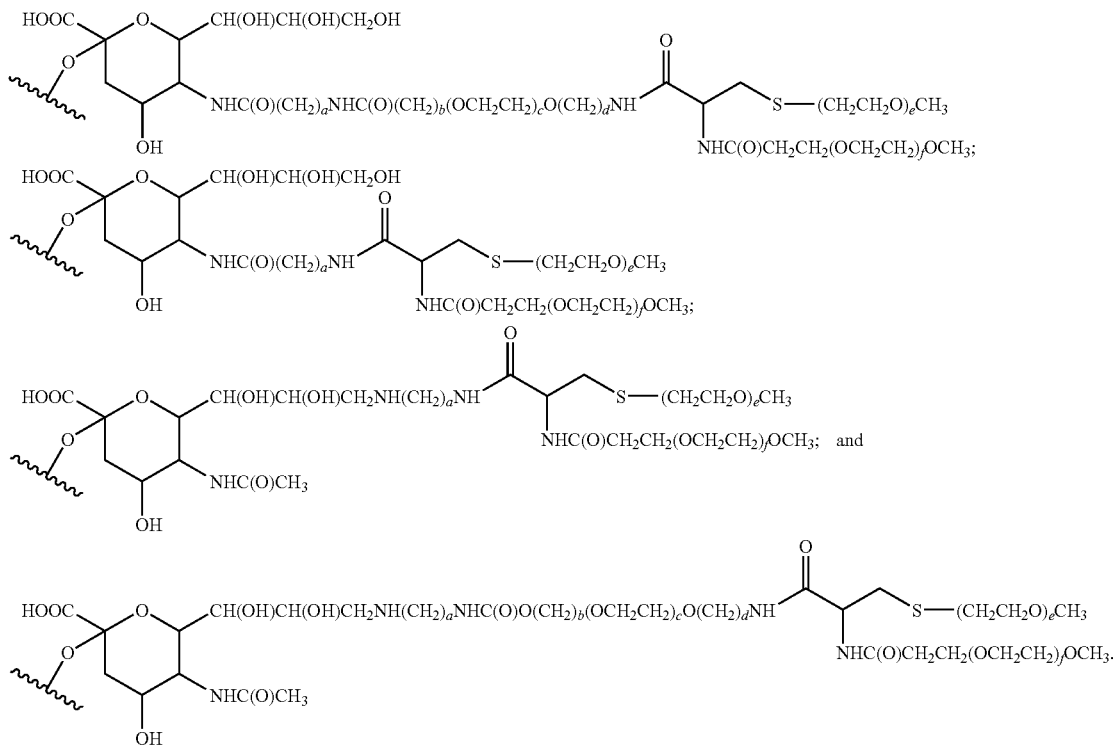

In each of the structures above, the linker fragment —NH(CH$_2$)$_a$— can be present or absent.

In other exemplary embodiments, the conjugate includes an $R^{15}$ moiety selected from the group:

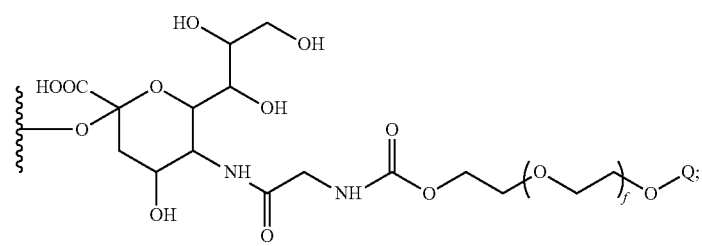

-continued
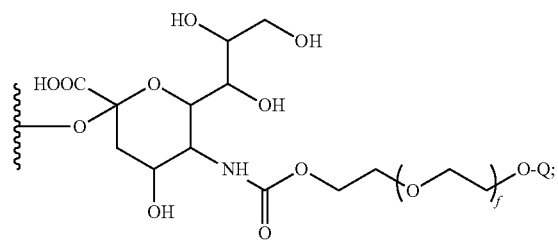
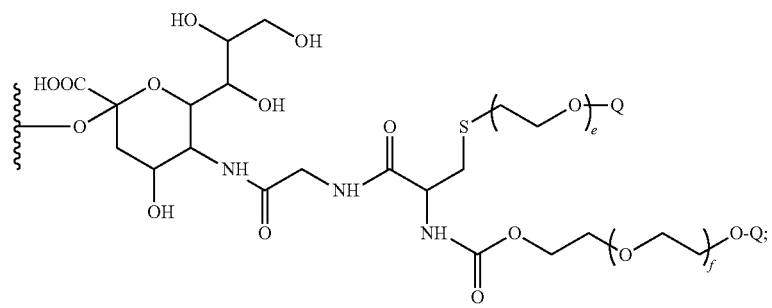
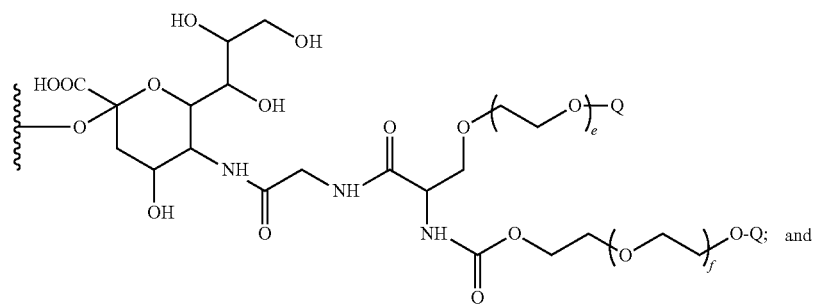
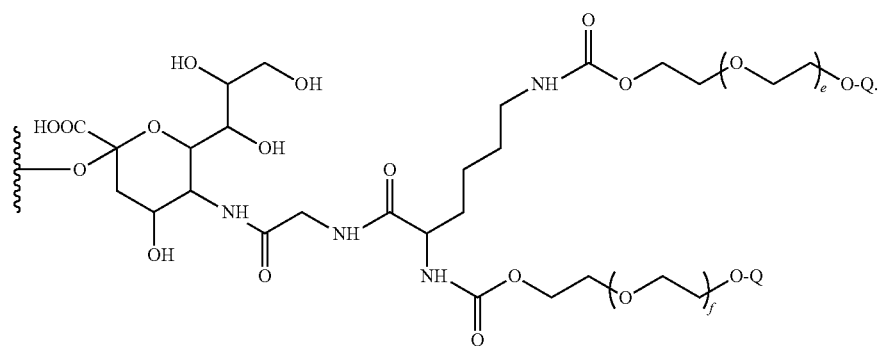

In each of the formulae above, the indices e and f are independently selected from the integers from 1 to 2500. In further exemplary embodiments, e and f are selected to provide a PEG moiety that is about 1 kDa, 2 kDa, 5 kDa, 10 kDa, 15 kDa, 20 kDa, 25 kDa, 30 kDa, 35 kDa, 40 kDa, 45 kDa, 50 kDa, 55 kDa, 60 kDa, 65 kDa, 70 kDa, 75 kDa or 80 kDa. The symbol Q represents substituted or unsubstituted alkyl (e.g., $C_1$-$C_6$ alkyl e.g., methyl), substituted or unsubstituted heteroalkyl or H.

-continued

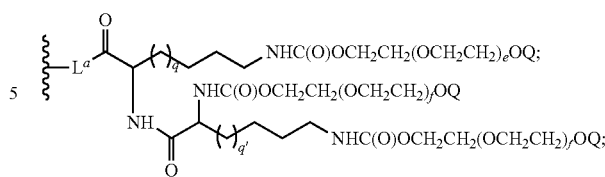

and tri-lysine peptides (Lys-Lys-Lys), e.g.:

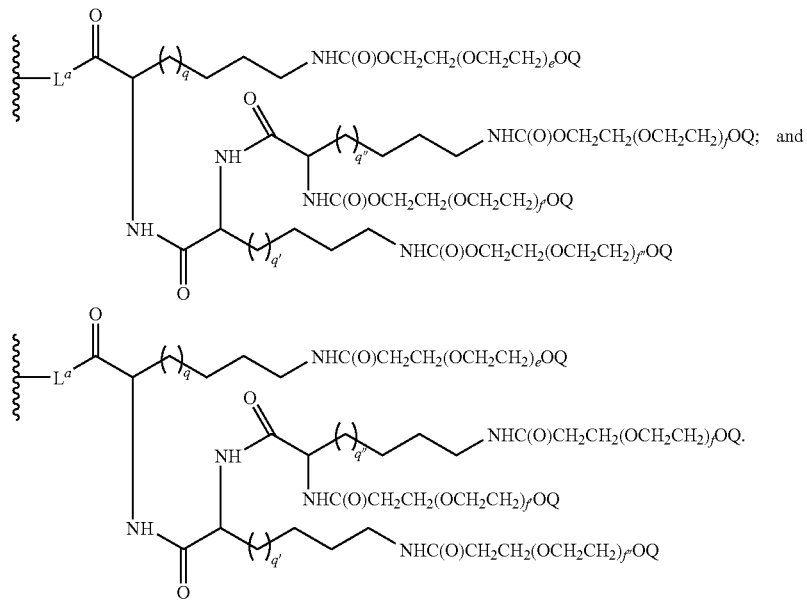

Other branched polymers have structures based on di-lysine (Lys-Lys) peptides, e.g.:

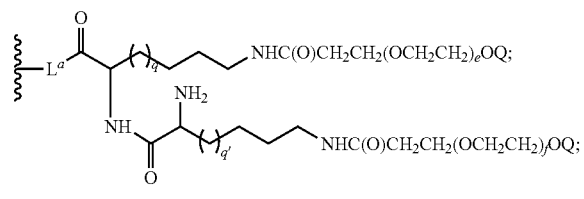

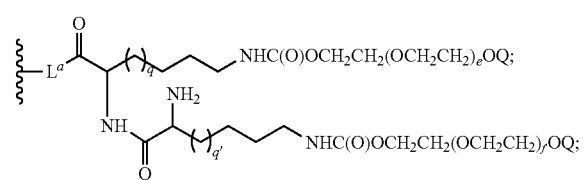

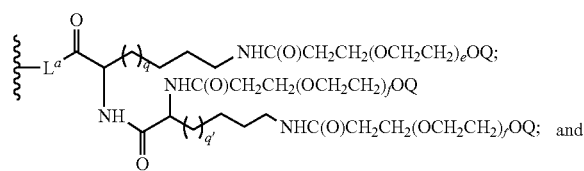

In each of the figures above, e, f, f' and f" represent integers independently selected from 1 to 2500. The indices q, q' and q" represent integers independently selected from 1 to 20.

Exemplary modifying groups are discussed below. The modifying groups can be selected for their ability to impart to a polypeptide one or more desirable properties. Exemplary properties include, but are not limited to, enhanced pharmacokinetics, enhanced pharmacodynamics, improved biodistribution, providing a polyvalent species, improved water solubility, enhanced or diminished lipophilicity, and tissue targeting.

Exemplary modified sugars are modified with water-soluble or water-insoluble polymers. Examples of useful polymer are further exemplified below.

Water-Soluble Polymers

Many water-soluble polymers are known to those of skill in the art and are useful in practicing the present invention. The term water-soluble polymer encompasses species such as saccharides (e.g., dextran, amylose, hyalouronic acid, poly (sialic acid), heparans, heparins, etc.); poly (amino acids), e.g., poly(aspartic acid) and poly(glutamic acid); nucleic acids; synthetic polymers (e.g., poly(acrylic acid), poly (ethers), e.g., poly(ethylene glycol); peptides, proteins, and the like. The present invention may be practiced with any water-soluble polymer with the sole limitation that the polymer must include a point at which the remainder of the conjugate can be attached.

Methods for activation of polymers can also be found in WO 94/17039, U.S. Pat. No. 5,324,844, WO 94/18247, WO 94/04193, U.S. Pat. Nos. 5,219,564, 5,122,614, WO 90/13540, U.S. Pat. No. 5,281,698, and more WO 93/15189, and for conjugation between activated polymers and peptides, e.g. Coagulation Factor VIII (WO 94/15625), hemoglobin (WO 94/09027), oxygen carrying molecule (U.S. Pat. No. 4,412,989), ribonuclease and superoxide dismutase (Veronese at al., *App. Biochem. Biotech.* 11: 141-45 (1985)).

Preferred water-soluble polymers are those in which a substantial proportion of the polymer molecules in a sample of the polymer are of approximately the same molecular weight; such polymers are "homodisperse."

The present invention is further illustrated by reference to a poly(ethylene glycol) conjugate. Several reviews and monographs on the functionalization and conjugation of PEG are available. See, for example, Harris, *Macronol. Chem. Phys.* C25: 325-373 (1985); Scouten, *Methods in Enzymology* 135: 30-65 (1987); Wong et al., *Enzyme Microb. Technol.* 14: 866-874 (1992); Delgado et al., *Critical Reviews in Therapeutic Drug Carrier Systems* 9: 249-304 (1992); Zalipsky, *Bioconjugate Chem.* 6: 150-165 (1995); and Bhadra, et al., *Pharmazie,* 57:5-29 (2002). Routes for preparing reactive PEG molecules and forming conjugates using the reactive molecules are known in the art. For example, U.S. Pat. No. 5,672,662 discloses a water soluble and isolatable conjugate of an active ester of a polymer acid selected from linear or branched poly(alkylene oxides), poly(oxyethylated polyols), poly(olefinic alcohols), and poly(acrylomorpholine).

U.S. Pat. No. 6,376,604 sets forth a method for preparing a water-soluble 1-benzotriazolylcarbonate ester of a water-soluble and non-peptidic polymer by reacting a terminal hydroxyl of the polymer with di(1-benzotriazoyl)carbonate in an organic solvent. The active ester is used to form conjugates with a biologically active agent such as a protein or peptide.

WO 99/45964 describes a conjugate comprising a biologically active agent and an activated water soluble polymer comprising a polymer backbone having at least one terminus linked to the polymer backbone through a stable linkage, wherein at least one terminus comprises a branching moiety having proximal reactive groups linked to the branching moiety, in which the biologically active agent is linked to at least one of the proximal reactive groups. Other branched poly (ethylene glycols) are described in WO 96/21469, U.S. Pat. No. 5,932,462 describes a conjugate formed with a branched PEG molecule that includes a branched terminus that includes reactive functional groups. The free reactive groups are available to react with a biologically active species, such as a protein or peptide, forming conjugates between the poly (ethylene glycol) and the biologically active species. U.S. Pat. No. 5,446,090 describes a bifunctional PEG linker and its use in forming conjugates having a peptide at each of the PEG linker termini.

Conjugates that include degradable PEG linkages are described in WO 99/34833; and WO 99/14259, as well as in U.S. Pat. No. 6,348,558. Such degradable linkages are applicable in the present invention.

The art-recognized methods of polymer activation set forth above are of use in the context of the present invention in the formation of the branched polymers set forth herein and also for the conjugation of these branched polymers to other species, e.g., sugars, sugar nucleotides and the like.

In other exemplary embodiments, the branched PEG is based upon a cysteine, serine or di-lysine core. Thus, further exemplary branched PEGs include:

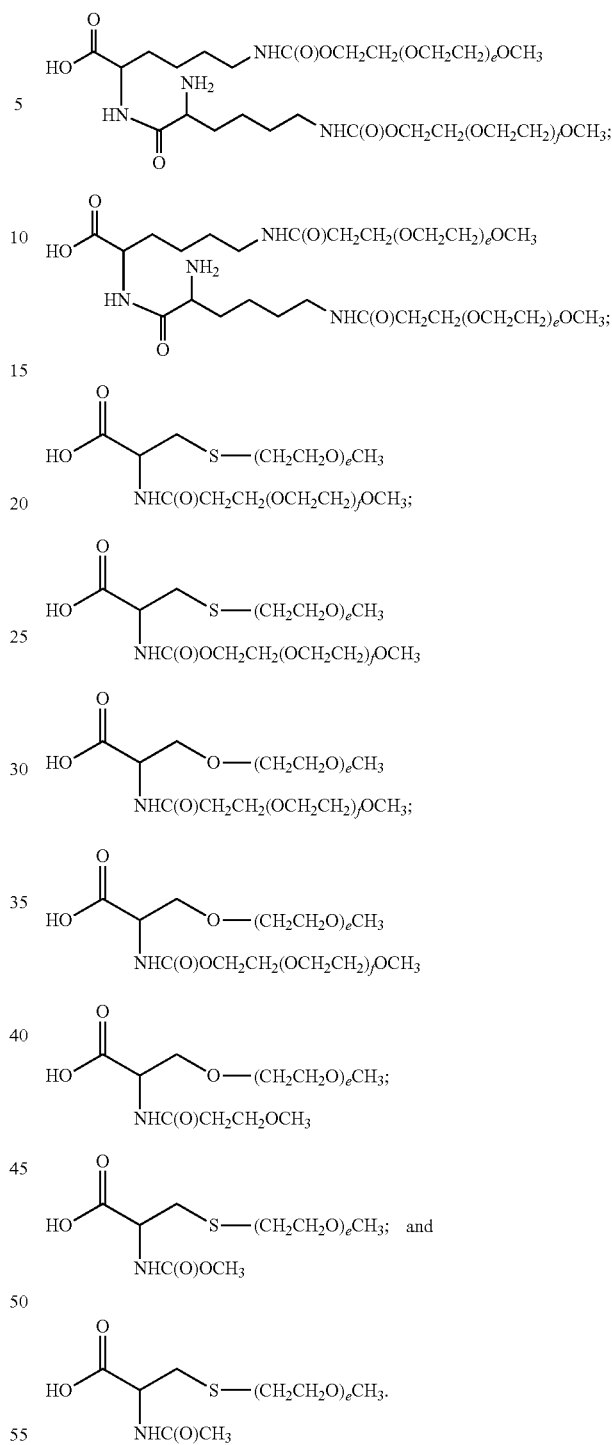

The modified sugars are prepared by reacting the glycosyl core (or a linker on the core) with a polymeric modifying moiety (or a linker on the polymeric modifying moiety). The discussion that follows provides examples of selected polymeric modifying moieties of use in the invention. For example, representative polymeric modifying moieties include structures that are based on side chain-containing amino acids, e.g., serine, cysteine, lysine, and small peptides, e.g., lys-lys.

Those of skill will appreciate that the free amine in the di-lysine structures can also be pegylated through an amide or urethane bond with a PEG moiety.

In yet another embodiment, the branched PEG moiety is based upon a tri-lysine peptide. The tri-lysine can be mono-, di-, tri-, or tetra-PEGylated. Exemplary species according to this embodiment have the formulae:

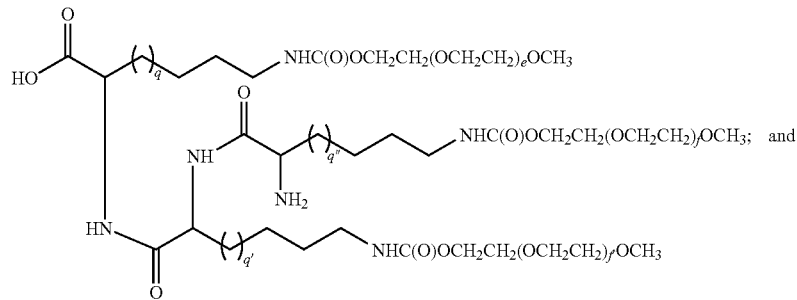

above can include three polymeric subunits, the third bonded to the α-amine shown as unmodified in the structure above. Similarly, the use of a tri-lysine functionalized with three or four polymeric subunits labeled with the polymeric modifying moiety in a desired manner is within the scope of the invention.

Exemplary PEG molecules that are activated with these and other activating group species and methods of making the activated PEGs are set forth in WO 04/083259.

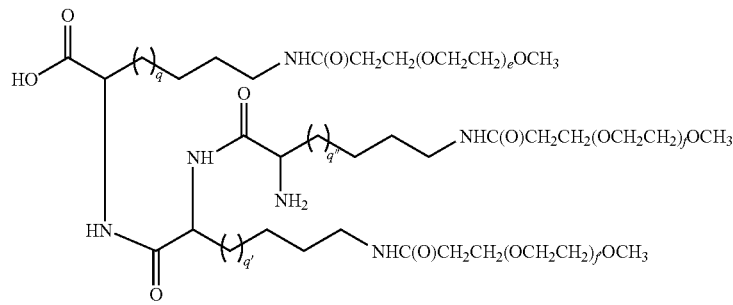

in which e, f and f' are independently selected integers from 1 to 2500; and q, q' and q" are independently selected integers from 1 to 20.

In exemplary embodiments of the invention, the PEG is m-PEG (5 kD, 10 kD, 15 kD, 20 kD or 30 kD). An exemplary branched PEG species is a serine- or cysteine-(m-PEG)$_2$ in which the m-PEG is a 20 kD m-PEG. In an exemplary embodiment, the branched PEG is the cysteine residue shown above with a 20 kD m-PEG attached to the sulfur and another attached to the nitrogen.

As will be apparent to those of skill, the branched polymers of use in the invention include variations on the themes set forth above. For example the di-lysine-PEG conjugate shown Those of skill in the art will appreciate that one or more of the m-PEG arms of the branched polymers shown above can be replaced by a PEG moiety with a different terminus, e.g., OH, COOH, NH$_2$, C$_2$-C$_{10}$-alkyl, etc. Moreover, the structures above are readily modified by inserting alkyl linkers (or removing carbon atoms) between the α-carbon atom and the functional group of the amino acid side chain. Thus, "homo" derivatives and higher homologues, as well as lower homologues, are within the scope of cores for branched PEGs of use in the present invention.

The branched PEG species set forth herein are readily prepared by methods such as that set forth in the scheme below:

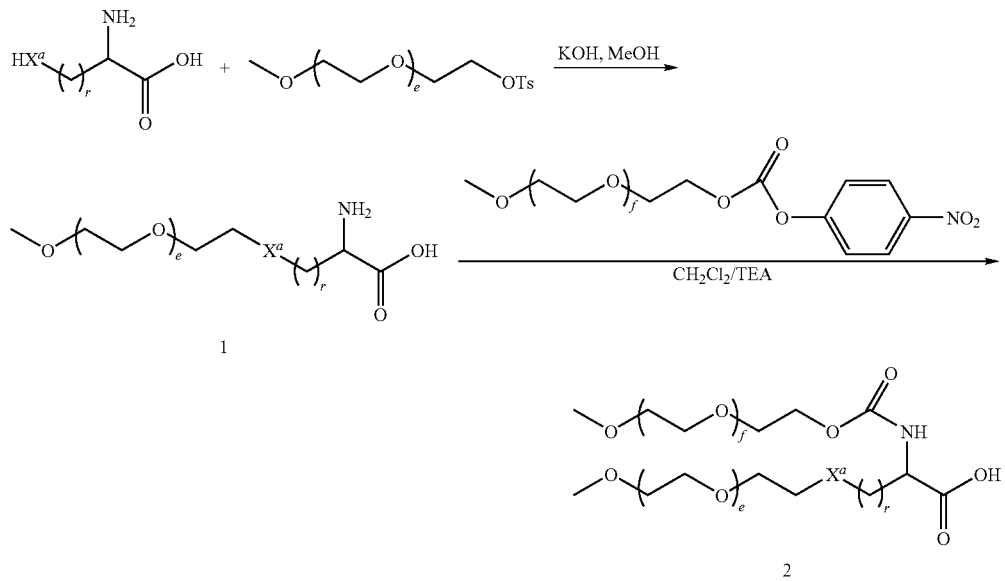

in which $X^a$ is O or S and r is an integer from 1 to 5. The indices e and f are independently selected integers from 1 to 2500. In an exemplary embodiment, one or both of these indices are selected such that the polymer is about 10 kD, 15 kD, or 20 kD in molecular weight.

Thus, according to this scheme, a natural or unnatural amino acid is contacted with an activated m-PEG derivative, in this case the tosylate, forming 1 by alkylating the side-chain heteroatom $X^a$. The mono-functionalized m-PEG amino acid is submitted to N-acylation conditions with a reactive m-PEG derivative, thereby assembling branched m-PEG 2. As one of skill will appreciate, the tosylate leaving group can be replaced with any suitable leaving group, e.g., halogen, mesylate, triflate, etc. Similarly, the reactive carbonate utilized to acylate the amine can be replaced with an active ester, e.g., N-hydroxysuccinimide, etc., or the acid can be activated in situ using a dehydrating agent such as dicyclohexylcarbodiimide, carbonyldiimidazole, etc.

In other exemplary embodiments, the urea moiety is replaced by a group such as a amide.

Water-Insoluble Polymers

In another embodiment, analogous to those discussed above, the modified sugars comprise a water-insoluble polymer, rather than a water-soluble polymer. The conjugates of the invention may also include one or more water-insoluble polymers. This embodiment of the invention is illustrated by the use of the conjugate as a vehicle with which to deliver a therapeutic peptide in a controlled manner. Polymeric drug delivery systems are known in the art. See, for example, Dunn et al., Eds. POLYMERIC DRUGS AND DRUG DELIVERY SYSTEMS, ACS Symposium Series Vol. 469, American Chemical Society, Washington, D.C. 1991. Those of skill in the art will appreciate that substantially any known drug delivery system is applicable to the conjugates of the present invention.

The motifs forth above for $R^1$, $L-R^1$, $R^{15}$, $R^{15'}$ and other radicals are equally applicable to water-insoluble polymers, which may be incorporated into the linear and branched structures without limitation utilizing chemistry readily accessible to those of skill in the art.

Representative water-insoluble polymers include, but are not limited to, polyphosphazines, poly(vinyl alcohols), polyamides, polycarbonates, polyalkylenes, polyacrylamides, polyalkylene glycols, polyalkylene oxides, polyalkylene terephthalates, polyvinyl ethers, polyvinyl esters, polyvinyl halides, polyvinylpyrrolidone, polyglycolides, polysiloxanes, polyurethanes, poly(methyl methacrylate), poly(ethyl methacrylate), poly(butyl methacrylate), poly(isobutyl methacrylate), poly(hexyl methacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate) polyethylene, polypropylene, poly(ethylene glycol), poly(ethylene oxide), poly (ethylene terephthalate), poly(vinyl acetate), polyvinyl chloride, polystyrene, polyvinyl pyrrolidone, pluronics and polyvinylphenol and copolymers thereof.

Synthetically modified natural polymers of use in hGH conjugates of the invention include, but are not limited to, alkyl celluloses, hydroxyalkyl celluloses, cellulose ethers, cellulose esters, and nitrocelluloses. Particularly preferred members of the broad classes of synthetically modified natural polymers include, but are not limited to, methyl cellulose, ethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, carboxymethyl cellulose, cellulose triacetate, cellulose sulfate sodium salt, and polymers of acrylic and methacrylic esters and alginic acid.

These and the other polymers discussed herein can be readily obtained from commercial sources such as Sigma Chemical Co. (St. Louis, Mo.), Polysciences (Warrenton, Pa.), Aldrich (Milwaukee, Wis.), Fluka (Ronkonkoma, N.Y.), and BioRad (Richmond, Calif.), or else synthesized from monomers obtained from these suppliers using standard techniques.

Representative biodegradable polymers of use in the hGH conjugates of the invention include, but are not limited to, polylactides, polyglycolides and copolymers thereof, poly (ethylene terephthalate), poly(butyric acid), poly(valeric acid), poly(lactide-co-caprolactone), poly(lactide-co-glycolide), polyanhydrides, polyorthoesters, blends and copolymers thereof. Of particular use are compositions that form gels, such as those including collagen, pluronics and the like.

The polymers of use in the invention include "hybrid" polymers that include water-insoluble materials having within at least a portion of their structure, a bioresorbable molecule. An example of such a polymer is one that includes a water-insoluble copolymer, which has a bioresorbable region, a hydrophilic region and a plurality of crosslinkable functional groups per polymer chain.

For purposes of the present invention, "water-insoluble materials" includes materials that are substantially insoluble in water or water-containing environments. Thus, although certain regions or segments of the copolymer may be hydrophilic or even water-soluble, the polymer molecule, as a whole, does not to any substantial measure dissolve in water.

For purposes of the present invention, the term "bioresorbable molecule" includes a region that is capable of being metabolized or broken down and resorbed and/or eliminated through normal excretory routes by the body. Such metabolites or break down products are preferably substantially non-toxic to the body.

The bioresorbable region may be either hydrophobic or hydrophilic, so long as the copolymer composition as a whole is not rendered water-soluble. Thus, the bioresorbable region is selected based on the preference that the polymer, as a whole, remains water-insoluble. Accordingly, the relative properties, i.e., the kinds of functional groups contained by, and the relative proportions of the bioresorbable region, and the hydrophilic region are selected to ensure that useful bioresorbable compositions remain water-insoluble.

Exemplary resorbable polymers include, for example, synthetically produced resorbable block copolymers of poly($\alpha$-hydroxy-carboxylic acid)/poly(oxyalkylene, (see, Cohn et al., U.S. Pat. No. 4,826,945). These copolymers are not crosslinked and are water-soluble so that the body can excrete the degraded block copolymer compositions. See, Younes et al., *J. Biomed. Mater. Res.* 21: 1301-1316 (1987); and Cohn et al., *J. Biomed. Mater. Res.* 22: 993-1009 (1988).

Presently preferred bioresorbable polymers include one or more components selected from poly(esters), poly(hydroxy acids), poly(lactones), poly(amides), poly(ester-amides), poly (amino acids), poly(anhydrides), poly(orthoesters), poly (carbonates), poly(phosphazines), poly(phosphoesters), poly (thioesters), polysaccharides and mixtures thereof. More preferably still, the bioresorbable polymer includes a poly (hydroxy) acid component. Of the poly(hydroxy) acids, polylactic acid, polyglycolic acid, polycaproic acid, polybutyric acid, polyvaleric acid and copolymers and mixtures thereof are preferred.

In addition to forming fragments that are absorbed in vivo ("bioresorbed"), preferred polymeric coatings for use in the methods of the invention can also form an excretable and/or metabolizable fragment.

Higher order copolymers can also be used in the present invention. For example, Casey et al., U.S. Pat. No. 4,438,253, which issued on Mar. 20, 1984, discloses tri-block copolymers produced from the transesterification of poly(glycolic acid) and an hydroxyl-ended poly(alkylene glycol). Such compositions are disclosed for use as resorbable monofilament sutures. The flexibility of such compositions is controlled by the incorporation of an aromatic orthocarbonate, such as tetra-p-tolyl orthocarbonate into the copolymer structure.

Other polymers based on lactic and/or glycolic acids can also be utilized. For example, Spinu, U.S. Pat. No. 5,202,413, which issued on Apr. 13, 1993, discloses biodegradable multi-block copolymers having sequentially ordered blocks of polylactide and/or polyglycolide produced by ring-opening polymerization of lactide and/or glycolide onto either an oligomeric diol or a diamine residue followed by chain extension with a di-functional compound, such as, a diisocyanate, diacylchloride or dichlorosilane.

Bioresorbable regions of coatings useful in the present invention can be designed to be hydrolytically and/or enzymatically cleavable. For purposes of the present invention, "hydrolytically cleavable" refers to the susceptibility of the copolymer, especially the bioresorbable region, to hydrolysis in water or a water-containing environment. Similarly, "enzymatically cleavable" as used herein refers to the susceptibility of the copolymer, especially the bioresorbable region, to cleavage by endogenous or exogenous enzymes.

When placed within the body, the hydrophilic region can be processed into excretable and/or metabolizable fragments. Thus, the hydrophilic region can include, for example, polyethers, polyalkylene oxides, polyols, poly(vinyl pyrrolidine), poly(vinyl alcohol), poly(alkyl oxazolines), polysaccharides, carbohydrates, peptides, proteins and copolymers and mixtures thereof. Furthermore, the hydrophilic region can also be, for example, a poly(alkylene) oxide. Such poly(alkylene) oxides can include, for example, poly(ethylene) oxide, poly (propylene) oxide and mixtures and copolymers thereof.

Polymers that are components of hydrogels are also useful in the present invention. Hydrogels are polymeric materials that are capable of absorbing relatively large quantities of water. Examples of hydrogel forming compounds include, but are not limited to, polyacrylic acids, sodium carboxymethylcellulose, polyvinyl alcohol, polyvinyl pyrrolidine, gelatin, carrageenan and other polysaccharides, hydroxyethylenemethacrylic acid (HEMA), as well as derivatives thereof, and the like. Hydrogels can be produced that are stable, biodegradable and bioresorbable. Moreover, hydrogel compositions can include subunits that exhibit one or more of these properties.

Bio-compatible hydrogel compositions whose integrity can be controlled through crosslinking are known and are presently preferred for use in the methods of the invention. For example, Hubbell et al., U.S. Pat. No. 5,410,016, which issued on Apr. 25, 1995 and U.S. Pat. No. 5,529,914, which issued on Jun. 25, 1996, disclose water-soluble systems, which are crosslinked block copolymers having a water-soluble central block segment sandwiched between two hydrolytically labile extensions. Such copolymers are further end-capped with photopolymerizable acrylate functionalities. When crosslinked, these systems become hydrogels. The water soluble central block of such copolymers can include poly(ethylene glycol); whereas, the hydrolytically labile extensions can be a poly($\alpha$-hydroxy acid), such as polyglycolic acid or polylactic acid. See, Sawhney et al., *Macromolecules* 26: 581-587 (1993).

In another preferred embodiment, the gel is a thermoreversible gel. Thermoreversible gels including components, such as pluronics, collagen, gelatin, hyalouronic acid, polysaccharides, polyurethane hydrogel, polyurethane-urea hydrogel and combinations thereof are presently preferred.

In yet another exemplary embodiment, the hGH conjugates of the invention include a component of a liposome. Liposomes can be prepared according to methods known to those skilled in the art, for example, as described in Eppstein et al., U.S. Pat. No. 4,522,811, which issued on Jun. 11, 1985. For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound or its pharmaceutically acceptable salt is then introduced into the container. The container is then swirled by hand to free lipid material from the sides of the container and to disperse lipid aggregates, thereby forming the liposomal suspension.

The above-recited microparticles and methods of preparing the microparticles are offered by way of example and they are not intended to define the scope of microparticles of use in the present invention. It will be apparent to those of skill in the art that an array of microparticles, fabricated by different methods, are of use in the present invention.

The structural formats discussed above in the context of the water-soluble polymers, both straight-chain and branched, are generally applicable with respect to the water-insoluble polymers as well. Thus, for example, the cysteine, serine, dilysine, and trilysine branching cores can be functionalized with two water-insoluble polymer moieties. The methods used to produce these species are generally closely analogous to those used to produce the water-soluble polymers.

The degree of PEG substitution of the modified sugars and hGH conjugates can be controlled by choice of stoichiometry, number of available glycosylation sites, selection of an enzyme that is selective for a particular site, and the like, see U.S. Pat. App. No. 60/690,728.

Biomolecules

In another preferred embodiment, the modified sugar bears a biomolecule. In still further preferred embodiments, the biomolecule is a functional protein, enzyme, antigen, antibody, peptide, nucleic acid (e.g., single nucleotides or nucleosides, oligonucleotides, polynucleotides and single- and higher-stranded nucleic acids), lectin, receptor or a combination thereof.

Preferred biomolecules are essentially non-fluorescent, or emit such a minimal amount of fluorescence that they are inappropriate for use as a fluorescent marker in an assay. Moreover, it is generally preferred to use biomolecules that are not sugars. An exception to this preference is the use of an otherwise naturally occurring sugar that is modified by covalent attachment of another entity (e.g., PEG, biomolecule, therapeutic moiety, diagnostic moiety, etc.). In an exemplary embodiment, a sugar moiety, which is a biomolecule, is conjugated to a linker arm and the sugar-linker arm cassette is subsequently conjugated to a peptide via a method of the invention.

Biomolecules useful in practicing the present invention can be derived from any source. The biomolecules can be isolated from natural sources or they can be produced by synthetic methods. Peptides can be natural peptides or mutated peptides. Mutations can be effected by chemical mutagenesis, site-directed mutagenesis or other means of inducing mutations known to those of skill in the art. Peptides useful in practicing the instant invention include, for example, enzymes, antigens, antibodies and receptors. Antibodies can be either polyclonal or monoclonal; either intact or fragments. The peptides are optionally the products of a program of directed evolution.

Both naturally derived and synthetic peptides and nucleic acids are of use in conjunction with the present invention; these molecules can be attached to a sugar residue component or a crosslinking agent by any available reactive group. For example, peptides can be attached through a reactive amine, carboxyl, sulfhydryl, or hydroxyl group. The reactive group can reside at a peptide terminus or at a site internal to the peptide chain. Nucleic acids can be attached through a reactive group on a base (e.g., exocyclic amine) or an available hydroxyl group on a sugar moiety (e.g., 3'- or 5'-hydroxyl). The peptide and nucleic acid chains can be further derivatized at one or more sites to allow for the attachment of appropriate reactive groups onto the chain. See, Chrisey et al. *Nucleic Acids Res.* 24: 3031-3039 (1996).

In a further preferred embodiment, the biomolecule is selected to direct the peptide modified by the methods of the invention to a specific tissue, thereby enhancing the delivery of the peptide to that tissue relative to the amount of underivatized peptide that is delivered to the tissue. In a still further preferred embodiment, the amount of derivatized peptide delivered to a specific tissue within a selected time period is enhanced by derivatization by at least about 20%, more preferably, at least about 40%, and more preferably still, at least about 100%. Presently, preferred biomolecules for targeting applications include antibodies, hormones and ligands for cell-surface receptors.

In still a further exemplary embodiment, there is provided as conjugate with biotin. Thus, for example, a selectively biotinylated peptide is elaborated by the attachment of an avidin or streptavidin moiety bearing one or more modifying groups.

Therapeutic Moieties

In another preferred embodiment, the modified sugar includes a therapeutic moiety. Those of skill in the art will appreciate that there is overlap between the category of therapeutic moieties and biomolecules; many biomolecules have therapeutic properties or potential.

The therapeutic moieties can be agents already accepted for clinical use or they can be drugs whose use is experimental, or whose activity or mechanism of action is under investigation. The therapeutic moieties can have a proven action in a given disease state or can be only hypothesized to show desirable action in a given disease state. In a preferred embodiment, the therapeutic moieties are compounds, which are being screened for their ability to interact with a tissue of choice. Therapeutic moieties, which are useful in practicing the instant invention include drugs from a broad range of drug classes having a variety of pharmacological activities. Preferred therapeutic moieties are essentially non-fluorescent, or emit such a minimal amount of fluorescence that they are inappropriate for use as a fluorescent marker in an assay. Moreover, it is generally preferred to use therapeutic moieties that are not sugars. An exception to this preference is the use of a sugar that is modified by covalent attachment of another entity, such as a PEG, biomolecule, therapeutic moiety, diagnostic moiety and the like. In another exemplary embodiment, a therapeutic sugar moiety is conjugated to a linker arm and the sugar-linker arm cassette is subsequently conjugated to a peptide via a method of the invention.

Methods of conjugating therapeutic and diagnostic agents to various other species are well known to those of skill in the art. See, for example Hermanson, BIOCONJUGATE TECHNIQUES, Academic Press, San Diego, 1996; and Dunn et al., Eds. POLYMERIC DRUGS AND DRUG DELIVERY SYSTEMS, ACS Symposium Series Vol. 469, American Chemical Society, Washington, D.C. 1991.

In an exemplary embodiment, the therapeutic moiety is attached to the modified sugar via a linkage that is cleaved under selected conditions. Exemplary conditions include, but are not limited to, a selected pH (e.g., stomach, intestine, endocytotic vacuole), the presence of an active enzyme (e.g., esterase, reductase, oxidase), light, heat and the like. Many cleaveable groups are known in the art. See, for example, Jung et al., *Biochem. Biophys. Acta*, 761: 152-162 (1983); Joshi et al., *J. Biol. Chem.*, 265: 14518-14525 (1990); Zarling et al., *J. Immunol.*, 124: 913-920 (1980); Bouizar et al., *Eur. J. Biochem.*, 155: 141-147 (1986); Park et al., *J. Biol. Chem.*, 261: 205-210 (1986); Browning et al., *J. Immunol.*, 143: 1859-1867 (1989).

Enzymes
Glycosyltransferases

Glycosyltransferases catalyze the addition of activated sugars (donor NDP-sugars), in a step-wise fashion, to a protein, glycopeptide, lipid or glycolipid or to the non-reducing end of a growing oligosaccharide. N-linked glycopeptides are synthesized via a transferase and a lipid-linked oligosaccharide donor Dol-PP-NAG$_2$Glc$_3$Man$_9$ in an en block transfer followed by trimming of the core. In this case the nature of the "core" saccharide is somewhat different from subsequent attachments. A very large number of glycosyltransferases are known in the art.

The glycosyltransferase to be used in the present invention may be any as long as it can utilize the modified sugar as a sugar donor. Examples of such enzymes include Leloir pathway glycosyltransferase, such as galactosyltransferase, N-acetylglucosaminyltransferase, N-acetylgalactosaminyltransferase, fucosyltransferase, sialyltransferase, mannosyltransferase, xylosyltransferase, glucurononyltransferase and the like.

For enzymatic saccharide syntheses that involve glycosyltransferase reactions, glycosyltransferase can be cloned, or isolated from any source. Many cloned glycosyltransferases are known, as are their polynucleotide sequences. See, e.g., "The WWW Guide To Cloned Glycosyltransferases," at www.vei.co.ulk/TCN/gt_guide.htm. Glycosyltransferase amino acid sequences and nucleotide sequences encoding glycosyltransferases from which the amino acid sequences can be deduced are also found in various publicly available databases, including GenBank, Swiss-Prot, EMBL, and others.

Glycosyltransferases that can be employed in the methods of the invention include, but are not limited to, galactosyltransferases, fucosyltransferases, glucosyltransferases, N-acetylgalactosaminyltransferases, N-acetylglucosaminyltransferases, glucuronyltransferases, sialyltransferases, mannosyltransferases, glucuronic acid transferases, galacturonic acid transferases, and oligosaccharyltransferases. Suitable glycosyltransferases include those obtained from eukaryotes, as well as from prokaryotes.

DNA encoding the enzyme glycosyltransferases may be obtained by chemical synthesis, by screening reverse transcripts of mRNA from appropriate cells or cell line cultures, by screening genomic libraries from appropriate cells, or by combinations of these procedures. Screening of mRNA or genomic DNA may be carried out with oligonucleotide probes generated from the glycosyltransferases gene sequence. Probes may be labeled with a detectable group such as a fluorescent group, a radioactive atom or a chemiluminescent group in accordance with known procedures and used in conventional hybridization assays. In the alternative, glycosyltransferases gene sequences may be obtained by use of the polymerase chain reaction (PCR) procedure, with the PCR oligonucleotide primers being produced from the glycosyltransferases gene sequence. See, U.S. Pat. No. 4,683,195 to Mullis et al. and U.S. Pat. No. 4,683,202 to Mullis.

The glycosyltransferases enzyme may be synthesized in host cells transformed with vectors containing DNA encoding the glycosyltransferases enzyme. A vector is a replicable DNA construct. Vectors are used either to amplify DNA encoding the glycosyltransferases enzyme and/or to express DNA which encodes the glycosyltransferases enzyme. An expression vector is a replicable DNA construct in which a DNA sequence encoding the glycosyltransferases enzyme is operably linked to suitable control sequences capable of effecting the expression of the glycosyltransferases enzyme in a suitable host. The need for such control sequences will vary depending upon the host selected and the transformation method chosen. Generally, control sequences include a transcriptional promoter, an optional operator sequence to control transcription, a sequence encoding suitable mRNA ribosomal binding sites, and sequences which control the termination of transcription and translation. Amplification vectors do not require expression control domains. All that is needed is the ability to replicate in a host, usually conferred by an origin of replication, and a selection gene to facilitate recognition of transformants.

Fucosyltransferases

In some embodiments, a glycosyltransferase used in the method of the invention is a fucosyltransferase. Fucosyltransferases are known to those of skill in the art. Exemplary fucosyltransferases include enzymes, which transfer L-fucose from GDP-fucose to a hydroxy position of an acceptor sugar. Fucosyltransferases that transfer non-nucleotide sugars to an acceptor are also of use in the present invention.

In some embodiments, the acceptor sugar is, for example, the GlcNAc in a Galβ(1→3,4)GlcNAcβ-group in an oligosaccharide glycoside. Suitable fucosyltransferases for this reaction include the Galβ(1→3,4)GlcNAc 1-α(1→3,4)fucosyltransferase (FTIII E.C. No. 2.4.1.65), which was first characterized from human milk (see, Palcic, et al., Carbohydrate Res. 190:1-11 (1989); Prieels, et al., J. Biol. Chem. 256: 10456-10463 (1981); and Nunez, et al., Can. J. Chem. 59: 2086-2095 (1981)) and the Galβ(1→4)GlcNAcβ-αfucosyltransferases (FTIV, FTV, FTVI) which are found in human serum. FTVII (E.C. No. 2.4.1.65), a sialyl α(2→3)Galβ ((1→3)GlcNAcβ fucosyltransferase, has also been characterized. A recombinant form of the Galβ(1→3,4) GlcNAcβ-α (1→3,4)fucosyltransferase has also been characterized (see, Dumas, et al., Bioorg. Med. Letters 1: 425-428 (1991) and Kukowska-Latallo, et al., Genes and Development 4: 1288-1303 (1990)). Other exemplary fucosyltransferases include, for example, α1,2 fucosyltransferase (E.C. No. 2.4.1.69). Enzymatic fucosylation can be carried out by the methods described in Mollicone, et al., Eur. J. Biochem. 191: 169-176 (1990) or U.S. Pat. No. 5,374,655. Cells that are used to produce a fucosyltransferase will also include an enzymatic system for synthesizing GDP-fucose.

Galactosyltransferases

In another group of embodiments, the glycosyltransferase is a galactosyltransferase. Exemplary galactosyltransferases include α(1,3) galactosyltransferases (E.C. No. 2.4.1.151, see, e.g., Dabkowski et al., Transplant Proc. 25:2921 (1993) and Yamamoto et al. Nature 345: 229-233 (1990), bovine (GenBank j04989, Joziasse et al, J. Biol. Chem. 264: 14290-14297 (1989)), murine (GenBank m26925; Larsen et al., Proc. Nat'l. Acad. Sci. USA 86: 8227-8231 (1989)), porcine (GenBank L36152; Strahan et al., Immunogenetics 41: 101-105 (1995)). Another suitable α1,3 galactosyltransferase is that which is involved in synthesis of the blood group B antigen (EC 2.4.1.37, Yamamoto et al., J. Biol. Chem. 265: 1146-1151 (1990) (human)).

Also suitable for use in the methods of the invention are β(1,4) galactosyltransferases, which include, for example, EC 2.4.1.90 (LacNAc synthetase) and EC 2.4.1.22 (lactose synthetase) (bovine (D'Agostaro et al., Eur. J. Biochem. 183: 211-217 (1989)), human (Masri et al., Biochem. Biophys. Res. Commun. 157: 657-663 (1988)), murine (Nakazawa et al., J. Biochem. 104: 165-168 (1988)), as well as E.C. 2.4.1.38 and the ceramide galactosyltransferase (EC 2.4.1.45, Stahl et al., J. Neurosci. Res. 38: 234-242 (1994)). Other suitable galactosyltransferases include, for example, α1,2 galactosyltransferases (from e.g., Schizosaccharomyces pombe, Chapell et al, Mol. Biol. Cell 5: 519-528 (1994)).

The production of proteins such as the enzyme GalNAc T$_{I-XIV}$ from cloned genes by genetic engineering is well known. See, eg., U.S. Pat. No. 4,761,371. One method involves collection of sufficient samples, then the amino acid sequence of the enzyme is determined by N-terminal sequencing. This information is then used to isolate a cDNA clone encoding a full-length (membrane bound) transferase which upon expression in the insect cell line Sf9 resulted in the synthesis of a fully active enzyme. The acceptor specificity of the enzyme is then determined using a semiquantitative analysis of the amino acids surrounding known glycosylation sites in 16 different proteins followed by in vitro glycosylation studies of synthetic peptides. This work has demonstrated that certain amino acid residues are overrepresented in glycosylated peptide segments and that residues in specific positions surrounding glycosylated serine and threonine residues may have a more marked influence on acceptor efficiency than other amino acid moieties.

Sialyltransferases

Sialyltransferases are another type of glycosyltransferase that is useful in the recombinant cells and reaction mixtures of the invention. Cells that produce recombinant sialyltransferases will also produce CMP-sialic acid, which is a sialic acid donor for sialyltransferases. Examples of sialyltransferases that are suitable for use in the present invention include ST3Gal III (e.g., a rat or human ST3Gal III), ST3Gal IV, ST3Gal I, ST6Gal I, ST3Gal V, ST6Gal II, ST6GalNAc I, ST6GalNAc III, and ST6GalNAc III (the sialyltransferase nomenclature used herein is as described in Tsuji et al., *Glycobiology* 6: v-xiv (1996)). An exemplary α(2,3)sialyltransferase referred to as α(2,3)sialyltransferase (EC 2.4.99.6) transfers sialic acid to the non-reducing terminal Gal of a Galβ1→3Glc disaccharide or glycoside. See, Van den Eijnden et al., *J. Biol. Chem.* 256: 3159 (1981), Weinstein et al., *J. Biol. Chem.* 257: 13845 (1982) and Wen et al, *J. Biol. Chem.* 267: 21011 (1992). Another exemplary α2,3-sialyltransferase (EC 2.4.99.4) transfers sialic acid to the non-reducing terminal Gal of the disaccharide or glycoside. see, Rearick et al., *J. Biol. Chem.* 254: 4444 (1979) and Gillespie et al., *J. Biol. Chem.* 267: 21004 (1992). Further exemplary enzymes include Gal-β-1,4-GlcNAc α-2,6 sialyltransferase (See, Kurosawa et al. *Eur. J. Biochem.* 219: 375-381 (1994)).

Preferably, for glycosylation of carbohydrates of glycopeptides the sialyltransferase will be able to transfer sialic acid to the sequence Galβ1,4GlcNAc-, the most common penultimate sequence underlying the terminal sialic acid on fully sialylated carbohydrate structures (see, Table 3).

TABLE 3

Sialyltransferases which use the Galβ1,4GlcNAc sequence as an acceptor substrate

| Sialyltransferase | Source | Sequence(s) formed | Ref. |
|---|---|---|---|
| ST6Gal I | Mammalian | NeuAcα2,6Galβ1,4GlCNAc— | 1 |
| ST3Gal III | Mammalian | NeuAcα2,3Galβ1,4GlCNAc— | 1 |
|  |  | NeuAcα2,3Galβ1,3GlCNAc— |  |
| ST3Gal IV | Mammalian | NeuAcα2,3Galβ1,4GlCNAc— | 1 |
|  |  | NeuAcα2,3Galβ1,3GlCNAc— |  |
| ST6Gal II | Mammalian | NeuAcα2,6Galβ1,4GlCNA |  |
| ST6Gal II | photobacterium | NeuAcα2,6Galβ1,4GlCNAc— | 2 |
| ST3Gal V | *N. meningitides* *N. gonorrhoeae* | NeuAcα2,3Galβ1,4GlCNAc— | 3 |

Goochee et al., *Bio/Technology* 9: 1347-1355 (1991)
Yamamoto et al., *J. Biochem.* 120: 104-110 (1996)
Gilbert et al., *J. Biol Chem.* 271: 28271-28276 (1996)

An example of a sialyltransferase that is useful in the claimed methods is ST3Gal III, which is also referred to as α(2,3)sialyltransferase (EC 2.4.99.6). This enzyme catalyzes the transfer of sialic acid to the Gal of a Galβ1,3GlcNAc or Galβ1,4GlcNAc glycoside (see, e.g., Wen et al., *J. Biol. Chem.* 267: 21011 (1992); Van den Eijnden et al., *J. Biol. Chem.* 256: 3159 (1991)) and is responsible for sialylation of asparagine-linked oligosaccharides in glycopeptides. The sialic acid is linked to a Gal with the formation of an α-linkage between the two saccharides. Bonding (linkage) between the saccharides is between the 2-position of NeuAc and the 3-position of Gal. This particular enzyme can be isolated from rat liver (Weinstein et al., *J. Biol. Chem.* 257: 13845 (1982)); the human cDNA (Sasaki et al. (1993) *J. Biol. Chem.* 268: 22782-22787; Kitagawa & Paulson (1994) *J. Biol. Chem.* 269:1394-1401) and genomic (Kitagawa et al. (1996) *J. Biol. Chem.* 271: 931-938) DNA sequences are known, facilitating production of this enzyme by recombinant expression. In a preferred embodiment, the claimed sialylation methods use a rat ST3Gal III.

Other exemplary sialyltransferases of use in the present invention include those isolated from *Campylobacter jejuni*, including the α(2,3). See, e.g., WO99/49051.

Sialyltransferases other than those listed in Table 3, are also useful in an economic and efficient large-scale process for sialylation of commercially important glycopeptides. As a simple test to find out the utility of these other enzymes, various amounts of each enzyme (1-100 mU/mg protein) are reacted with asialo-α$_1$ AGP (at 1-10 mg/ml) to compare the ability of the sialyltransferase of interest to sialylate glycopeptides relative to either bovine ST6Gal I, ST3Gal III or both sialyltransferases. Alternatively, other glycopeptides or glycopeptides, or N-linked oligosaccharides enzymatically released from the peptide backbone can be used in place of asialo-α$_1$ AGP for this evaluation. Sialyltransferases with the ability to sialylate N-linked oligosaccharides of glycopeptides more efficiently than ST6Gal I are useful in a practical large-scale process for peptide sialylation (as illustrated for ST3Gal III in this disclosure).

Other Glycosyltransferases

One of skill in the art will understand that other glycosyltransferases can be substituted into similar transferase cycles as have been described in detail for the sialyltransferase. In particular, the glycosyltransferase can also be, for instance, glucosyltransferases, e.g., Alg8 (Stagljov et al., *Proc. Natl. Acad. Sci. USA* 91: 5977 (1994)) or Alg5 (Heesen et al, *Eur. J. Biochem.* 224: 71 (1994)).

N-acetylgalactosaminyltransferases are also of use in practicing the present invention. Suitable N-acetylgalactosaminyltransferases include, but are not limited to, α(1,3) N-acetylgalactosaminyltransferase, β(1,4) N-acetylgalactosaminyltransferases (Nagata et al., *J. Biol. Chem.* 267: 12082-12089 (1992) and Smith et al., *J. Biol. Chem.* 269: 15162 (1994)) and polypeptide N-acetylgalactosaminyltransferase (Homa et al., *J. Biol. Chem.* 268: 12609 (1993)). Suitable N-acetylglucosaminyltransferases include GnTI (2.4.1.101, Hull et al., *BBRC* 176: 608 (1991)), GnTII, GnTIII (Ihara et al., *J. Biochem.* 113: 692 (1993)), GnTIV, and GnTV (Shoreiban et al, *J. Biol. Chem.* 268: 15381 (1993)), O-linked N-acetylglucosaminyltransferase (Bierhuizen et al., *Proc. Natl. Acad. Sci. USA* 89: 9326 (1992)), N-acetylglucosamine-1-phosphate transferase (Rajput et al, *Biochem J.* 285: 985 (1992), and hyaluronan synthase.

Mannosyltransferases are of use to transfer modified mannose moieties. Suitable mannosyltransferases include α(1,2) mannosyltransferase, α(1,3) mannosyltransferase, α(1,6) mannosyltransferase, β(1,4) mannosyltransferase, Dol-P-

Man synthase, OCh1, and Pmt1 (see, Kornfeld et al., *Annu. Rev. Biochem.* 54: 631-664 (1985)).

Xylosyltransferases are also useful in the present invention. See, for example, Rodgers, et al., Biochem. J., 288:817-822 (1992); and Elbain, et al., U.S. Pat. No. 6,168,937.

Other suitable glycosyltransferase cycles are described in Ichikawa et al., *JACS* 114: 9283 (1992), Wong et al., *J. Org. Chem.* 57: 4343 (1992), and Ichikawa et al. in CARBOHYDRATES AND CARBOHYDRATE POLYMERS. Yaltami, ed. (ATL Press, 1993).

Prokaryotic glycosyltransferases are also useful in practicing the invention. Such glycosyltransferases include enzymes involved in synthesis of lipooligosaccharides (LOS), which are produced by many gram negative bacteria. The LOS typically have terminal glycan sequences that mimic glycoconjugates found on the surface of human epithelial cells or in host secretions (Preston et al., *Critical Reviews in Microbiology* 23(3): 139-180 (1996)). Such enzymes include, but are not limited to, the proteins of the rfa operons of species such as *E. coli* and *Salmonella typhimurium*, which include a β1,6 galactosyltransferase and a β1,3 galactosyltransferase (see, e.g., EMBL Accession Nos. M80599 and M86935 (*E. coli*); EMBL Accession No. S56361 (*S. typhimurium*)), a glucosyltransferase (Swiss-Prot Accession No. P25740 (*E. coli*), an β1,2-glucosyltransferase (rfaJ)(Swiss-Prot Accession No. P27129 (*E. coli*) and Swiss-Prot Accession No. P19817 (*S. typhimurium*)), and an β1,2-N-acetylglucosaminyltransferase (rfaK)(EMBL Accession No. U00039 (*E. coli*). Other glycosyltransferases for which amino acid sequences are known include those that are encoded by operons such as rfaB, which have been characterized in organisms such as *Klebsiella pneumoniae, E. coli, Salmonella typhimurium, Salmonella enterica, Yersinia enterocolitica, Mycobacterium leprosum*, and the rh1 operon of *Pseudomonas aeruginosa*.

Also suitable for use in the present invention are glycosyltransferases that are involved in producing structures containing lacto-N-neotetraose, D-galactosyl-β-1,4-N-acetyl-D-glucosaminyl-β-1,3-D-galactosyl-β-1,4-D-glucose, and the $P^k$ blood group trisaccharide sequence, D-galactosyl-α-1,4-D-galactosyl-β-1,4-D-glucose, which have been identified in the LOS of the mucosal pathogens *Neisseria gonnorhoeae* and *N. meningitidis* (Scholten et al., *J. Med. Microbiol.* 41: 236-243 (1994)). The genes from *N. meningitidis* and *N. gonorrhoeae* that encode the glycosyltransferases involved in the biosynthesis of these structures have been identified from *N. meningitidis* immunotypes L3 and L1 (Jennings et al., *Mol. Microbiol.* 18: 729-740 (1995)) and the *N. gonorrhoeae* mutant F62 (Gotshlich, *J. Exp. Med.* 180: 2181-2190 (1994)). In *N. meningitidis*, a locus consisting of three genes, IgtA, IgtB and Ig E, encodes the glycosyltransferase enzymes required for addition of the last three of the sugars in the lacto-N-neotetraose chain (Wakarchuk et al., *J. Biol. Chem.* 271: 19166-73 (1996)). Recently the enzymatic activity of the IgtB and IgtA gene product was demonstrated, providing the first direct evidence for their proposed glycosyltransferase function (Wakarchuk et al., *J. Biol. Chem.* 271(45): 28271-276 (1996)). In *N. gonorrhoeae*, there are two additional genes, IgtD which adds β-D-GalNAc to the 3 position of the terminal galactose of the lacto-N-neotetraose structure and IgtC which adds a terminal α-D-Gal to the lactose element of a truncated LOS, thus creating the $P^k$ blood group antigen structure (Gotshlich (1994), supra.). In *N. meningitidis*, a separate immunotype L1 also expresses the $P^k$ blood group antigen and has been shown to carry an IgtC gene (Jennings et al., (1995), supra.). *Neisseria* glycosyltransferases and associated genes are also described in U.S. Pat. No. 5,545,553 (Gotschlich). Genes for α1,2-fucosyltransferase and α1,3-fucosyltransferase from *Helicobacter pylori* has also been characterized (Martin et al., *J. Biol. Chem.* 272: 21349-21356 (1997)). Also of use in the present invention are the glycosyltransferases of *Campylobacter jejuni* (see, for example, http://afmb.cnrs-mrs.fr/~pedro/CAZY/gtf_42.html).

Sulfotransferases

The invention also provides methods for producing peptides that include sulfated molecules, including, for example sulfated polysaccharides such as heparin, heparan sulfate, carragenen, and related compounds. Suitable sulfotransferases include, for example, chondroitin-6-sulphotransferase (chicken cDNA described by Fukuta et al., *J. Biol. Chem.* 270: 18575-18580 (1995); GenBank Accession No. D49915), glycosaminoglycan N-acetylglucosamine N-deacetylase/N-sulphotransferase 1 (Dixon et al., *Genomics* 26: 239-241 (1995); UL 18918), and glycosaminoglycan N-acetylglucosamine N-deacetylase/N-sulphotransferase 2 (murine cDNA described in Orellana et al., *J. Biol. Chem.* 269: 2270-2276 (1994) and Eriksson et al., *J. Biol. Chem.* 269: 10438-10443 (1994); human cDNA described in GenBank Accession No. U2304).

Cell-Bound Glycosyltransferases

In another embodiment, the enzymes utilized in the method of the invention are cell-bound glycosyltransferases. Although many soluble glycosyltransferases are known (see, for example, U.S. Pat. No. 5,032,519), glycosyltransferases are generally in membrane-bound form when associated with cells. Many of the membrane-bound enzymes studied thus far are considered to be intrinsic proteins; that is, they are not released from the membranes by sonication and require detergents for solubilization. Surface glycosyltransferases have been identified on the surfaces of vertebrate and invertebrate cells, and it has also been recognized that these surface transferases maintain catalytic activity under physiological conditions. However, the more recognized function of cell surface glycosyltransferases is for intercellular recognition (Roth, MOLECULAR APPROACHES to SUPRACELLULAR PHENOMENA, 1990).

Methods have been developed to alter the glycosyltransferases expressed by cells. For example, Larsen et al., *Proc. Natl. Acad. Sci. USA* 86: 8227-8231 (1989), report a genetic approach to isolate cloned cDNA sequences that determine expression of cell surface oligosaccharide structures and their cognate glycosyltransferases. A cDNA library generated from mRNA isolated from a murine cell line known to express UDP-galactose:.β.-D-galactosyl-1,4-N-acetyl-D-glucosaminide α-1,3-galactosyltransferase was transfected into COS-1 cells. The transfected cells were then cultured and assayed for α-1-3 galactosyltransferase activity.

Francisco et al, *Proc. Natl. Acad. Sci. USA* 89: 2713-2717 (1992), disclose a method of anchoring β-lactamase to the external surface of *Escherichia coli*. A tripartite fusion consisting of (i) a signal sequence of an outer membrane protein, (ii) a membrane-spanning section of an outer membrane protein, and (iii) a complete mature β-lactamase sequence is produced resulting in an active surface bound β-lactamase molecule. However, the Francisco method is limited only to procaryotic cell systems and as recognized by the authors, requires the complete tripartite fusion for proper functioning.

Fusion Proteins

In other exemplary embodiments, the methods of the invention utilize fusion proteins that have more than one enzymatic activity that is involved in synthesis of a desired glycopeptide conjugate. The fusion polypeptides can be composed of, for example, a catalytically active domain of a glycosyltransferase that is joined to a catalytically active domain of an accessory enzyme. The accessory enzyme catalytic domain can, for example, catalyze a step in the formation of a nucleotide sugar that is a donor for the glycosyltransferase, or catalyze a reaction involved in a glycosyltransferase cycle. For example, a polynucleotide that encodes a glycosyltransferase can be joined, in-frame, to a polynucleotide that encodes an enzyme involved in nucleotide sugar synthesis. The resulting fusion protein can then catalyze not only the synthesis of the nucleotide sugar, but also the transfer of the sugar moiety to the acceptor molecule. The fusion protein can be two or more cycle enzymes linked into one expressible nucleotide sequence. In other embodiments the fusion protein includes the catalytically active domains of two or more glycosyltransferases. See, for example, U.S. Pat. No. 5,641,668. The modified glycopeptides of the present invention can be readily designed and manufactured utilizing various suitable fusion proteins (see, for example, PCT Patent Application PCT/CA98/01180, which was published as WO 99/31224 on Jun. 24, 1999.)

Immobilized Enzymes

In addition to cell-bound enzymes, the present invention also provides for the use of enzymes that are immobilized on a solid and/or soluble support. In an exemplary embodiment, there is provided a glycosyltransferase that is conjugated to a PEG via an intact glycosyl linker according to the methods of the invention. The PEG-linker-enzyme conjugate is optionally attached to solid support. The use of solid supported enzymes in the methods of the invention simplifies the work up of the reaction mixture and purification of the reaction product, and also enables the facile recovery of the enzyme. The glycosyltransferase conjugate is utilized in the methods of the invention. Other combinations of enzymes and supports will be apparent to those of skill in the art.

Exemplary peptides with which the present invention can be practiced, methods of adding or removing glycosylation sites, and adding or removing glycosyl structures or substructures are described in detail in WO03/031464 and related U.S. and PCT applications.

The present invention also takes advantage of adding to (or removing from) a peptide one or more selected glycosyl residues, after which a modified sugar is conjugated to at least one of the selected glycosyl residues of the peptide. The present embodiment is useful, for example, when it is desired to conjugate the modified sugar to a selected glycosyl residue that is either not present on a peptide or is not present in a desired amount. Thus, prior to coupling a modified sugar to a peptide, the selected glycosyl residue is conjugated to the peptide by enzymatic or chemical coupling. In another embodiment, the glycosylation pattern of a glycopeptide is altered prior to the conjugation of the modified sugar by the removal of a carbohydrate residue from the glycopeptide. See, for example WO 98/31826.

Addition or removal of any carbohydrate moieties present on the glycopeptide is accomplished either chemically or enzymatically. An exemplary chemical deglycosylation is brought about by exposure of the polypeptide variant to the compound trifluoromethanesulfonic acid, or an equivalent compound. This treatment results in the cleavage of most or all sugars except the linking sugar (N-acetylglucosamine or N-acetylgalactosamine), while leaving the peptide intact. Chemical deglycosylation is described by Hakimuddin et al., *Arch. Biochem. Biophys.* 259: 52 (1987) and by Edge et al., *Anal Biochem.* 118: 131 (1981). Enzymatic cleavage of carbohydrate moieties on polypeptide variants can be achieved by the use of a variety of endo- and exo-glycosidases as described by Thotakura et al., *Meth. Enzymol.* 138: 350 (1987).

In an exemplary embodiment, the peptide is essentially completely desialylated with neuraminidase prior to performing glycoconjugation or remodeling steps on the peptide. Following the glycoconjugation or remodeling, the peptide is optionally re-sialylated using a sialyltransferase. In an exemplary embodiment, the re-sialylation occurs at essentially each (e.g., >80%, preferably greater than 85%, greater than 90%, preferably greater than 95% and more preferably greater than 96%, 97%, 98% or 99%) terminal saccharyl acceptor in a population of sialyl acceptors. In a preferred embodiment, the saccharide has a substantially uniform sialylation pattern (i.e., substantially uniform glycosylation pattern).

Chemical addition of glycosyl moieties is carried out by any art-recognized method. Enzymatic addition of sugar moieties is preferably achieved using a modification of the methods set forth herein, substituting native glycosyl units for the modified sugars used in the invention. Other methods of adding sugar moieties are disclosed in U.S. Pat. Nos. 5,876,980, 6,030,815, 5,728,554, and 5,922,577.

Exemplary attachment points for selected glycosyl residue include, but are not limited to: (a) consensus sites for N-linked glycosylation, and sites for O-linked glycosylation; (b) terminal glycosyl moieties that are acceptors for a glycosyltransferase; (c) arginine, asparagine and histidine; (d) free carboxyl groups; (e) free sulfhydryl groups such as those of cysteine; (f) free hydroxyl groups such as those of serine, threonine, or hydroxyproline; (g) aromatic residues such as those of phenylalanine, tyrosine, or tryptophan; or (h) the amide group of glutamine. Exemplary methods of use in the present invention are described in WO 87/05330 published Sep. 11, 1987, and in Aplin and Wriston, CRC Crit. Rev. Biochem., pp. 259-306 (1981).

In an exemplary embodiment, the peptide that is modified by a method of the invention is a glycopeptide that is produced in mammalian cells (e.g., CHO cells) or in a transgenic animal and thus, contains N- and/or O-linked oligosaccharide chains, which are incompletely sialylated. The oligosaccharide chains of the glycopeptide lacking a sialic acid and containing a terminal galactose residue can be PEGylated, PPGylated or otherwise modified with a modified sialic acid.

Exemplary PEG-sialic acid derivative include:

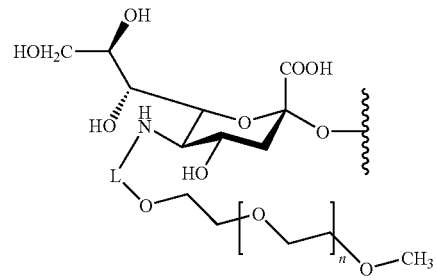

in which L is a substituted or unsubstituted alkyl or substituted or unsubstituted heteroalkyl linker moiety joining the sialic acid moiety and the PEG moiety, and "n" is 1 or greater; and

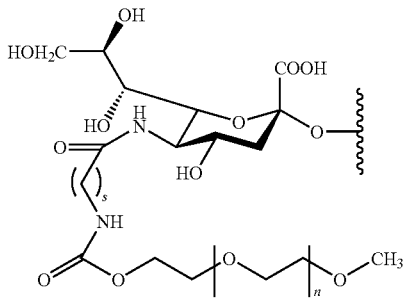

in which the index "s" represents an integer from 0 to 20, and "n" is 1 or greater.

Linker Groups (Cross-linking Groups)

Preparation of the Modified Sugar for Use in the Methods of the Present Invention includes attachment of a modifying group to a sugar residue and forming a stable adduct, which is a substrate for a glycosyltransferase. The sugar and modifying group can be coupled by a zero- or higher-order cross-linking agent. Exemplary bifunctional compounds which can be used for attaching modifying groups to carbohydrate moieties include, but are not limited to, bifunctional poly(ethylene glycols), polyamides, polyethers, polyesters and the like. General approaches for linking carbohydrates to other molecules are known in the literature. See, for example, Lee et al., *Biochemistry* 28: 1856 (1989); Bhatia et al., *Anal. Biochem.* 178: 408 (1989); Janda et al., *J. Am. Chem. Soc.* 112: 8886 (1990) and Bednarski et al., WO 92/18135. In the discussion that follows, the reactive groups are treated as benign on the sugar moiety of the nascent modified sugar. The focus of the discussion is for clarity of illustration. Those of skill in the art will appreciate that the discussion is relevant to reactive groups on the modifying group as well.

Cleavable Linker Groups

In yet a further embodiment, the linker group is provided with a group that can be cleaved to release the modifying group from the sugar residue. Many cleaveable groups are known in the art. See, for example, Jung et al., *Biochem. Biophys. Acta* 761: 152-162 (1983); Joshi et al., *J. Biol. Chem.* 265: 14518-14525 (1990); Zarling et al., *J. Immunol.* 124: 913-920 (1980); Bouizar et al., *Eur. J. Biochem.* 155: 141-147 (1986); Park et al., *J. Biol. Chem.* 261: 205-210 (1986); Browning et al., *J. Immunol.* 143: 1859-1867 (1989). Moreover a broad range of cleavable, bifunctional (both homo- and hetero-bifunctional) linker groups is commercially available from suppliers such as Pierce.

Exemplary cleaveable moieties can be cleaved using light, heat or reagents such as thiols, hydroxylamine, bases, periodate and the like. Moreover, certain preferred groups are cleaved in vivo in response to being endocytized (e.g., cis-aconityl; see, Shen et al., *Biochem. Biophys. Res. Commun.* 102: 1048 (1991)). Preferred cleaveable groups comprise a cleaveable moiety which is a member selected from the group consisting of disulfide, ester, imide, carbonate, nitrobenzyl, phenacyl and benzoin groups.

Conjugation of Modified Sugars to Peptides

The modified sugars are conjugated to a glycosylated or non-glycosylated peptide using an appropriate enzyme to mediate the conjugation. Preferably, the concentrations of the modified donor sugar(s), enzyme(s) and acceptor peptide(s) are selected such that glycosylation proceeds until the acceptor is consumed. The considerations discussed below, while set forth in the context of a sialyltransferase, are generally applicable to other glycosyltransferase reactions.

A number of methods of using glycosyltransferases to synthesize desired oligosaccharide structures are known and are generally applicable to the instant invention. Exemplary methods are described, for instance, WO 96/32491, Ito et al., *Pure Appl. Chem.* 65: 753 (1993), and U.S. Pat. Nos. 5,352,670, 5,374,541, 5,545,553, commonly owned U.S. Pat. Nos. 6,399,336, and 6,440,703, and commonly owned published PCT applications, WO 03/031464, WO 04/033651, WO 04/099231, which are incorporated herein by reference.

The present invention is practiced using a single glycosyltransferase or a combination of glycosyltransferases. For example, one can use a combination of a sialyltransferase and a galactosyltransferase. In those embodiments using more than one enzyme, the enzymes and substrates are preferably combined in an initial reaction mixture, or the enzymes and reagents for a second enzymatic reaction are added to the reaction medium once the first enzymatic reaction is complete or nearly complete. By conducting two enzymatic reactions in sequence in a single vessel, overall yields are improved over procedures in which an intermediate species is isolated. Moreover, cleanup and disposal of extra solvents and by-products is reduced.

In a preferred embodiment, each of the first and second enzyme is a glycosyltransferase. In another preferred embodiment, one enzyme is an endoglycosidase. In an additional preferred embodiment, more than two enzymes are used to assemble the modified glycoprotein of the invention. The enzymes are used to alter a saccharide structure on the peptide at any point either before or after the addition of the modified sugar to the peptide.

In another embodiment, the method makes use of one or more exo- or endoglycosidase. The glycosidase is typically a mutant, which is engineered to form glycosyl bonds rather than cleave them. The mutant glycanase typically includes a substitution of an amino acid residue for an active site acidic amino acid residue. For example, when the endoglycanase is endo-H, the substituted active site residues will typically be Asp at position 130, Glu at position 132 or a combination thereof. The amino acids are generally replaced with serine, alanine, asparagine, or glutamine.

The mutant enzyme catalyzes the reaction, usually by a synthesis step that is analogous to the reverse reaction of the endoglycanase hydrolysis step. In these embodiments, the glycosyl donor molecule (e.g., a desired oligo- or monosaccharide structure) contains a leaving group and the reaction proceeds with the addition of the donor molecule to a GlcNAc residue on the protein. For example, the leaving group can be a halogen, such as fluoride. In other embodiments, the leaving group is a Asn, or a Asn-peptide moiety. In yet further embodiments, the GlcNAc residue on the glycosyl donor molecule is modified. For example, the GlcNAc residue may comprise a 1,2 oxazoline moiety.

In a preferred embodiment, each of the enzymes utilized to produce a conjugate of the invention are present in a catalytic amount. The catalytic amount of a particular enzyme varies according to the concentration of that enzyme's substrate as well as to reaction conditions such as temperature, time and pH value. Means for determining the catalytic amount for a given enzyme under preselected substrate concentrations and reaction conditions are well known to those of skill in the art.

The temperature at which an above process is carried out can range from just above freezing to the temperature at which the most sensitive enzyme denatures. Preferred temperature ranges are about 0° C. to about 55° C., and more preferably about 20° C. to about 30° C. In another exemplary embodiment, one or more components of the present method are conducted at an elevated temperature using a thermophilic enzyme.

The reaction mixture is maintained for a period of time sufficient for the acceptor to be glycosylated, thereby forming the desired conjugate. Some of the conjugate can often be detected after a few hours, with recoverable amounts usually being obtained within 24 hours or less. Those of skill in the art understand that the rate of reaction is dependent on a number of variable factors (e.g., enzyme concentration, donor concentration, acceptor concentration, temperature, solvent volume), which are optimized for a selected system.

The present invention also provides for the industrial-scale production of modified peptides. As used herein, an industrial scale generally produces at least 1 gram of finished, purified conjugate.

In the discussion that follows, the invention is exemplified by the conjugation of modified sialic acid moieties to a glycosylated peptide. The exemplary modified sialic acid is labeled with m-PEG. The focus of the following discussion on the use of PEG-modified sialic acid and glycosylated peptides is for clarity of illustration and is not intended to imply that the invention is limited to the conjugation of these two partners. One of skill understands that the discussion is generally applicable to the additions of modified glycosyl moieties other than sialic acid. Moreover, the discussion is equally applicable to the modification of a glycosyl unit with agents other than m-PEG including other PEG moieties, therapeutic moieties, and biomolecules.

An enzymatic approach can be used for the selective introduction of m-PEGylated or m-PPGylated carbohydrates onto a peptide or glycopeptide. The method utilizes modified sugars containing PEG, PPG, or a masked reactive functional group, and is combined with the appropriate glycosyltransferase or glycosynthase. By selecting the glycosyltransferase that will make the desired carbohydrate linkage and utilizing the modified sugar as the donor substrate, the PEG or PPG can be introduced directly onto the peptide backbone, onto existing sugar residues of a glycopeptide or onto sugar residues that have been added to a peptide.

In an exemplary embodiment, an acceptor for a sialyltransferase is present on the peptide to be modified either as a naturally occurring structure or is placed there recombinantly, enzymatically or chemically. Suitable acceptors, include, for example, galactosyl acceptors such as Galβ1,4GlcNAc, Galβ1,4GalNAc, Galβ1,3GalNAc, lacto-N-tetraose, Galβ1, 3GlcNAc, GalNAc, Galβ1,3GalNAc, Galβ1,6GlcNAc, Galβ1,4Glc (lactose), and other acceptors known to those of skill in the art (see, e.g., Paulson et al., *J. Biol. Chem.* 253: 5617-5624 (1978)). Exemplary sialytransferases are set forth herein.

In one embodiment, an acceptor for the sialyltransferase is present on the glycopeptide to be modified upon in vivo synthesis of the glycopeptide. Such glycopeptides can be sialylated using the claimed methods without prior modification of the glycosylation pattern of the glycopeptide. Alternatively, the methods of the invention can be used to sialylate a peptide that does not include a suitable acceptor; one first modifies the peptide to include an acceptor by methods known to those of skill in the art. In an exemplary embodiment, a GalNAc residue is added by the action of a GalNAc transferase.

In an exemplary embodiment, the galactosyl acceptor is assembled by attaching a galactose residue to an appropriate acceptor linked to the peptide, e.g., a GlcNAc. The method includes incubating the peptide to be modified with a reaction mixture that contains a suitable amount of a galactosyltransferase (e.g., Galβ1,3 or Galβ1,4), and a suitable galactosyl donor (e.g., UDP-galactose). The reaction is allowed to proceed substantially to completion or, alternatively, the reaction is terminated when a preselected amount of the galactose residue is added. Other methods of assembling a selected saccharide acceptor will be apparent to those of skill in the art.

In yet another embodiment, glycopeptide-linked oligosaccharides are first "trimmed," either in whole or in part, to expose either an acceptor for the sialyltransferase or a moiety to which one or more appropriate residues can be added to obtain a suitable acceptor. Enzymes such as glycosyltransferases and endoglycosidases (see, for example U.S. Pat. No. 5,716,812) are useful for the attaching and trimming reactions. In another embodiment of this method, the sialic acid moieties of the peptide are essentially completely removed (e.g., at least 90, at least 95 or at least 99%), exposing an acceptor for a modified sialic acid.

In the discussion that follows, the method of the invention is exemplified by the use of modified sugars having a PEG moiety attached thereto. The focus of the discussion is for clarity of illustration. Those of skill will appreciate that the discussion is equally relevant to those embodiments in which the modified sugar bears a therapeutic moiety, biomolecule or the like.

In an exemplary embodiment of the invention in which a carbohydrate residue is "trimmed" prior to the addition of the modified sugar, high mannose is trimmed back to the first generation biantennary structure. A modified sugar bearing a PEG moiety is conjugated to one or more of the sugar residues exposed by the "trimming back." In one example, a PEG moiety is added via a GlcNAc conjugated to the PEG moiety. The modified GlcNAc is attached to one or both of the terminal mannose residues of the biantennary structure. Alternatively, an unmodified GlcNAc can be added to one or both of the termini of the branched species.

In another exemplary embodiment, a PEG moiety is added to one or both of the terminal mannose residues of the biantennary structure via a modified sugar having a galactose residue, which is conjugated to a GlcNAc residue added onto the terminal mannose residues. Alternatively, an unmodified Gal can be added to one or both terminal GlcNAc residues.

In yet a further example, a PEG moiety is added onto a Gal residue using a modified sialic acid such as those discussed above.

In another exemplary embodiment, an O-linked glycosyl residue is "trimmed back" to the GalNAc attached to the amino acid. In one example, a water-soluble polymer is added via a Gal modified with the polymer. Alternatively, an unmodified Gal is added to the GalNAc, followed by a Gal with an attached water-soluble polymer. In yet another embodiment, one or more unmodified Gal residue is added to the GalNAc, followed by a sialic acid moiety modified with a water-soluble polymer.

A high mannose structure can also be trimmed back to the elementary tri-mannosyl core.

In a further exemplary embodiment, high mannose is "trimmed back" to the GlcNAc to which the first mannose is attached. The GlcNAc is conjugated to a Gal residue bearing a PEG moiety. Alternatively, an unmodified Gal is added to the GlcNAc, followed by the addition of a sialic acid modified with a water-soluble sugar. In yet a further example, the terminal GlcNAc is conjugated with Gal and the GlcNAc is subsequently fucosylated with a modified fucose bearing a PEG moiety.

High mannose may also be trimmed back to the first GlcNAc attached to the Asn of the peptide. In one example, the GlcNAc of the GlcNAc-(Fuc)$_a$ residue is conjugated with ha GlcNAc bearing a water soluble polymer. In another example, the GlcNAc of the GlcNAc-(Fuc)$_a$ residue is modified with Gal, which bears a water soluble polymer. In a still further embodiment, the GlcNAc is modified with Gal, followed by conjugation to the Gal of a sialic acid modified with a PEG moiety.

Other exemplary embodiments are set forth in commonly owned U.S. Patent application Publications: 20040132640; 20040063911; 20040137557; U.S. patent application Ser. Nos. 10/369,979; 10/410,913; 10/360,770; 10/410,945 and PCT/US02/32263 each of which is incorporated herein by reference.

The Examples set forth above provide an illustration of the power of the methods set forth herein. Using the methods of the invention, it is possible to "trim back" and build up a carbohydrate residue of substantially any desired structure.

The modified sugar can be added to the termini of the carbohydrate moiety as set forth above, or it can be intermediate between the peptide core and the terminus of the carbohydrate.

Glycosylation by Recombinant Methods

Glycosylation of a mutant human growth hormone may also be accomplished intracellularly by recombinant means. A polynucleotide sequence encoding a mutant human growth hormone, which comprises at least one newly introduced N- or O-linked glycosylation site, may be transfected into a suitable host cell line, e.g., a eukaryotic cell line derived from yeast, insect, or mammalian origin. The mutant human growth hormone recombinantly produced from such a cell line is glycosylated by the host cell glycosylation machinery.

In a selected embodiment, a hGH peptide, expressed in insect cells, is remodeled such that glycans on the remodeled glycopeptide include a GlcNAc-Gal glycosyl residue. The addition of GlcNAc and Gal can occur as separate reactions or as a single reaction in a single vessel. In this example, GlcNAc-transferase I and Gal-transferase I are used. The modified sialyl moiety is added using ST3Gal-III.

In another embodiment, the addition of GlcNAc, Gal and modified Sia can also occur in a single reaction vessel, using the enzymes set forth above. Each of the enzymatic remodeling and glycoPEGylation steps are carried out individually.

When the peptide is expressed in mammalian cells, different methods are of use. In one embodiment, the peptide is conjugated without need for remodeling prior to conjugation by contacting the peptide with a sialyltransferase that transfers the modified sialic acid directly onto a sialic acid on the peptide forming Sia-Sia-L-$R^1$, or exchanges a sialic acid on the peptide for the modified sialic acid, forming Sia-L-$R^1$. An exemplary enzyme of use in this method is CST-II. Other enzymes that add sialic acid to sialic acid are known to those of skill in the art and examples of such enzymes are set forth the figures appended hereto.

In yet another method of preparing the conjugates of the invention, the peptide expressed in a mammalian system is desialylated using a sialidase. The exposed Gal residue is sialylated with a modified sialic acid using a sialyltransferase specific for O-linked glycans, providing an hGH peptide with an O-linked modified glycan. The desialylated, modified hGH peptide is optionally partially or fully re-sialylated by using a sialyltransferase such as ST3GalIII.

In another aspect, the invention provides a method of making a PEGylated hGH of the invention. The method includes: (a) contacting a substrate hGH peptide comprising a glycosyl group selected from:

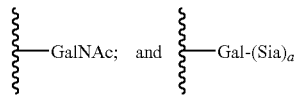

with a sugar donor and an enzyme for which the sugar donor is a substrate under conditions appropriate to transfer a sugar moiety from the sugar donor to the hGH peptide. In an exemplary embodiment, the sugar moiety is a modified sugar moiety. In another exemplary embodiment, the modified sugar moiety is a modified sialic acid residue with a water-soluble polymer (e.g., PEG) covalently attached thereto. An exemplary PEG-sialic acid sugar donor has the formula:

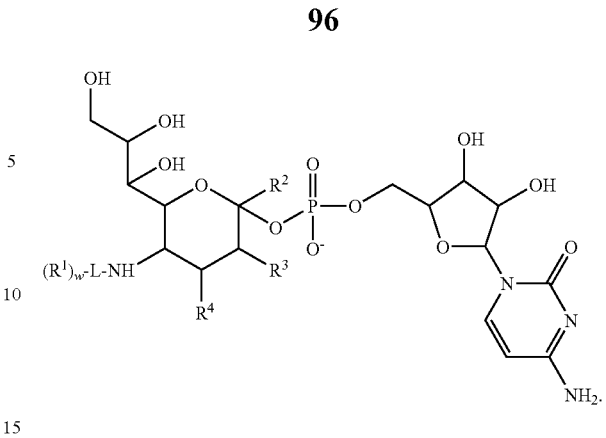

A preferred enzyme transfers PEG-sialic acid from said donor onto a member selected from the GalNAc, Gal and the Sia of a glycosyl group, under conditions appropriate for the transfer. An exemplary modified sialic acid donor is CMP-sialic acid modified, through a linker moiety, with a polymer, e.g., a straight chain or branched poly(ethylene glycol) moiety. As discussed herein, the peptide is optionally glycosylated with GalNAc and/or Gal and/or Sia ("Remodeled") prior to attaching the modified sugar. The remodeling steps can occur in sequence in the same vessel without purification of the glycosylated peptide between steps. Alternatively, following one or more remodeling step, the glycosylated peptide can be purified prior to submitting it to the next glycosylation or glycPEGylation step.

As illustrated in the examples and discussed further below, placement of an acceptor moiety for the PEG-sugar is accomplished in any desired number of steps. For example, in one embodiment, the addition of GalNAc to the peptide can be followed by a second step in which the PEG-sugar is conjugated to the GalNAc in the same reaction vessel. Alternatively, these two steps can be carried out in a single vessel approximately simultaneously.

In a further exemplary embodiment, the hGH peptide is expressed in an appropriate expression system prior to being glycopegylated or remodeled. Exemplary expression systems include Sf-9/baculovirus and Chinese Hamster Ovary (CHO) cells.

In another exemplary embodiment, the invention provides methods of forming a conjugate of hGH such as those set forth herein in which the hGH in the conjugate is essentially unoxidized. Oxidation of methionine residues of PEG-hGH can be detected by N-terminal sequencing and peptide mapping. Oxidation or its absence can be confirmed using RP-HPLC. For example, using RP-HPLC, a peak in addition the major PEG-hGH peak was detected, which represents a PEG-hGH species in which methionine is oxidized (Met-Ox). For hGH this peak has been identified as Met127/Met138 oxidation, eluting 0.2 min before the main peak. Additionally, a small peak eluting approximately 3 min before the main peak as Met122 oxidation has been identified. Met1 oxidation was detected by RP-HPLC using the 60° C. method, but coelutes with the main peak. This N-terminal methionine oxidation is detected by peptide mapping and is referred to as G1-Ox.

Thus, in an exemplary embodiment, the invention provides a population of hGH conjugates, as described herein, in which less than 10%, preferably less than 5%, more preferably less than 1%, more preferably less than 0.5%, still more preferably less than 0.1%, preferably less than 0.05%, more preferably less than 0.01%, even more preferably less than 0.005% and still more preferably less than 0.001% of the members of the population include a methionine residue selected from Met127, Met138, Met 122, N-terminal Met and combinations thereof which is oxidized.

In an exemplary method according to the invention, the enzymatic conjugation of the modified sugar to the peptide is performed under conditions that prevent or retard the oxidation of methionine residues of the peptide. In an exemplary embodiment, the reaction mixture includes added methionine. Exemplary methods of the invention use up to about 20 mM methionine in the conjugation reaction mixture.

Purification of Glycosylated Mutant hGH

The products produced by the above processes can be used without purification. However, it is usually preferred to recover the product and one or more of the intermediates, e.g., nucleotide sugars, branched and linear PEG species, modified sugars and modified nucleotide sugars. Standard, well known techniques for recovery of glycosylated saccharides such as thin or thick layer chromatography, column chromatography, ion exchange chromatography, or membrane filtration can be used. It is preferred to use membrane filtration, more preferably utilizing a reverse osmotic membrane, or one or more column chromatographic techniques for the recovery as is discussed hereinafter and in the literature cited herein. For instance, membrane filtration wherein the membranes have molecular weight cutoff of about 3000 to about 10,000 can be used to remove proteins such as glycosyl transferases. Nanofiltration or reverse osmosis can then be used to remove salts and/or purify the product saccharides (see, e.g., WO 98/15581). Nanofilter membranes are a class of reverse osmosis membranes that pass monovalent salts but retain polyvalent salts and uncharged solutes larger than about 100 to about 2,000 Daltons, depending upon the membrane used. Thus, in a typical application, saccharides prepared by the methods of the present invention will be retained in the membrane and contaminating salts will pass through.

If the glycosylated mutant human growth hormone is produced intracellularly, as a first step, the particulate debris, either host cells or lysed fragments, is removed. Following glycoPEGylation, the PEGylated peptide is purified by art-recognized methods, for example, by centrifugation or ultrafiltration; optionally, the protein may be concentrated with a commercially available protein concentration filter, followed by separating the polypeptide variant from other impurities by one or more steps selected from immunoaffinity chromatography, ion-exchange column fractionation (e.g., on diethylaminoethyl (DEAE) or matrices containing carboxymethyl or sulfopropyl groups), chromatography on Blue-Sepharose, CM Blue-Sepharose, MONO-Q, MONO-S, lentil lectin-Sepharose, WGA-Sepharose, Con A-Sepharose, Ether Toyopearl, Butyl Toyopearl, Phenyl Toyopearl, SP-Sepharose, or protein A Sepharose, SDS-PAGE chromatography, silica chromatography, chromatofocusing, reverse phase HPLC (e.g., silica gel with appended aliphatic groups), gel filtration using, e.g., Sephadex molecular sieve or size-exclusion chromatography, chromatography on columns that selectively bind the polypeptide, and ethanol or ammonium sulfate precipitation.

Modified glycopeptides produced in culture are usually isolated by initial extraction from cells, cell lysate, culture media, etc., followed by one or more concentration, salting-out, aqueous ion-exchange, or size-exclusion chromatography steps. Additionally, the modified glycoprotein may be purified by affinity chromatography. Finally, HPLC may be employed for final purification steps.

A protease inhibitor, e.g., methylsulfonylfluoride (PMSF) may be included in any of the foregoing steps to inhibit proteolysis and antibiotics or preservatives may be included to prevent the growth of adventitious contaminants.

In another embodiment, supernatants from systems that produce the modified human growth hormone of the invention are first concentrated using a commercially available protein concentration filter, for example, an Amicon or Millipore Pellicon ultrafiltration unit. Following the concentration step, the concentrate may be applied to a suitable purification matrix. For example, a suitable affinity matrix may comprise a ligand for the peptide, a lectin or antibody molecule bound to a suitable support. Alternatively, an anion-exchange resin may be employed, for example, a matrix or substrate having pendant DEAE groups. Suitable matrices include acrylamide, agarose, dextran, cellulose, or other types commonly employed in protein purification. Alternatively, a cation-exchange step may be employed. Suitable cation exchangers include various insoluble matrices comprising sulfopropyl or carboxymethyl groups. Sulfopropyl groups are particularly preferred.

Other methods of use in purification include size exclusion chromatography (SEC), hydroxyapatite chromatography, hydrophobic interaction chromatography and chromatography on Blue Sepharose. These and other useful methods are illustrated in co-assigned U.S. Provisional Patent Application No. 60/678,822, filed May 6, 2005.

One or more RP-HPLC steps employing hydrophobic RP-HPLC media, e.g., silica gel having pendant methyl or other aliphatic groups, may be employed to further purify a polypeptide conjugate composition. Some or all of the foregoing purification steps, in various combinations, can also be employed to provide a homogeneous or essentially homogeneous modified glycoprotein.

The modified glycopeptide of the invention resulting from a large-scale fermentation may be purified by standard methods analogous to those disclosed by Urdal et al., *J. Chromatog.* 296: 171 (1984). This reference describes two sequential, RP-HPLC steps for purification of recombinant human IL-2 on a preparative HPLC column. Alternatively, techniques such as affinity chromatography may be utilized to purify the modified glycoprotein. For instance, chemically PEGylated mutant hGH products of the invention may be fractionated using standard chromatographic techniques known in the art to obtain a more homogenous product containing specific numbers of PEG or fractions of PEG (e.g. 1-3, 2-4, etc.).

In an exemplary embodiment, the purification is accomplished by the methods set forth in commonly owned, co-assigned U.S. Provisional Patent No. 60/665,588, filed Mar. 24, 2005.

In another exemplary embodiment, the purification is effected by SPHP chromatography using an appropriate buffer as an eluent. Exemplary buffers include citrate and acetate buffers, with citrate presently preferred.

In a further exemplary embodiment, a phosphate salt, e.g, sodium phosphate is added to the enzymatic conjugation reaction mixture. The reaction mixture is centrifuged and the resulting mixture is purified by SPHP. In this embodiment, free methionine, which is not covalently attached to the hGH peptide, is either present or absent during the purification step.

An exemplary purification process, as set forth above, results in the isolation of a population of hGH conjugates, as described herein, in which less than 10%, preferably less than 5%, more preferably less than 1%, more preferably less than 0.5%, still more preferably less than 0.1%, preferably less than 0.05%, more preferably less than 0.01%, even more preferably less than 0.005% and still more preferably less than 0.001% of the members of the population include a methionine residue selected from Met127, Met138, Met 122, N-terminal Met and combinations thereof which is oxidized.

In yet another exemplary embodiment, the purified hGH conjugate composition includes a population of hGH peptides in which less than 10%, preferably less than 5%, more preferably less than 1%, more preferably less than 0.5%, still more preferably less than 0.1%, preferably less than 0.05%, more preferably less than 0.01%, even more preferably less than 0.005% and still more preferably less than 0.001% of the population of peptides is associated in a peptide aggregate as determined by size-exclusion chromatography.

Protease Resistant Mutant hGH

The present invention also provides protease resistant hGH mutants. As used herein, the terms "protease resistant" and "proteolysis resistant" refer to hGH peptides (e.g., mutants) that enhance the stability of the mutant hGH peptide relative to the wild type hGH peptide in the presence of a protease. In a preferred embodiment, the protease recognition site of the wild type is completely inactivated in the mutant and is not a site of cleavage by the protease that cleaved the corresponding site in the wild type. In exemplary embodiments, the rate of cleavage is reduced by about 30%, more preferably by about 60%, and even more preferably by about 90%.

In an exemplary embodiment, protease resistance is imbued by mutation of one or more amino acids within a protease recognition site. In another exemplary embodiment, protease resistance is imparted by the presence of one or more water-soluble polymer moieties covalently bound to the peptide proximate the protease recognition site. The water-soluble peptide can be placed by reaction with an activated water-soluble polymer (e.g., NHS-ester of PEG) or enzymatically (e.g., by glycoPEGylation). Those of skill will appreciate that a combination of mutation and conjugation of a water-soluble polymer can be used.

In an exemplary embodiment, chemical PEGylation of hGH prior to and/or after glycoPEGylation is used to achieve the protease resistant hGH of the present invention. These two types of peptide PEGylation can be performed in any combinations and order. Chemical PEGylation, as contemplated in the present invention, involves the binding of PEG, or other blocking group, i.e. a group inhibiting proteolysis, either in or near various protease recognition sites, thereby allowing the PEG, or other group, to serve essentially as a protease inhibitor. Peptides chemically PEGylated in this manner show enhanced resistance to protease degradation.

Methods for chemically PEGylating peptides are widely-known in the art (e.g. see Background section). Chemical PEGylation is performed with any acceptable PEGylation reagent. Exemplary standard activated PEG groups known in the art can be used for this process (see, Shearwater Polymers, Nektar Therapeutics catalogs). Moreover, the linear and branched PEG species set forth herein are similarly of use in practicing the present methods. It will be apparent to those of skill that the PEG molecules set forth herein are readily conversted to useful activated derivatives by methods known in the art.

In preferred embodiments, the molecular weights of PEG to be used include 500 MW, 2 kDa, 5 kDa, 10 kDa, 20 kDa, 30 kDa, and 40 kDa, etc. Other acceptable branched and linear PEG structures are discussed in the preceding sections.

It should be noted that protease inhibiting groups other than PEG, including other water-soluble polymers, water-insoluble polymers, therapeutic moieties, and biomolecules, are also useful in practicing the present invention.

Functional Assays for the Mutant hGH

Following the production and, preferably, purification of a glycosylated mutant human growth hormone, the biological functions of the glycoprotein are tested using several methods known in the art. The functional assays are based on various characteristics of human growth hormone, such as its specific binding to human growth hormone receptor, activation of the hGH receptor, and its activity in promoting cell growth. In each assay, wild-type human growth hormone is included as a positive control.

A radioreceptor binding assay can be carried out to measure the binding between a radio-labeled hGH receptor and a mutant human growth hormone of the present invention. Detailed description for such an assay can be found in the literature, e.g., Tsushima et al., *J. Clin. Endocrinol. Metab.*, 37: 334-337 (1973); Chin et al., *Endocr. Meta.* 37: 334 (1973); and U.S. Pat. Nos. 4,871,835, 5,079,230.

The ability of a mutant human growth hormone to promote cell growth is assessed by methods such as the tibia test (Parlow et al., *Endocrinology* 77: 1126 (1965); U.S. Pat. No. 4,871,835). Briefly, rats are hypophysectomized at 28-30 days of age and kept for 10-14 days without treatment. Human growth hormone mutants derived from recombinant source is then given to the rats by daily subcutaneous injections. The animals are sacrificed on the sixth day, their foreleg knee bones taken out and the width of the epiphyseal plates measured. The weight of these rats at the start of the experiment and before being sacrificed is also monitored and compared among different groups receiving daily injections of the mutant human growth hormone at different concentrations.

Furthermore, the biological activity of a mutant human growth hormone can be demonstrated in its ability to cause hGH-dependent tyrosine phosphorylation in IM-9 cells, which are derived from a clone of human lymphoblastoma and express human growth hormone receptor on the cell surface. Other cell types such as MB-2 cells may also be suitable for hGH functional assays. The level of tyrosine phosphorylation of cellular proteins upon exposure to the mutant human growth hormone is shown by a monoclonal antibody against phosphorylated tyrosine, as described by Silva et al., *Endocrinology*, 132: 101 (1993) and U.S. Pat. No. 6,238,915.

Pharmaceutical Composition and Administration

The glycosylated mutant human growth hormone having desired oligosaccharide determinants described above can be used as therapeutics for treating a variety of diseases and conditions related to deficiency in growth hormone. Growth-related conditions that can be treated with the mutant human growth hormone of the present invention include: dwarfism, short-stature in children and adults, cachexia/muscle wasting, general muscular atrophy, and sex chromosome abnormality (e.g., Turner's Syndrome). Other conditions may be treated using the mutant hGH of the present invention include: short-bowel syndrome, lipodystrophy, osteoporosis, uraemaia, burns, female infertility, bone regeneration, general diabetes, type II diabetes, osteo-arthritis, chronic obstructive pulmonary disease (COPD), and insomia. The mutant hGH of the invention may also be used to promote various healing processes, e.g., general tissue regeneration, bone regeneration, and wound healing, or as a vaccine adjunct. Thus, the present invention also provides pharmaceutical compositions comprising an effective amount of glycosylated mutant human growth hormone, which is produced according to the methods described above.

In some embodiments of the present invention, the pharmaceutical composition includes a pharmaceutically acceptable diluent and a covalent conjugate between a non-naturally-occurring, PEG moiety, therapeutic moiety or biomolecule and a glycosylated or non-glycosylated peptide. The polymer, therapeutic moiety or biomolecule is conjugated to the peptide via an intact glycosyl linking group interposed between and covalently linked to both the peptide and the polymer, therapeutic moiety or biomolecule.

Pharmaceutical compositions of the invention are suitable for use in a variety of drug delivery systems. Suitable formulations for use in the present invention are found in *Remington's Pharmaceutical Sciences*, Mace Publishing Company, Philadelphia, Pa., 17th ed. (1985). For a brief review of methods for drug delivery, see, Langer, *Science* 249: 1527-1533 (1990).

The pharmaceutical compositions may be formulated for any appropriate manner of administration, including for example, topical, oral, nasal, intravenous, intracranial, intraperitoneal, subcutaneous or intramuscular administration. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactate polyglycolate) may also be employed as carriers for the pharmaceutical compositions of this invention. Suitable biodegradable microspheres are disclosed, for example, in U.S. Pat. Nos. 4,897,268 and 5,075,109.

Commonly, the pharmaceutical compositions are administered parenterally, e.g., subcutaneously or intravenously. Thus, the invention provides compositions for parenteral administration that include the compound dissolved or suspended in an acceptable carrier, preferably an aqueous carrier, e.g., water, buffered water, saline, PBS and the like. The compositions may also contain detergents such as Tween 20 and Tween 80; stablizers such as mannitol, sorbitol, sucrose, and trehalose; and preservatives such as EDTA and m-cresol. The compositions may contain pharmaceutically acceptable auxiliary substances as required to approximate physiological conditions, such as pH adjusting and buffering agents, tonicity adjusting agents, wetting agents, detergents and the like.

In some embodiments the glycopeptides of the invention can be incorporated into liposomes formed from standard vesicle-forming lipids. A variety of methods are available for preparing liposomes, as described in, e.g., Szoka et al., *Ann. Rev. Biophys. Bioeng.* 9: 467 (1980), U.S. Pat. Nos. 4,235,871, 4,501,728 and 4,837,028. The targeting of liposomes using a variety of targeting agents (e.g., the sialyl galactosides of the invention) is well known in the art (see, e.g., U.S. Pat. Nos. 4,957,773 and 4,603,044).

Standard methods for coupling targeting agents to liposomes can be used. These methods generally involve incorporation into liposomes of lipid components, such as phosphatidylethanolamine, which can be activated for attachment of targeting agents, or derivatized lipophilic compounds, such as lipid-derivatized glycopeptides of the invention.

Targeting mechanisms generally require that the targeting agents be positioned on the surface of the liposome in such a manner that the target moieties are available for interaction with the target, for example, a cell surface receptor. The carbohydrates of the invention may be attached to a lipid molecule before the liposome is formed using methods known to those of skill in the art (e.g., alkylation or acylation of a hydroxyl group present on the carbohydrate with a long chain alkyl halide or with a fatty acid, respectively).

Alternatively, the liposome may be fashioned in such a way that a connector portion is first incorporated into the membrane at the time of forming the membrane. The connector portion must have a lipophilic portion, which is firmly embedded and anchored in the membrane. It must also have a reactive portion, which is chemically available on the aqueous surface of the liposome. The reactive portion is selected so that it will be chemically suitable to form a stable chemical bond with the targeting agent or carbohydrate, which is added later. In some cases it is possible to attach the target agent to the connector molecule directly, but in most instances it is more suitable to use a third molecule to act as a chemical bridge, thus linking the connector molecule which is in the membrane with the target agent or carbohydrate which is extended, three dimensionally, off of the vesicle surface.

The compounds prepared by the methods of the invention may also find use as diagnostic reagents. For example, labeled compounds can be used to locate areas of inflammation or tumor metastasis in a patient suspected of having an inflammation. For this use, the compounds can be labeled with $^{125}$I, $^{14}$C, or tritium.

The active ingredient used in the pharmaceutical compositions of the present invention is glycopegylated hGH and its derivatives having the biological properties of stimulating granulocyte production. Preferably, the hGH composition of the present invention is administered parenterally (e.g. IV, IM, SC or IP). Effective dosages are expected to vary considerably depending on the condition being treated and the route of administration but are expected to be in the range of about 0.1 (~7 U) to 100 (~7000 U) μg/kg body weight of the active material. Preferable doses for treatment of anemic conditions are about 50 to about 300 Units/kg three times a week. Because the present invention provides a hGH with an enhanced in vivo residence time, the stated dosages are optionally lowered when a composition of the invention is administered.

Preparative methods for species of use in preparing the compositions of the invention are generally set forth in various patent publications, e.g., US 20040137557; WO 04/083258; and WO 04/033651. The following examples are provided to illustrate the conjugates, and methods and of the present invention, but not to limit the claimed invention.

In an exemplary embodiment, the present invention provides a pharmaceutical formulation that includes a population of hGH conjugates, such as described herein, in combination with a pharmaceutically acceptable diluent. A preferred formulation of the invention includes a buffer, a detergent, and a polyol.

An exemplary formulation includes the peptide conjugate in an amount from about 1 mg/mL to about 100 mg/mL, preferably from about 5 mg/mL to about 75 mg/mL, and more preferably from about 10 mg/mL to about 50 mg/mL.

An exemplary formulation includes a buffer at a concentration of about 1 mM to about 100 mM, preferably from about 5 mM to about 75 mM, and more preferably from about 10 mM to about 50 mM.

In an exemplary formulation, the detergent is present in an amount from about 0.00001% to about 10%, preferably from about 0.00005% to about 1%, more preferably from about 0.0001% to about 0.1%, more preferably from about 0.0005% to about 0.005%, and even more preferably from about 0.001% to about 0.01%.

In an exemplary formulation, the polyol is present in an amount of about 1 mg/mL to 100 mg/mL, preferably from about 10 mg/mL to about 75 mg/mL, more preferably from about 15 mg/mL to about 50 mg/mL.

In an exemplary embodiment, the pH of the formulation is from about 3 to about 7.5, preferably from about 4 to about 6.5 and more preferably from about 5 to about 6. Whatever the structure of the peptide conjugate, it is generally preferred that it be formulated at a pH that is within a range of about 0.5 pH units of the pI of the peptide.

In an exemplary embodiment, the detergent is Tween, e.g., Tween 20. In a further exemplary embodiment the polyol is sorbitol. In another embodiment, the buffer is sodium acetate.

An exemplary formulation of the invention includes hGH conjugate (2 mg/mL) in a mixture with 10 mM NaOAc, 0.003% Tween 20, and 50 mg/mL of sorbitol at pH 4.0.

These compositions may be sterilized by conventional sterilization techniques, or may be sterile filtered. The resulting aqueous solutions may be packaged for use as is, or lyophilized, the lyophilized preparation being combined with a sterile aqueous carrier prior to administration. The pH of the preparations typically will be between 3 and 11, more preferably from 5 to 9, and most preferably from 7 and 8.

The compositions containing the glycosylated mutant human growth hormone can be administered for prophylactic and/or therapeutic treatments. In therapeutic applications, compositions are administered to a patient already suffering from a disease or condition related to growth hormone deficiency, in an amount sufficient to cure or at least partially arrest the symptoms of the disease and its complications. An amount adequate to accomplish this is defined as a "therapeutically effective dose." Amounts effective for this use will depend on the severity of the disease or condition and the weight and general state of the patient, but generally range from about 0.1 mg to about 2,000 mg of glycosylated mutant human growth hormone per day for a 70 kg patient, with dosages of from about 5 mg to about 200 mg of the compounds per day being more commonly used.

In prophylactic applications, compositions containing the glycosylated mutant human growth hormone of the invention are administered to a patient susceptible to or otherwise at risk of a particular disease. Such an amount is defined to be a "prophylactically effective dose." In this use, the precise amounts again depend on the patient's state of health and weight, but generally range from about 0.1 mg to about 1,000 mg per 70 kilogram patient, more commonly from about 5 mg to about 200 mg per 70 kg of body weight.

Single or multiple administrations of the compositions can be carried out with dose levels and pattern being selected by the treating physician. In any event, the pharmaceutical formulations should provide a quantity of the glycosylated mutant human growth hormone of this invention sufficient to effectively treat the patient.

EXAMPLES

The following examples are provided by way of illustration only and not by way of limitation. Those of skill in the art will readily recognize a variety of non-critical parameters that could be changed or modified to yield essentially similar results.

Example 1

Human growth hormone occurs in a variety of different isoforms and different amino acid sequences. The two best characterized forms include placental derived hGH, which is also known as GH-V (PDB P01242) and pituitary derived hGH, which is also known as somatotropin or GH-N (P01241); see FIG. 26. The pituitary derived hGH is not glycosylated and is produced in *Escherichia coli* as a therapeutic. The placental derived hGH (GH-V) has one N-glycosylation site at amino acid 140 (see Table 4 and FIG. 26, see arrow).

TABLE 4

| Human Growth Hormone (GH-V), Placenta Derived; P01242 (SEQ ID NO: 2) |
|---|
| fptiplsrlfdnamlrarrlyqlaydtyqefeeayilkeqkysflqnpqtslcfsesiptpsnrvktqqksnle<br>llrislllilqswlepvqllrsvfanslvygasdsnvyrhlkdleegiqtlmwrledgsprtgqifnqsyskfdt<br>kshnddallknygllycfrkdmdkvetflrivqcrsvegscgf            ↑ |

Figure 27:
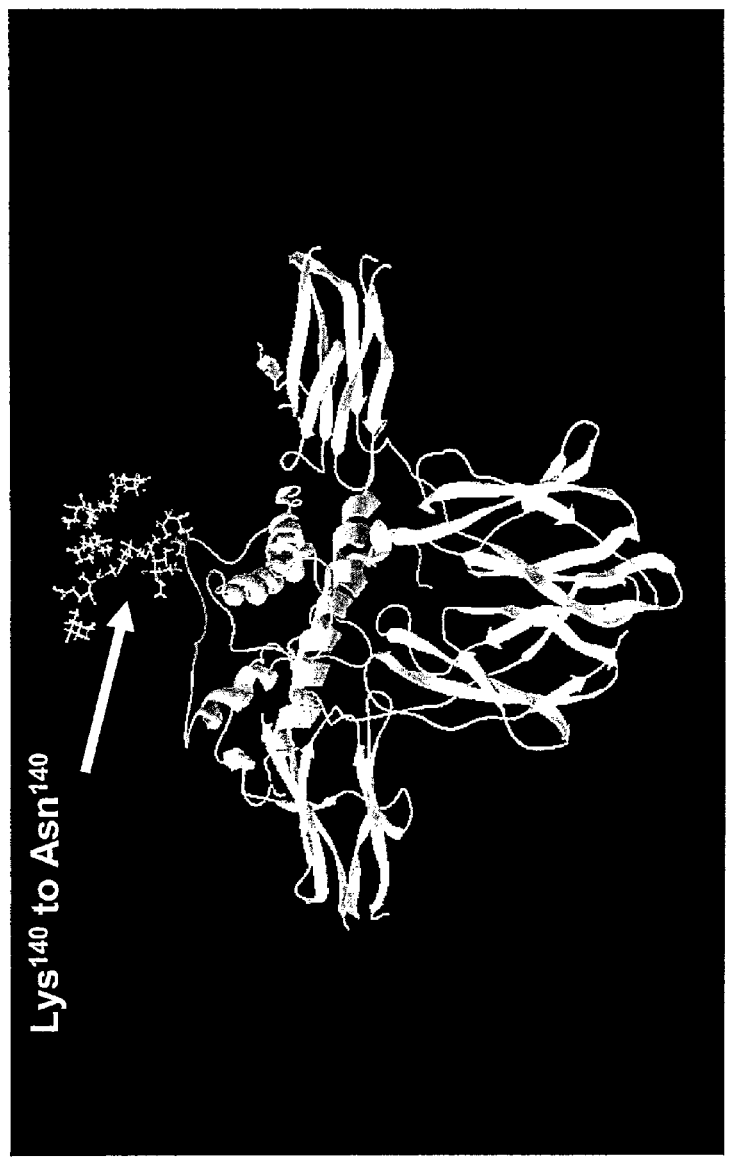
FIG. 27 is the crystal structure depiction of a glycosylated GH-N mutant hGH (Lys140 to Asn140) and its receptor polypeptide.

The pituitary derived hGH (GH-N) can be modified at amino acid position 140 to introduce an N-linked glycosylation site by mutating the nucleotide sequence encoding this polypeptide so that instead of encoding the wild-type lysine (abbreviated as "k" at amino acid 140 of the GH-N polypeptide sequence in Table 5 and FIG. 26, see arrow), the nucleotide sequence will encode an asparagine (abbreviated "n") at amino acid position 140 of GH-N (see also FIG. 27).

TABLE 5

| Human Growth Hormone (GH-N), Pituitary Derived; P01241 (SEQ ID NO: 1) |
|---|
| fptiplsrlfdnamlrahrlhqlafdtyqefeeayipkeqkysflqnpqtslcfsesiptpsnreetqqksnle<br>llrislllilqswlepvqflrsvfanslvygasdsnvydllkdleegiqtlmgrledgsprtgqifkqtyskfdt<br>nshnddallknygllycfrkdmdkvetflrivqcrsvegscgf            ↑ |

This mutated pituitary derived hGH, regardless of the expression system used to produce this polypeptide, can then be glycosylated or glycoconjugated (see WO 03/31464). Preferably, the mutated pituitary derived hGH is glycoPEGylated, wherein a polyethylene glycol (PEG) moiety is conjugated to the mutated pituitary derived hGH polypeptide via a glycosyl linkage (see WO 03/31464, incorporated herein by reference). FIG. 1 describes the GlycoPEGylation of an hGH N-linked glycan mutant produced in either Sf9 insect cells or mammalian cells. GlycoPEGylation of the mutated pituitary derived hGH is expected to result in improved biophysical properties that may include but are not limited to improved half-life, improved area under the curve (AUC) values, reduced clearance, and reduced immunogenicity.

Example 2

Figure 28:
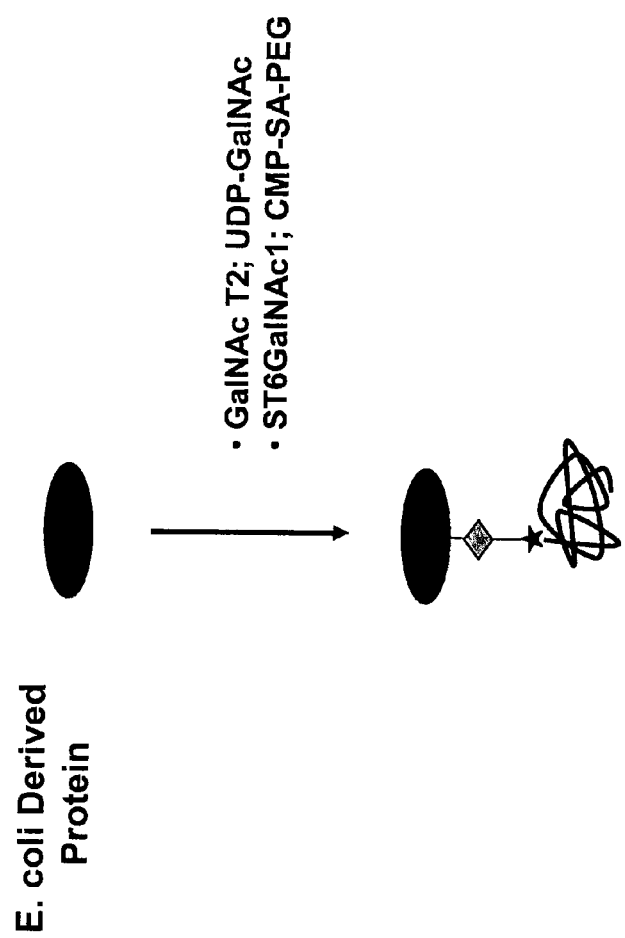
FIG. 28 shows the glycoPEGylation of an *Escherichia coli* produced hGH O-linked glycan mutant.

An alternative approach is to create an O-linked glycosylation site into the pituitary derived hGH polypeptide. This O-linked glycosylation site may then be used as a site on which the mutated hGH polypeptide can be glycoPEGylated using a GalNAcT$_2$ enzyme or the like. One or more additional transferases may then be used to add glycans or glycoconjugates to that site. Preferably, the mutated pituitary derived hGH polypeptide is glycoPEGylated. FIG. 28 describes the glycoPEGylation of an hGH O-linked glycan mutant produced in *Escherichia coli*.

Example 3

Figure 29:
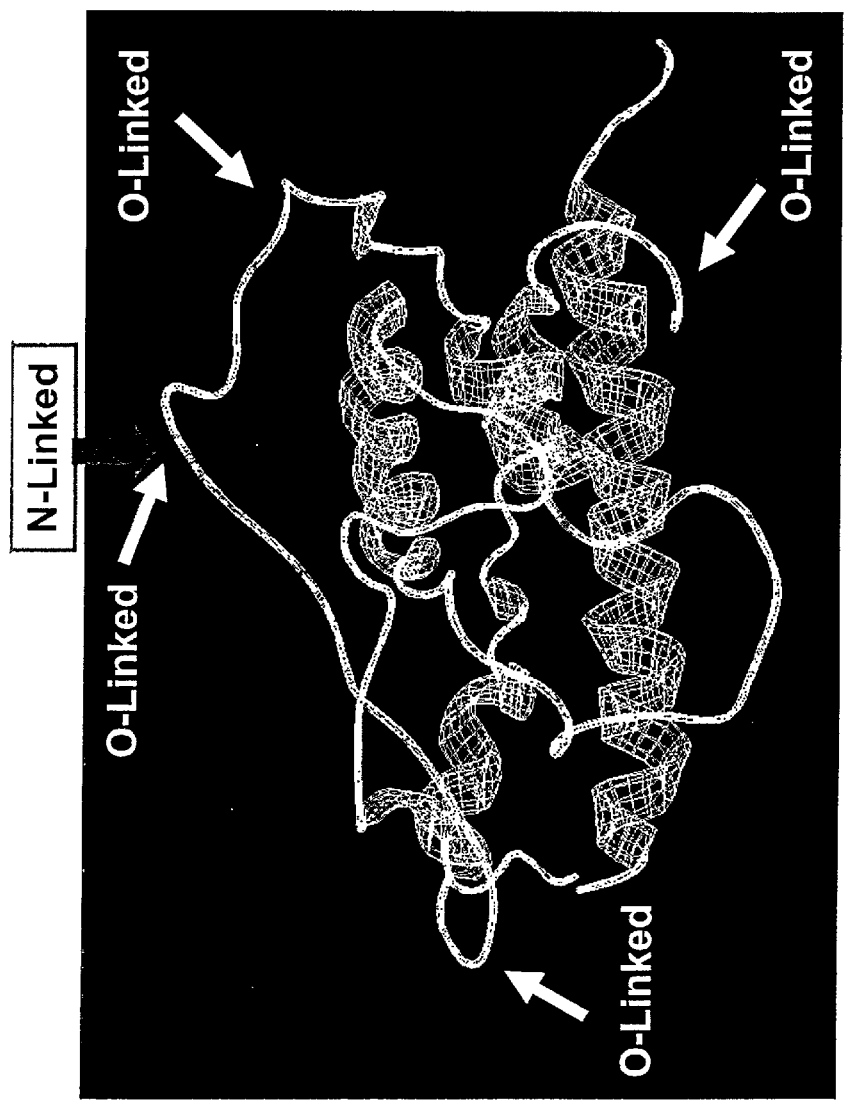
FIG. 29 displays alternate mutants of GH-N to introduce glycosylation sites. The arrows indicate the protein loop regions of GH-N into which a glycosylation site may be introduced.

As identified by the crystal structure of hGH and its receptor, the protein loop regions on pituitary derived hGH are best suited for mutation to introduce a glycosylation site (FIG. 29). Specifically, the nucleotide sequence that encodes amino acids 1-6 (FPTIPL; SEQ ID NO:10), amino acids 48-52 (PQTSL; SEQ ID NO:11), amino acids 59-64 (PTPSNR; SEQ ID NO:12), amino acids 133-139 (PRTGQIF; SEQ ID NO:13), amino acids 133-145 (PRTGQIFKQTYSK; SEQ ID NO:14), or amino acids 139-142 (FKQT; SEQ ID NO:15) of the wild-type pituitary derived hGH amino acid sequence (see Table 5 and FIG. 26) can be mutated so that either an N-linked or an O-linked glycosylation site is introduced into the resulting mutated pituitary-derived hGH polypeptide.

FIG. 2 illustrates six (6) of these introduced O-linked glycosylation sites. The arrows in FIG. 2 each represent the threonine residue on which O-linked glycosylation will occur in the GH-N O-linked glycan hGH mutant.

FIG. 3 and FIG. 4 each illustrates two additional GH-N O-linked glycan hGH mutants.

Example 4

This example describes amino acid sequence mutations introducing O-linked glycosylation sites, i.e., serine or threonine residues, into a preferably proline-containing site of a wild-type human growth hormone sequence or any modified version thereof.

N-terminal Mutations

In the N-terminal mutants, the N-terminus of a wild-type hGH, FP$^2$TIP$^5$LS; SEQ ID NO:16, is replaced with either MXnTP$^2$TIP$^5$LS or MAPTSSXnP$^2$TIP$^5$LS. Preferred examples include:

```
MVTPTIPLS;                    SEQ ID NO: 17

MQTPTIPLS;                    SEQ ID NO: 18

MAPTSSPTIPLS;                 SEQ ID NO: 19

MAPTSSSPTIPLS (IL-2 N-terminus);  SEQ ID NO: 20

MPTTFPTIPLS;                  SEQ ID NO: 21

MPTSSPTIPLS;                  SEQ ID NO: 22

MPTSSSPTIPLS;                 SEQ ID NO: 23
```

Internal Mutation Site 1

In this type of mutants, the N-terminus of a wild-type hGH, FP$^2$TIP$^5$LS; SEQ ID NO:24, is replaced with Zmp$^2$TXnBoP$^5$LS. Preferred mutations include:

```
MFPTQIPLS;        SEQ ID NO: 25

MFPTSIPLS;        SEQ ID NO: 26

MFPTSSPLS;        SEQ ID NO: 27

MFPTQIPLS;        SEQ ID NO: 28

MFPTTTPLS;        SEQ ID NO: 29
```

Internal Mutation Site 2

In this type of mutants, the amino acid sequence surrounding P$^{37}$, AYIP$^{37}$KEQKY; SEQ ID NO:30, is replace with AZmJqP$^{37}$OrXnBoΔpY, where at least one of Z, J, O, X, and B is independently selected from either Thr or Ser; Δ may include Lys (K) and X may be Asp (D). Preferred examples include:

```
AYIP37TQGAY;      SEQ ID NO: 31

AYIP37TSSSY;      SEQ ID NO: 32

AQITP37TEQKY;     SEQ ID NO: 33

AYIP37TEQSY;      SEQ ID NO: 34
```

Internal Mutation Site 3

In this type of mutants, the amino acid sequence surrounding P$^{48}$, LQNP$^{48}$QTSLC; SEQ ID NO:35, is replaced with LZmJqP$^{48}$OrXnBoLC, where at least one of Z, J, O, and X are independently selected from either Thr or Ser. Preferred examples include:

```
LQTP48QTSLC;      SEQ ID NO: 36

LQNP48TTSLC;      SEQ ID NO: 37
```

Internal Mutation Site 4

In this type of mutants, the amino acid sequence surrounding P$^{59}$, SESIP$^{59}$TPNREET; SEQ ID NO:38, is replaced with SZmUsJqP$^{59}$TPOrXnBoΔrT, where at least one of Z, J, O, B, Δ, U, and X is independently selected from either Thr or Ser; B, Δ, and Z may include charged amino acids. Preferred examples include:

```
SESTP59TPNREET;   SEQ ID NO: 39

SSSTP59TPNREET;   SEQ ID NO: 40

SESIP59TPNTEET;   SEQ ID NO: 41

SESIP59TPNTQET;   SEQ ID NO: 42

SESIP59TPTQGAT;   SEQ ID NO: 43

SESIP59TPTESST;   SEQ ID NO: 44

SQSTP59TPNREET;   SEQ ID NO: 45

SQSTP59TPNQEET;   SEQ ID NO: 46

SESTP59TPTSSST;   SEQ ID NO: 47
```

Internal Mutation Site 5

In this type of mutants, the amino acid sequence surrounding P$^{89}$, SWLEP$^{89}$VQFLRS; SEQ ID NO:48, is replaced with SZmUsJqP$^{89}$OrXnBoΔrλtS, where at least one of Z, U, J, O, B, and X is independently selected from either Thr or Ser; J and λ may include charged amino acids. Preferred examples include:

```
SWLEP89TQGLRS;    SEQ ID NO: 49

SWLEP89TQGATS;    SEQ ID NO: 50
```

-continued

| | |
|---|---|
| SSQTP$^{89}$VQFLRS; | SEQ ID NO: 51 |
| SWLEP$^{89}$TSSLSS; | SEQ ID NO: 52 |
| SMVTP$^{89}$VQFLRS; | SEQ ID NO: 53 |

Internal Mutation Site 6

In this type of mutants, the amino acid sequence surrounding $P^{133}$, EDGSP$^{133}$RTGQIF; SEQ ID NO:54, has been replace with EZmUsJqP$^{133}$OrXnBoΔrλtF, where at least one of Z, U, J, O, B, and X is independently selected from either Thr or Ser. Preferred examples include:

| | |
|---|---|
| EDGSP$^{133}$TTGQIF; | SEQ ID NO: 55 |
| EDGSP$^{133}$NTGQIF; | SEQ ID NO: 56 |
| EDGSP$^{133}$TQGQIF; | SEQ ID NO: 57 |
| EDGSP$^{133}$TVGQIF; | SEQ ID NO: 58 |
| EDGSP$^{133}$TTTQIF; | SEQ ID NO: 59 |
| EDGSP$^{133}$TSSQIF; | SEQ ID NO: 60 |
| EDGSP$^{133}$TTQGIF; | SEQ ID NO: 61 |
| EDGSP$^{133}$QTGQIF; | SEQ ID NO: 62 |
| EDGTP$^{133}$NTGQIF; | SEQ ID NO: 63 |
| EDQTP$^{133}$NTGQIF; | SEQ ID NO: 64 |

Internal Mutation Site 7

In this type of mutants, the amino acid sequence surrounding $P^{140}$, GQIFK$^{140}$QTYS; SEQ ID NO:65, is replace with GZmUsJqΔr$^{140}$OrXnBoS, where at least one of Z, U, J, O, B, and X is independently selected from either Thr or Ser. Preferred examples include:

| | |
|---|---|
| GQIFN$^{140}$QTYS; | SEQ ID NO: 66 |
| GQIFN$^{140}$ITYS; | SEQ ID NO: 67 |

-continued

| | |
|---|---|
| GQIST$^{140}$QTYS; | SEQ ID NO: 72 |
| GQIPT$^{140}$TTYS; | SEQ ID NO: 73 |

C-Terminal Mutations

In this type of mutants, the amino acid sequence at the C-terminus of a wild-type hGH, VEGSCG$^{109}$F; SEQ ID NO:74, is replaced with VEGSCG$^{190}$PXnBoZmUsP, where at least one of Z, U, B, and X is independently selected from either Thr or Ser. Preferred examples include:

| | |
|---|---|
| VEGSCGPTTTP; | SEQ ID NO: 75 |
| VEGSCGPTSSP; | SEQ ID NO: 76 |
| VEGSCGPTQGAMP; | SEQ ID NO: 77 |
| VEGSCGPTTIP; | SEQ ID NO: 78 |
| VEGSCGPMVTP; | SEQ ID NO: 79 |

In all above cases, X, Z, B, Δ, J, U, O, and A are independently selected from E (glutamate), any uncharged amino acid or dipeptide combination including M, F, MF, and the like; m, n, o, p, q, r, s, and t are independently selected from integers from 0 to 3. In all cases, the N-terminal Met may be present or absent on any hGH mutant. The numbering of the amino acid residues is based on the initial unmodified sequence in which the left most residue is numbered 1. The numbering of unmodified amino acids remains unchanged following the modification. More than one of the above described sequence modifications may be present in a hGH mutant of the present invention.

Example 5

This example illustrates one embodiment of the present invention, wherein a mutant hGH with the $P^{134}$TINT glycosylation site motif first undergoes glycoPEGylation with the use of $GalNAcT_2$ and UDP-GalNAc in combination with ST6GalNAc-I and CMP-SA-PEG (30 kDa), then chemical PEGylation, resulting in a hGH with protease resistance.

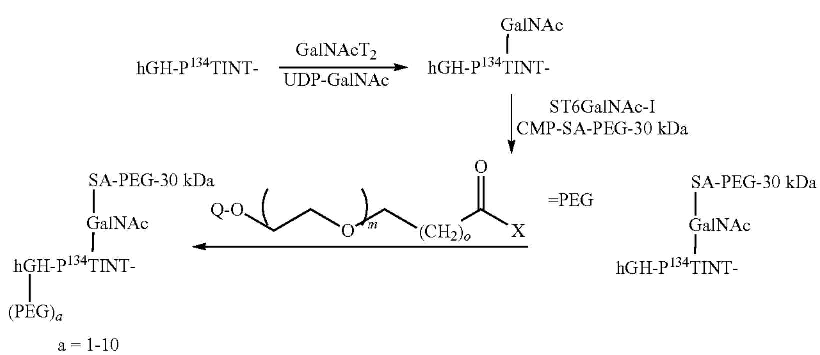

-continued

| | |
|---|---|
| GQIFP$^{140}$QTSS; | SEQ ID NO: 68 |
| GQIFP$^{140}$TTTS; | SEQ ID NO: 69 |
| GQITP$^{140}$QTYS; | SEQ ID NO: 70 |
| GQIFT$^{140}$QTYS; | SEQ ID NO: 71 |

Example 6

This example illustrates one embodiment of the present invention, wherein a mutant hGH with the $P^{134}$TQGAM glycosylation site motif first undergoes chemical PEGylation, then glycoPEGylation with the use of $GalNAcT_2$, core-1-$GalT_1$, $ST3Gal_1$ in combination with CMP-SA-PEG-Cys (40 kDa), thereby resulting in a hGH with protease resistance.

CMP-SA-PEGCys (40kDa)

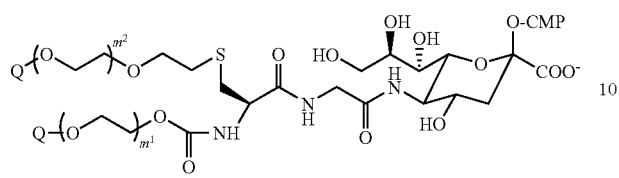

$m^1$ = 20 kDaPEG
$m^2$ = 20 kDaPEG
Q = CH$_3$

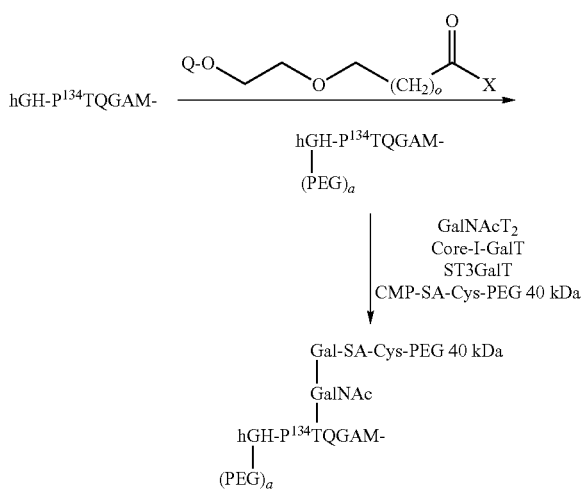

Example 7

This example illustrates one embodiment of the present invention, wherein a mutant hGH with the P$^{134}$TINT glycosylation site motif first undergoes glycoPEGylation with the use of GalNAcT$_2$ and UDP-GalNAc in combination with core-1-GalT$_1$/UDP-Gal and ST3Gal$_1$/CMP-SA-PEG (40 kDa), then chemical PEGylation, resulting in a hGH with protease resistance. It should be noted that only one size form should be used for any single reaction and product.

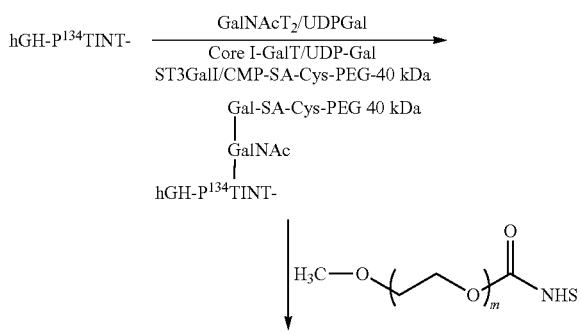

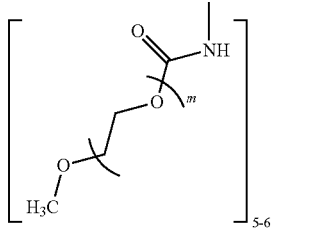

m = (independently selected)
10, 11, 12, 13, 14, 15, 16, 17
18, 19, 20

Example 8

Figure 30:
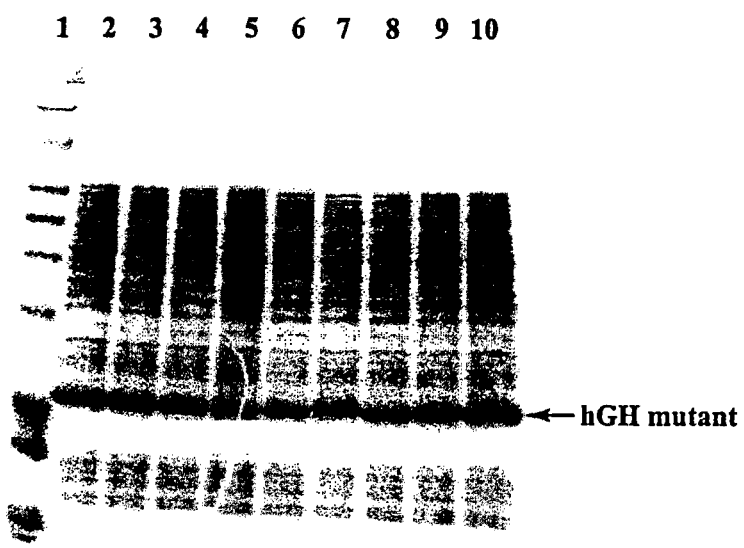
FIG. 30 are SDS-PAGE analysis results for nine exemplary hGH mutant proteins.

This example illustrates one embodiment of the present invention, wherein hGH mutants are expressed in *E. coli* JM109 and W3110. Miniprep plasmid DNA from hGH mutants were used to transform *E. coli* JM109 and W3110, respectively. The resulting transformants were inoculated into 2 ml Martone LB containing 10 µg/ml kanamycin and grown overnight at 37° C. as starter cultures. One half milliliter of the starter culture were transferred to 50 ml Martone LB containing 10 µg/ml kanamycin and allowed to grow at 37° C./250 rpm until OD$_{600}$ reached 0.8~1.0. IPTG was then added to a final concentration of 1 mM and the induction was performed for 5 hrs at 37° C. with a reduced agitation rate of 150 rpm. One hundred microliters of each culture before and after induction were taken and the bacteria were harvested by centrifugation in a bench top centrifuge. Each pellet was resuspended in 20 µl H$_2$O plus 20 µl 2× SDS-PAGE sample buffer and 4 µl DTT stock solution (1 M). The cells were lysed and the proteins denatured by heating at 95° C. for 5 min. Ten microliters from each sample were loaded onto a 14% acrylamide Tris-Glycine precast gels. The electrophoresis was performed at constant voltage (125 V) until the dye moved to the bottom of the gel. The gel was stained with Simple blue Safestain (see FIG. 30).

Induction of hGH Mutant Expression in Shake Flask
Small Scale Induction for GlycoPEGylation Screening Plasmid DNA for each hGH mutant were transformed into *E. coli* W3110. Several colonies from each transformation plate were inoculated into 20 ml Martone LB containing 10 µg/ml kanamycin and grown at 37° C./250 rpm for ~6 hrs as starter culture. Ten milliliters of the starter culture were then transferred to 500 ml Martone LB containing 10 µg/ml kanamycin and grown at 37° C./250 rpm until OD$_{600}$ reached 0.8-1.0. IPTG was added to a final concentration of 1 mM and the induction was performed overnight at 37° C. with 150 rpm. For some of the mutants, the hGH mutant expression was analyzed by SDS-PAGE as described above.

Induction at 1 L Scale

The starter culture was inoculated using a scraping from a glycerol stock of each individual mutant. The bacteria were incubated at 37° C., 135 rpm overnight. Ten milliliters of starter culture were transferred to 1 L Martone LB containing Kanamycin (10 µg/ml) in 2 L-shaking flask (baffled or non-baffled) and grown at 37° C., 250 rpm until OD$_{600}$ of 0.8~1.0 (around 3 hrs). IPTG was added to a final concentration of 1 mM and the induction was performed at 37° C., 135 rpm for 15 hrs. The Martone LB media contained 1% Martone B-1, 0.5% Marcor Yeast Extract, 1% NaCl. The pH was adjusted to 7.0 by adding 3.25 ml 1N NaOH to 1 L medium.

Induction of hGH Mutant Expression in 10-L Fermentor

8 L of media were prepared containing 1% Martone B-1, 0.5% Marcor Yeast Extract, 1% NaCl. The pH was brought to 7.0 after autoclaving and then the acid/base valves were turned off. Kanamycin at a final concentration of fifteen μg/ml was added. The growth was performed under full air flow at 37° C., 250 rpm until $OD_{600}$ reached 0.5-1.0 using 180 ml overnight culture as the inoculum. The protein expression was induced by the addition of 1 mM IPTG (final concentration) under ½ air flow rate at 125 rpm for 24-30 hrs. Cells were harvested by centrifugation.

Induction of hGH Mutant Expression in 150-L Fermentor

The parameters for the 150-L fermentor were designed to mimic those of the above mentioned 10-L fermentor. Kanamycin was used through all stages of culture at a final concentration of 10 μg/ml. A 200 ml shake flask seed culture was inoculated with 100 μl from a thawed 1 ml glycerol stock and grown at 37° C./135 rpm for 16-18 hrs. The shake flask seed culture was then transferred to 15-L seed fermentor containing 10 L media and grown overnight. Two to ten liters of the seed culture, preferably 2 L, were used to inoculate up to 98 L production culture (with combined volume of 100 L in a 150-L fermentor). The cultures were grown to an $OD_{600}$ of 0.6 to 3.0, preferably 0.6, at 37° C. and 25% $pO_2$ under cascade mode. The expression of each hGH mutant was induced by the addition of IPTG at a final concentration of 1 mM. The fermentation was continued at an agitation of 75 rpm and 10% $pO_2$ (cascade mode) at 37° C. for 24 hrs. Cells were harvested using a disc stack centrifuge.

Preparation of Inclusion Bodies (IBs) for hGH Mutants

Small Scale IB Preparation for GlycoPEGylation Screening

Figure 31:
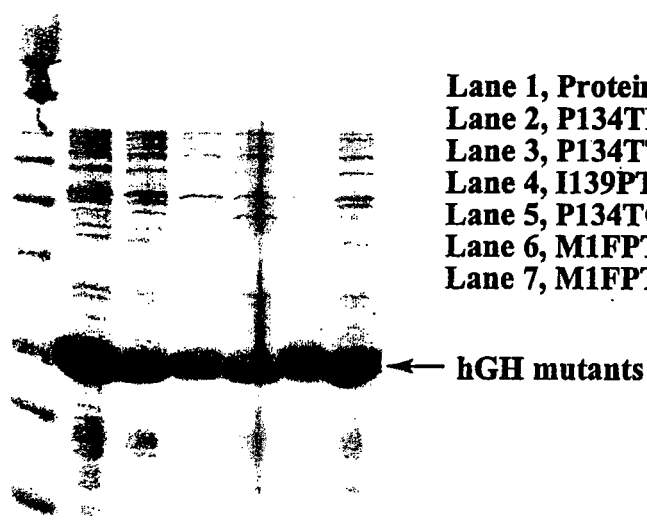
FIG. 31 are SDS-PAGE analysis results for inclusion bodies of six exemplary hGH mutants.

Induced cultures were harvested by centrifugation at 4° C./5000 rpm for 15 min. The pellets obtained were resuspended in a buffer containing 20 mM Tris-HCl, pH 8.5, 5 mM EDTA. The resuspended bacterial cells were disrupted by passing through a microfluidizer twice at ~16,000 Psi. The IBs were collected by centrifugation at 4° C., 5000 rpm for 10 min and washed twice, first with 35 ml and second with 10 ml washing buffer containing 20 mM Tris-HCl, pH 8.5, 5 mM EDTA, 100 mM NaCl, 1% Triton X-100 and 1% sodium deoxycholate. The IBs were finally resuspended in 30 ml $H_2O$ and aliquoted equally into 3 50-ml conical tubes. The IBs were collected and stored at −80° C. Five to ten microliter aliquots were analyzed on 14% acrylamide Tris-Glycine precast gels as described above (see FIG. 31).

Large Scale IB Preparation for GlycoPEGylation

The induced cultures were harvested by centrifugation at 4° C. with 5000 rpm for 10 min. The pellets obtained were resuspended (4 g/100 ml) in a buffer containing 20 mM Tris-HCl, pH 8.5, 5 mM EDTA. The resuspended bacterial cells were disrupted by passing through a microfluidizer twice. The IBs were collected by centrifugation at 4° C., 4150 rpm for 10 min and washed repeatedly as shown in Table 6 below.

TABLE 6

Procedures of scaled-up IB washing

| Step | Wash | Collection (g) × time (min) | Note |
|---|---|---|---|
| 1 | 150 ml wash buffer | 5000 g × 10 min | IBs from 9 L culture |
| 2 | 150 ml wash Buffer | 5000 g × 10 min | |
| 3 | 150 ml $H_2O$ | 5000 g × 10 min | Top loose layer removed |
| 4 | 150 ml Wash buffer | 5000 g × 10 min | |
| 5 | 150 ml Wash buffer | 5000 g × 10 min | |
| 6 | 150 ml $H_2O$ | 5000 g × 10 min | Top loose layer removed |
| 7 | 150 ml Wash buffer | 5000 g × 10 min | |
| 8 | 150 ml $H_2O$ | 5000 g × 10 min | Top loose layer removed |

Refolding of Inclusion Bodies for hGH Mutants:

hGH Mutants Refolded in a Buffer Containing Redox Couple 150 mg washed IBs were first solubilized in 7.5 ml buffer containing 6 M guanidine HCl, 5 mM EDTA, 100 mM NaCl, and 50 mM Tris-HCl (pH 8.5) by constant stirring at room temperature. The solubilized IBs were then diluted slowly into a refolding buffer with combined volume of 150 ml containing, 0.5 M L-Arg+, 250 mM NaCl, 10 mM KCl, 0.05% PEG 3350, 50 mM MES, 1 mM GSH, 0.1 mM GSSG, 0.3 mM lauryl maltoside, pH approximately 10.5. The refolding was performed at 4° C. for 2.5 hrs with slow, constant stirring and then dialyzed overnight against 2 L buffer containing 50 mM NaOAc, pH 4.0, 50 mM NaCl and 10% glycerol. The pH of the dialysis buffer can be varied from 4.0 to 7.4, but preferably 7.4.

hGH Mutants Refolded by alkaline Solubilization

Figure 32:
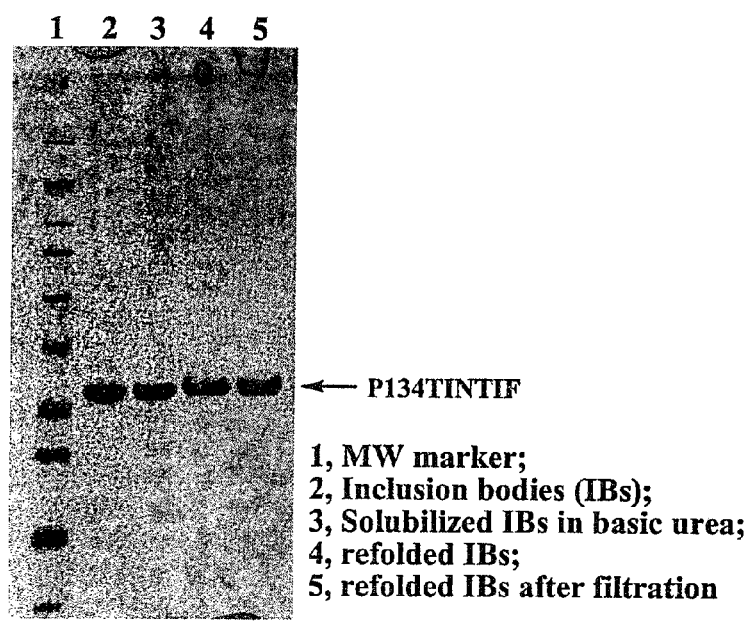
FIG. 32 are SDS-PAGE analysis results of pre- and post-refolding inclusion bodies for an exemplary hGH mutant.

The refolding of IBs was carried out in ~200 mg aliquots using the following procedure (see FIG. 32):

1. Solubilization of each IB aliquot at a ratio of 5 mg/ml in ice-cold buffer containing 100 mM Tris, pH 12.5, 2 M urea by constant stirring until no significant pellets were visible;
2. Dilution by adding 4 volumes of cold water batchwise without stirring;
3. Adjusting pH to 8.5 using 1 N HCl with constant, mild stirring;

The refolded aliquots were pooled and filtered through a 0.45 μm membrane prior to loading onto DEAE ion exchange chromatography.

Example 9

Acute Toxicity Study of Glycopegylated hGH Compounds Administered by either the Intravenous or Subcutaneous Route to Rats The formulation was used as received for dose administration. All animals were dosed once, intravenous or subcutaneous, on Study Day 1. Dose volume was dependent upon final Dosage Concentration to yield a final dose per animal of 90 μg/rat (see Table 7 below).

TABLE 7

| Group Number | Test Article | Route of Administration | Dosage Level (μg/rat) | Number of Males |
|---|---|---|---|---|
| 1 | AA | subcutaneous | 90 | 12 |
| 2 | AV | subcutaneous | 90 | 12 |

TABLE 7-continued

| Group Number | Test Article | Route of Administration | Dosage Level (μg/rat) | Number of Males |
|---|---|---|---|---|
| 3 | AW | subcutaneous | 90 | 12 |
| 4 | AS | subcutaneous | 90 | 12 |
| 5 | AQ | subcutaneous | 90 | 12 |
| 6 | AP | subcutaneous | 90 | 12 |
| 7 | AU | subcutaneous | 90 | 12 |
| 8 | AO | subcutaneous | 90 | 12 |
| 9 | AR | subcutaneous | 90 | 12 |
| 10 | AA | intravenous | 90 | 12 |
| 11 | AV | intravenous | 90 | 12 |
| 12 | AW | intravenous | 90 | 12 |
| 13 | AS | intravenous | 90 | 12 |
| 14 | AQ | intravenous | 90 | 12 |
| 15 | AP | intravenous | 90 | 12 |
| 16 | AU | intravenous | 90 | 12 |
| 17 | AO | intravenous | 90 | 12 |
| 18 | AR | intravenous | 90 | 12 |

Blood for evaluation of pharmacokinetics was collected from 4 rats/subgroup according to Table 8 below.

TABLE 8

| Intravenous | Number of samples/group collected at each time-point (postdose) | | |
|---|---|---|---|
| Subgroup/test article | 5 min, 1 hour, 8 hour, 48 hour | 15 min, 2 hour, 12 hour, 72 hour | 30 min, 4 hour, 24 hour, 96 hour |
| A | 4 | | |
| B | | 4 | |
| C | | | 4 |

| Subcutaneous | Number of samples/group collected at each time-point (postdose) | | |
|---|---|---|---|
| Subgroup/test article | 1 hour, 12 hour, 48 hour, 96 hour | 4 hour, 24 hour, 60 hour | 8 hour, 36 hour, 72 hour |
| A | 4 | | |
| B | | 3 | |
| C | | | 3 |

Blood was processed to serum, frozen (−70° C.±5° C.) and shipped overnight to Neose Technologies, Inc. for concentration analysis. An ELISA was used to measure the concentration of hGH. Pharmacokinetic analysis was then performed.

Example 10

10-Day Study Comparing the Efficacy of Glycopegylated and Non-Glycopegylated Human Growth Hormone Following Subcutaneous Administration in Hypophysectomized Female Rats A total of 65 hypophysectomized female Sprague-Dawley rats were assigned to 13 groups (5/group). Animals were administered either 200 μL of Vehicle (a solution of phosphate buffered saline at pH 7.4, 0.3% Pluronic F-68, and 2% Mannitol), 180 μg or 30 μg/dose of the reference control article (P148), or 180 μg of one of the test articles (P241, P242, P249-64, P249-72, P250, P256, P257, P258, P259, or P240) via subcutaneous injection. All animals were administered a single dose on Study Day 1, with the exception of animals dosed with 30 μg/dose reference control (P148) which were administered 10 consecutive daily doses beginning on SD 1. (See Table 9 below)

TABLE 9

| Group | Treatment | Test Article | Protein Concentration (μg/mL) | Dose Level (μL/dose) | Protein Dosage (μg/dose) | Number of Animals | Animal Numbers |
|---|---|---|---|---|---|---|---|
| 1 | Vehicle-62 | | 0 | 200 | 0 | 5 | 20565-20569 |
| 2 | AA | P148 | 1310 | 137 | 180 | 5 | 20570-20574 |
| 3 | AA | P148 | 1310 | 23 | 30 | 5 | 20575-20579 |
| 4 | AV | P241 | 1130 | 159 | 180 | 5 | 20580-20584 |
| 5 | AW | P242 | 1140 | 158 | 180 | 5 | 20585-20589 |
| 6 | AS-64 | P249-64 | 970 | 186 | 180 | 5 | 20590-20594 |
| 7 | AS-72 | P249-72 | 1000 | 180 | 180 | 5 | 20595-20599 |
| 8 | AQ | P250 | 897 | 200 | 180 | 5 | 20600-20604 |
| 9 | AP | P256 | 1030 | 175 | 180 | 5 | 20605-20609 |
| 10 | AU | P257 | 1620 | 111 | 180 | 5 | 20610-20614 |
| 11 | AO | P258 | 1290 | 139 | 180 | 5 | 20615-20619 |
| 12 | AR | P259 | 980 | 184 | 180 | 5 | 20620-20624 |
| 13 | AX | P240 | 1190 | 151 | 180 | 5 | 20625-20629 |

Different reference control groups (Groups 2 and 3) were established to evaluate the efficacy of the test articles compared to different injection frequencies of an established hGH formulation.

Rats were administered a subcutaneous injection once on Study Day 1 for Groups 1, 2, and 4-13 and once daily (approximately the same time each day, ±1 hour) on Study Day 1-10 for Group 3. Dosing materials were maintained on wet ice prior to and during dosing. All animals were checked for general health/mortality twice daily, clinical observations predose and termination and body weights recorded predose, Study Day 1 and daily thereafter.

Blood was collected for IGF-1 evaluation on Study Day-3 (prestudy), 1, 2, 4, 7, and 10, stored on wet ice, and centrifuged at ~3000 rpm for 10 min at 4° C. Plasma was transferred to microcentrifuge tubes and stored at −75±10° C. Plasma was shipped to Ani Lytics on dry ice for insulin-like growth factor 1 (IGF-1) plasma concentration (IGF-1 analysis).

A gross necropsy, which included examination of the external surface of the body, injection site, all orifices, the cranial, thoracic, and abdominal cavities, and their contents, was performed on surviving animals on Study Day 11. Organs were weighed as soon as possible after dissection at scheduled necropsies. Paired organs were weighed together. Moribund animals were subjected to a gross necropsy and protocol specified-tissues were collected; however no organ weights were collected. At scheduled termination, the absence of the pituitary gland was documented. The eyes were fixed in modified Davidson's fixative for approximately 24 hours and then transferred to 70% alcohol. All gross lesions and protocol-required tissues were preserved in 10% neutral buffered formalin (NBF).

Body weights, body weight changes, absolute and relative organ weights, and IGF-1 concentration were statistically analyzed. Analysis was performed for all test articles against each reference control group (Groups 2 and 3).

Example 11

DEAE Purification

The refolded hGH (2 L) was passed through a 0.2 micron in-line filter and was loaded on a DEAE Sepharose column (200 mL) pre-equilibrated with 20 mM tris buffer pH 8.5, 5 mM EDTA, 0.4 M urea and connected to an HPLC system that monitored the absorbance at 280 nm. The hGH was eluted with a step gradient from 20 mM tris buffer pH 8.5, 5 mM EDTA to 20 mM tris buffer pH 8.5, 5 mM EDTA, 50 mM NaCl followed by a linear gradient to 20 mM tris buffer pH 8.5, 5 mM EDTA, 2 M NaCl. Fractions were collected in a chilled fraction collector and concentrated to approximately 1 mg/mL using a centrifugal filter (5 kDa MWCO). Samples were stored at 4° C.

Superdex 200 Purification

The concentrated DEAE-sepharose purified hGH samples (approximately 9 mL) were loaded on a Superdex 75 column connected to an HPLC system monitoring absorbance at 280 nm. The hGH product was eluted with 50 mM Tris, pH 7.4, 20 mM NaCl at a flow rate of 4 mL/min. Fractions containing monomeric product were collected and stored at 4° C.

Example 12

Table of Mutants:

TABLE 10

| AA sequence of hGH mutants | | In vitro activity (Nb2-11 cell proliferation) |
|---|---|---|
| P134TTGQIF | (SEQ ID NO: 96) | Active |
| P134TTAQIF | (SEQ ID NO: 97) | Active |
| P134TATQIF | (SEQ ID NO: 98) | Active |
| P134TQGAMF | (SEQ ID NO: 99) | Active |
| P134TQGAIF | (SEQ ID NO: 100) | Active |
| P134TQGQIF | (SEQ ID NO: 101) | Active |
| P134TTLYVF | (SEQ ID NO: 102) | Active |
| P134TINTIF | (SEQ ID NO: 103) | Active |
| P134TTVSIF | (SEQ ID NO: 104) | Active |
| I139PTQTYS | (SEQ ID NO: 105) | Active |
| I139PTQAYS | (SEQ ID NO: 106) | Active |
| P134TTLQIF | (SEQ ID NO: 107) | Active |
| P134TTVQIF | (SEQ ID NO: 108) | Active |
| P134TTNQIF | (SEQ ID NO: 109) | Active |
| P134TTQQIF | (SEQ ID NO: 110) | Active |
| P134TIGQIF | (SEQ ID NO: 111) | Active |
| P134TILQIF | (SEQ ID NO: 112) | Active |
| P134TIVQIF | (SEQ ID NO: 113) | Active |
| P134TINQIF | (SEQ ID NO: 114) | Active |
| P134TIQQIF | (SEQ ID NO: 115) | Active |
| P134TIAQIF | (SEQ ID NO: 116) | Active |
| L129ETETPRT | (SEQ ID NO: 117) | Active |
| L129VTETPRT | (SEQ ID NO: 118) | Active |
| L129ETQSPRT | (SEQ ID NO: 119) | Active |
| L129VTQSPRT | (SEQ ID NO: 120) | Active |
| L129VTETPAT | (SEQ ID NO: 121) | Active |
| L129ETETPAT | (SEQ ID NO: 122) | Active |

TABLE 10-continued

| AA sequence of hGH mutants | | In vitro activity (Nb2-11 cell proliferation) |
|---|---|---|
| L129ATGSPRT | (SEQ ID NO: 123) | Active |
| L129ETQSPST | (SEQ ID NO: 124) | Active |
| L129ETQSPAT | (SEQ ID NO: 125) | Active |
| L129ETQSPLT | (SEQ ID NO: 126) | Active |
| Y43 change to A; P134TINTIFKQTYS | (SEQ ID NO: 127) | Active |
| Y43 change to A; P134TINTIFKQTA | (SEQ ID NO: 128) | Active |
| Y43 change to A; P134TINTIANQTA | (SEQ ID NO: 129) | Active |
| Y43 change to A; I139PTQAYS | (SEQ ID NO: 130) | Active |
| V1TPT | (SEQ ID NO: 131) | Active |
| P134TQGAMP | (SEQ ID NO: 132) | Active |
| P134TTTQIF | (SEQ ID NO: 133) | Active |
| P134NTGQIF | (SEQ ID NO: 134) | Active |
| M1FPTEIP | (SEQ ID NO: 135) | Active |
| M1FPTVLP | (SEQ ID NO: 136) | Active |

Example 13

Preparation of hGH-GalNAc-SA-PEG-30 kDa (Two Sugar Preparation)

The hGH mutant (14.0 mg, 0.63 micromole) was adjusted to 0.001% Polysorbate 80 and concentrated to a volume of 2-3 mL using a centrifugal filter (5 kDa MWCO). The UDP-GalNAc (6.3 micromoles) and 1M MnCl$_2$ (to a final concentration of 10 mM MnCl$_2$) were then added to the concentrated hGH solution. The GalNAcT2 (50 microliters, 105 mU) was added, mixed very gently and incubated at room temperature for 18.5 hrs. The addition of GalNAc was determined to be complete by MALDI analysis of the reaction mixture. The CMP-SA-PEG-30 kDa (1.9 micromoles) was added to the hGH-GalNAc reaction mixture as a concentrated solution in reaction buffer and ST6GalNAc1 (0.72 mL, 0.7 U) was added with gentle mixing. The reaction mixture was incubated at room temperature for 20 hrs and was monitored for extent of PEGylation by SDS PAGE and RP-HPLC. The product, hGH-GalNAc-SA-PEG-30 kDa, was purified using SP Sepharose and SEC (Superdex 200) chromatography. The purified hGH-GalNAc-SA-PEG-30 kDa was concentrated and then formulated. The product was analyzed by a BCA protein assay, SDS-PAGE gels (silver stain), MALDI, SEC for aggregation, and for cell proliferation. (See Table 11 below)

TABLE 11

| hGH mutant | GalNAc Addition - GalNAcT2 Conversion Yield (MALDI) | SA-PEG-30 kDa Addition (2 sugar product) Conversion Yield by RP-HPLC |
|---|---|---|
| P134TINTIF | 100% | 83-89% |
| P134TTVSIF | 100% | 74-85% |
| I139PTQAYS | 100% | 66-86% |
| P134TQGAMF | 100% | 86% |
| M1FPTEIP | 100% | 27% |
| M1FPTVLP | 100% | 11-18% |

Preparation of hGH-GalNAc-Gal-SA-Cys-PEG-40 kDa (Three Sugar Preparation)

The hGH mutant (42 mg, 1.9 micromoles) was adjusted to 0.001% Polysorbate 80 and concentrated to a volume of 6-7 mL using a centrifugal filter (5 kDa MWCO). The UDP-GalNAc (19.1 micromoles) was added as a concentrated solution in Reaction buffer: 50 mM Tris, 20 mM NaCl, 0.001% Polysorbate 80, 0.02% NaN$_3$, pH 7.4 (0.2 mL) and the resulting solution was adjusted to 10 mM MnCl$_2$ (1 M MnCl$_2$, 0.08 mL). The GalNAcT2 (200-400 mU) was added, mixed very gently and incubated at room temperature for 18.5 hours. The addition of GalNAc was determined to be complete by MALDI analysis of the reaction mixture. A concentrated solution of UDP-Gal in Reaction buffer (19 micromoles, 0.1 mL) and Core-1-GalT1 enzyme (0.42 U) were added to the hGH-GalNAc reaction mixture with gentle mixing and the resulting solution was incubated for 16.5 hrs at room temperature. The addition of Gal was determined to be complete by MALDI analysis of the reaction mixture. The CMP-SA-cys-PEG-40 kDa (3.8 micromoles) was added to the hGH-GalNAc-Gal reaction mixture as a concentrated solution in reaction buffer (0.8 mL) and ST3Gal1 enzyme (1.68 U) was added with gentle mixing. The reaction mixture was incubated at room temperature for 20-65 hrs and was monitored for extent of PEGylation by SDS PAGE and RP-HPLC. The product, hGH-GalNAc-Gal-SA-cys-PEG-40 kDa, was purified using SP Sepharose and SEC (Superdex 200) chromatography. The purified hGH-GalNAc-Gal-SA-cys-PEG-40 kDa was concentrated and then formulated. The product was analyzed by a BCA protein assay, SDS-PAGE gels (silver stain), MALDI, SEC for aggregation, and for cell proliferation. (See Table 12 below)

TABLE 12

| hGH mutant | GalNAc Addition GalNAcT2 Conversion Yield (MALDI) | Gal Addition Core-1GalT1 Conversion Yield (MALDI) | SA-PEG-cys-40 kDa Addition (3 sugar product) Conversion Yield RP-HPLC |
|---|---|---|---|
| P134TINTIF | 100% | 100% | 25-45% |
| P134TTVSIF | 100% | 100% | (40% SDS-PAGE) |
| I139PTQAYS | 100% | 100% | 23-24% |
| P134TQGAMF | 100% | 100% | 32% |
| M1FPTEIP | 100% | 100% | (20% SDS-PAGE) |
| M1FPTVLP | 100% | 100% | 20-40% |
| Y43 change to A; P134TINTIFKQTYS | 100% | 100% | 28-32% |
| Y43 change to A; P134TINTIFKQTA, | 100% | 100% | 22-24% |
| Y43 change to A; P134TINTIANQTA | 100% | 100% | 50% |
| Y43 change to A; I139PTQAYS | 100% | 100% | 28-38% |

SP Sepharose Chromatography: The hGH-GalNAc-SA-PEG-30 kDa and hGH-GalNAc-Gal-SA-Cys-PEG-40 kDa were purified using an SP Sepharose column (20 mL) connected to an HPLC system that monitored the absorbance at 280 nm. The hGH reaction mixtures were diluted into 5 volumes of cold 25 mM sodium acetate (pH 4.2) and were injected onto the column. The product was eluted at a flow rate of 5.0 mL/min. using a NaCl gradient. Product containing fractions were collected, neutralized to pH>7 with 1 M Tris, pH 8 and concentrated to approximately 1.0 mL using a centrifugal filter, 5 kDa MWCO. Samples were stored at 4° C.

Size Exclusion Chromatography: The hGH-GalNAc-SA-PEG-30 kDa and hGH-GalNAc-Gal-SA-cys-PEG-40 kDa were purified on a Superdex 200 column using an HPLC that monitored absorbance at 280 nm. The concentrated SP-sepharose purified samples (approximately 1 mL) were loaded and the products were eluted with PBS (pH 7.4) at a flow rate of 1-2 mL/min. Product containing fractions were collected and stored at 4° C.

SDS PAGE Analysis: The 4-20% polyacrylamide gradient slab gels were used. Samples (approximately 10 mcg of protein) were mixed with 10 microliters SDS Sample Buffer containing 0.1 M DTT, and heated at 85° C. for 6 min, unless otherwise noted. Gels were run at a constant voltage of 125 V for 1 hr 50 min. After electrophoresis, the proteins were stained with a colloidal stain solution for 2-24 hours at room temperature as necessary to visualize the protein or with a silver stain kit.

Example 14

Cell Proliferation Assay

An Nb2-11 cell proliferation assay was used to determine the in vitro activity of the hGH mutants and glycoPEGylated hGH mutants. The assay was based that described in Patra, A. K., Mukhopadhyay, R., Mukhiga, R., Krishnan, A., Garg, L. C. and Panda, A. K. Optimization of inclusion body solubilization and renaturation of recombinant human growth hormone from *Escherichia coli*. Protein Expr. Purif. 18, 182-192 (2000). Nb2-11 cells were grown in Fischer's media with lactogen-free 10% horse serum and 10% fetal bovine serum, 2 mM glutamine, 0.05 mM 2-mercaptoethanol in a humidified chamber at 37° C., 5% $CO_2$. Nb2-11 cells were washed twice with PBS to remove the growth media and then resuspended and incubated in Arrest Media containing Fischer's media with lactogen-free 10% horse serum and 1% fetal bovine serum, 2 mM glutamine, 0.05 mM 2-mercaptoethanol at 37° C., 5% $CO_2$ for 24 h. After incubating the cells under starving conditions, Nb2-11 cells were dispensed into a 96-well plate at a density of $5\times10^4$ cells/mL. hGH samples were sterile filtered and diluted at different concentrations in dilution medium (Fischer's media with lactogen-free 10% horse serum, 2 mM glutamine, 0.05 mM 2-mercaptoethanol and 2 mM HEPES). The diluted hGH samples were added to the plated cells in 6 replicates. The cells were then incubated for 72 hours in a humidified chamber at 37° C. with 5% $CO_2$. After incubating for 72 hours, MTS reagent was added to each plate as a calorimetric indicator of cell density. The reduced by-product of MTS was measured calorimetrically at an absorbance of 490 nm using an ELISA Plate. Prior to addition of the MTS, Nb2-11 cells, maintained separately under normal growth conditions, were dispensed at known cell densities into reserved empty wells on each plate were used to generate a standard curve. Using a linear regression analysis of the standard curve, the cell density at each sample concentration was interpolated from the average of the 6 replicates.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims. All publications, patents, and patent applications cited herein are hereby incorporated by reference in their entirety for all purposes.

What is claimed is:

1. An isolated human growth hormone peptide comprising the amino acid sequence of SEQ ID NO: 1 or SEQ ID NO: 2 except (a) one or more protease recognition sites of SEQ ID NO: 1 or SEQ ID NO: 2 are mutated to be resistant to proteolysis, wherein the protease recognition sites are selected from the group consisting of positions 4, 10, 23, 25, 28, 31, 42, 44-45, 103, 133-137, 139-140, 142-143, 146, 150, and 151, (b) one or more O-linked glycosylation sites are present that are not present in SEQ ID NO: 1 or SEQ ID NO: 2, wherein the O-linked glycosylation sites are selected from the group consisting of positions 1-6, 48-52, 59-64, and 133-145, (c) optionally one or more N-linked glycosylation sites are present that are not present in SEQ ID NO: 1 or SEQ ID NO: 2, wherein the N-linked glycosylation sites are selected from the group consisting of positions 1-6, 48-52, 59-64, and 133-145, and (d) optionally an N-terminal methionine is present or absent, wherein the human growth hormone peptide retains at least one lysine or histidine residue of SEQ ID NO: 1 or SEQ ID NO: 2.

2. The human growth hormone peptide of claim 1, wherein an O-linked glycosylation site not present in SEQ ID NO: 1 or SEQ ID NO: 2 is present and proximate a proline residue.

3. The human growth hormone peptide of claim 1, comprising the amino acid sequence of SEQ ID NO: 81, 82, 83, 84, 85, 86, 87, 88, or 89.

4. The human growth hormone peptide of claim 1, wherein more than one O-linked glycosylation site is present that is not present in SEQ ID NO: 1 or SEQ ID NO: 2.

5. The human growth hormone peptide of claim 1, comprising a water-soluble polymer attached through a glycosyl linker to at least one O-linked glycosylation site that is not present in SEQ ID NO: 1 or SEQ ID NO: 2.

6. The human growth hormone peptide of claim 5, wherein the glycosyl linker is an intact glycosyl linker.

7. The human growth hormone peptide of claim 5, wherein the intact glycosyl linker is a member selected from a galactosyl, an N-acetylgalactosyl, and a sialic acid residue.

8. The human growth hormone peptide of claim 5, wherein the water-soluble polymer is poly(ethylene glycol).

9. The human growth hormone peptide of claim 5, wherein the O-glycosylation site that is not present in SEQ ID NO: 1 or SEQ ID NO: 2 comprises an amino acid that is either threonine or serine and the glycosyl linker is covalently attached to the threonine or serine.

10. The human growth hormone peptide of claim 1, wherein the human growth hormone peptide further comprises a water-soluble polymer covalently bound to an amino acid not present in SEQ ID NO: 1 or SEQ ID NO: 2 but present in the human growth hormone peptide to render a protease recognition site of SEQ ID NO: 1 or SEQ ID NO: 2 proteolysis resistant.

11. The human growth hormone peptide of claim 10, wherein the water-soluble polymer is a poly(ethylene glycol).

12. The human growth hormone peptide of claim 10, wherein the amino acid is lysine.

13. The human growth hormone peptide of claim 1, wherein the human growth hormone peptide further comprises a water-soluble polymer covalently bound to an amino acid proximate to an amino acid not present in SEQ ID NO: 1 or SEQ ID NO: 2 but present in the human growth hormone peptide to render a protease recognition site of SEQ ID NO: 1 or SEQ ID NO: 2 proteolysis resistant.

14. The human growth hormone peptide of claim 13, wherein the water-soluble polymer is a poly(ethylene glycol).

15. The human growth hormone peptide of claim 13, wherein the amino acid proximate to an amino acid not present in SEQ ID NO: 1 or SEQ ID NO: 2 is lysine.

16. The human growth hormone peptide of claim 1, wherein more than one protease recognition site of SEQ ID NO: 1 or SEQ ID NO: 2 is mutated to be resistant to proteolysis.

17. The human growth hormone peptide of claim 1, wherein more than one protease recognition site of SEQ ID NO: 1 or SEQ ID NO: 2 is mutated to be resistant to proteolysis, and wherein more than one O-linked glycosylation site is present that is not present in SEQ ID NO: 1 or SEQ ID NO: 2.

18. The human growth hormone peptide of claim 1, wherein more than one N-linked glycosylation site is present that is not present in SEQ ID NO: 1 or SEQ ID NO: 2.

19. The human growth hormone peptide of claim 1, wherein the human growth hormone peptide retains a biological activity of a human growth hormone.

20. The human growth hormone peptide of claim 1, wherein the human growth hormone peptide comprises one or more mutations selected from the group consisting of phenylalanine$_{10}$ to alanine, leucine$_{23}$ to alanine, phenylalanine$_{25}$ to alanine, tyrosine$_{28}$ to alanine, phenylalanine$_{31}$ to alanine, tyrosine$_{42}$ to alanine, phenylalanine$_{44}$ to alanine, leucine$_{45}$ to alanine, tyrosine$_{103}$ to alanine, arginine$_{134}$ to threonine, threonine$_{135}$ to isoleucine, threonine$_{135}$ to glutamine, glycine$_{136}$ to valine, glycine$_{136}$ to asparagine, glutamine$_{137}$ to threonine, glutamine$_{137}$ to serine, glutamine$_{137}$ to alanine, isoleucine$_{138}$ to proline, isoleucine$_{138}$ to methionine, phenylalanine$_{139}$ to proline, phenylalanine$_{139}$ to alanine, lysine$_{140}$ to alanine, lysine$_{140}$ to threonine, lysine$_{140}$ to asparagine, threonine$_{142}$ to alanine, tyrosine$_{143}$ to alanine, phenylalanine$_{146}$ to alanine, serine$_{150}$ to alanine, histidine$_{151}$ to alanine, isoleucine$_4$ to valine-leucine, and insertion of glutamate preceding isoleucine$_4$.

21. The human growth hormone peptide of claim 20, wherein the human growth hormone peptide comprises eight or fewer mutations.

22. A pharmaceutical formulation comprising a human growth hormone peptide according to claim 1 and a pharmaceutically acceptable carrier.

23. An isolated human growth hormone peptide comprising the amino acid sequence of SEQ ID NO: 3, 4, 5, 6, 7, 8, 9, or 80.

24. A method of producing a human growth hormone, which method comprises:
 (a) transfecting a cell with a nucleic acid encoding the human growth hormone according to claim 23; and
 (b) expressing the nucleic acid in the cell to produce the human growth hormone.

25. A method of treating a subject in need of supplementation of endogenously produced human growth hormone, which method comprises administering to the subject a therapeutically effective amount of a human growth hormone peptide of claim 1.

26. A method of producing a human growth hormone, which method comprises:
 (a) transfecting a cell with a nucleic acid encoding the human growth hormone according to claim 1; and
 (b) expressing the nucleic acid in the cell to produce the human growth hormone.

27. The method of claim 26, further comprising:
 (c) contacting the human growth hormone with a sugar donor and an enzyme for which the sugar donor is a substrate under conditions appropriate to transfer a sugar moiety from the donor to an O-linked glycosylation site not present in SEQ ID NO: 1 or SEQ ID NO: 2.

28. The method of claim 27, wherein the sugar moiety is a modified sugar moiety.

29. The method of claim 28, wherein the sugar moiety is modified by a water-soluble polymer covalently attached thereto.

30. The method of claim 29, wherein the water-soluble polymer is a poly(ethylene glycol).

31. The method of claim 27, wherein the sugar moiety is a member selected from a galactosyl, N-acetylgalactosyl and a sialic acid moiety.

32. The method of claim 27, which method further comprises:
(d) contacting the human growth hormone with an activated water-soluble polymer under conditions appropriate to form a covalent bond between a water-soluble polymer moiety of the activated water-soluble polymer and an amino acid of the human growth hormone.

33. The method of claim 32, wherein the amino acid residue is (1) an amino acid not present in SEQ ID NO: 1 or SEQ ID NO: 2 but present in the human growth hormone peptide to render a protease recognition site of SEQ ID NO: 1 or SEQ ID NO: 2 proteolysis resistant or (2) an amino acid proximate to the amino acid of (1).

34. The method of claim 32, wherein the amino acid is proximate to the protease recognition site.

35. The method of claim 27, which method further comprises:
(d) isolating the human growth hormone prior to step (c).

36. The method of claim 26, wherein an O-linked glycosylation site not present in SEQ ID NO: 1 or SEQ ID NO: 2 is present and proximate a proline residue.

37. The method of claim 36, wherein the O-linked glycosylation site that is not present in SEQ ID NO: 1 or SEQ ID NO: 2 comprises an amino acid that is either threonine or serine.

38. The method of claim 26, wherein the human growth hormone comprises an amino acid sequence selected from SEQ ID NO: 81, 82, 83, 84, 85, 86, 87, 88, and 89.

39. The method of claim 26, wherein more than one O-linked glycosylation site is present that is not present in SEQ ID NO: 1 or SEQ ID NO: 2.

* * * * *

UNITED STATES PATENT AND TRADEMARK OFFICE
CERTIFICATE OF CORRECTION

| | | |
|---|---|---|
| PATENT NO. | : 9,187,546 B2 | Page 1 of 1 |
| APPLICATION NO. | : 11/910958 | |
| DATED | : November 17, 2015 | |
| INVENTOR(S) | : Shawn DeFrees | |

It is certified that error appears in the above-identified patent and that said Letters Patent is hereby corrected as shown below:

In the claims

In Column 221, line 38, "claim 5," should read --claim 6,--

Signed and Sealed this
Twenty-eighth Day of June, 2016

Michelle K. Lee
*Director of the United States Patent and Trademark Office*

SEQUENCE LISTING

<160> NUMBER OF SEQ ID NOS: 136

<210> SEQ ID NO 1
<211> LENGTH: 191
<212> TYPE: PRT
<213> ORGANISM: Homo sapiens

<400> SEQUENCE: 1

Phe Pro Thr Ile Pro Leu Ser Arg Leu Phe Asp Asn Ala Met Leu Arg
 1               5                  10                  15

Ala His Arg Leu His Gln Leu Ala Phe Asp Thr Tyr Gln Glu Phe Glu
             20                  25                  30

```
Glu Ala Tyr Ile Pro Lys Glu Gln Lys Tyr Ser Phe Leu Gln Asn Pro
            35                  40                  45

Gln Thr Ser Leu Cys Phe Ser Glu Ser Ile Pro Thr Pro Ser Asn Arg
 50                  55                  60

Glu Glu Thr Gln Gln Lys Ser Asn Leu Glu Leu Leu Arg Ile Ser Leu
 65                  70                  75                  80

Leu Leu Ile Gln Ser Trp Leu Glu Pro Val Gln Phe Leu Arg Ser Val
                85                  90                  95

Phe Ala Asn Ser Leu Val Tyr Gly Ala Ser Asp Ser Asn Val Tyr Asp
                100                 105                 110

Leu Leu Lys Asp Leu Glu Glu Gly Ile Gln Thr Leu Met Gly Arg Leu
                115                 120                 125

Glu Asp Gly Ser Pro Arg Thr Gly Gln Ile Phe Lys Gln Thr Tyr Ser
 130                 135                 140

Lys Phe Asp Thr Asn Ser His Asn Asp Asp Ala Leu Leu Lys Asn Tyr
145                  150                 155                 160

Gly Leu Leu Tyr Cys Phe Arg Lys Asp Met Asp Lys Val Glu Thr Phe
                165                 170                 175

Leu Arg Ile Val Gln Cys Arg Ser Val Glu Gly Ser Cys Gly Phe
                180                 185                 190

<210> SEQ ID NO 2
<211> LENGTH: 191
<212> TYPE: PRT
<213> ORGANISM: Homo sapiens

<400> SEQUENCE: 2

Phe Pro Thr Ile Pro Leu Ser Arg Leu Phe Asp Asn Ala Met Leu Arg
 1                   5                  10                  15

Ala Arg Arg Leu Tyr Gln Leu Ala Tyr Asp Thr Tyr Gln Glu Phe Glu
                20                  25                  30

Glu Ala Tyr Ile Leu Lys Glu Gln Lys Tyr Ser Phe Leu Gln Asn Pro
            35                  40                  45

Gln Thr Ser Leu Cys Phe Ser Glu Ser Ile Pro Thr Pro Ser Asn Arg
 50                  55                  60

Val Lys Thr Gln Gln Lys Ser Asn Leu Glu Leu Leu Arg Ile Ser Leu
 65                  70                  75                  80

Leu Leu Ile Gln Ser Trp Leu Glu Pro Val Gln Leu Leu Arg Ser Val
                85                  90                  95

Phe Ala Asn Ser Leu Val Tyr Gly Ala Ser Asp Ser Asn Val Tyr Arg
                100                 105                 110

His Leu Lys Asp Leu Glu Glu Gly Ile Gln Thr Leu Met Trp Arg Leu
                115                 120                 125

Glu Asp Gly Ser Pro Arg Thr Gly Gln Ile Phe Asn Gln Ser Tyr Ser
 130                 135                 140

Lys Phe Asp Thr Lys Ser His Asn Asp Asp Ala Leu Leu Lys Asn Tyr
145                  150                 155                 160

Gly Leu Leu Tyr Cys Phe Arg Lys Asp Met Asp Lys Val Glu Thr Phe
                165                 170                 175

Leu Arg Ile Val Gln Cys Arg Ser Val Glu Gly Ser Cys Gly Phe
                180                 185                 190

<210> SEQ ID NO 3
<211> LENGTH: 191
<212> TYPE: PRT
```

<213> ORGANISM: Artificial Sequence
<220> FEATURE:
<223> OTHER INFORMATION: synthetic mutant human growth hormone

<400> SEQUENCE: 3

```
Phe Pro Thr Ile Pro Leu Ser Arg Leu Phe Asp Asn Ala Met Leu Arg
  1               5                  10                  15

Ala His Arg Leu His Gln Leu Ala Phe Asp Thr Tyr Gln Glu Phe Glu
             20                  25                  30

Glu Ala Tyr Ile Pro Lys Glu Gln Lys Tyr Ser Phe Leu Gln Asn Pro
         35                  40                  45

Gln Thr Ser Leu Cys Phe Ser Glu Ser Ile Pro Thr Pro Ser Asn Arg
     50                  55                  60

Glu Glu Thr Gln Gln Lys Ser Asn Leu Glu Leu Leu Arg Ile Ser Leu
 65                  70                  75                  80

Leu Leu Ile Gln Ser Trp Leu Glu Pro Val Gln Phe Leu Arg Ser Val
                 85                  90                  95

Phe Ala Asn Ser Leu Val Tyr Gly Ala Ser Asp Ser Asn Val Tyr Asp
            100                 105                 110

Leu Leu Lys Asp Leu Glu Glu Gly Ile Gln Thr Leu Met Gly Arg Leu
        115                 120                 125

Glu Asp Gly Ser Pro Thr Thr Thr Gln Ile Phe Lys Gln Thr Tyr Ser
    130                 135                 140

Lys Phe Asp Thr Asn Ser His Asn Asp Asp Ala Leu Leu Lys Asn Tyr
145                 150                 155                 160

Gly Leu Leu Tyr Cys Phe Arg Lys Asp Met Asp Lys Val Glu Thr Phe
                165                 170                 175

Leu Arg Ile Val Gln Cys Arg Ser Val Glu Gly Ser Cys Gly Phe
            180                 185                 190
```

<210> SEQ ID NO 4
<211> LENGTH: 194
<212> TYPE: PRT
<213> ORGANISM: Artificial Sequence
<220> FEATURE:
<223> OTHER INFORMATION: synthetic mutant human growth hormone

<400> SEQUENCE: 4

```
Pro Thr Thr Phe Pro Thr Ile Pro Leu Ser Arg Leu Phe Asp Asn Ala
  1               5                  10                  15

Met Leu Arg Ala His Arg Leu His Gln Leu Ala Phe Asp Thr Tyr Gln
             20                  25                  30

Glu Phe Glu Glu Ala Tyr Ile Pro Lys Glu Gln Lys Tyr Ser Phe Leu
         35                  40                  45

Gln Asn Pro Gln Thr Ser Leu Cys Phe Ser Glu Ser Ile Pro Thr Pro
     50                  55                  60

Ser Asn Arg Glu Glu Thr Gln Gln Lys Ser Asn Leu Glu Leu Leu Arg
 65                  70                  75                  80

Ile Ser Leu Leu Leu Ile Gln Ser Trp Leu Glu Pro Val Gln Phe Leu
                 85                  90                  95

Arg Ser Val Phe Ala Asn Ser Leu Val Tyr Gly Ala Ser Asp Ser Asn
            100                 105                 110

Val Tyr Asp Leu Leu Lys Asp Leu Glu Glu Gly Ile Gln Thr Leu Met
        115                 120                 125

Gly Arg Leu Glu Asp Gly Ser Pro Arg Thr Gly Gln Ile Phe Lys Gln
    130                 135                 140
```

```
Thr Tyr Ser Lys Phe Asp Thr Asn Ser His Asn Asp Asp Ala Leu Leu
145                 150                 155                 160

Lys Asn Tyr Gly Leu Leu Tyr Cys Phe Arg Lys Asp Met Asp Lys Val
            165                 170                 175

Glu Thr Phe Leu Arg Ile Val Gln Cys Arg Ser Val Glu Gly Ser Cys
        180                 185                 190

Gly Phe

<210> SEQ ID NO 5
<211> LENGTH: 191
<212> TYPE: PRT
<213> ORGANISM: Artificial Sequence
<220> FEATURE:
<223> OTHER INFORMATION: synthetic mutant human growth hormone

<400> SEQUENCE: 5

Phe Pro Thr Ile Pro Leu Ser Arg Leu Phe Asp Asn Ala Met Leu Arg
1               5                   10                  15

Ala His Arg Leu His Gln Leu Ala Phe Asp Thr Tyr Gln Glu Phe Glu
            20                  25                  30

Glu Ala Tyr Ile Pro Lys Glu Gln Lys Tyr Ser Phe Leu Gln Asn Pro
        35                  40                  45

Gln Thr Ser Leu Cys Phe Ser Glu Ser Ile Pro Thr Pro Ser Asn Arg
    50                  55                  60

Glu Glu Thr Gln Gln Lys Ser Asn Leu Glu Leu Leu Arg Ile Ser Leu
65                  70                  75                  80

Leu Leu Ile Gln Ser Trp Leu Glu Pro Val Gln Phe Leu Arg Ser Val
                85                  90                  95

Phe Ala Asn Ser Leu Val Tyr Gly Ala Ser Asp Ser Asn Val Tyr Asp
            100                 105                 110

Leu Leu Lys Asp Leu Glu Glu Gly Ile Gln Thr Leu Met Gly Arg Leu
        115                 120                 125

Glu Asp Gly Ser Pro Thr Thr Gly Gln Ile Phe Lys Gln Thr Tyr Ser
    130                 135                 140

Lys Phe Asp Thr Asn Ser His Asn Asp Asp Ala Leu Leu Lys Asn Tyr
145                 150                 155                 160

Gly Leu Leu Tyr Cys Phe Arg Lys Asp Met Asp Lys Val Glu Thr Phe
                165                 170                 175

Leu Arg Ile Val Gln Cys Arg Ser Val Glu Gly Ser Cys Gly Phe
            180                 185                 190

<210> SEQ ID NO 6
<211> LENGTH: 193
<212> TYPE: PRT
<213> ORGANISM: Artificial Sequence
<220> FEATURE:
<223> OTHER INFORMATION: synthetic mutant human growth hormone

<400> SEQUENCE: 6

Met Val Thr Pro Thr Ile Pro Leu Ser Arg Leu Phe Asp Asn Ala Met
1               5                   10                  15

Leu Arg Ala His Arg Leu His Gln Leu Ala Phe Asp Thr Tyr Gln Glu
            20                  25                  30

Phe Glu Glu Ala Tyr Ile Pro Lys Glu Gln Lys Tyr Ser Phe Leu Gln
        35                  40                  45

Asn Pro Gln Thr Ser Leu Cys Phe Ser Glu Ser Ile Pro Thr Pro Ser
    50                  55                  60
```

```
Asn Arg Glu Glu Thr Gln Gln Lys Ser Asn Leu Glu Leu Leu Arg Ile
 65                  70                  75                  80

Ser Leu Leu Leu Ile Gln Ser Trp Leu Glu Pro Val Gln Phe Leu Arg
                 85                  90                  95

Ser Val Phe Ala Asn Ser Leu Val Tyr Gly Ala Ser Asp Ser Asn Val
            100                 105                 110

Tyr Asp Leu Leu Lys Asp Leu Glu Glu Gly Ile Gln Thr Leu Met Gly
        115                 120                 125

Arg Leu Glu Asp Gly Ser Pro Arg Thr Gly Gln Ile Phe Lys Gln Thr
    130                 135                 140

Tyr Ser Lys Phe Asp Thr Asn Ser His Asn Asp Asp Ala Leu Leu Lys
145                 150                 155                 160

Asn Tyr Gly Leu Leu Tyr Cys Phe Arg Lys Asp Met Asp Lys Val Glu
                165                 170                 175

Thr Phe Leu Arg Ile Val Gln Cys Arg Ser Val Glu Gly Ser Cys Gly
                180                 185                 190

Phe

<210> SEQ ID NO 7
<211> LENGTH: 193
<212> TYPE: PRT
<213> ORGANISM: Artificial Sequence
<220> FEATURE:
<223> OTHER INFORMATION: synthetic mutant human growth hormone

<400> SEQUENCE: 7

Met Val Thr Pro Thr Ile Pro Leu Ser Arg Leu Phe Asp Asn Ala Met
  1               5                  10                  15

Leu Arg Ala His Arg Leu His Gln Leu Ala Phe Asp Thr Tyr Gln Glu
             20                  25                  30

Phe Glu Glu Ala Tyr Ile Pro Lys Glu Gln Lys Tyr Ser Phe Leu Gln
         35                  40                  45

Asn Pro Gln Thr Ser Leu Cys Phe Ser Glu Ser Ile Pro Thr Pro Ser
 50                  55                  60

Asn Arg Glu Glu Thr Gln Gln Lys Ser Asn Leu Glu Leu Leu Arg Ile
 65                  70                  75                  80

Ser Leu Leu Leu Ile Gln Ser Trp Leu Glu Pro Val Gln Phe Leu Arg
                 85                  90                  95

Ser Val Phe Ala Asn Ser Leu Val Tyr Gly Ala Ser Asp Ser Asn Val
            100                 105                 110

Tyr Asp Leu Leu Lys Asp Leu Glu Glu Gly Ile Gln Thr Leu Met Gly
        115                 120                 125

Arg Leu Glu Asp Gly Ser Pro Arg Thr Gly Gln Ile Phe Lys Gln Thr
    130                 135                 140

Tyr Ser Lys Phe Asp Thr Asn Ser His Asn Asp Asp Ala Leu Leu Lys
145                 150                 155                 160

Asn Tyr Gly Leu Leu Tyr Cys Phe Arg Lys Asp Met Asp Lys Val Glu
                165                 170                 175

Thr Phe Leu Arg Ile Val Gln Cys Arg Ser Val Glu Gly Ser Cys Gly
                180                 185                 190

Phe

<210> SEQ ID NO 8
<211> LENGTH: 192
<212> TYPE: PRT
<213> ORGANISM: Artificial Sequence
```

-continued

```
<220> FEATURE:
<223> OTHER INFORMATION: synthetic mutant human growth hormone

<400> SEQUENCE: 8

Met Phe Pro Thr Ile Pro Leu Ser Arg Leu Phe Asp Asn Ala Met Leu
1               5                   10                  15

Arg Ala His Arg Leu His Gln Leu Ala Phe Asp Thr Tyr Gln Glu Phe
            20                  25                  30

Glu Glu Ala Tyr Ile Pro Lys Glu Gln Lys Tyr Ser Phe Leu Gln Asn
        35                  40                  45

Pro Gln Thr Ser Leu Cys Phe Ser Glu Ser Ile Pro Thr Pro Ser Asn
    50                  55                  60

Arg Glu Glu Thr Gln Gln Lys Ser Asn Leu Glu Leu Leu Arg Ile Ser
65                  70                  75                  80

Leu Leu Leu Ile Gln Ser Trp Leu Glu Pro Val Gln Phe Leu Arg Ser
                85                  90                  95

Val Phe Ala Asn Ser Leu Val Tyr Gly Ala Ser Asp Ser Asn Val Tyr
            100                 105                 110

Asp Leu Leu Lys Asp Leu Glu Glu Gly Ile Gln Thr Leu Met Gly Arg
        115                 120                 125

Leu Glu Asp Gly Ser Pro Thr Val Gly Gln Ile Phe Lys Gln Thr Tyr
    130                 135                 140

Ser Lys Phe Asp Thr Asn Ser His Asn Asp Asp Ala Leu Leu Lys Asn
145                 150                 155                 160

Tyr Gly Leu Leu Tyr Cys Phe Arg Lys Asp Met Asp Lys Val Glu Thr
                165                 170                 175

Phe Leu Arg Ile Val Gln Cys Arg Ser Val Glu Gly Ser Cys Gly Phe
            180                 185                 190

<210> SEQ ID NO 9
<211> LENGTH: 192
<212> TYPE: PRT
<213> ORGANISM: Artificial Sequence
<220> FEATURE:
<223> OTHER INFORMATION: synthetic mutant human growth hormone

<400> SEQUENCE: 9

Met Phe Pro Thr Ile Pro Leu Ser Arg Leu Phe Asp Asn Ala Met Leu
1               5                   10                  15

Arg Ala His Arg Leu His Gln Leu Ala Phe Asp Thr Tyr Gln Glu Phe
            20                  25                  30

Glu Glu Ala Tyr Ile Pro Lys Glu Gln Lys Tyr Ser Phe Leu Gln Asn
        35                  40                  45

Pro Gln Thr Ser Leu Cys Phe Ser Glu Ser Ile Pro Thr Pro Ser Asn
    50                  55                  60

Arg Glu Glu Thr Gln Gln Lys Ser Asn Leu Glu Leu Leu Arg Ile Ser
65                  70                  75                  80

Leu Leu Leu Ile Gln Ser Trp Leu Glu Pro Val Gln Phe Leu Arg Ser
                85                  90                  95

Val Phe Ala Asn Ser Leu Val Tyr Gly Ala Ser Asp Ser Asn Val Tyr
            100                 105                 110

Asp Leu Leu Lys Asp Leu Glu Glu Gly Ile Gln Thr Leu Met Gly Arg
        115                 120                 125

Leu Glu Asp Gly Ser Pro Thr Thr Gln Ile Phe Lys Gln Thr Tyr
    130                 135                 140

Ser Lys Phe Asp Thr Asn Ser His Asn Asp Asp Ala Leu Leu Lys Asn
```

```
                145                 150                 155                 160
Tyr Gly Leu Leu Tyr Cys Phe Arg Lys Asp Met Asp Lys Val Glu Thr
                    165                 170                 175
Phe Leu Arg Ile Val Gln Cys Arg Ser Val Glu Gly Ser Cys Gly Phe
                    180                 185                 190

<210> SEQ ID NO 10
<211> LENGTH: 6
<212> TYPE: PRT
<213> ORGANISM: Artificial Sequence
<220> FEATURE:
<223> OTHER INFORMATION: synthetic mutant human growth hormone

<400> SEQUENCE: 10

Phe Pro Thr Ile Pro Leu
1               5

<210> SEQ ID NO 11
<211> LENGTH: 5
<212> TYPE: PRT
<213> ORGANISM: Artificial Sequence
<220> FEATURE:
<223> OTHER INFORMATION: synthetic mutant human growth hormone

<400> SEQUENCE: 11

Pro Gln Thr Ser Leu
1               5

<210> SEQ ID NO 12
<211> LENGTH: 6
<212> TYPE: PRT
<213> ORGANISM: Artificial Sequence
<220> FEATURE:
<223> OTHER INFORMATION: synthetic mutant human growth hormone

<400> SEQUENCE: 12

Pro Thr Pro Ser Asn Arg
1               5

<210> SEQ ID NO 13
<211> LENGTH: 7
<212> TYPE: PRT
<213> ORGANISM: Artificial Sequence
<220> FEATURE:
<223> OTHER INFORMATION: synthetic mutant human growth hormone

<400> SEQUENCE: 13

Pro Arg Thr Gly Gln Ile Phe
1               5

<210> SEQ ID NO 14
<211> LENGTH: 13
<212> TYPE: PRT
<213> ORGANISM: Artificial Sequence
<220> FEATURE:
<223> OTHER INFORMATION: synthetic mutant human growth hormone

<400> SEQUENCE: 14

Pro Arg Thr Gly Gln Ile Phe Lys Gln Thr Tyr Ser Lys
1               5                   10

<210> SEQ ID NO 15
<211> LENGTH: 4
<212> TYPE: PRT
<213> ORGANISM: Artificial Sequence
<220> FEATURE:
```

<223> OTHER INFORMATION: synthetic mutant human growth hormone

<400> SEQUENCE: 15

Phe Lys Gln Thr
 1

<210> SEQ ID NO 16
<211> LENGTH: 7
<212> TYPE: PRT
<213> ORGANISM: Artificial Sequence
<220> FEATURE:
<223> OTHER INFORMATION: synthetic mutant human growth hormone

<400> SEQUENCE: 16

Phe Pro Thr Ile Pro Leu Ser
 1               5

<210> SEQ ID NO 17
<211> LENGTH: 9
<212> TYPE: PRT
<213> ORGANISM: Artificial Sequence
<220> FEATURE:
<223> OTHER INFORMATION: synthetic mutant human growth hormone

<400> SEQUENCE: 17

Met Val Thr Pro Thr Ile Pro Leu Ser
 1               5

<210> SEQ ID NO 18
<211> LENGTH: 9
<212> TYPE: PRT
<213> ORGANISM: Artificial Sequence
<220> FEATURE:
<223> OTHER INFORMATION: synthetic mutant human growth hormone

<400> SEQUENCE: 18

Met Gln Thr Pro Thr Ile Pro Leu Ser
 1               5

<210> SEQ ID NO 19
<211> LENGTH: 12
<212> TYPE: PRT
<213> ORGANISM: Artificial Sequence
<220> FEATURE:
<223> OTHER INFORMATION: synthetic mutant human growth hormone

<400> SEQUENCE: 19

Met Ala Pro Thr Ser Ser Pro Thr Ile Pro Leu Ser
 1               5                   10

<210> SEQ ID NO 20
<211> LENGTH: 13
<212> TYPE: PRT
<213> ORGANISM: Artificial Sequence
<220> FEATURE:
<223> OTHER INFORMATION: synthetic mutant human growth hormone

<400> SEQUENCE: 20

Met Ala Pro Thr Ser Ser Ser Pro Thr Ile Pro Leu Ser
 1               5                   10

<210> SEQ ID NO 21
<211> LENGTH: 11
<212> TYPE: PRT
<213> ORGANISM: Artificial Sequence
<220> FEATURE:
<223> OTHER INFORMATION: synthetic mutant human growth hormone

```
<400> SEQUENCE: 21

Met Pro Thr Thr Phe Pro Thr Ile Pro Leu Ser
1               5                   10

<210> SEQ ID NO 22
<211> LENGTH: 11
<212> TYPE: PRT
<213> ORGANISM: Artificial Sequence
<220> FEATURE:
<223> OTHER INFORMATION: synthetic mutant human growth hormone

<400> SEQUENCE: 22

Met Pro Thr Thr Phe Pro Thr Ile Pro Leu Ser
1               5                   10

<210> SEQ ID NO 23
<211> LENGTH: 11
<212> TYPE: PRT
<213> ORGANISM: Artificial Sequence
<220> FEATURE:
<223> OTHER INFORMATION: synthetic mutant human growth hormone

<400> SEQUENCE: 23

Met Pro Thr Ser Ser Pro Thr Ile Pro Leu Ser
1               5                   10

<210> SEQ ID NO 24
<211> LENGTH: 7
<212> TYPE: PRT
<213> ORGANISM: Artificial Sequence
<220> FEATURE:
<223> OTHER INFORMATION: synthetic mutant human growth hormone

<400> SEQUENCE: 24

Phe Pro Thr Ile Pro Leu Ser
1               5

<210> SEQ ID NO 25
<211> LENGTH: 7
<212> TYPE: PRT
<213> ORGANISM: Artificial Sequence
<220> FEATURE:
<223> OTHER INFORMATION: synthetic mutant human growth hormone

<400> SEQUENCE: 25

Phe Pro Thr Ile Pro Leu Ser
1               5

<210> SEQ ID NO 26
<211> LENGTH: 9
<212> TYPE: PRT
<213> ORGANISM: Artificial Sequence
<220> FEATURE:
<223> OTHER INFORMATION: synthetic mutant human growth hormone

<400> SEQUENCE: 26

Met Phe Pro Thr Gln Ile Pro Leu Ser
1               5

<210> SEQ ID NO 27
<211> LENGTH: 9
<212> TYPE: PRT
<213> ORGANISM: Artificial Sequence
<220> FEATURE:
<223> OTHER INFORMATION: synthetic mutant human growth hormone
```

```
<400> SEQUENCE: 27

Met Phe Pro Thr Ser Ile Pro Leu Ser
1               5

<210> SEQ ID NO 28
<211> LENGTH: 9
<212> TYPE: PRT
<213> ORGANISM: Artificial Sequence
<220> FEATURE:
<223> OTHER INFORMATION: synthetic mutant human growth hormone

<400> SEQUENCE: 28

Met Phe Pro Thr Ser Ser Pro Leu Ser
1               5

<210> SEQ ID NO 29
<211> LENGTH: 9
<212> TYPE: PRT
<213> ORGANISM: Artificial Sequence
<220> FEATURE:
<223> OTHER INFORMATION: synthetic mutant human growth hormone

<400> SEQUENCE: 29

Met Phe Pro Thr Thr Thr Pro Leu Ser
1               5

<210> SEQ ID NO 30
<211> LENGTH: 9
<212> TYPE: PRT
<213> ORGANISM: Artificial Sequence
<220> FEATURE:
<223> OTHER INFORMATION: synthetic mutant human growth hormone

<400> SEQUENCE: 30

Ala Tyr Ile Pro Lys Glu Gln Lys Tyr
1               5

<210> SEQ ID NO 31
<211> LENGTH: 9
<212> TYPE: PRT
<213> ORGANISM: Artificial Sequence
<220> FEATURE:
<223> OTHER INFORMATION: synthetic mutant human growth hormone

<400> SEQUENCE: 31

Ala Tyr Ile Pro Lys Glu Gln Lys Tyr
1               5

<210> SEQ ID NO 32
<211> LENGTH: 9
<212> TYPE: PRT
<213> ORGANISM: Artificial Sequence
<220> FEATURE:
<223> OTHER INFORMATION: synthetic mutant human growth hormone

<400> SEQUENCE: 32

Ala Tyr Ile Pro Thr Ser Ser Ser Tyr
1               5

<210> SEQ ID NO 33
<211> LENGTH: 10
<212> TYPE: PRT
<213> ORGANISM: Artificial Sequence
<220> FEATURE:
<223> OTHER INFORMATION: synthetic mutant human growth hormone

<400> SEQUENCE: 33
```

```
Ala Gln Ile Thr Pro Thr Glu Gln Lys Tyr
1               5                   10

<210> SEQ ID NO 34
<211> LENGTH: 9
<212> TYPE: PRT
<213> ORGANISM: Artificial Sequence
<220> FEATURE:
<223> OTHER INFORMATION: synthetic mutant human growth hormone

<400> SEQUENCE: 34

Ala Tyr Ile Pro Thr Glu Gln Ser Tyr
1               5

<210> SEQ ID NO 35
<211> LENGTH: 9
<212> TYPE: PRT
<213> ORGANISM: Artificial Sequence
<220> FEATURE:
<223> OTHER INFORMATION: synthetic mutant human growth hormone

<400> SEQUENCE: 35

Leu Gln Asn Pro Gln Thr Ser Leu Cys
1               5

<210> SEQ ID NO 36
<211> LENGTH: 9
<212> TYPE: PRT
<213> ORGANISM: Artificial Sequence
<220> FEATURE:
<223> OTHER INFORMATION: synthetic mutant human growth hormone

<400> SEQUENCE: 36

Leu Gln Thr Pro Gln Thr Ser Leu Cys
1               5

<210> SEQ ID NO 37
<211> LENGTH: 9
<212> TYPE: PRT
<213> ORGANISM: Artificial Sequence
<220> FEATURE:
<223> OTHER INFORMATION: synthetic mutant human growth hormone

<400> SEQUENCE: 37

Leu Gln Asn Pro Thr Thr Ser Leu Cys
1               5

<210> SEQ ID NO 38
<211> LENGTH: 12
<212> TYPE: PRT
<213> ORGANISM: Artificial Sequence
<220> FEATURE:
<223> OTHER INFORMATION: synthetic mutant human growth hormone

<400> SEQUENCE: 38

Ser Glu Ser Ile Pro Thr Pro Asn Arg Glu Glu Thr
1               5                   10

<210> SEQ ID NO 39
<211> LENGTH: 12
<212> TYPE: PRT
<213> ORGANISM: Artificial Sequence
<220> FEATURE:
<223> OTHER INFORMATION: synthetic mutant human growth hormone

<400> SEQUENCE: 39
```

Ser Glu Ser Thr Pro Thr Pro Asn Arg Glu Glu Thr
1               5                   10

<210> SEQ ID NO 40
<211> LENGTH: 12
<212> TYPE: PRT
<213> ORGANISM: Artificial Sequence
<220> FEATURE:
<223> OTHER INFORMATION: synthetic mutant human growth hormone

<400> SEQUENCE: 40

Ser Ser Ser Thr Pro Thr Pro Asn Arg Glu Glu Thr
1               5                   10

<210> SEQ ID NO 41
<211> LENGTH: 12
<212> TYPE: PRT
<213> ORGANISM: Artificial Sequence
<220> FEATURE:
<223> OTHER INFORMATION: synthetic mutant human growth hormone

<400> SEQUENCE: 41

Ser Glu Ser Ile Pro Thr Pro Asn Thr Glu Glu Thr
1               5                   10

<210> SEQ ID NO 42
<211> LENGTH: 12
<212> TYPE: PRT
<213> ORGANISM: Artificial Sequence
<220> FEATURE:
<223> OTHER INFORMATION: synthetic mutant human growth hormone

<400> SEQUENCE: 42

Ser Glu Ser Ile Pro Thr Pro Asn Thr Gln Glu Thr
1               5                   10

<210> SEQ ID NO 43
<211> LENGTH: 12
<212> TYPE: PRT
<213> ORGANISM: Artificial Sequence
<220> FEATURE:
<223> OTHER INFORMATION: synthetic mutant human growth hormone

<400> SEQUENCE: 43

Ser Glu Ser Ile Pro Thr Pro Thr Gln Gly Ala Thr
1               5                   10

<210> SEQ ID NO 44
<211> LENGTH: 12
<212> TYPE: PRT
<213> ORGANISM: Artificial Sequence
<220> FEATURE:
<223> OTHER INFORMATION: synthetic mutant human growth hormone

<400> SEQUENCE: 44

Ser Glu Ser Ile Pro Thr Pro Thr Glu Ser Ser Thr
1               5                   10

<210> SEQ ID NO 45
<211> LENGTH: 12
<212> TYPE: PRT
<213> ORGANISM: Artificial Sequence
<220> FEATURE:
<223> OTHER INFORMATION: synthetic mutant human growth hormone

<400> SEQUENCE: 45

Ser Gln Ser Thr Pro Thr Pro Asn Arg Glu Glu Thr

```
<210> SEQ ID NO 46
<211> LENGTH: 12
<212> TYPE: PRT
<213> ORGANISM: Artificial Sequence
<220> FEATURE:
<223> OTHER INFORMATION: synthetic mutant human growth hormone

<400> SEQUENCE: 46

Ser Gln Ser Thr Pro Thr Pro Asn Gln Glu Glu Thr
1               5                   10

<210> SEQ ID NO 47
<211> LENGTH: 12
<212> TYPE: PRT
<213> ORGANISM: Artificial Sequence
<220> FEATURE:
<223> OTHER INFORMATION: synthetic mutant human growth hormone

<400> SEQUENCE: 47

Ser Glu Ser Thr Pro Thr Pro Thr Ser Ser Ser Thr
1               5                   10

<210> SEQ ID NO 48
<211> LENGTH: 11
<212> TYPE: PRT
<213> ORGANISM: Artificial Sequence
<220> FEATURE:
<223> OTHER INFORMATION: synthetic mutant human growth hormone

<400> SEQUENCE: 48

Ser Trp Leu Glu Pro Val Gln Phe Leu Arg Ser
1               5                   10

<210> SEQ ID NO 49
<211> LENGTH: 11
<212> TYPE: PRT
<213> ORGANISM: Artificial Sequence
<220> FEATURE:
<223> OTHER INFORMATION: synthetic mutant human growth hormone

<400> SEQUENCE: 49

Ser Trp Leu Glu Pro Thr Gln Gly Leu Arg Ser
1               5                   10

<210> SEQ ID NO 50
<211> LENGTH: 11
<212> TYPE: PRT
<213> ORGANISM: Artificial Sequence
<220> FEATURE:
<223> OTHER INFORMATION: synthetic mutant human growth hormone

<400> SEQUENCE: 50

Ser Ser Gln Thr Pro Val Gln Phe Leu Arg Ser
1               5                   10

<210> SEQ ID NO 51
<211> LENGTH: 11
<212> TYPE: PRT
<213> ORGANISM: Artificial Sequence
<220> FEATURE:
<223> OTHER INFORMATION: synthetic mutant human growth hormone

<400> SEQUENCE: 51

Ser Trp Leu Glu Pro Thr Ser Ser Leu Ser Ser
1               5                   10
```

```
<210> SEQ ID NO 52
<211> LENGTH: 11
<212> TYPE: PRT
<213> ORGANISM: Artificial Sequence
<220> FEATURE:
<223> OTHER INFORMATION: synthetic mutant human growth hormone

<400> SEQUENCE: 52

Ser Met Val Thr Pro Val Gln Phe Leu Arg Ser
1               5                   10

<210> SEQ ID NO 53
<211> LENGTH: 11
<212> TYPE: PRT
<213> ORGANISM: Artificial Sequence
<220> FEATURE:
<223> OTHER INFORMATION: synthetic mutant human growth hormone

<400> SEQUENCE: 53

Glu Asp Gly Ser Pro Arg Thr Gly Gln Ile Phe
1               5                   10

<210> SEQ ID NO 54
<211> LENGTH: 11
<212> TYPE: PRT
<213> ORGANISM: Artificial Sequence
<220> FEATURE:
<223> OTHER INFORMATION: synthetic mutant human growth hormone

<400> SEQUENCE: 54

Glu Asp Gly Ser Pro Thr Thr Gly Gln Ile Phe
1               5                   10

<210> SEQ ID NO 55
<211> LENGTH: 11
<212> TYPE: PRT
<213> ORGANISM: Artificial Sequence
<220> FEATURE:
<223> OTHER INFORMATION: synthetic mutant human growth hormone

<400> SEQUENCE: 55

Glu Asp Gly Ser Pro Asn Thr Gly Gln Ile Phe
1               5                   10

<210> SEQ ID NO 56
<211> LENGTH: 11
<212> TYPE: PRT
<213> ORGANISM: Artificial Sequence
<220> FEATURE:
<223> OTHER INFORMATION: synthetic mutant human growth hormone

<400> SEQUENCE: 56

Glu Asp Gly Ser Pro Thr Gln Gly Gln Ile Phe
1               5                   10

<210> SEQ ID NO 57
<211> LENGTH: 11
<212> TYPE: PRT
<213> ORGANISM: Artificial Sequence
<220> FEATURE:
<223> OTHER INFORMATION: synthetic mutant human growth hormone

<400> SEQUENCE: 57

Glu Asp Gly Ser Pro Thr Val Gly Gln Ile Phe
1               5                   10
```

```
<210> SEQ ID NO 58
<211> LENGTH: 11
<212> TYPE: PRT
<213> ORGANISM: Artificial Sequence
<220> FEATURE:
<223> OTHER INFORMATION: synthetic mutant human growth hormone

<400> SEQUENCE: 58

Glu Asp Gly Ser Pro Thr Thr Thr Gln Ile Phe
1               5                   10

<210> SEQ ID NO 59
<211> LENGTH: 11
<212> TYPE: PRT
<213> ORGANISM: Artificial Sequence
<220> FEATURE:
<223> OTHER INFORMATION: synthetic mutant human growth hormone

<400> SEQUENCE: 59

Glu Asp Gly Ser Pro Thr Ser Ser Gln Ile Phe
1               5                   10

<210> SEQ ID NO 60
<211> LENGTH: 11
<212> TYPE: PRT
<213> ORGANISM: Artificial Sequence
<220> FEATURE:
<223> OTHER INFORMATION: synthetic mutant human growth hormone

<400> SEQUENCE: 60

Glu Asp Gly Ser Pro Thr Thr Gln Gly Ile Phe
1               5                   10

<210> SEQ ID NO 61
<211> LENGTH: 11
<212> TYPE: PRT
<213> ORGANISM: Artificial Sequence
<220> FEATURE:
<223> OTHER INFORMATION: synthetic mutant human growth hormone

<400> SEQUENCE: 61

Glu Asp Gly Ser Pro Gln Thr Gly Gln Ile Phe
1               5                   10

<210> SEQ ID NO 62
<211> LENGTH: 11
<212> TYPE: PRT
<213> ORGANISM: Artificial Sequence
<220> FEATURE:
<223> OTHER INFORMATION: synthetic mutant human growth hormone

<400> SEQUENCE: 62

Glu Asp Gly Thr Pro Asn Thr Gly Gln Ile Phe
1               5                   10

<210> SEQ ID NO 63
<211> LENGTH: 11
<212> TYPE: PRT
<213> ORGANISM: Artificial Sequence
<220> FEATURE:
<223> OTHER INFORMATION: synthetic mutant human growth hormone

<400> SEQUENCE: 63

Glu Asp Gln Thr Pro Asn Thr Gly Gln Ile Phe
1               5                   10
```

```
-continued

<210> SEQ ID NO 64
<211> LENGTH: 9
<212> TYPE: PRT
<213> ORGANISM: Artificial Sequence
<220> FEATURE:
<223> OTHER INFORMATION: synthetic mutant human growth hormone

<400> SEQUENCE: 64

Gly Gln Ile Phe Lys Gln Thr Tyr Ser
1               5

<210> SEQ ID NO 65
<211> LENGTH: 9
<212> TYPE: PRT
<213> ORGANISM: Artificial Sequence
<220> FEATURE:
<223> OTHER INFORMATION: synthetic mutant human growth hormone

<400> SEQUENCE: 65

Gly Gln Ile Phe Asn Gln Thr Tyr Ser
1               5

<210> SEQ ID NO 66
<211> LENGTH: 9
<212> TYPE: PRT
<213> ORGANISM: Artificial Sequence
<220> FEATURE:
<223> OTHER INFORMATION: synthetic mutant human growth hormone

<400> SEQUENCE: 66

Gly Gln Ile Phe Asn Ile Thr Tyr Ser
1               5

<210> SEQ ID NO 67
<211> LENGTH: 9
<212> TYPE: PRT
<213> ORGANISM: Artificial Sequence
<220> FEATURE:
<223> OTHER INFORMATION: synthetic mutant human growth hormone

<400> SEQUENCE: 67

Gly Gln Ile Phe Pro Gln Thr Ser Ser
1               5

<210> SEQ ID NO 68
<211> LENGTH: 9
<212> TYPE: PRT
<213> ORGANISM: Artificial Sequence
<220> FEATURE:
<223> OTHER INFORMATION: synthetic mutant human growth hormone

<400> SEQUENCE: 68

Gly Gln Ile Phe Pro Thr Thr Thr Ser
1               5

<210> SEQ ID NO 69
<211> LENGTH: 9
<212> TYPE: PRT
<213> ORGANISM: Artificial Sequence
<220> FEATURE:
<223> OTHER INFORMATION: synthetic mutant human growth hormone

<400> SEQUENCE: 69

Gly Gln Ile Thr Pro Gln Thr Tyr Ser
1               5

<210> SEQ ID NO 70
```

```
<211> LENGTH: 9
<212> TYPE: PRT
<213> ORGANISM: Artificial Sequence
<220> FEATURE:
<223> OTHER INFORMATION: synthetic mutant human growth hormone

<400> SEQUENCE: 70

Gly Gln Ile Phe Thr Gln Thr Tyr Ser
 1               5

<210> SEQ ID NO 71
<211> LENGTH: 9
<212> TYPE: PRT
<213> ORGANISM: Artificial Sequence
<220> FEATURE:
<223> OTHER INFORMATION: synthetic mutant human growth hormone

<400> SEQUENCE: 71

Gly Gln Ile Ser Thr Gln Thr Tyr Ser
 1               5

<210> SEQ ID NO 72
<211> LENGTH: 9
<212> TYPE: PRT
<213> ORGANISM: Artificial Sequence
<220> FEATURE:
<223> OTHER INFORMATION: synthetic mutant human growth hormone

<400> SEQUENCE: 72

Gly Gln Ile Pro Thr Thr Thr Tyr Ser
 1               5

<210> SEQ ID NO 73
<211> LENGTH: 7
<212> TYPE: PRT
<213> ORGANISM: Artificial Sequence
<220> FEATURE:
<223> OTHER INFORMATION: synthetic mutant human growth hormone

<400> SEQUENCE: 73

Val Glu Gly Ser Cys Gly Phe
 1               5

<210> SEQ ID NO 74
<211> LENGTH: 11
<212> TYPE: PRT
<213> ORGANISM: Artificial Sequence
<220> FEATURE:
<223> OTHER INFORMATION: synthetic mutant human growth hormone

<400> SEQUENCE: 74

Val Glu Gly Ser Cys Gly Pro Thr Thr Thr Pro
 1               5                   10

<210> SEQ ID NO 75
<211> LENGTH: 11
<212> TYPE: PRT
<213> ORGANISM: Artificial Sequence
<220> FEATURE:
<223> OTHER INFORMATION: synthetic mutant human growth hormone

<400> SEQUENCE: 75

Val Glu Gly Ser Cys Gly Pro Thr Thr Thr Pro
 1               5                   10

<210> SEQ ID NO 76
<211> LENGTH: 11
```

```
<212> TYPE: PRT
<213> ORGANISM: Artificial Sequence
<220> FEATURE:
<223> OTHER INFORMATION: synthetic mutant human growth hormone

<400> SEQUENCE: 76

Val Glu Gly Ser Cys Gly Pro Thr Ser Ser Pro
1               5                   10

<210> SEQ ID NO 77
<211> LENGTH: 13
<212> TYPE: PRT
<213> ORGANISM: Artificial Sequence
<220> FEATURE:
<223> OTHER INFORMATION: synthetic mutant human growth hormone

<400> SEQUENCE: 77

Val Glu Gly Ser Cys Gly Pro Thr Gln Gly Ala Met Pro
1               5                   10

<210> SEQ ID NO 78
<211> LENGTH: 11
<212> TYPE: PRT
<213> ORGANISM: Artificial Sequence
<220> FEATURE:
<223> OTHER INFORMATION: synthetic mutant human growth hormone

<400> SEQUENCE: 78

Val Glu Gly Ser Cys Gly Pro Thr Thr Ile Pro
1               5                   10

<210> SEQ ID NO 79
<211> LENGTH: 11
<212> TYPE: PRT
<213> ORGANISM: Artificial Sequence
<220> FEATURE:
<223> OTHER INFORMATION: synthetic mutant human growth hormone

<400> SEQUENCE: 79

Val Glu Gly Ser Cys Gly Pro Met Val Thr Pro
1               5                   10

<210> SEQ ID NO 80
<211> LENGTH: 193
<212> TYPE: PRT
<213> ORGANISM: Artificial Sequence
<220> FEATURE:
<223> OTHER INFORMATION: synthetic mutant human growth hormone

<400> SEQUENCE: 80

Met Phe Pro Thr Glu Ile Pro Leu Ser Arg Leu Phe Asp Asn Ala Met
1               5                   10                  15

Leu Arg Ala His Arg Leu His Gln Leu Ala Phe Asp Thr Tyr Gln Glu
            20                  25                  30

Phe Glu Glu Ala Tyr Ile Pro Lys Glu Gln Lys Tyr Ser Phe Leu Gln
        35                  40                  45

Asn Pro Gln Thr Ser Leu Cys Phe Ser Glu Ser Ile Pro Thr Pro Ser
    50                  55                  60

Asn Arg Glu Glu Thr Gln Gln Lys Ser Asn Leu Glu Leu Leu Arg Ile
65                  70                  75                  80

Ser Leu Leu Leu Ile Gln Ser Trp Leu Glu Pro Val Gln Phe Leu Arg
                85                  90                  95

Ser Val Phe Ala Asn Ser Leu Val Tyr Gly Ala Ser Asp Ser Asn Val
            100                 105                 110
```

-continued

```
Tyr Asp Leu Leu Lys Asp Leu Glu Glu Gly Ile Gln Thr Leu Met Gly
        115                 120                 125

Arg Leu Glu Asp Gly Ser Pro Arg Thr Gly Gln Ile Phe Lys Gln Thr
    130                 135                 140

Tyr Ser Lys Phe Asp Thr Asn Ser His Asn Asp Ala Leu Leu Lys
145                 150                 155                 160

Asn Tyr Gly Leu Leu Tyr Cys Phe Arg Lys Asp Met Asp Lys Val Glu
                165                 170                 175

Thr Phe Leu Arg Ile Val Gln Cys Arg Ser Val Glu Gly Ser Cys Gly
                180                 185                 190

Phe
```

<210> SEQ ID NO 81
<211> LENGTH: 192
<212> TYPE: PRT
<213> ORGANISM: Artificial Sequence
<220> FEATURE:
<223> OTHER INFORMATION: synthetic mutant human growth hormone

<400> SEQUENCE: 81

```
Met Phe Pro Thr Ile Pro Leu Ser Arg Leu Phe Asp Asn Ala Met Leu
1               5                   10                  15

Arg Ala His Arg Leu His Gln Leu Ala Phe Asp Thr Tyr Gln Glu Phe
            20                  25                  30

Glu Glu Ala Tyr Ile Pro Lys Glu Gln Lys Tyr Ser Phe Leu Gln Asn
        35                  40                  45

Pro Gln Thr Ser Leu Cys Phe Ser Glu Ser Ile Pro Thr Pro Ser Asn
    50                  55                  60

Arg Glu Glu Thr Gln Gln Lys Ser Asn Leu Glu Leu Leu Arg Ile Ser
65                  70                  75                  80

Leu Leu Leu Ile Gln Ser Trp Leu Glu Pro Val Gln Phe Leu Arg Ser
                85                  90                  95

Val His Ala Asn Ser Leu Val Tyr Gly Ala Ser Asp Ser Asn Val Tyr
            100                 105                 110

Asp Leu Leu Lys Asp Leu Glu Glu Gly Ile Gln Thr Leu Met Gly Arg
        115                 120                 125

Leu Glu Asp Gly Ser Pro Thr Thr Val Ser Ile Phe Lys Gln Thr Tyr
    130                 135                 140

Ser Lys Phe Asp Thr Asn Ser His Asn Asp Asp Ala Leu Leu Lys Asn
145                 150                 155                 160

Tyr Gly Leu Leu Tyr Cys Phe Arg Lys Asp Met Asp Lys Val Glu Thr
                165                 170                 175

Phe Leu Arg Ile Val Gln Cys Arg Ser Val Glu Gly Ser Cys Gly Phe
                180                 185                 190
```

<210> SEQ ID NO 82
<211> LENGTH: 192
<212> TYPE: PRT
<213> ORGANISM: Artificial Sequence
<220> FEATURE:
<223> OTHER INFORMATION: synthetic mutant human growth hormone

<400> SEQUENCE: 82

```
Met Phe Pro Thr Ile Pro Leu Ser Arg Leu Phe Asp Asn Ala Met Leu
1               5                   10                  15

Arg Ala His Arg Leu His Gln Leu Ala Phe Asp Thr Tyr Gln Glu Phe
            20                  25                  30
```

```
Glu Glu Ala Tyr Ile Pro Lys Glu Gln Lys Tyr Ser Phe Leu Gln Asn
            35                  40                  45

Pro Gln Thr Ser Leu Cys Phe Ser Glu Ser Ile Pro Thr Pro Ser Asn
 50                  55                  60

Arg Glu Glu Thr Gln Gln Lys Ser Asn Leu Glu Leu Leu Arg Ile Ser
 65                  70                  75                  80

Leu Leu Leu Ile Gln Ser Trp Leu Glu Pro Val Gln Phe Leu Arg Ser
                 85                  90                  95

Val Phe Ala Asn Ser Leu Val Tyr Gly Ala Ser Asp Ser Asn Val Tyr
                100                 105                 110

Asp Leu Leu Lys Asp Leu Glu Glu Gly Ile Gln Thr Leu Met Gly Arg
                115                 120                 125

Leu Glu Asp Gly Ser Pro Arg Thr Gly Gln Ile Pro Thr Gln Ala Tyr
            130                 135                 140

Ser Lys Phe Asp Thr Asn Ser His Asn Asp Asp Ala Leu Leu Lys Asn
145                 150                 155                 160

Tyr Gly Leu Leu Tyr Cys Phe Arg Lys Asp Met Asp Lys Val Glu Thr
                165                 170                 175

Phe Leu Arg Ile Val Gln Cys Arg Ser Val Glu Gly Ser Cys Gly Phe
                180                 185                 190
```

<210> SEQ ID NO 83
<211> LENGTH: 192
<212> TYPE: PRT
<213> ORGANISM: Artificial Sequence
<220> FEATURE:
<223> OTHER INFORMATION: synthetic mutant human growth hormone

<400> SEQUENCE: 83

```
Met Phe Pro Thr Ile Pro Leu Ser Arg Leu Phe Asp Asn Ala Met Leu
 1               5                  10                  15

Arg Ala His Arg Leu His Gln Leu Ala Phe Asp Thr Tyr Gln Glu Phe
                20                  25                  30

Glu Glu Ala Tyr Ile Pro Lys Glu Gln Lys Tyr Ser Phe Leu Gln Asn
            35                  40                  45

Pro Gln Thr Ser Leu Cys Glu Ser Glu Ser Ile Pro Thr Pro Ser Asn
 50                  55                  60

Arg Glu Glu Thr Gln Gln Lys Ser Asn Leu Glu Leu Leu Arg Ile Ser
 65                  70                  75                  80

Leu Leu Leu Ile Gln Ser Trp Leu Glu Arg Val Gln Phe Leu Arg Ser
                 85                  90                  95

Val Phe Ala Asn Ser Leu Val Tyr Gly Ala Ser Asp Ser Asn Val Tyr
                100                 105                 110

Asp Leu Leu Lys Asp Leu Glu Glu Gly Ile Gln Thr Leu Met Gly Arg
                115                 120                 125

Leu Glu Asp Gly Ser Pro Thr Ile Asn Thr Ile Phe Lys Gln Thr Tyr
            130                 135                 140

Ser Lys Phe Asp Thr Asn Ser His Asn Asp Asp Ala Leu Leu Lys Asn
145                 150                 155                 160

Tyr Gly Leu Leu Tyr Cys Phe Arg Lys Asp Met Asp Lys Val Glu Thr
                165                 170                 175

Phe Leu Arg Ile Val Gln Cys Arg Ser Val Glu Gly Ser Cys Gly Phe
                180                 185                 190
```

<210> SEQ ID NO 84

<211> LENGTH: 192
<212> TYPE: PRT
<213> ORGANISM: Artificial Sequence
<220> FEATURE:
<223> OTHER INFORMATION: synthetic mutant human growth hormone

<400> SEQUENCE: 84

```
Met Phe Pro Thr Ile Pro Leu Ser Arg Leu Phe Asp Asn Ala Met Leu
 1               5                  10                  15

Arg Ala His Arg Leu His Gln Leu Ala Phe Asp Thr Tyr Gln Glu Phe
            20                  25                  30

Glu Glu Ala Tyr Ile Pro Lys Glu Gln Lys Ala Ser Phe Leu Gln Asn
        35                  40                  45

Pro Gln Thr Ser Leu Cys Phe Ser Glu Ser Ile Pro Thr Pro Ser Asn
 50                  55                  60

Arg Glu Glu Thr Gln Gln Lys Ser Asn Leu Glu Leu Leu Arg Ile Ser
 65                  70                  75                  80

Leu Leu Leu Ile Gln Ser Trp Leu Glu Pro Val Gln Phe Leu Arg Ser
                85                  90                  95

Val Phe Ala Asn Ser Leu Val Tyr Gly Ala Ser Asp Ser Asn Val Tyr
            100                 105                 110

Asp Leu Leu Lys Asp Leu Glu Glu Gly Ile Gln Thr Leu Met Gly Arg
        115                 120                 125

Leu Glu Asp Gly Ser Pro Thr Ile Asn Thr Ile Phe Lys Gln Thr Tyr
130                 135                 140

Ser Lys Phe Asp Thr Asn Ser His Asn Asp Asp Ala Leu Leu Lys Asn
145                 150                 155                 160

Tyr Gly Leu Leu Tyr Cys Phe Arg Lys Asp Met Asp Lys Val Glu Thr
                165                 170                 175

Phe Leu Arg Ile Val Gln Cys Arg Ser Val Glu Gly Ser Cys Gly Phe
            180                 185                 190
```

<210> SEQ ID NO 85
<211> LENGTH: 192
<212> TYPE: PRT
<213> ORGANISM: Artificial Sequence
<220> FEATURE:
<223> OTHER INFORMATION: synthetic mutant human growth hormone

<400> SEQUENCE: 85

```
Met Phe Pro Thr Ile Pro Leu Ser Arg Leu Phe Asp Asn Ala Met Leu
 1               5                  10                  15

Arg Ala His Arg Leu His Gln Leu Ala Phe Asp Thr Tyr Gln Glu Phe
            20                  25                  30

Glu Glu Ala Tyr Ile Pro Lys Glu Gln Lys Ala Ser Phe Leu Gln Asn
        35                  40                  45

Pro Gln Thr Ser Leu Cys Phe Ser Glu Ser Ile Pro Thr Pro Ser Asn
 50                  55                  60

Arg Glu Glu Thr Gln Gln Lys Ser Asn Leu Glu Leu Leu Arg Ile Ser
 65                  70                  75                  80

Leu Leu Leu Ile Gln Ser Trp Leu Glu Pro Val Gln Phe Leu Arg Ser
                85                  90                  95

Val Phe Ala Asn Ser Leu Val Tyr Gly Ala Ser Asp Ser Asn Val Tyr
            100                 105                 110

Asp Leu Leu Lys Asp Leu Glu Glu Gly Ile Gln Thr Leu Met Gly Arg
        115                 120                 125

Leu Glu Asp Gly Ser Pro Thr Ile Asn Thr Ile Phe Lys Gln Thr Ala
```

```
                130                 135                 140
Ser Lys Phe Asp Thr Asn Ser His Asn Asp Asp Ala Leu Leu Lys Asn
145                 150                 155                 160

Tyr Gly Leu Leu Tyr Cys Phe Arg Lys Asp Met Asp Lys Val Glu Thr
                165                 170                 175

Phe Leu Arg Ile Val Gln Cys Arg Ser Val Glu Gly Ser Cys Gly Phe
                180                 185                 190

<210> SEQ ID NO 86
<211> LENGTH: 192
<212> TYPE: PRT
<213> ORGANISM: Artificial Sequence
<220> FEATURE:
<223> OTHER INFORMATION: synthetic mutant human growth hormone

<400> SEQUENCE: 86

Met Phe Pro Thr Ile Pro Leu Ser Arg Leu Phe Asp Asn Ala Met Leu
1               5                   10                  15

Arg Ala His Arg Leu His Gln Leu Ala Phe Asp Thr Tyr Gln Glu Phe
                20                  25                  30

Glu Glu Ala Tyr Ile Pro Lys Glu Gln Lys Ala Ser Phe Leu Gln Asn
            35                  40                  45

Pro Gln Thr Ser Leu Cys Phe Ser Glu Ser Ile Pro Thr Pro Ser Asn
    50                  55                  60

Arg Glu Glu Thr Gln Gln Lys Ser Asn Leu Glu Leu Leu Arg Ile Ser
65                  70                  75                  80

Leu Leu Leu Ile Gln Ser Trp Leu Glu Pro Val Gln Phe Leu Arg Ser
                85                  90                  95

Val Phe Ala Asn Ser Leu Val Tyr Gly Ala Ser Asp Ser Asn Val Tyr
                100                 105                 110

Asp Leu Leu Lys Asp Leu Glu Glu Gly Ile Gln Thr Leu Met Gly Arg
            115                 120                 125

Leu Glu Asp Gly Ser Pro Thr Ile Asn Thr Ile Ala Asn Gln Thr Ala
    130                 135                 140

Ser Lys Phe Asp Thr Asn Ser His Asn Asp Asp Ala Leu Leu Lys Asn
145                 150                 155                 160

Tyr Gly Leu Leu Tyr Cys Phe Arg Lys Asp Met Asp Lys Val Glu Thr
                165                 170                 175

Phe Leu Arg Ile Val Gln Cys Arg Ser Val Glu Gly Ser Cys Gly Phe
                180                 185                 190

<210> SEQ ID NO 87
<211> LENGTH: 192
<212> TYPE: PRT
<213> ORGANISM: Artificial Sequence
<220> FEATURE:
<223> OTHER INFORMATION: synthetic mutant human growth hormone

<400> SEQUENCE: 87

Met Phe Pro Thr Ile Pro Leu Ser Arg Leu Phe Asp Asn Ala Met Leu
1               5                   10                  15

Arg Ala His Arg Leu His Gln Leu Ala Phe Asp Thr Tyr Gln Glu Phe
                20                  25                  30

Glu Glu Ala Tyr Ile Pro Lys Glu Gln Lys Ala Ser Phe Leu Gln Asn
            35                  40                  45

Pro Gln Thr Ser Leu Cys Phe Ser Glu Ser Ile Pro Thr Pro Ser Asn
    50                  55                  60
```

-continued

Arg Glu Glu Thr Gln Gln Lys Ser Asn Leu Glu Leu Leu Arg Ile Ser
65                  70                  75                  80

Leu Leu Leu Ile Gln Ser Trp Leu Glu Pro Val Gln Phe Leu Arg Ser
                85                  90                  95

Val Phe Ala Asn Ser Leu Val Tyr Gly Ala Ser Asp Ser Asn Val Tyr
            100                 105                 110

Asp Leu Leu Lys Asp Leu Glu Glu Gly Ile Gln Thr Leu Met Gly Arg
        115                 120                 125

Leu Glu Asp Gly Ser Pro Arg Thr Gly Gln Ile Pro Thr Gln Ala Tyr
    130                 135                 140

Ser Lys Phe Asp Thr Asn Ser His Asn Asp Asp Ala Leu Leu Lys Asn
145                 150                 155                 160

Tyr Gly Leu Leu Tyr Cys Phe Arg Lys Asp Met Asp Lys Val Glu Thr
                165                 170                 175

Phe Leu Arg Ile Val Gln Cys Arg Ser Val Glu Gly Ser Cys Gly Phe
            180                 185                 190

<210> SEQ ID NO 88
<211> LENGTH: 192
<212> TYPE: PRT
<213> ORGANISM: Artificial Sequence
<220> FEATURE:
<223> OTHER INFORMATION: synthetic mutant human growth hormone

<400> SEQUENCE: 88

Met Phe Pro Thr Ile Pro Leu Ser Arg Leu Phe Asp Asn Ala Met Leu
1               5                   10                  15

Arg Ala His Arg Leu His Gln Leu Ala Phe Asp Thr Tyr Gln Glu Phe
            20                  25                  30

Glu Glu Ala Tyr Ile Pro Lys Glu Gln Lys Tyr Ser Phe Leu Gln Asn
        35                  40                  45

Pro Gln Thr Ser Leu Cys Phe Ser Glu Ser Ile Pro Thr Pro Ser Asn
    50                  55                  60

Arg Glu Glu Thr Gln Gln Lys Ser Asn Leu Glu Leu Leu Arg Ile Ser
65                  70                  75                  80

Leu Leu Leu Ile Gln Ser Trp Leu Glu Pro Val Gln Phe Leu Arg Ser
                85                  90                  95

Val Phe Ala Asn Ser Leu Val Tyr Gly Ala Ser Asp Ser Asn Val Tyr
            100                 105                 110

Asp Leu Leu Lys Asp Leu Glu Glu Gly Ile Gln Thr Leu Met Gly Arg
        115                 120                 125

Leu Glu Asp Gly Ser Pro Thr Thr Val Ser Ile Phe Lys Gln Thr Tyr
    130                 135                 140

Ser Lys Phe Asp Thr Asn Ser His Asn Asp Asp Ala Leu Leu Lys Asn
145                 150                 155                 160

Tyr Gly Leu Leu Tyr Cys Phe Arg Lys Asp Met Asp Lys Val Glu Thr
                165                 170                 175

Phe Leu Arg Ile Val Gln Cys Arg Ser Val Glu Gly Ser Cys Gly Phe
            180                 185                 190

<210> SEQ ID NO 89
<211> LENGTH: 192
<212> TYPE: PRT
<213> ORGANISM: Artificial Sequence
<220> FEATURE:
<223> OTHER INFORMATION: synthetic mutant human growth hormone

<400> SEQUENCE: 89

```
Met Phe Pro Thr Ile Pro Leu Ser Arg Leu Phe Asp Asn Ala Met Leu
 1               5                  10                  15

Arg Ala His Arg Leu His Gln Leu Ala Phe Asp Thr Tyr Gln Glu Phe
            20                  25                  30

Glu Glu Ala Tyr Ile Pro Lys Glu Gln Lys Tyr Ser Phe Leu Gln Asn
        35                  40                  45

Pro Gln Thr Ser Leu Cys Phe Ser Glu Ser Ile Pro Thr Pro Ser Asn
50                  55                  60

Arg Glu Glu Thr Gln Gln Lys Ser Asn Leu Glu Leu Leu Arg Ile Ser
65                  70                  75                  80

Leu Leu Leu Ile Gln Ser Trp Leu Glu Pro Val Gln Phe Leu Arg Ser
            85                  90                  95

Val Phe Ala Asn Ser Leu Val Tyr Gly Ala Ser Asp Ser Asn Val Tyr
        100                 105                 110

Asp Leu Leu Lys Asp Leu Glu Glu Gly Ile Gln Thr Leu Met Gly Arg
    115                 120                 125

Leu Glu Asp Gly Ser Pro Thr Ile Asn Thr Ile Phe Lys Gln Thr Tyr
130                 135                 140

Ser Lys Phe Asp Thr Asn Ser His Asn Asp Asp Ala Leu Leu Lys Asn
145                 150                 155                 160

Tyr Gly Leu Leu Tyr Cys Phe Arg Lys Asp Met Asp Lys Val Glu Thr
            165                 170                 175

Phe Leu Arg Ile Val Gln Cys Arg Ser Val Glu Gly Ser Cys Gly Phe
        180                 185                 190

<210> SEQ ID NO 90
<211> LENGTH: 194
<212> TYPE: PRT
<213> ORGANISM: Artificial Sequence
<220> FEATURE:
<223> OTHER INFORMATION: synthetic mutant human growth hormone

<400> SEQUENCE: 90

Pro Thr Thr Phe Pro Thr Thr Pro Leu Ser Arg Leu Phe Asp Asn Ala
 1               5                  10                  15

Met Leu Arg Ala His Arg Leu His Gln Leu Ala Phe Asp Thr Tyr Gln
            20                  25                  30

Glu Phe Glu Glu Ala Tyr Ile Pro Lys Glu Gln Lys Tyr Ser Phe Leu
        35                  40                  45

Gln Asn Pro Thr Thr Ser Leu Cys Phe Ser Glu Ser Ile Pro Thr Pro
    50                  55                  60

Thr Thr Thr Glu Glu Thr Gly Gly Lys Ser Asn Leu Glu Leu Leu Arg
65                  70                  75                  80

Ile Ser Leu Leu Leu Ile Gln Ser Trp Leu Glu Pro Val Gln Phe Leu
            85                  90                  95

Arg Ser Val Phe Ala Asn Ser Ile Val Tyr Gly Ala Ser Asp Ser Asn
        100                 105                 110

Val Tyr Asp Leu Leu Lys Asp Leu Glu Glu Gly Ile Gln Thr Leu Met
    115                 120                 125

Gly Arg Leu Glu Asp Gly Ser Pro Thr Thr Gln Ile Phe Lys Thr
130                 135                 140

Thr Thr Ser Lys Phe Asp Thr Asn Ser His Asn Asp Asp Ala Leu Leu
145                 150                 155                 160

Lys Asn Tyr Gly Leu Leu Tyr Cys Phe Arg Lys Asp Met Asp Lys Val
            165                 170                 175
```

```
Glu Thr Phe Leu Arg Ile Val Gln Cys Arg Ser Val Glu Gly Ser Cys
                180                 185                 190

Gly Phe

<210> SEQ ID NO 91
<211> LENGTH: 191
<212> TYPE: PRT
<213> ORGANISM: Artificial Sequence
<220> FEATURE:
<223> OTHER INFORMATION: synthetic mutant human growth hormone

<400> SEQUENCE: 91

Phe Pro Thr Ile Pro Leu Ser Arg Leu Phe Asp Asn Ala Met Leu Arg
  1               5                  10                  15

Ala His Arg Leu Lys Gln Leu Ala Phe Asp Thr Tyr Gln Glu Phe Glu
                 20                  25                  30

Glu Ala Tyr Ile Pro Lys Glu Gln Lys Tyr Ser Phe Leu Gln Asn Pro
             35                  40                  45

Gln Thr Ser Leu Cys Phe Ser Glu Ser Ile Pro Thr Pro Ser Asn Arg
         50                  55                  60

Glu Glu Thr Gln Gln Lys Ser Asn Leu Glu Leu Leu Arg Ile Ser Leu
 65                  70                  75                  80

Leu Leu Ile Gln Ser Trp Leu Glu Pro Val Gln Phe Leu Arg Ser Val
                 85                  90                  95

Phe Ala Asn Ser Leu Val Tyr Gly Ala Ser Asp Ser Asn Val Tyr Asp
            100                 105                 110

Leu Leu Lys Asp Leu Glu Glu Gly Ile Gln Thr Leu Met Gly Arg Leu
        115                 120                 125

Glu Asp Gly Ser Pro Thr Thr Thr Gln Ile Phe Lys Gln Thr Tyr Ser
130                 135                 140

Lys Phe Asp Thr Asn Ser His Asn Asp Asp Ala Leu Leu Lys Asn Tyr
145                 150                 155                 160

Gly Leu Leu Tyr Cys Phe Arg Lys Asp Met Asp Lys Val Glu Thr Phe
                165                 170                 175

Leu Arg Ile Val Gln Cys Arg Ser Val Glu Gly Ser Cys Gly Phe
            180                 185                 190

<210> SEQ ID NO 92
<211> LENGTH: 193
<212> TYPE: PRT
<213> ORGANISM: Artificial Sequence
<220> FEATURE:
<223> OTHER INFORMATION: synthetic mutant human growth hormone

<400> SEQUENCE: 92

Pro Thr Thr Pro Thr Ile Pro Leu Ser Arg Leu Pro Asp Asn Ala Met
  1               5                  10                  15

Leu Arg Ala His Arg Leu His Gln Leu Ala Phe Asp Thr Tyr Gln Glu
                 20                  25                  30

Phe Glu Glu Ala Tyr Ile Pro Lys Glu Gln Lys Tyr Ser Phe Leu Gln
             35                  40                  45

Asn Pro Gln Thr Ser Leu Cys Phe Ser Glu Ser Ile Pro Thr Pro Ser
         50                  55                  60

Asn Arg Glu Glu Thr Gln Gln Lys Ser Asn Leu Glu Leu Leu Arg Ile
 65                  70                  75                  80

Ser Leu Leu Leu Ile Gln Ser Trp Leu Glu Pro Val Gln Phe Leu Arg
                 85                  90                  95
```

```
Ser Val Phe Ala Asn Ser Leu Val Tyr Gly Ala Ser Asp Ser Asn Val
            100                 105                 110

Tyr Asp Leu Leu Lys Asp Leu Glu Glu Gly Ile Gln Thr Leu Met Gly
            115                 120                 125

Arg Leu Glu Asp Gly Ser Pro Arg Thr Gly Gln Ile Phe Lys Gln Thr
130                 135                 140

Tyr Ser Lys Phe Asp Thr Asn Ser His Asn Asp Asp Ala Leu Leu Lys
145                 150                 155                 160

Asn Tyr Gly Leu Leu Tyr Cys Phe Arg Lys Asp Met Asp Lys Val Glu
                165                 170                 175

Thr Phe Leu Arg Ile Val Gln Cys Arg Ser Val Glu Gly Ser Cys Gly
            180                 185                 190

Phe

<210> SEQ ID NO 93
<211> LENGTH: 191
<212> TYPE: PRT
<213> ORGANISM: Artificial Sequence
<220> FEATURE:
<223> OTHER INFORMATION: synthetic mutant human growth hormone

<400> SEQUENCE: 93

Phe Pro Thr Ile Pro Leu Ser Arg Leu Phe Asp Asn Ala Met Leu Arg
1               5                   10                  15

Ala His Arg Leu His Gln Leu Ala Phe Asp Thr Tyr Gln Glu Phe Glu
            20                  25                  30

Glu Ala Tyr Ile Pro Lys Glu Gln Lys Tyr Ser Phe Leu Gln Asn Pro
        35                  40                  45

Gln Thr Ser Leu Cys Phe Ser Glu Ser Ile Pro Thr Pro Ser Asn Arg
    50                  55                  60

Glu Glu Thr Gln Gln Lys Ser Asn Leu Glu Leu Leu Arg Ile Ser Leu
65                  70                  75                  80

Leu Leu Ile Gln Ser Trp Leu Glu Pro Val Gln Phe Leu Arg Ser Val
                85                  90                  95

Phe Ala Asn Ser Leu Val Tyr Gly Ala Ser Asp Ser Asn Val Tyr Asp
            100                 105                 110

Leu Leu Lys Asp Leu Glu Glu Gly Ile Gln Thr Leu Met Gly Arg Leu
        115                 120                 125

Glu Asp Gly Ser Pro Arg Thr Gly Gln Ile Phe Lys Gln Thr Tyr Ser
    130                 135                 140

Lys Phe Asp Thr Asn Ser His Asn Asp Asp Ala Leu Leu Lys Asn Tyr
145                 150                 155                 160

Gly Leu Leu Tyr Cys Phe Arg Lys Asp Met Asp Lys Val Glu Thr Phe
                165                 170                 175

Leu Arg Ile Val Gln Cys Arg Ser Val Glu Gly Ser Cys Gly Phe
            180                 185                 190

<210> SEQ ID NO 94
<211> LENGTH: 193
<212> TYPE: PRT
<213> ORGANISM: Artificial Sequence
<220> FEATURE:
<223> OTHER INFORMATION: synthetic mutant human growth hormone

<400> SEQUENCE: 94

Met Val Thr Pro Thr Ile Pro Leu Ser Arg Leu Phe Asp Asn Ala Met
1               5                   10                  15
```

Leu Arg Ala Asn Arg Leu Arg Gln Leu Ala Phe Asp Thr Tyr Gln Glu
            20                  25                  30

Phe Glu Glu Ala Tyr Ile Pro Lys Glu Gln Lys Tyr Ser Phe Leu Gln
            35                  40                  45

Asn Pro Gln Thr Ser Leu Cys Phe Ser Glu Ser Ile Pro Thr Pro Ser
 50                  55                  60

Asn Arg Glu Glu Thr Gln Gln Lys Ser Asn Leu Glu Leu Leu Arg Ile
 65                  70                  75                  80

Ser Leu Leu Leu Ile Gln Ser Trp Leu Glu Pro Val Gln Phe Leu Arg
            85                  90                  95

Ser Val Phe Ala Asn Ser Leu Val Tyr Gly Ala Ser Asp Ser Asn Val
            100                 105                 110

Tyr Asp Leu Leu Lys Asp Leu Glu Glu Gly Ile Gln Thr Leu Met Gly
            115                 120                 125

Arg Leu Glu Asp Gly Ser Pro Arg Thr Gly Gln Ile Phe Lys Gln Thr
130                 135                 140

Tyr Ser Lys Phe Asp Thr Asn Ser His Asn Asp Asp Ala Leu Leu Lys
145                 150                 155                 160

Asn Tyr Gly Leu Leu Tyr Cys Phe Arg Lys Asp Met Asp Lys Val Glu
            165                 170                 175

Thr Phe Leu Arg Ile Val Gln Cys Arg Ser Val Glu Gly Ser Cys Gly
            180                 185                 190

Phe

<210> SEQ ID NO 95
<211> LENGTH: 192
<212> TYPE: PRT
<213> ORGANISM: Artificial Sequence
<220> FEATURE:
<223> OTHER INFORMATION: synthetic mutant human growth hormone

<400> SEQUENCE: 95

Met Phe Pro Thr Ile Pro Leu Ser Arg Leu Phe Asp Asn Ala Met Leu
 1               5                   10                  15

Arg Ala His Arg Leu His Gln Leu Ala Phe Asp Thr Tyr Gln Glu Phe
            20                  25                  30

Glu Glu Ala Tyr Ile Pro Lys Glu Gln Lys Tyr Ser Phe Leu Gln Asn
            35                  40                  45

Pro Gln Thr Ser Leu Cys Phe Ser Glu Ser Ile Pro Thr Pro Ser Asn
 50                  55                  60

Arg Glu Glu Thr Gln Gln Lys Ser Asn Leu Glu Leu Leu Arg Ile Ser
 65                  70                  75                  80

Leu Leu Leu Ile Gln Ser Trp Leu Glu Pro Val Gln Phe Leu Arg Ser
            85                  90                  95

Val Phe Ala Asn Ser Leu Val Tyr Gly Ala Ser Asp Ser Asn Val Tyr
            100                 105                 110

Asp Leu Leu Lys Asp Leu Glu Glu Gly Ile Gln Thr Leu Met Gly Arg
            115                 120                 125

Leu Glu Asp Gly Ser Pro Arg Thr Gly Gln Ile Phe Lys Gln Thr Tyr
130                 135                 140

Ser Lys Phe Asp Thr Asn Ser His Asn Asp Asp Ala Leu Leu Lys Asn
145                 150                 155                 160

Tyr Gly Leu Leu Tyr Cys Phe Arg Lys Asp Met Asp Lys Val Glu Thr
            165                 170                 175

```
Phe Leu Arg Ile Val Gln Cys Arg Ser Val Glu Gly Ser Cys Gly Phe
            180                 185                 190
```

<210> SEQ ID NO 96
<211> LENGTH: 192
<212> TYPE: PRT
<213> ORGANISM: Artificial Sequence
<220> FEATURE:
<223> OTHER INFORMATION: hGH glycosylation variant

<400> SEQUENCE: 96

```
Met Phe Pro Thr Ile Pro Leu Ser Arg Leu Phe Asp Asn Ala Met Leu
  1               5                  10                  15

Arg Ala His Arg Leu His Gln Leu Ala Phe Asp Thr Tyr Gln Glu Phe
             20                  25                  30

Glu Glu Ala Tyr Ile Pro Lys Glu Gln Lys Tyr Ser Phe Leu Gln Asn
         35                  40                  45

Pro Gln Thr Ser Leu Cys Phe Ser Glu Ser Ile Pro Thr Pro Ser Asn
     50                  55                  60

Arg Glu Glu Thr Gln Gln Lys Ser Asn Leu Glu Leu Leu Arg Ile Ser
 65                  70                  75                  80

Leu Leu Leu Ile Gln Ser Trp Leu Glu Pro Val Gln Phe Leu Arg Ser
                 85                  90                  95

Val Phe Ala Asn Ser Leu Val Tyr Gly Ala Ser Asp Ser Asn Val Tyr
            100                 105                 110

Asp Leu Leu Lys Asp Leu Glu Glu Gly Ile Gln Thr Leu Met Gly Arg
        115                 120                 125

Leu Glu Asp Gly Ser Pro Thr Thr Gly Gln Ile Phe Lys Gln Thr Tyr
    130                 135                 140

Ser Lys Phe Asp Thr Asn Ser His Asn Asp Ala Leu Leu Lys Asn
145                 150                 155                 160

Tyr Gly Leu Leu Tyr Cys Phe Arg Lys Asp Met Asp Lys Val Glu Thr
                165                 170                 175

Phe Leu Arg Ile Val Gln Cys Arg Ser Val Glu Gly Ser Cys Gly Phe
            180                 185                 190
```

<210> SEQ ID NO 97
<211> LENGTH: 192
<212> TYPE: PRT
<213> ORGANISM: Artificial Sequence
<220> FEATURE:
<223> OTHER INFORMATION: hGH glycosylation variant

<400> SEQUENCE: 97

```
Met Phe Pro Thr Ile Pro Leu Ser Arg Leu Phe Asp Asn Ala Met Leu
  1               5                  10                  15

Arg Ala His Arg Leu His Gln Leu Ala Phe Asp Thr Tyr Gln Glu Phe
             20                  25                  30

Glu Glu Ala Tyr Ile Pro Lys Glu Gln Lys Tyr Ser Phe Leu Gln Asn
         35                  40                  45

Pro Gln Thr Ser Leu Cys Phe Ser Glu Ser Ile Pro Thr Pro Ser Asn
     50                  55                  60

Arg Glu Glu Thr Gln Gln Lys Ser Asn Leu Glu Leu Leu Arg Ile Ser
 65                  70                  75                  80

Leu Leu Leu Ile Gln Ser Trp Leu Glu Pro Val Gln Phe Leu Arg Ser
                 85                  90                  95

Val Phe Ala Asn Ser Leu Val Tyr Gly Ala Ser Asp Ser Asn Val Tyr
            100                 105                 110
```

```
Asp Leu Leu Lys Asp Leu Glu Glu Gly Ile Gln Thr Leu Met Gly Arg
        115                 120                 125

Leu Glu Asp Gly Ser Pro Thr Thr Ala Gln Ile Phe Lys Gln Thr Tyr
130                 135                 140

Ser Lys Phe Asp Thr Asn Ser His Asn Asp Asp Ala Leu Leu Lys Asn
145                 150                 155                 160

Tyr Gly Leu Leu Tyr Cys Phe Arg Lys Asp Met Asp Lys Val Glu Thr
                165                 170                 175

Phe Leu Arg Ile Val Gln Cys Arg Ser Val Glu Gly Ser Cys Gly Phe
            180                 185                 190

<210> SEQ ID NO 98
<211> LENGTH: 192
<212> TYPE: PRT
<213> ORGANISM: Artificial Sequence
<220> FEATURE:
<223> OTHER INFORMATION: hGH glycosylation variant

<400> SEQUENCE: 98

Met Phe Pro Thr Ile Pro Leu Ser Arg Leu Phe Asp Asn Ala Met Leu
1               5                   10                  15

Arg Ala His Arg Leu His Gln Leu Ala Phe Asp Thr Tyr Gln Glu Phe
            20                  25                  30

Glu Glu Ala Tyr Ile Pro Lys Glu Gln Lys Tyr Ser Phe Leu Gln Asn
        35                  40                  45

Pro Gln Thr Ser Leu Cys Phe Ser Glu Ser Ile Pro Thr Pro Ser Asn
    50                  55                  60

Arg Glu Glu Thr Gln Gln Lys Ser Asn Leu Glu Leu Leu Arg Ile Ser
65                  70                  75                  80

Leu Leu Leu Ile Gln Ser Trp Leu Glu Pro Val Gln Phe Leu Arg Ser
                85                  90                  95

Val Phe Ala Asn Ser Leu Val Tyr Gly Ala Ser Asp Ser Asn Val Tyr
            100                 105                 110

Asp Leu Leu Lys Asp Leu Glu Glu Gly Ile Gln Thr Leu Met Gly Arg
        115                 120                 125

Leu Glu Asp Gly Ser Pro Thr Ala Thr Gln Ile Phe Lys Gln Thr Tyr
130                 135                 140

Ser Lys Phe Asp Thr Asn Ser His Asn Asp Asp Ala Leu Leu Lys Asn
145                 150                 155                 160

Tyr Gly Leu Leu Tyr Cys Phe Arg Lys Asp Met Asp Lys Val Glu Thr
                165                 170                 175

Phe Leu Arg Ile Val Gln Cys Arg Ser Val Glu Gly Ser Cys Gly Phe
            180                 185                 190

<210> SEQ ID NO 99
<211> LENGTH: 192
<212> TYPE: PRT
<213> ORGANISM: Artificial Sequence
<220> FEATURE:
<223> OTHER INFORMATION: hGH glycosylation variant

<400> SEQUENCE: 99

Met Phe Pro Thr Ile Pro Leu Ser Arg Leu Phe Asp Asn Ala Met Leu
1               5                   10                  15

Arg Ala His Arg Leu His Gln Leu Ala Phe Asp Thr Tyr Gln Glu Phe
            20                  25                  30

Glu Glu Ala Tyr Ile Pro Lys Glu Gln Lys Tyr Ser Phe Leu Gln Asn
```

```
                35                  40                  45
Pro Gln Thr Ser Leu Cys Phe Ser Glu Ser Ile Pro Thr Pro Ser Asn
 50                  55                  60

Arg Glu Glu Thr Gln Gln Lys Ser Asn Leu Glu Leu Leu Arg Ile Ser
 65                  70                  75                  80

Leu Leu Leu Ile Gln Ser Trp Leu Glu Pro Val Gln Phe Leu Arg Ser
                 85                  90                  95

Val Phe Ala Asn Ser Leu Val Tyr Gly Ala Ser Asp Ser Asn Val Tyr
                100                 105                 110

Asp Leu Leu Lys Asp Leu Glu Glu Gly Ile Gln Thr Leu Met Gly Arg
                115                 120                 125

Leu Glu Asp Gly Ser Pro Thr Gln Gly Ala Met Phe Lys Gln Thr Tyr
                130                 135                 140

Ser Lys Phe Asp Thr Asn Ser His Asn Asp Asp Ala Leu Leu Lys Asn
145                 150                 155                 160

Tyr Gly Leu Leu Tyr Cys Phe Arg Lys Asp Met Asp Lys Val Glu Thr
                165                 170                 175

Phe Leu Arg Ile Val Gln Cys Arg Ser Val Glu Gly Ser Cys Gly Phe
                180                 185                 190

<210> SEQ ID NO 100
<211> LENGTH: 192
<212> TYPE: PRT
<213> ORGANISM: Artificial Sequence
<220> FEATURE:
<223> OTHER INFORMATION: hGH glycosylation variant

<400> SEQUENCE: 100

Met Phe Pro Thr Ile Pro Leu Ser Arg Leu Phe Asp Asn Ala Met Leu
 1               5                  10                  15

Arg Ala His Arg Leu His Gln Leu Ala Phe Asp Thr Tyr Gln Glu Phe
                 20                  25                  30

Glu Glu Ala Tyr Ile Pro Lys Glu Gln Lys Tyr Ser Phe Leu Gln Asn
                 35                  40                  45

Pro Gln Thr Ser Leu Cys Phe Ser Glu Ser Ile Pro Thr Pro Ser Asn
 50                  55                  60

Arg Glu Glu Thr Gln Gln Lys Ser Asn Leu Glu Leu Leu Arg Ile Ser
 65                  70                  75                  80

Leu Leu Leu Ile Gln Ser Trp Leu Glu Pro Val Gln Phe Leu Arg Ser
                 85                  90                  95

Val Phe Ala Asn Ser Leu Val Tyr Gly Ala Ser Asp Ser Asn Val Tyr
                100                 105                 110

Asp Leu Leu Lys Asp Leu Glu Glu Gly Ile Gln Thr Leu Met Gly Arg
                115                 120                 125

Leu Glu Asp Gly Ser Pro Thr Gln Gly Ala Ile Phe Lys Gln Thr Tyr
                130                 135                 140

Ser Lys Phe Asp Thr Asn Ser His Asn Asp Asp Ala Leu Leu Lys Asn
145                 150                 155                 160

Tyr Gly Leu Leu Tyr Cys Phe Arg Lys Asp Met Asp Lys Val Glu Thr
                165                 170                 175

Phe Leu Arg Ile Val Gln Cys Arg Ser Val Glu Gly Ser Cys Gly Phe
                180                 185                 190

<210> SEQ ID NO 101
<211> LENGTH: 192
<212> TYPE: PRT
```

<213> ORGANISM: Artificial Sequence
<220> FEATURE:
<223> OTHER INFORMATION: hGH glycosylation variant

<400> SEQUENCE: 101

```
Met Phe Pro Thr Ile Pro Leu Ser Arg Leu Phe Asp Asn Ala Met Leu
  1               5                  10                  15

Arg Ala His Arg Leu His Gln Leu Ala Phe Asp Thr Tyr Gln Glu Phe
             20                  25                  30

Glu Glu Ala Tyr Ile Pro Lys Glu Gln Lys Tyr Ser Phe Leu Gln Asn
         35                  40                  45

Pro Gln Thr Ser Leu Cys Phe Ser Glu Ser Ile Pro Thr Pro Ser Asn
 50                  55                  60

Arg Glu Glu Thr Gln Gln Lys Ser Asn Leu Glu Leu Leu Arg Ile Ser
 65                  70                  75                  80

Leu Leu Leu Ile Gln Ser Trp Leu Glu Pro Val Gln Phe Leu Arg Ser
                 85                  90                  95

Val Phe Ala Asn Ser Leu Val Tyr Gly Ala Ser Asp Ser Asn Val Tyr
            100                 105                 110

Asp Leu Leu Lys Asp Leu Glu Glu Gly Ile Gln Thr Leu Met Gly Arg
            115                 120                 125

Leu Glu Asp Gly Ser Pro Thr Gln Gly Gln Ile Phe Lys Gln Thr Tyr
130                 135                 140

Ser Lys Phe Asp Thr Asn Ser His Asn Asp Asp Ala Leu Leu Lys Asn
145                 150                 155                 160

Tyr Gly Leu Leu Tyr Cys Phe Arg Lys Asp Met Asp Lys Val Glu Thr
                165                 170                 175

Phe Leu Arg Ile Val Gln Cys Arg Ser Val Glu Gly Ser Cys Gly Phe
            180                 185                 190
```

<210> SEQ ID NO 102
<211> LENGTH: 192
<212> TYPE: PRT
<213> ORGANISM: Artificial Sequence
<220> FEATURE:
<223> OTHER INFORMATION: hGH glycosylation variant

<400> SEQUENCE: 102

```
Met Phe Pro Thr Ile Pro Leu Ser Arg Leu Phe Asp Asn Ala Met Leu
  1               5                  10                  15

Arg Ala His Arg Leu His Gln Leu Ala Phe Asp Thr Tyr Gln Glu Phe
             20                  25                  30

Glu Glu Ala Tyr Ile Pro Lys Glu Gln Lys Tyr Ser Phe Leu Gln Asn
         35                  40                  45

Pro Gln Thr Ser Leu Cys Phe Ser Glu Ser Ile Pro Thr Pro Ser Asn
 50                  55                  60

Arg Glu Glu Thr Gln Gln Lys Ser Asn Leu Glu Leu Leu Arg Ile Ser
 65                  70                  75                  80

Leu Leu Leu Ile Gln Ser Trp Leu Glu Pro Val Gln Phe Leu Arg Ser
                 85                  90                  95

Val Phe Ala Asn Ser Leu Val Tyr Gly Ala Ser Asp Ser Asn Val Tyr
            100                 105                 110

Asp Leu Leu Lys Asp Leu Glu Glu Gly Ile Gln Thr Leu Met Gly Arg
            115                 120                 125

Leu Glu Asp Gly Ser Pro Thr Thr Leu Tyr Val Phe Lys Gln Thr Tyr
130                 135                 140
```

```
Ser Lys Phe Asp Thr Asn Ser His Asn Asp Asp Ala Leu Leu Lys Asn
145                 150                 155                 160

Tyr Gly Leu Leu Tyr Cys Phe Arg Lys Asp Met Asp Lys Val Glu Thr
                165                 170                 175

Phe Leu Arg Ile Val Gln Cys Arg Ser Val Glu Gly Ser Cys Gly Phe
            180                 185                 190
```

<210> SEQ ID NO 103
<211> LENGTH: 192
<212> TYPE: PRT
<213> ORGANISM: Artificial Sequence
<220> FEATURE:
<223> OTHER INFORMATION: hGH glycosylation variant

<400> SEQUENCE: 103

```
Met Phe Pro Thr Ile Pro Leu Ser Arg Leu Phe Asp Asn Ala Met Leu
1               5                   10                  15

Arg Ala His Arg Leu His Gln Leu Ala Phe Asp Thr Tyr Gln Glu Phe
            20                  25                  30

Glu Glu Ala Tyr Ile Pro Lys Glu Gln Lys Tyr Ser Phe Leu Gln Asn
        35                  40                  45

Pro Gln Thr Ser Leu Cys Phe Ser Glu Ser Ile Pro Thr Pro Ser Asn
    50                  55                  60

Arg Glu Glu Thr Gln Gln Lys Ser Asn Leu Glu Leu Leu Arg Ile Ser
65                  70                  75                  80

Leu Leu Leu Ile Gln Ser Trp Leu Glu Pro Val Gln Phe Leu Arg Ser
                85                  90                  95

Val Phe Ala Asn Ser Leu Val Tyr Gly Ala Ser Asp Ser Asn Val Tyr
            100                 105                 110

Asp Leu Leu Lys Asp Leu Glu Glu Gly Ile Gln Thr Leu Met Gly Arg
        115                 120                 125

Leu Glu Asp Gly Ser Pro Thr Ile Asn Thr Ile Phe Lys Gln Thr Tyr
    130                 135                 140

Ser Lys Phe Asp Thr Asn Ser His Asn Asp Asp Ala Leu Leu Lys Asn
145                 150                 155                 160

Tyr Gly Leu Leu Tyr Cys Phe Arg Lys Asp Met Asp Lys Val Glu Thr
                165                 170                 175

Phe Leu Arg Ile Val Gln Cys Arg Ser Val Glu Gly Ser Cys Gly Phe
            180                 185                 190
```

<210> SEQ ID NO 104
<211> LENGTH: 192
<212> TYPE: PRT
<213> ORGANISM: Artificial Sequence
<220> FEATURE:
<223> OTHER INFORMATION: hGH glycosylation variant

<400> SEQUENCE: 104

```
Met Phe Pro Thr Ile Pro Leu Ser Arg Leu Phe Asp Asn Ala Met Leu
1               5                   10                  15

Arg Ala His Arg Leu His Gln Leu Ala Phe Asp Thr Tyr Gln Glu Phe
            20                  25                  30

Glu Glu Ala Tyr Ile Pro Lys Glu Gln Lys Tyr Ser Phe Leu Gln Asn
        35                  40                  45

Pro Gln Thr Ser Leu Cys Phe Ser Glu Ser Ile Pro Thr Pro Ser Asn
    50                  55                  60

Arg Glu Glu Thr Gln Gln Lys Ser Asn Leu Glu Leu Leu Arg Ile Ser
65                  70                  75                  80
```

```
Leu Leu Leu Ile Gln Ser Trp Leu Glu Pro Val Gln Phe Leu Arg Ser
                85                  90                  95

Val Phe Ala Asn Ser Leu Val Tyr Gly Ala Ser Asp Ser Asn Val Tyr
            100                 105                 110

Asp Leu Leu Lys Asp Leu Glu Glu Gly Ile Gln Thr Leu Met Gly Arg
        115                 120                 125

Leu Glu Asp Gly Ser Pro Thr Thr Val Ser Ile Phe Lys Gln Thr Tyr
    130                 135                 140

Ser Lys Phe Asp Thr Asn Ser His Asn Asp Asp Ala Leu Leu Lys Asn
145                 150                 155                 160

Tyr Gly Leu Leu Tyr Cys Phe Arg Lys Asp Met Asp Lys Val Glu Thr
                165                 170                 175

Phe Leu Arg Ile Val Gln Cys Arg Ser Val Glu Gly Ser Cys Gly Phe
            180                 185                 190

<210> SEQ ID NO 105
<211> LENGTH: 192
<212> TYPE: PRT
<213> ORGANISM: Artificial Sequence
<220> FEATURE:
<223> OTHER INFORMATION: hGH glycosylation variant

<400> SEQUENCE: 105

Met Phe Pro Thr Ile Pro Leu Ser Arg Leu Phe Asp Asn Ala Met Leu
1               5                   10                  15

Arg Ala His Arg Leu His Gln Leu Ala Phe Asp Thr Tyr Gln Glu Phe
            20                  25                  30

Glu Glu Ala Tyr Ile Pro Lys Glu Gln Lys Tyr Ser Phe Leu Gln Asn
        35                  40                  45

Pro Gln Thr Ser Leu Cys Phe Ser Glu Ser Ile Pro Thr Pro Ser Asn
    50                  55                  60

Arg Glu Glu Thr Gln Gln Lys Ser Asn Leu Glu Leu Leu Arg Ile Ser
65                  70                  75                  80

Leu Leu Leu Ile Gln Ser Trp Leu Glu Pro Val Gln Phe Leu Arg Ser
                85                  90                  95

Val Phe Ala Asn Ser Leu Val Tyr Gly Ala Ser Asp Ser Asn Val Tyr
            100                 105                 110

Asp Leu Leu Lys Asp Leu Glu Glu Gly Ile Gln Thr Leu Met Gly Arg
        115                 120                 125

Leu Glu Asp Gly Ser Pro Arg Thr Gly Gln Ile Pro Thr Gln Thr Tyr
    130                 135                 140

Ser Lys Phe Asp Thr Asn Ser His Asn Asp Asp Ala Leu Leu Lys Asn
145                 150                 155                 160

Tyr Gly Leu Leu Tyr Cys Phe Arg Lys Asp Met Asp Lys Val Glu Thr
                165                 170                 175

Phe Leu Arg Ile Val Gln Cys Arg Ser Val Glu Gly Ser Cys Gly Phe
            180                 185                 190

<210> SEQ ID NO 106
<211> LENGTH: 192
<212> TYPE: PRT
<213> ORGANISM: Artificial Sequence
<220> FEATURE:
<223> OTHER INFORMATION: hGH glycosylation variant

<400> SEQUENCE: 106

Met Phe Pro Thr Ile Pro Leu Ser Arg Leu Phe Asp Asn Ala Met Leu
```

```
              1               5                  10                 15
            Arg Ala His Arg Leu His Gln Leu Ala Phe Asp Thr Tyr Gln Glu Phe
                         20                  25                 30

Glu Glu Ala Tyr Ile Pro Lys Glu Gln Lys Tyr Ser Phe Leu Gln Asn
                         35                  40                 45

Pro Gln Thr Ser Leu Cys Phe Ser Glu Ser Ile Pro Thr Pro Ser Asn
                         50                  55                 60

Arg Glu Glu Thr Gln Gln Lys Ser Asn Leu Glu Leu Leu Arg Ile Ser
             65                  70                  75                 80

Leu Leu Leu Ile Gln Ser Trp Leu Glu Pro Val Gln Phe Leu Arg Ser
                             85                  90                 95

Val Phe Ala Asn Ser Leu Val Tyr Gly Ala Ser Asp Ser Asn Val Tyr
                            100                 105                110

Asp Leu Leu Lys Asp Leu Glu Glu Gly Ile Gln Thr Leu Met Gly Arg
                            115                 120                125

Leu Glu Asp Gly Ser Pro Arg Thr Gly Gln Ile Pro Thr Gln Ala Tyr
                        130                 135                 140

Ser Lys Phe Asp Thr Asn Ser His Asn Asp Asp Ala Leu Leu Lys Asn
            145                 150                 155                160

Tyr Gly Leu Leu Tyr Cys Phe Arg Lys Asp Met Asp Lys Val Glu Thr
                            165                 170                175

Phe Leu Arg Ile Val Gln Cys Arg Ser Val Glu Gly Ser Cys Gly Phe
                        180                 185                 190

<210> SEQ ID NO 107
<211> LENGTH: 192
<212> TYPE: PRT
<213> ORGANISM: Artificial Sequence
<220> FEATURE:
<223> OTHER INFORMATION: hGH glycosylation variant

<400> SEQUENCE: 107

Met Phe Pro Thr Ile Pro Leu Ser Arg Leu Phe Asp Asn Ala Met Leu
             1               5                  10                 15

Arg Ala His Arg Leu His Gln Leu Ala Phe Asp Thr Tyr Gln Glu Phe
                         20                  25                 30

Glu Glu Ala Tyr Ile Pro Lys Glu Gln Lys Tyr Ser Phe Leu Gln Asn
                         35                  40                 45

Pro Gln Thr Ser Leu Cys Phe Ser Glu Ser Ile Pro Thr Pro Ser Asn
                         50                  55                 60

Arg Glu Glu Thr Gln Gln Lys Ser Asn Leu Glu Leu Leu Arg Ile Ser
             65                  70                  75                 80

Leu Leu Leu Ile Gln Ser Trp Leu Glu Pro Val Gln Phe Leu Arg Ser
                             85                  90                 95

Val Phe Ala Asn Ser Leu Val Tyr Gly Ala Ser Asp Ser Asn Val Tyr
                            100                 105                110

Asp Leu Leu Lys Asp Leu Glu Glu Gly Ile Gln Thr Leu Met Gly Arg
                            115                 120                125

Leu Glu Asp Gly Ser Pro Thr Thr Leu Gln Ile Phe Lys Gln Thr Tyr
                        130                 135                 140

Ser Lys Phe Asp Thr Asn Ser His Asn Asp Asp Ala Leu Leu Lys Asn
            145                 150                 155                160

Tyr Gly Leu Leu Tyr Cys Phe Arg Lys Asp Met Asp Lys Val Glu Thr
                            165                 170                175

Phe Leu Arg Ile Val Gln Cys Arg Ser Val Glu Gly Ser Cys Gly Phe
```

```
                    180                 185                 190

<210> SEQ ID NO 108
<211> LENGTH: 192
<212> TYPE: PRT
<213> ORGANISM: Artificial Sequence
<220> FEATURE:
<223> OTHER INFORMATION: hGH glycosylation variant

<400> SEQUENCE: 108

Met Phe Pro Thr Ile Pro Leu Ser Arg Leu Phe Asp Asn Ala Met Leu
  1               5                  10                  15

Arg Ala His Arg Leu His Gln Leu Ala Phe Asp Thr Tyr Gln Glu Phe
                 20                  25                  30

Glu Glu Ala Tyr Ile Pro Lys Glu Gln Lys Tyr Ser Phe Leu Gln Asn
             35                  40                  45

Pro Gln Thr Ser Leu Cys Phe Ser Glu Ser Ile Pro Thr Pro Ser Asn
     50                  55                  60

Arg Glu Glu Thr Gln Gln Lys Ser Asn Leu Glu Leu Leu Arg Ile Ser
 65                  70                  75                  80

Leu Leu Leu Ile Gln Ser Trp Leu Glu Pro Val Gln Phe Leu Arg Ser
                 85                  90                  95

Val Phe Ala Asn Ser Leu Val Tyr Gly Ala Ser Asp Ser Asn Val Tyr
            100                 105                 110

Asp Leu Leu Lys Asp Leu Glu Glu Gly Ile Gln Thr Leu Met Gly Arg
        115                 120                 125

Leu Glu Asp Gly Ser Pro Thr Thr Val Gln Ile Phe Lys Gln Thr Tyr
    130                 135                 140

Ser Lys Phe Asp Thr Asn Ser His Asn Asp Asp Ala Leu Leu Lys Asn
145                 150                 155                 160

Tyr Gly Leu Leu Tyr Cys Phe Arg Lys Asp Met Asp Lys Val Glu Thr
                165                 170                 175

Phe Leu Arg Ile Val Gln Cys Arg Ser Val Glu Gly Ser Cys Gly Phe
            180                 185                 190

<210> SEQ ID NO 109
<211> LENGTH: 192
<212> TYPE: PRT
<213> ORGANISM: Artificial Sequence
<220> FEATURE:
<223> OTHER INFORMATION: hGH glycosylation variant

<400> SEQUENCE: 109

Met Phe Pro Thr Ile Pro Leu Ser Arg Leu Phe Asp Asn Ala Met Leu
  1               5                  10                  15

Arg Ala His Arg Leu His Gln Leu Ala Phe Asp Thr Tyr Gln Glu Phe
                 20                  25                  30

Glu Glu Ala Tyr Ile Pro Lys Glu Gln Lys Tyr Ser Phe Leu Gln Asn
             35                  40                  45

Pro Gln Thr Ser Leu Cys Phe Ser Glu Ser Ile Pro Thr Pro Ser Asn
     50                  55                  60

Arg Glu Glu Thr Gln Gln Lys Ser Asn Leu Glu Leu Leu Arg Ile Ser
 65                  70                  75                  80

Leu Leu Leu Ile Gln Ser Trp Leu Glu Pro Val Gln Phe Leu Arg Ser
                 85                  90                  95

Val Phe Ala Asn Ser Leu Val Tyr Gly Ala Ser Asp Ser Asn Val Tyr
            100                 105                 110
```

```
Asp Leu Leu Lys Asp Leu Glu Glu Gly Ile Gln Thr Leu Met Gly Arg
            115                 120                 125

Leu Glu Asp Gly Ser Pro Thr Thr Asn Gln Ile Phe Lys Gln Thr Tyr
        130                 135                 140

Ser Lys Phe Asp Thr Asn Ser His Asn Asp Asp Ala Leu Leu Lys Asn
145                 150                 155                 160

Tyr Gly Leu Leu Tyr Cys Phe Arg Lys Asp Met Asp Lys Val Glu Thr
                165                 170                 175

Phe Leu Arg Ile Val Gln Cys Arg Ser Val Glu Gly Ser Cys Gly Phe
            180                 185                 190
```

<210> SEQ ID NO 110
<211> LENGTH: 192
<212> TYPE: PRT
<213> ORGANISM: Artificial Sequence
<220> FEATURE:
<223> OTHER INFORMATION: hGH glycosylation variant

<400> SEQUENCE: 110

```
Met Phe Pro Thr Ile Pro Leu Ser Arg Leu Phe Asp Asn Ala Met Leu
1               5                   10                  15

Arg Ala His Arg Leu His Gln Leu Ala Phe Asp Thr Tyr Gln Glu Phe
            20                  25                  30

Glu Glu Ala Tyr Ile Pro Lys Glu Gln Lys Tyr Ser Phe Leu Gln Asn
        35                  40                  45

Pro Gln Thr Ser Leu Cys Phe Ser Glu Ser Ile Pro Thr Pro Ser Asn
    50                  55                  60

Arg Glu Glu Thr Gln Gln Lys Ser Asn Leu Glu Leu Leu Arg Ile Ser
65                  70                  75                  80

Leu Leu Leu Ile Gln Ser Trp Leu Glu Pro Val Gln Phe Leu Arg Ser
                85                  90                  95

Val Phe Ala Asn Ser Leu Val Tyr Gly Ala Ser Asp Ser Asn Val Tyr
            100                 105                 110

Asp Leu Leu Lys Asp Leu Glu Glu Gly Ile Gln Thr Leu Met Gly Arg
            115                 120                 125

Leu Glu Asp Gly Ser Pro Thr Thr Gln Gln Ile Phe Lys Gln Thr Tyr
        130                 135                 140

Ser Lys Phe Asp Thr Asn Ser His Asn Asp Asp Ala Leu Leu Lys Asn
145                 150                 155                 160

Tyr Gly Leu Leu Tyr Cys Phe Arg Lys Asp Met Asp Lys Val Glu Thr
                165                 170                 175

Phe Leu Arg Ile Val Gln Cys Arg Ser Val Glu Gly Ser Cys Gly Phe
            180                 185                 190
```

<210> SEQ ID NO 111
<211> LENGTH: 192
<212> TYPE: PRT
<213> ORGANISM: Artificial Sequence
<220> FEATURE:
<223> OTHER INFORMATION: hGH glycosylation variant

<400> SEQUENCE: 111

```
Met Phe Pro Thr Ile Pro Leu Ser Arg Leu Phe Asp Asn Ala Met Leu
1               5                   10                  15

Arg Ala His Arg Leu His Gln Leu Ala Phe Asp Thr Tyr Gln Glu Phe
            20                  25                  30

Glu Glu Ala Tyr Ile Pro Lys Glu Gln Lys Tyr Ser Phe Leu Gln Asn
        35                  40                  45
```

Pro Gln Thr Ser Leu Cys Phe Ser Glu Ser Ile Pro Thr Pro Ser Asn
        50                  55                  60

Arg Glu Glu Thr Gln Gln Lys Ser Asn Leu Glu Leu Leu Arg Ile Ser
65                  70                  75                  80

Leu Leu Leu Ile Gln Ser Trp Leu Glu Pro Val Gln Phe Leu Arg Ser
                85                  90                  95

Val Phe Ala Asn Ser Leu Val Tyr Gly Ala Ser Asp Ser Asn Val Tyr
                100                 105                 110

Asp Leu Leu Lys Asp Leu Glu Glu Gly Ile Gln Thr Leu Met Gly Arg
                115                 120                 125

Leu Glu Asp Gly Ser Pro Thr Ile Gly Gln Ile Phe Lys Gln Thr Tyr
                130                 135                 140

Ser Lys Phe Asp Thr Asn Ser His Asn Asp Asp Ala Leu Leu Lys Asn
145                 150                 155                 160

Tyr Gly Leu Leu Tyr Cys Phe Arg Lys Asp Met Asp Lys Val Glu Thr
                165                 170                 175

Phe Leu Arg Ile Val Gln Cys Arg Ser Val Glu Gly Ser Cys Gly Phe
                180                 185                 190

<210> SEQ ID NO 112
<211> LENGTH: 192
<212> TYPE: PRT
<213> ORGANISM: Artificial Sequence
<220> FEATURE:
<223> OTHER INFORMATION: hGH glycosylation variant

<400> SEQUENCE: 112

Met Phe Pro Thr Ile Pro Leu Ser Arg Leu Phe Asp Asn Ala Met Leu
1               5                   10                  15

Arg Ala His Arg Leu His Gln Leu Ala Phe Asp Thr Tyr Gln Glu Phe
                20                  25                  30

Glu Glu Ala Tyr Ile Pro Lys Glu Gln Lys Tyr Ser Phe Leu Gln Asn
            35                  40                  45

Pro Gln Thr Ser Leu Cys Phe Ser Glu Ser Ile Pro Thr Pro Ser Asn
        50                  55                  60

Arg Glu Glu Thr Gln Gln Lys Ser Asn Leu Glu Leu Leu Arg Ile Ser
65                  70                  75                  80

Leu Leu Leu Ile Gln Ser Trp Leu Glu Pro Val Gln Phe Leu Arg Ser
                85                  90                  95

Val Phe Ala Asn Ser Leu Val Tyr Gly Ala Ser Asp Ser Asn Val Tyr
                100                 105                 110

Asp Leu Leu Lys Asp Leu Glu Glu Gly Ile Gln Thr Leu Met Gly Arg
                115                 120                 125

Leu Glu Asp Gly Ser Pro Thr Ile Leu Gln Ile Phe Lys Gln Thr Tyr
                130                 135                 140

Ser Lys Phe Asp Thr Asn Ser His Asn Asp Asp Ala Leu Leu Lys Asn
145                 150                 155                 160

Tyr Gly Leu Leu Tyr Cys Phe Arg Lys Asp Met Asp Lys Val Glu Thr
                165                 170                 175

Phe Leu Arg Ile Val Gln Cys Arg Ser Val Glu Gly Ser Cys Gly Phe
                180                 185                 190

<210> SEQ ID NO 113
<211> LENGTH: 192
<212> TYPE: PRT
<213> ORGANISM: Artificial Sequence

```
<220> FEATURE:
<223> OTHER INFORMATION: hGH glycosylation variant

<400> SEQUENCE: 113

Met Phe Pro Thr Ile Pro Leu Ser Arg Leu Phe Asp Asn Ala Met Leu
 1               5                  10                  15

Arg Ala His Arg Leu His Gln Leu Ala Phe Asp Thr Tyr Gln Glu Phe
            20                  25                  30

Glu Glu Ala Tyr Ile Pro Lys Glu Gln Lys Tyr Ser Phe Leu Gln Asn
        35                  40                  45

Pro Gln Thr Ser Leu Cys Phe Ser Glu Ser Ile Pro Thr Pro Ser Asn
    50                  55                  60

Arg Glu Glu Thr Gln Gln Lys Ser Asn Leu Glu Leu Leu Arg Ile Ser
65                  70                  75                  80

Leu Leu Leu Ile Gln Ser Trp Leu Glu Pro Val Gln Phe Leu Arg Ser
                85                  90                  95

Val Phe Ala Asn Ser Leu Val Tyr Gly Ala Ser Asp Ser Asn Val Tyr
            100                 105                 110

Asp Leu Leu Lys Asp Leu Glu Glu Gly Ile Gln Thr Leu Met Gly Arg
        115                 120                 125

Leu Glu Asp Gly Ser Pro Thr Ile Val Gln Ile Phe Lys Gln Thr Tyr
    130                 135                 140

Ser Lys Phe Asp Thr Asn Ser His Asn Asp Asp Ala Leu Leu Lys Asn
145                 150                 155                 160

Tyr Gly Leu Leu Tyr Cys Phe Arg Lys Asp Met Asp Lys Val Glu Thr
                165                 170                 175

Phe Leu Arg Ile Val Gln Cys Arg Ser Val Glu Gly Ser Cys Gly Phe
            180                 185                 190

<210> SEQ ID NO 114
<211> LENGTH: 192
<212> TYPE: PRT
<213> ORGANISM: Artificial Sequence
<220> FEATURE:
<223> OTHER INFORMATION: hGH glycosylation variant

<400> SEQUENCE: 114

Met Phe Pro Thr Ile Pro Leu Ser Arg Leu Phe Asp Asn Ala Met Leu
 1               5                  10                  15

Arg Ala His Arg Leu His Gln Leu Ala Phe Asp Thr Tyr Gln Glu Phe
            20                  25                  30

Glu Glu Ala Tyr Ile Pro Lys Glu Gln Lys Tyr Ser Phe Leu Gln Asn
        35                  40                  45

Pro Gln Thr Ser Leu Cys Phe Ser Glu Ser Ile Pro Thr Pro Ser Asn
    50                  55                  60

Arg Glu Glu Thr Gln Gln Lys Ser Asn Leu Glu Leu Leu Arg Ile Ser
65                  70                  75                  80

Leu Leu Leu Ile Gln Ser Trp Leu Glu Pro Val Gln Phe Leu Arg Ser
                85                  90                  95

Val Phe Ala Asn Ser Leu Val Tyr Gly Ala Ser Asp Ser Asn Val Tyr
            100                 105                 110

Asp Leu Leu Lys Asp Leu Glu Glu Gly Ile Gln Thr Leu Met Gly Arg
        115                 120                 125

Leu Glu Asp Gly Ser Pro Thr Ile Asn Gln Ile Phe Lys Gln Thr Tyr
    130                 135                 140

Ser Lys Phe Asp Thr Asn Ser His Asn Asp Asp Ala Leu Leu Lys Asn
```

```
                    145                 150                 155                 160

Tyr Gly Leu Leu Tyr Cys Phe Arg Lys Asp Met Asp Lys Val Glu Thr
                165                 170                 175

Phe Leu Arg Ile Val Gln Cys Arg Ser Val Glu Gly Ser Cys Gly Phe
                180                 185                 190

<210> SEQ ID NO 115
<211> LENGTH: 192
<212> TYPE: PRT
<213> ORGANISM: Artificial Sequence
<220> FEATURE:
<223> OTHER INFORMATION: hGH glycosylation variant

<400> SEQUENCE: 115

Met Phe Pro Thr Ile Pro Leu Ser Arg Leu Phe Asp Asn Ala Met Leu
1               5                   10                  15

Arg Ala His Arg Leu His Gln Leu Ala Phe Asp Thr Tyr Gln Glu Phe
                20                  25                  30

Glu Glu Ala Tyr Ile Pro Lys Glu Gln Lys Tyr Ser Phe Leu Gln Asn
            35                  40                  45

Pro Gln Thr Ser Leu Cys Phe Ser Glu Ser Ile Pro Thr Pro Ser Asn
        50                  55                  60

Arg Glu Glu Thr Gln Gln Lys Ser Asn Leu Glu Leu Leu Arg Ile Ser
65                  70                  75                  80

Leu Leu Leu Ile Gln Ser Trp Leu Glu Pro Val Gln Phe Leu Arg Ser
                85                  90                  95

Val Phe Ala Asn Ser Leu Val Tyr Gly Ala Ser Asp Ser Asn Val Tyr
                100                 105                 110

Asp Leu Leu Lys Asp Leu Glu Glu Gly Ile Gln Thr Leu Met Gly Arg
            115                 120                 125

Leu Glu Asp Gly Ser Pro Thr Ile Gln Gln Ile Phe Lys Gln Thr Tyr
        130                 135                 140

Ser Lys Phe Asp Thr Asn Ser His Asn Asp Asp Ala Leu Leu Lys Asn
145                 150                 155                 160

Tyr Gly Leu Leu Tyr Cys Phe Arg Lys Asp Met Asp Lys Val Glu Thr
                165                 170                 175

Phe Leu Arg Ile Val Gln Cys Arg Ser Val Glu Gly Ser Cys Gly Phe
                180                 185                 190

<210> SEQ ID NO 116
<211> LENGTH: 192
<212> TYPE: PRT
<213> ORGANISM: Artificial Sequence
<220> FEATURE:
<223> OTHER INFORMATION: hGH glycosylation variant

<400> SEQUENCE: 116

Met Phe Pro Thr Ile Pro Leu Ser Arg Leu Phe Asp Asn Ala Met Leu
1               5                   10                  15

Arg Ala His Arg Leu His Gln Leu Ala Phe Asp Thr Tyr Gln Glu Phe
                20                  25                  30

Glu Glu Ala Tyr Ile Pro Lys Glu Gln Lys Tyr Ser Phe Leu Gln Asn
            35                  40                  45

Pro Gln Thr Ser Leu Cys Phe Ser Glu Ser Ile Pro Thr Pro Ser Asn
        50                  55                  60

Arg Glu Glu Thr Gln Gln Lys Ser Asn Leu Glu Leu Leu Arg Ile Ser
65                  70                  75                  80
```

```
Leu Leu Leu Ile Gln Ser Trp Leu Glu Pro Val Gln Phe Leu Arg Ser
                85                  90                  95

Val Phe Ala Asn Ser Leu Val Tyr Gly Ala Ser Asp Ser Asn Val Tyr
            100                 105                 110

Asp Leu Leu Lys Asp Leu Glu Glu Gly Ile Gln Thr Leu Met Gly Arg
            115                 120                 125

Leu Glu Asp Gly Ser Pro Thr Ile Ala Gln Ile Phe Lys Gln Thr Tyr
        130                 135                 140

Ser Lys Phe Asp Thr Asn Ser His Asn Asp Asp Ala Leu Leu Lys Asn
145                 150                 155                 160

Tyr Gly Leu Leu Tyr Cys Phe Arg Lys Asp Met Asp Lys Val Glu Thr
                165                 170                 175

Phe Leu Arg Ile Val Gln Cys Arg Ser Val Glu Gly Ser Cys Gly Phe
            180                 185                 190

<210> SEQ ID NO 117
<211> LENGTH: 192
<212> TYPE: PRT
<213> ORGANISM: Artificial Sequence
<220> FEATURE:
<223> OTHER INFORMATION: hGH glycosylation variant

<400> SEQUENCE: 117

Met Phe Pro Thr Ile Pro Leu Ser Arg Leu Phe Asp Asn Ala Met Leu
1               5                   10                  15

Arg Ala His Arg Leu His Gln Leu Ala Phe Asp Thr Tyr Gln Glu Phe
            20                  25                  30

Glu Glu Ala Tyr Ile Pro Lys Glu Gln Lys Tyr Ser Phe Leu Gln Asn
        35                  40                  45

Pro Gln Thr Ser Leu Cys Phe Ser Glu Ser Ile Pro Thr Pro Ser Asn
50                  55                  60

Arg Glu Glu Thr Gln Gln Lys Ser Asn Leu Glu Leu Leu Arg Ile Ser
65                  70                  75                  80

Leu Leu Leu Ile Gln Ser Trp Leu Glu Pro Val Gln Phe Leu Arg Ser
                85                  90                  95

Val Phe Ala Asn Ser Leu Val Tyr Gly Ala Ser Asp Ser Asn Val Tyr
            100                 105                 110

Asp Leu Leu Lys Asp Leu Glu Glu Gly Ile Gln Thr Leu Met Gly Arg
            115                 120                 125

Leu Glu Thr Glu Thr Pro Arg Thr Gly Gln Ile Phe Lys Gln Thr Tyr
        130                 135                 140

Ser Lys Phe Asp Thr Asn Ser His Asn Asp Asp Ala Leu Leu Lys Asn
145                 150                 155                 160

Tyr Gly Leu Leu Tyr Cys Phe Arg Lys Asp Met Asp Lys Val Glu Thr
                165                 170                 175

Phe Leu Arg Ile Val Gln Cys Arg Ser Val Glu Gly Ser Cys Gly Phe
            180                 185                 190

<210> SEQ ID NO 118
<211> LENGTH: 192
<212> TYPE: PRT
<213> ORGANISM: Artificial Sequence
<220> FEATURE:
<223> OTHER INFORMATION: hGH glycosylation variant

<400> SEQUENCE: 118

Met Phe Pro Thr Ile Pro Leu Ser Arg Leu Phe Asp Asn Ala Met Leu
1               5                   10                  15
```

Arg Ala His Arg Leu His Gln Leu Ala Phe Asp Thr Tyr Gln Glu Phe
            20                  25                  30

Glu Glu Ala Tyr Ile Pro Lys Glu Gln Lys Tyr Ser Phe Leu Gln Asn
        35                  40                  45

Pro Gln Thr Ser Leu Cys Phe Ser Glu Ser Ile Pro Thr Pro Ser Asn
    50                  55                  60

Arg Glu Glu Thr Gln Gln Lys Ser Asn Leu Glu Leu Leu Arg Ile Ser
65                  70                  75                  80

Leu Leu Leu Ile Gln Ser Trp Leu Glu Pro Val Gln Phe Leu Arg Ser
                85                  90                  95

Val Phe Ala Asn Ser Leu Val Tyr Gly Ala Ser Asp Ser Asn Val Tyr
            100                 105                 110

Asp Leu Leu Lys Asp Leu Glu Glu Gly Ile Gln Thr Leu Met Gly Arg
        115                 120                 125

Leu Val Thr Glu Thr Pro Arg Thr Gly Gln Ile Phe Lys Gln Thr Tyr
    130                 135                 140

Ser Lys Phe Asp Thr Asn Ser His Asn Asp Asp Ala Leu Leu Lys Asn
145                 150                 155                 160

Tyr Gly Leu Leu Tyr Cys Phe Arg Lys Asp Met Asp Lys Val Glu Thr
                165                 170                 175

Phe Leu Arg Ile Val Gln Cys Arg Ser Val Glu Gly Ser Cys Gly Phe
            180                 185                 190

<210> SEQ ID NO 119
<211> LENGTH: 192
<212> TYPE: PRT
<213> ORGANISM: Artificial Sequence
<220> FEATURE:
<223> OTHER INFORMATION: hGH glycosylation variant

<400> SEQUENCE: 119

Met Phe Pro Thr Ile Pro Leu Ser Arg Leu Phe Asp Asn Ala Met Leu
1               5                   10                  15

Arg Ala His Arg Leu His Gln Leu Ala Phe Asp Thr Tyr Gln Glu Phe
            20                  25                  30

Glu Glu Ala Tyr Ile Pro Lys Glu Gln Lys Tyr Ser Phe Leu Gln Asn
        35                  40                  45

Pro Gln Thr Ser Leu Cys Phe Ser Glu Ser Ile Pro Thr Pro Ser Asn
    50                  55                  60

Arg Glu Glu Thr Gln Gln Lys Ser Asn Leu Glu Leu Leu Arg Ile Ser
65                  70                  75                  80

Leu Leu Leu Ile Gln Ser Trp Leu Glu Pro Val Gln Phe Leu Arg Ser
                85                  90                  95

Val Phe Ala Asn Ser Leu Val Tyr Gly Ala Ser Asp Ser Asn Val Tyr
            100                 105                 110

Asp Leu Leu Lys Asp Leu Glu Glu Gly Ile Gln Thr Leu Met Gly Arg
        115                 120                 125

Leu Glu Thr Gln Ser Pro Arg Thr Gly Gln Ile Phe Lys Gln Thr Tyr
    130                 135                 140

Ser Lys Phe Asp Thr Asn Ser His Asn Asp Asp Ala Leu Leu Lys Asn
145                 150                 155                 160

Tyr Gly Leu Leu Tyr Cys Phe Arg Lys Asp Met Asp Lys Val Glu Thr
                165                 170                 175

Phe Leu Arg Ile Val Gln Cys Arg Ser Val Glu Gly Ser Cys Gly Phe
            180                 185                 190

<210> SEQ ID NO 120
<211> LENGTH: 192
<212> TYPE: PRT
<213> ORGANISM: Artificial Sequence
<220> FEATURE:
<223> OTHER INFORMATION: hGH glycosylation variant

<400> SEQUENCE: 120

```
Met Phe Pro Thr Ile Pro Leu Ser Arg Leu Phe Asp Asn Ala Met Leu
 1               5                  10                  15

Arg Ala His Arg Leu His Gln Leu Ala Phe Asp Thr Tyr Gln Glu Phe
            20                  25                  30

Glu Glu Ala Tyr Ile Pro Lys Glu Gln Lys Tyr Ser Phe Leu Gln Asn
        35                  40                  45

Pro Gln Thr Ser Leu Cys Phe Ser Glu Ser Ile Pro Thr Pro Ser Asn
    50                  55                  60

Arg Glu Glu Thr Gln Gln Lys Ser Asn Leu Glu Leu Leu Arg Ile Ser
65                  70                  75                  80

Leu Leu Leu Ile Gln Ser Trp Leu Glu Pro Val Gln Phe Leu Arg Ser
                85                  90                  95

Val Phe Ala Asn Ser Leu Val Tyr Gly Ala Ser Asp Ser Asn Val Tyr
            100                 105                 110

Asp Leu Leu Lys Asp Leu Glu Glu Gly Ile Gln Thr Leu Met Gly Arg
        115                 120                 125

Leu Val Thr Gln Ser Pro Arg Thr Gly Gln Ile Phe Lys Gln Thr Tyr
    130                 135                 140

Ser Lys Phe Asp Thr Asn Ser His Asn Asp Asp Ala Leu Leu Lys Asn
145                 150                 155                 160

Tyr Gly Leu Leu Tyr Cys Phe Arg Lys Asp Met Asp Lys Val Glu Thr
                165                 170                 175

Phe Leu Arg Ile Val Gln Cys Arg Ser Val Glu Gly Ser Cys Gly Phe
            180                 185                 190
```

<210> SEQ ID NO 121
<211> LENGTH: 192
<212> TYPE: PRT
<213> ORGANISM: Artificial Sequence
<220> FEATURE:
<223> OTHER INFORMATION: hGH glycosylation variant

<400> SEQUENCE: 121

```
Met Phe Pro Thr Ile Pro Leu Ser Arg Leu Phe Asp Asn Ala Met Leu
 1               5                  10                  15

Arg Ala His Arg Leu His Gln Leu Ala Phe Asp Thr Tyr Gln Glu Phe
            20                  25                  30

Glu Glu Ala Tyr Ile Pro Lys Glu Gln Lys Tyr Ser Phe Leu Gln Asn
        35                  40                  45

Pro Gln Thr Ser Leu Cys Phe Ser Glu Ser Ile Pro Thr Pro Ser Asn
    50                  55                  60

Arg Glu Glu Thr Gln Gln Lys Ser Asn Leu Glu Leu Leu Arg Ile Ser
65                  70                  75                  80

Leu Leu Leu Ile Gln Ser Trp Leu Glu Pro Val Gln Phe Leu Arg Ser
                85                  90                  95

Val Phe Ala Asn Ser Leu Val Tyr Gly Ala Ser Asp Ser Asn Val Tyr
            100                 105                 110

Asp Leu Leu Lys Asp Leu Glu Glu Gly Ile Gln Thr Leu Met Gly Arg
```

```
                115                 120                 125
Leu Val Thr Glu Thr Pro Ala Thr Gly Gln Ile Phe Lys Gln Thr Tyr
            130                 135                 140

Ser Lys Phe Asp Thr Asn Ser His Asn Asp Asp Ala Leu Leu Lys Asn
145                 150                 155                 160

Tyr Gly Leu Leu Tyr Cys Phe Arg Lys Asp Met Asp Lys Val Glu Thr
                165                 170                 175

Phe Leu Arg Ile Val Gln Cys Arg Ser Val Glu Gly Ser Cys Gly Phe
            180                 185                 190

<210> SEQ ID NO 122
<211> LENGTH: 192
<212> TYPE: PRT
<213> ORGANISM: Artificial Sequence
<220> FEATURE:
<223> OTHER INFORMATION: hGH glycosylation variant

<400> SEQUENCE: 122

Met Phe Pro Thr Ile Pro Leu Ser Arg Leu Phe Asp Asn Ala Met Leu
 1               5                  10                  15

Arg Ala His Arg Leu His Gln Leu Ala Phe Asp Thr Tyr Gln Glu Phe
            20                  25                  30

Glu Glu Ala Tyr Ile Pro Lys Glu Gln Lys Tyr Ser Phe Leu Gln Asn
        35                  40                  45

Pro Gln Thr Ser Leu Cys Phe Ser Glu Ser Ile Pro Thr Pro Ser Asn
    50                  55                  60

Arg Glu Glu Thr Gln Gln Lys Ser Asn Leu Glu Leu Leu Arg Ile Ser
65                  70                  75                  80

Leu Leu Leu Ile Gln Ser Trp Leu Glu Pro Val Gln Phe Leu Arg Ser
                85                  90                  95

Val Phe Ala Asn Ser Leu Val Tyr Gly Ala Ser Asp Ser Asn Val Tyr
            100                 105                 110

Asp Leu Leu Lys Asp Leu Glu Glu Gly Ile Gln Thr Leu Met Gly Arg
        115                 120                 125

Leu Glu Thr Glu Thr Pro Ala Thr Gly Gln Ile Phe Lys Gln Thr Tyr
    130                 135                 140

Ser Lys Phe Asp Thr Asn Ser His Asn Asp Asp Ala Leu Leu Lys Asn
145                 150                 155                 160

Tyr Gly Leu Leu Tyr Cys Phe Arg Lys Asp Met Asp Lys Val Glu Thr
                165                 170                 175

Phe Leu Arg Ile Val Gln Cys Arg Ser Val Glu Gly Ser Cys Gly Phe
            180                 185                 190

<210> SEQ ID NO 123
<211> LENGTH: 192
<212> TYPE: PRT
<213> ORGANISM: Artificial Sequence
<220> FEATURE:
<223> OTHER INFORMATION: hGH glycosylation variant

<400> SEQUENCE: 123

Met Phe Pro Thr Ile Pro Leu Ser Arg Leu Phe Asp Asn Ala Met Leu
 1               5                  10                  15

Arg Ala His Arg Leu His Gln Leu Ala Phe Asp Thr Tyr Gln Glu Phe
            20                  25                  30

Glu Glu Ala Tyr Ile Pro Lys Glu Gln Lys Tyr Ser Phe Leu Gln Asn
        35                  40                  45
```

```
Pro Gln Thr Ser Leu Cys Phe Ser Glu Ser Ile Pro Thr Pro Ser Asn
 50                  55                  60

Arg Glu Glu Thr Gln Gln Lys Ser Asn Leu Glu Leu Leu Arg Ile Ser
 65                  70                  75                  80

Leu Leu Leu Ile Gln Ser Trp Leu Glu Pro Val Gln Phe Leu Arg Ser
                 85                  90                  95

Val Phe Ala Asn Ser Leu Val Tyr Gly Ala Ser Asp Ser Asn Val Tyr
                100                 105                 110

Asp Leu Leu Lys Asp Leu Glu Glu Gly Ile Gln Thr Leu Met Gly Arg
                115                 120                 125

Leu Ala Thr Gly Ser Pro Arg Thr Gly Gln Ile Phe Lys Gln Thr Tyr
            130                 135                 140

Ser Lys Phe Asp Thr Asn Ser His Asn Asp Asp Ala Leu Leu Lys Asn
145                 150                 155                 160

Tyr Gly Leu Leu Tyr Cys Phe Arg Lys Asp Met Asp Lys Val Glu Thr
                165                 170                 175

Phe Leu Arg Ile Val Gln Cys Arg Ser Val Glu Gly Ser Cys Gly Phe
            180                 185                 190
```

<210> SEQ ID NO 124
<211> LENGTH: 192
<212> TYPE: PRT
<213> ORGANISM: Artificial Sequence
<220> FEATURE:
<223> OTHER INFORMATION: hGH glycosylation variant

<400> SEQUENCE: 124

```
Met Phe Pro Thr Ile Pro Leu Ser Arg Leu Phe Asp Asn Ala Met Leu
 1               5                  10                  15

Arg Ala His Arg Leu His Gln Leu Ala Phe Asp Thr Tyr Gln Glu Phe
                 20                  25                  30

Glu Glu Ala Tyr Ile Pro Lys Glu Gln Lys Tyr Ser Phe Leu Gln Asn
             35                  40                  45

Pro Gln Thr Ser Leu Cys Phe Ser Glu Ser Ile Pro Thr Pro Ser Asn
 50                  55                  60

Arg Glu Glu Thr Gln Gln Lys Ser Asn Leu Glu Leu Leu Arg Ile Ser
 65                  70                  75                  80

Leu Leu Leu Ile Gln Ser Trp Leu Glu Pro Val Gln Phe Leu Arg Ser
                 85                  90                  95

Val Phe Ala Asn Ser Leu Val Tyr Gly Ala Ser Asp Ser Asn Val Tyr
                100                 105                 110

Asp Leu Leu Lys Asp Leu Glu Glu Gly Ile Gln Thr Leu Met Gly Arg
                115                 120                 125

Leu Glu Thr Gln Ser Pro Ser Thr Gly Gln Ile Phe Lys Gln Thr Tyr
            130                 135                 140

Ser Lys Phe Asp Thr Asn Ser His Asn Asp Asp Ala Leu Leu Lys Asn
145                 150                 155                 160

Tyr Gly Leu Leu Tyr Cys Phe Arg Lys Asp Met Asp Lys Val Glu Thr
                165                 170                 175

Phe Leu Arg Ile Val Gln Cys Arg Ser Val Glu Gly Ser Cys Gly Phe
            180                 185                 190
```

<210> SEQ ID NO 125
<211> LENGTH: 192
<212> TYPE: PRT
<213> ORGANISM: Artificial Sequence
<220> FEATURE:

<223> OTHER INFORMATION: hGH glycosylation variant

<400> SEQUENCE: 125

```
Met Phe Pro Thr Ile Pro Leu Ser Arg Leu Phe Asp Asn Ala Met Leu
1               5                   10                  15

Arg Ala His Arg Leu His Gln Leu Ala Phe Asp Thr Tyr Gln Glu Phe
            20                  25                  30

Glu Glu Ala Tyr Ile Pro Lys Glu Gln Lys Tyr Ser Phe Leu Gln Asn
        35                  40                  45

Pro Gln Thr Ser Leu Cys Phe Ser Glu Ser Ile Pro Thr Pro Ser Asn
    50                  55                  60

Arg Glu Glu Thr Gln Gln Lys Ser Asn Leu Glu Leu Leu Arg Ile Ser
65                  70                  75                  80

Leu Leu Leu Ile Gln Ser Trp Leu Glu Pro Val Gln Phe Leu Arg Ser
                85                  90                  95

Val Phe Ala Asn Ser Leu Val Tyr Gly Ala Ser Asp Ser Asn Val Tyr
            100                 105                 110

Asp Leu Leu Lys Asp Leu Glu Glu Gly Ile Gln Thr Leu Met Gly Arg
        115                 120                 125

Leu Glu Thr Gln Ser Pro Ala Thr Gly Gln Ile Phe Lys Gln Thr Tyr
    130                 135                 140

Ser Lys Phe Asp Thr Asn Ser His Asn Asp Asp Ala Leu Leu Lys Asn
145                 150                 155                 160

Tyr Gly Leu Leu Tyr Cys Phe Arg Lys Asp Met Asp Lys Val Glu Thr
                165                 170                 175

Phe Leu Arg Ile Val Gln Cys Arg Ser Val Glu Gly Ser Cys Gly Phe
            180                 185                 190
```

<210> SEQ ID NO 126
<211> LENGTH: 192
<212> TYPE: PRT
<213> ORGANISM: Artificial Sequence
<220> FEATURE:
<223> OTHER INFORMATION: hGH glycosylation variant

<400> SEQUENCE: 126

```
Met Phe Pro Thr Ile Pro Leu Ser Arg Leu Phe Asp Asn Ala Met Leu
1               5                   10                  15

Arg Ala His Arg Leu His Gln Leu Ala Phe Asp Thr Tyr Gln Glu Phe
            20                  25                  30

Glu Glu Ala Tyr Ile Pro Lys Glu Gln Lys Tyr Ser Phe Leu Gln Asn
        35                  40                  45

Pro Gln Thr Ser Leu Cys Phe Ser Glu Ser Ile Pro Thr Pro Ser Asn
    50                  55                  60

Arg Glu Glu Thr Gln Gln Lys Ser Asn Leu Glu Leu Leu Arg Ile Ser
65                  70                  75                  80

Leu Leu Leu Ile Gln Ser Trp Leu Glu Pro Val Gln Phe Leu Arg Ser
                85                  90                  95

Val Phe Ala Asn Ser Leu Val Tyr Gly Ala Ser Asp Ser Asn Val Tyr
            100                 105                 110

Asp Leu Leu Lys Asp Leu Glu Glu Gly Ile Gln Thr Leu Met Gly Arg
        115                 120                 125

Leu Glu Thr Gln Ser Pro Leu Thr Gly Gln Ile Phe Lys Gln Thr Tyr
    130                 135                 140

Ser Lys Phe Asp Thr Asn Ser His Asn Asp Asp Ala Leu Leu Lys Asn
145                 150                 155                 160
```

```
Tyr Gly Leu Leu Tyr Cys Phe Arg Lys Asp Met Asp Lys Val Glu Thr
            165                 170                 175

Phe Leu Arg Ile Val Gln Cys Arg Ser Val Glu Gly Ser Cys Gly Phe
            180                 185                 190
```

<210> SEQ ID NO 127
<211> LENGTH: 192
<212> TYPE: PRT
<213> ORGANISM: Artificial Sequence
<220> FEATURE:
<223> OTHER INFORMATION: hGH glycosylation variant

<400> SEQUENCE: 127

```
Met Phe Pro Thr Ile Pro Leu Ser Arg Leu Phe Asp Asn Ala Met Leu
  1               5                  10                  15

Arg Ala His Arg Leu His Gln Leu Ala Phe Asp Thr Tyr Gln Glu Phe
             20                  25                  30

Glu Glu Ala Tyr Ile Pro Lys Glu Gln Lys Ala Ser Phe Leu Gln Asn
         35                  40                  45

Pro Gln Thr Ser Leu Cys Phe Ser Glu Ser Ile Pro Thr Pro Ser Asn
     50                  55                  60

Arg Glu Glu Thr Gln Gln Lys Ser Asn Leu Glu Leu Leu Arg Ile Ser
 65                  70                  75                  80

Leu Leu Leu Ile Gln Ser Trp Leu Glu Pro Val Gln Phe Leu Arg Ser
                 85                  90                  95

Val Phe Ala Asn Ser Leu Val Tyr Gly Ala Ser Asp Ser Asn Val Tyr
            100                 105                 110

Asp Leu Leu Lys Asp Leu Glu Glu Gly Ile Gln Thr Leu Met Gly Arg
            115                 120                 125

Leu Glu Asp Gly Ser Pro Thr Ile Asn Thr Ile Phe Lys Gln Thr Tyr
        130                 135                 140

Ser Lys Phe Asp Thr Asn Ser His Asn Asp Asp Ala Leu Leu Lys Asn
145                 150                 155                 160

Tyr Gly Leu Leu Tyr Cys Phe Arg Lys Asp Met Asp Lys Val Glu Thr
            165                 170                 175

Phe Leu Arg Ile Val Gln Cys Arg Ser Val Glu Gly Ser Cys Gly Phe
            180                 185                 190
```

<210> SEQ ID NO 128
<211> LENGTH: 192
<212> TYPE: PRT
<213> ORGANISM: Artificial Sequence
<220> FEATURE:
<223> OTHER INFORMATION: hGH glycosylation variant

<400> SEQUENCE: 128

```
Met Phe Pro Thr Ile Pro Leu Ser Arg Leu Phe Asp Asn Ala Met Leu
  1               5                  10                  15

Arg Ala His Arg Leu His Gln Leu Ala Phe Asp Thr Tyr Gln Glu Phe
             20                  25                  30

Glu Glu Ala Tyr Ile Pro Lys Glu Gln Lys Ala Ser Phe Leu Gln Asn
         35                  40                  45

Pro Gln Thr Ser Leu Cys Phe Ser Glu Ser Ile Pro Thr Pro Ser Asn
     50                  55                  60

Arg Glu Glu Thr Gln Gln Lys Ser Asn Leu Glu Leu Leu Arg Ile Ser
 65                  70                  75                  80

Leu Leu Leu Ile Gln Ser Trp Leu Glu Pro Val Gln Phe Leu Arg Ser
```

```
                  85                  90                  95

Val Phe Ala Asn Ser Leu Val Tyr Gly Ala Ser Asp Ser Asn Val Tyr
                100                 105                 110

Asp Leu Leu Lys Asp Leu Glu Glu Gly Ile Gln Thr Leu Met Gly Arg
                115                 120                 125

Leu Glu Asp Gly Ser Pro Thr Ile Asn Thr Ile Phe Lys Gln Thr Ala
            130                 135                 140

Ser Lys Phe Asp Thr Asn Ser His Asn Asp Asp Ala Leu Leu Lys Asn
145                 150                 155                 160

Tyr Gly Leu Leu Tyr Cys Phe Arg Lys Asp Met Asp Lys Val Glu Thr
                165                 170                 175

Phe Leu Arg Ile Val Gln Cys Arg Ser Val Glu Gly Ser Cys Gly Phe
                180                 185                 190

<210> SEQ ID NO 129
<211> LENGTH: 192
<212> TYPE: PRT
<213> ORGANISM: Artificial Sequence
<220> FEATURE:
<223> OTHER INFORMATION: hGH glycosylation variant

<400> SEQUENCE: 129

Met Phe Pro Thr Ile Pro Leu Ser Arg Leu Phe Asp Asn Ala Met Leu
  1               5                  10                  15

Arg Ala His Arg Leu His Gln Leu Ala Phe Asp Thr Tyr Gln Glu Phe
                 20                  25                  30

Glu Glu Ala Tyr Ile Pro Lys Glu Gln Lys Ala Ser Phe Leu Gln Asn
                 35                  40                  45

Pro Gln Thr Ser Leu Cys Phe Ser Glu Ser Ile Pro Thr Pro Ser Asn
         50                  55                  60

Arg Glu Glu Thr Gln Gln Lys Ser Asn Leu Glu Leu Leu Arg Ile Ser
 65                  70                  75                  80

Leu Leu Leu Ile Gln Ser Trp Leu Glu Pro Val Gln Phe Leu Arg Ser
                 85                  90                  95

Val Phe Ala Asn Ser Leu Val Tyr Gly Ala Ser Asp Ser Asn Val Tyr
                100                 105                 110

Asp Leu Leu Lys Asp Leu Glu Glu Gly Ile Gln Thr Leu Met Gly Arg
                115                 120                 125

Leu Glu Asp Gly Ser Pro Thr Ile Asn Thr Ile Ala Asn Gln Thr Ala
            130                 135                 140

Ser Lys Phe Asp Thr Asn Ser His Asn Asp Asp Ala Leu Leu Lys Asn
145                 150                 155                 160

Tyr Gly Leu Leu Tyr Cys Phe Arg Lys Asp Met Asp Lys Val Glu Thr
                165                 170                 175

Phe Leu Arg Ile Val Gln Cys Arg Ser Val Glu Gly Ser Cys Gly Phe
                180                 185                 190

<210> SEQ ID NO 130
<211> LENGTH: 192
<212> TYPE: PRT
<213> ORGANISM: Artificial Sequence
<220> FEATURE:
<223> OTHER INFORMATION: hGH glycosylation variant

<400> SEQUENCE: 130

Met Phe Pro Thr Ile Pro Leu Ser Arg Leu Phe Asp Asn Ala Met Leu
  1               5                  10                  15
```

Arg Ala His Arg Leu His Gln Leu Ala Phe Asp Thr Tyr Gln Glu Phe
            20                  25                  30

Glu Glu Ala Tyr Ile Pro Lys Glu Gln Lys Ala Ser Phe Leu Gln Asn
            35                  40                  45

Pro Gln Thr Ser Leu Cys Phe Ser Glu Ser Ile Pro Thr Pro Ser Asn
    50                  55                  60

Arg Glu Glu Thr Gln Gln Lys Ser Asn Leu Glu Leu Leu Arg Ile Ser
65                  70                  75                  80

Leu Leu Leu Ile Gln Ser Trp Leu Glu Pro Val Gln Phe Leu Arg Ser
                85                  90                  95

Val Phe Ala Asn Ser Leu Val Tyr Gly Ala Ser Asp Ser Asn Val Tyr
                100                 105                 110

Asp Leu Leu Lys Asp Leu Glu Glu Gly Ile Gln Thr Leu Met Gly Arg
            115                 120                 125

Leu Glu Asp Gly Ser Pro Arg Thr Gly Gln Ile Pro Thr Gln Ala Tyr
        130                 135                 140

Ser Lys Phe Asp Thr Asn Ser His Asn Asp Ala Leu Leu Lys Asn
145                 150                 155                 160

Tyr Gly Leu Leu Tyr Cys Phe Arg Lys Asp Met Asp Lys Val Glu Thr
                165                 170                 175

Phe Leu Arg Ile Val Gln Cys Arg Ser Val Glu Gly Ser Cys Gly Phe
            180                 185                 190

<210> SEQ ID NO 131
<211> LENGTH: 192
<212> TYPE: PRT
<213> ORGANISM: Artificial Sequence
<220> FEATURE:
<223> OTHER INFORMATION: hGH glycosylation variant

<400> SEQUENCE: 131

Val Thr Pro Thr Ile Pro Leu Ser Arg Leu Phe Asp Asn Ala Met Leu
1               5                   10                  15

Arg Ala His Arg Leu His Gln Leu Ala Phe Asp Thr Tyr Gln Glu Phe
            20                  25                  30

Glu Glu Ala Tyr Ile Pro Lys Glu Gln Lys Tyr Ser Phe Leu Gln Asn
            35                  40                  45

Pro Gln Thr Ser Leu Cys Phe Ser Glu Ser Ile Pro Thr Pro Ser Asn
    50                  55                  60

Arg Glu Glu Thr Gln Gln Lys Ser Asn Leu Glu Leu Leu Arg Ile Ser
65                  70                  75                  80

Leu Leu Leu Ile Gln Ser Trp Leu Glu Pro Val Gln Phe Leu Arg Ser
                85                  90                  95

Val Phe Ala Asn Ser Leu Val Tyr Gly Ala Ser Asp Ser Asn Val Tyr
                100                 105                 110

Asp Leu Leu Lys Asp Leu Glu Glu Gly Ile Gln Thr Leu Met Gly Arg
            115                 120                 125

Leu Glu Asp Gly Ser Pro Arg Thr Gly Gln Ile Phe Lys Gln Thr Tyr
        130                 135                 140

Ser Lys Phe Asp Thr Asn Ser His Asn Asp Ala Leu Leu Lys Asn
145                 150                 155                 160

Tyr Gly Leu Leu Tyr Cys Phe Arg Lys Asp Met Asp Lys Val Glu Thr
                165                 170                 175

Phe Leu Arg Ile Val Gln Cys Arg Ser Val Glu Gly Ser Cys Gly Phe
            180                 185                 190

<210> SEQ ID NO 132
<211> LENGTH: 192
<212> TYPE: PRT
<213> ORGANISM: Artificial Sequence
<220> FEATURE:
<223> OTHER INFORMATION: hGH glycosylation variant

<400> SEQUENCE: 132

```
Met Phe Pro Thr Ile Pro Leu Ser Arg Leu Phe Asp Asn Ala Met Leu
 1               5                  10                  15

Arg Ala His Arg Leu His Gln Leu Ala Phe Asp Thr Tyr Gln Glu Phe
            20                  25                  30

Glu Glu Ala Tyr Ile Pro Lys Glu Gln Lys Tyr Ser Phe Leu Gln Asn
        35                  40                  45

Pro Gln Thr Ser Leu Cys Phe Ser Glu Ser Ile Pro Thr Pro Ser Asn
    50                  55                  60

Arg Glu Glu Thr Gln Gln Lys Ser Asn Leu Glu Leu Leu Arg Ile Ser
 65                  70                  75                  80

Leu Leu Leu Ile Gln Ser Trp Leu Glu Pro Val Gln Phe Leu Arg Ser
                85                  90                  95

Val Phe Ala Asn Ser Leu Val Tyr Gly Ala Ser Asp Ser Asn Val Tyr
            100                 105                 110

Asp Leu Leu Lys Asp Leu Glu Glu Gly Ile Gln Thr Leu Met Gly Arg
        115                 120                 125

Leu Glu Asp Gly Ser Pro Thr Gln Gly Ala Met Pro Lys Gln Thr Tyr
    130                 135                 140

Ser Lys Phe Asp Thr Asn Ser His Asn Asp Asp Ala Leu Leu Lys Asn
145                 150                 155                 160

Tyr Gly Leu Leu Tyr Cys Phe Arg Lys Asp Met Asp Lys Val Glu Thr
                165                 170                 175

Phe Leu Arg Ile Val Gln Cys Arg Ser Val Glu Gly Ser Cys Gly Phe
            180                 185                 190
```

<210> SEQ ID NO 133
<211> LENGTH: 192
<212> TYPE: PRT
<213> ORGANISM: Artificial Sequence
<220> FEATURE:
<223> OTHER INFORMATION: hGH glycosylation variant

<400> SEQUENCE: 133

```
Met Phe Pro Thr Ile Pro Leu Ser Arg Leu Phe Asp Asn Ala Met Leu
 1               5                  10                  15

Arg Ala His Arg Leu His Gln Leu Ala Phe Asp Thr Tyr Gln Glu Phe
            20                  25                  30

Glu Glu Ala Tyr Ile Pro Lys Glu Gln Lys Tyr Ser Phe Leu Gln Asn
        35                  40                  45

Pro Gln Thr Ser Leu Cys Phe Ser Glu Ser Ile Pro Thr Pro Ser Asn
    50                  55                  60

Arg Glu Glu Thr Gln Gln Lys Ser Asn Leu Glu Leu Leu Arg Ile Ser
 65                  70                  75                  80

Leu Leu Leu Ile Gln Ser Trp Leu Glu Pro Val Gln Phe Leu Arg Ser
                85                  90                  95

Val Phe Ala Asn Ser Leu Val Tyr Gly Ala Ser Asp Ser Asn Val Tyr
            100                 105                 110

Asp Leu Leu Lys Asp Leu Glu Glu Gly Ile Gln Thr Leu Met Gly Arg
        115                 120                 125
```

-continued

Leu Glu Asp Gly Ser Pro Thr Thr Thr Gln Ile Phe Lys Gln Thr Tyr
130                 135                 140

Ser Lys Phe Asp Thr Asn Ser His Asn Asp Asp Ala Leu Leu Lys Asn
145                 150                 155                 160

Tyr Gly Leu Leu Tyr Cys Phe Arg Lys Asp Met Asp Lys Val Glu Thr
                165                 170                 175

Phe Leu Arg Ile Val Gln Cys Arg Ser Val Glu Gly Ser Cys Gly Phe
            180                 185                 190

<210> SEQ ID NO 134
<211> LENGTH: 192
<212> TYPE: PRT
<213> ORGANISM: Artificial Sequence
<220> FEATURE:
<223> OTHER INFORMATION: hGH glycosylation variant

<400> SEQUENCE: 134

Met Phe Pro Thr Ile Pro Leu Ser Arg Leu Phe Asp Asn Ala Met Leu
1               5                   10                  15

Arg Ala His Arg Leu His Gln Leu Ala Phe Asp Thr Tyr Gln Glu Phe
            20                  25                  30

Glu Glu Ala Tyr Ile Pro Lys Glu Gln Lys Tyr Ser Phe Leu Gln Asn
        35                  40                  45

Pro Gln Thr Ser Leu Cys Phe Ser Glu Ser Ile Pro Thr Pro Ser Asn
50                  55                  60

Arg Glu Glu Thr Gln Gln Lys Ser Asn Leu Glu Leu Leu Arg Ile Ser
65                  70                  75                  80

Leu Leu Leu Ile Gln Ser Trp Leu Glu Pro Val Gln Phe Leu Arg Ser
                85                  90                  95

Val Phe Ala Asn Ser Leu Val Tyr Gly Ala Ser Asp Ser Asn Val Tyr
            100                 105                 110

Asp Leu Leu Lys Asp Leu Glu Glu Gly Ile Gln Thr Leu Met Gly Arg
        115                 120                 125

Leu Glu Asp Gly Ser Pro Asn Thr Gly Gln Ile Phe Lys Gln Thr Tyr
130                 135                 140

Ser Lys Phe Asp Thr Asn Ser His Asn Asp Asp Ala Leu Leu Lys Asn
145                 150                 155                 160

Tyr Gly Leu Leu Tyr Cys Phe Arg Lys Asp Met Asp Lys Val Glu Thr
                165                 170                 175

Phe Leu Arg Ile Val Gln Cys Arg Ser Val Glu Gly Ser Cys Gly Phe
            180                 185                 190

<210> SEQ ID NO 135
<211> LENGTH: 193
<212> TYPE: PRT
<213> ORGANISM: Artificial Sequence
<220> FEATURE:
<223> OTHER INFORMATION: hGH glycosylation variant

<400> SEQUENCE: 135

Met Phe Pro Thr Glu Ile Pro Leu Ser Arg Leu Phe Asp Asn Ala Met
1               5                   10                  15

Leu Arg Ala His Arg Leu His Gln Leu Ala Phe Asp Thr Tyr Gln Glu
            20                  25                  30

Phe Glu Glu Ala Tyr Ile Pro Lys Glu Gln Lys Tyr Ser Phe Leu Gln
        35                  40                  45

Asn Pro Gln Thr Ser Leu Cys Phe Ser Glu Ser Ile Pro Thr Pro Ser

```
                50                  55                  60
Asn Arg Glu Glu Thr Gln Gln Lys Ser Asn Leu Glu Leu Leu Arg Ile
 65                  70                  75                  80

Ser Leu Leu Leu Ile Gln Ser Trp Leu Glu Pro Val Gln Phe Leu Arg
                 85                  90                  95

Ser Val Phe Ala Asn Ser Leu Val Tyr Gly Ala Ser Asp Ser Asn Val
                100                 105                 110

Tyr Asp Leu Leu Lys Asp Leu Glu Glu Gly Ile Gln Thr Leu Met Gly
                115                 120                 125

Arg Leu Glu Asp Gly Ser Pro Arg Thr Gly Gln Ile Phe Lys Gln Thr
                130                 135                 140

Tyr Ser Lys Phe Asp Thr Asn Ser His Asn Asp Asp Ala Leu Leu Lys
145                 150                 155                 160

Asn Tyr Gly Leu Leu Tyr Cys Phe Arg Lys Asp Met Asp Lys Val Glu
                165                 170                 175

Thr Phe Leu Arg Ile Val Gln Cys Arg Ser Val Glu Gly Ser Cys Gly
                180                 185                 190

Phe

<210> SEQ ID NO 136
<211> LENGTH: 193
<212> TYPE: PRT
<213> ORGANISM: Artificial Sequence
<220> FEATURE:
<223> OTHER INFORMATION: hGH glycosylation variant

<400> SEQUENCE: 136

Met Phe Pro Thr Val Leu Pro Leu Ser Arg Leu Phe Asp Asn Ala Met
 1                   5                  10                  15

Leu Arg Ala His Arg Leu His Gln Leu Ala Phe Asp Thr Tyr Gln Glu
                 20                  25                  30

Phe Glu Glu Ala Tyr Ile Pro Lys Glu Gln Lys Tyr Ser Phe Leu Gln
                 35                  40                  45

Asn Pro Gln Thr Ser Leu Cys Phe Ser Glu Ser Ile Pro Thr Pro Ser
 50                  55                  60

Asn Arg Glu Glu Thr Gln Gln Lys Ser Asn Leu Glu Leu Leu Arg Ile
 65                  70                  75                  80

Ser Leu Leu Leu Ile Gln Ser Trp Leu Glu Pro Val Gln Phe Leu Arg
                 85                  90                  95

Ser Val Phe Ala Asn Ser Leu Val Tyr Gly Ala Ser Asp Ser Asn Val
                100                 105                 110

Tyr Asp Leu Leu Lys Asp Leu Glu Glu Gly Ile Gln Thr Leu Met Gly
                115                 120                 125

Arg Leu Glu Asp Gly Ser Pro Arg Thr Gly Gln Ile Phe Lys Gln Thr
                130                 135                 140

Tyr Ser Lys Phe Asp Thr Asn Ser His Asn Asp Asp Ala Leu Leu Lys
145                 150                 155                 160

Asn Tyr Gly Leu Leu Tyr Cys Phe Arg Lys Asp Met Asp Lys Val Glu
                165                 170                 175

Thr Phe Leu Arg Ile Val Gln Cys Arg Ser Val Glu Gly Ser Cys Gly
                180                 185                 190

Phe
```